(12) United States Patent
Gagner et al.

(10) Patent No.: US 12,345,641 B2
(45) Date of Patent: Jul. 1, 2025

(54) FLUORESCENCE QUENCHING IMMUNOASSAY

(71) Applicant: IDEXX Laboratories, Inc., Westbrook, ME (US)

(72) Inventors: Jennifer E. Gagner, Portland, ME (US); Kiamars Hajizadeh, Yarmouth, ME (US); Evan M. Peck, Gorham, ME (US); James R. Salter, Marietta, GA (US); Paul J. Travers, Scarborough, ME (US); Christopher P. Turmel, Westbrook, ME (US); Yingzi Wu, Johns Creek, GA (US); Hongzhi Xie, Falmouth, ME (US); Murthy V. S. N. Yerramilli, Scarborough, ME (US)

(73) Assignee: IDEZZ Laboratories, Inc., Westbrook, ME (US)

( * ) Notice: Subject to any disclaimer, the term of this patent is extended or adjusted under 35 U.S.C. 154(b) by 594 days.

(21) Appl. No.: 17/232,647

(22) Filed: Apr. 16, 2021

(65) Prior Publication Data

US 2022/0082501 A1 Mar. 17, 2022

Related U.S. Application Data

(60) Provisional application No. 63/152,365, filed on Feb. 23, 2021, provisional application No. 63/011,403, filed on Apr. 17, 2020.

(51) Int. Cl.
| | |
|---|---|
| *G01N 21/64* | (2006.01) |
| *C07D 311/82* | (2006.01) |
| *G01N 33/542* | (2006.01) |

(52) U.S. Cl.
CPC ....... *G01N 21/6428* (2013.01); *C07D 311/82* (2013.01); *G01N 33/542* (2013.01);
(Continued)

(58) Field of Classification Search
CPC .............. C07D 405/12; C07D 499/883; C07D 499/21; C07D 311/82; C07D 495/04;
(Continued)

(56) References Cited

U.S. PATENT DOCUMENTS

| | | | |
|---|---|---|---|
| 3,092,465 | A | 6/1963 | Adams et al. |
| 3,715,192 | A | 2/1973 | Wenz et al. |

(Continued)

FOREIGN PATENT DOCUMENTS

| | | |
|---|---|---|
| CA | 2799536 C | 12/2011 |
| CN | 110596396 A | 7/2022 |

(Continued)

OTHER PUBLICATIONS

Wei et al. Use of Synthetic Peptides as Tracer Antigens in Fluorescence Polarization Immunoassays of High Molecular Weight Analytes. Anal. Chem. 1993, vol. 65, pp. 3372-3377. (Year: 1993).*

(Continued)

*Primary Examiner* — Shafiqul Haq
(74) *Attorney, Agent, or Firm* — Parker Poe Adams & Bernstein, LLP; Paul E. Dietze

(57) ABSTRACT

The present invention relates to a method and reagents for determining the presence of or the amount of an analyte in a sample.

19 Claims, 61 Drawing Sheets

Specification includes a Sequence Listing.

(52) U.S. Cl.
CPC ............... *G01N 2021/6432* (2013.01); *G01N 2021/6441* (2013.01); *G01N 2470/12* (2021.08)

(58) Field of Classification Search
CPC ............. G01N 33/542; G01N 21/6428; G01N 33/9446; G01N 2470/12; G01N 33/78; G01N 2021/6441; G01N 33/6812; G01N 33/743; G01N 2021/6432; G01N 33/582
See application file for complete search history.

(56) References Cited

U.S. PATENT DOCUMENTS

| | | | |
|---|---|---|---|
| 3,992,158 A | 11/1976 | Przybylowicz et al. | |
| 3,996,345 A | 12/1976 | Ullman et al. | |
| 3,998,943 A | 12/1976 | Ullman | |
| 4,042,335 A | 8/1977 | Clement | |
| 4,050,898 A | 9/1977 | Goffe et al. | |
| 4,066,403 A | 1/1978 | Bruschi | |
| 4,144,306 A | 3/1979 | Figureas | |
| 4,160,016 A | 7/1979 | Ullman | |
| 4,174,384 A | 11/1979 | Ullman et al. | |
| 4,258,001 A | 3/1981 | Pierce et al. | |
| 4,261,968 A | 4/1981 | Ullman et al. | |
| 4,292,272 A | 9/1981 | Kitajima et al. | |
| 4,323,536 A | 4/1982 | Columbus | |
| 4,459,358 A | 7/1984 | Berke | |
| 4,614,823 A | 9/1986 | Kirkemo et al. | |
| 4,868,132 A | 9/1989 | Byrnes et al. | |
| 5,371,241 A | 12/1994 | Brush | |
| 5,427,960 A | 6/1995 | Wang et al. | |
| 5,489,668 A | 3/1996 | Scott | |
| 7,179,658 B2 | 2/2007 | Cheng et al. | |
| 7,371,562 B2 | 5/2008 | Cunningham et al. | |
| 7,939,164 B2 | 5/2011 | Koops et al. | |
| 8,012,720 B2 | 9/2011 | Fujita et al. | |
| 8,158,259 B2 | 4/2012 | Ramamurthy et al. | |
| 8,309,369 B2 | 11/2012 | Tan et al. | |
| 8,415,172 B2 | 4/2013 | Zuk | |
| 8,481,690 B2 | 7/2013 | Murthy et al. | |
| 8,492,139 B2 | 7/2013 | Tan et al. | |
| 8,608,984 B1 | 12/2013 | Taranekar et al. | |
| 8,628,973 B2 | 1/2014 | Woloszczuk et al. | |
| 8,629,412 B2 | 1/2014 | Sakai | |
| 8,778,699 B2 | 7/2014 | Yerramilli et al. | |
| 8,877,898 B2 | 11/2014 | Markiv et al. | |
| 9,005,901 B2 | 4/2015 | Gayda et al. | |
| 9,005,984 B2 | 4/2015 | Woloszczuk et al. | |
| 9,034,655 B2 | 5/2015 | Patsenker et al. | |
| 9,128,055 B2 | 9/2015 | Sekino et al. | |
| 9,157,910 B2 | 10/2015 | Dowell et al. | |
| 9,427,181 B2 | 8/2016 | Emken et al. | |
| 9,427,182 B2 | 8/2016 | Emken et al. | |
| 9,434,789 B2 | 9/2016 | Zuk | |
| 9,566,353 B2 | 2/2017 | Markiv et al. | |
| 9,591,979 B2 | 3/2017 | Taranekar et al. | |
| 9,605,068 B2 | 3/2017 | Woloszczuk et al. | |
| 9,612,238 B2 | 4/2017 | Lasmezas et al. | |
| 9,709,562 B2 | 7/2017 | Jakubowicz et al. | |
| 9,933,428 B2 | 4/2018 | Chan et al. | |
| 9,970,927 B2 | 5/2018 | Yerramilli et al. | |
| 10,064,573 B2 | 9/2018 | Emken et al. | |
| 10,073,090 B2 | 9/2018 | Dowell et al. | |
| 10,131,178 B2 | 11/2018 | Pudleiner et al. | |
| 10,321,864 B2 | 6/2019 | Zhu | |
| 10,379,046 B2 | 8/2019 | Katzlinger et al. | |
| 10,379,116 B2 | 8/2019 | Tan et al. | |
| 10,393,665 B2 | 8/2019 | Ahuja et al. | |
| 10,408,713 B2 | 9/2019 | Borch et al. | |
| 10,509,029 B2 | 12/2019 | Tamura | |
| 10,570,500 B2 | 2/2020 | Kim | |
| 10,571,396 B2 | 2/2020 | Schramm et al. | |
| 10,725,052 B2 | 7/2020 | Yerramilli et al. | |
| 10,942,179 B2 | 3/2021 | Dowell et al. | |
| 10,948,640 B2 | 3/2021 | Ockenfuss et al. | |
| 11,175,229 B1 | 11/2021 | Wang et al. | |
| 2011/0053076 A1 | 3/2011 | Sweeney et al. | |
| 2013/0130285 A1 | 5/2013 | Atkinson et al. | |
| 2013/0224884 A1 | 8/2013 | Briand et al. | |
| 2013/0280740 A1 | 10/2013 | Yerramilli et al. | |
| 2014/0011811 A1 | 1/2014 | Dudley et al. | |
| 2016/0025639 A1* | 1/2016 | Jakubowicz ............... B01L 9/52 435/7.1 |
| 2018/0335423 A1 | 11/2018 | Yerramilli et al. | |
| 2018/0353113 A1 | 12/2018 | Emken et al. | |
| 2019/0120856 A1 | 4/2019 | Xie et al. | |
| 2019/0219569 A1 | 7/2019 | Sun et al. | |
| 2019/0370447 A1 | 12/2019 | Houck et al. | |
| 2020/0181486 A1 | 6/2020 | Iwamoto et al. | |
| 2021/0055222 A1 | 2/2021 | Katzlinger | |
| 2021/0102919 A1 | 4/2021 | Foerderung et al. | |
| 2021/0247555 A1 | 8/2021 | Ockenfuss et al. | |
| 2022/0034879 A1 | 2/2022 | Elztov | |

FOREIGN PATENT DOCUMENTS

| | | | |
|---|---|---|---|
| EP | 0002963 B1 | 12/1983 | |
| EP | 0310940 A2 | 4/1989 | |
| EP | 0884591 A1 | 12/1998 | |
| EP | 2364845 A1 | 9/2011 | |
| EP | 2364846 A1 | 9/2011 | |
| EP | 3441766 A1 * | 2/2019 | ......... A61K 47/6889 |
| WO | 2005123105 A1 | 12/2005 | |
| WO | WO-2019079707 A1 * | 4/2019 | ....... G01N 33/54353 |
| WO | 2021069902 A1 | 4/2021 | |

OTHER PUBLICATIONS

Feldman et al. Cystatin B as a tissue and urinary biomarker of bladder cancer recurrence and disease progression. Clin Cancer Res. Feb. 1, 2009; 15(3): 1024-1031. (Year: 2009).*
Nanda et al. Labeling a Protein with Fluorophores Using NHS Ester Derivitization. Methods in Enzymology, 2014, vol. 536; pp. 87-93. (Year: 2014).*
Ullman et al. Fluorescent Excitation Transfer Immunoassay a general method for determination of antigens. The journal of Biological Chemistry, 1976, vol. 251, No. 14, Issue of Jul. 25, pp. 4172-4178. (Year: 1976).*
International Search Report and Written Opinion issued in International Application No. PCT/US2021/27684 as filed on Apr. 16, 2021, and mailed on Nov. 26, 2021.
Results of structure search for 2-(2,4,5, 7-tetrabromo-3-hydroxy-6-oxoxanthen-9-yl}benzoic acid provided with the International Search Report.
B. Kannan, et al., Printed Paper Sensors for Serum Lactate Dehydrogenase using Pullulan-Based Inks to Immobilize Reagents, Anal. Chem.,87, 9288-9293, (2015).
S. Jahanshahi-Anbuhi et al., Pullulan Encapsulation of Labile Biomolecules to Give Stable Bioassay Tablets, Angew. Chem. Int. Ed., 53, 6155-6158, (2014).
S. Jahanshahi-Anbuhi et al., Simple and Ultrastable All-inclusive Pullulan Tablets for Challenging Bioassays, Chem. Sci., 7, 2342, (2016).
A. Schou-Pederson et al., Comparison of Three Sample Preparation Procedures for the Quantification of L-Arginine, Asymmetric Dimethylarginine, and Symmetric Dimethylarginine in Human Plasma Using HPLC-FLD, J. Anal. Methods Chem., 1-7, (2018).
C. Tan et al., A New One Step Antigen Heterologous Homogenous Fluorescence Immunoassay for Progesterone Detection in Serum, Talanta, 134, 508-13, (2015).
M. Jolly et al., Fluorescence Polarization Immunoassay I. Monitoring Aminoglycoside Antibiotics in Serum and Plasma, Clin. Chem., 27(7):1190-1197, (1981).
J. Kada et al., Accurate Measurement of Avadin and Streptavadin in Biofluids with a New, Optimized Biotin Flourescein Conjugate, Biochimicha et Biophysica Acta 1427, 33-43, (1999).
J. Kada et al., Rapid Estimation of Avadin and Streptavadin by Fluoresence Quenching of Fluoresence Polarization, iochimicha et Biophysica Acta 1427, 44-48, (1999).

(56) References Cited

OTHER PUBLICATIONS

E. Shaw et al., Estimation of Serum Gentamicin by Quenching Fluoroimmunoassay, J. Cin. Path., 30, 526-531, (1977).

M. Shipchandler et al., 4'-[Aminomethyl]fluorescein and Its N-Alkyl Derivatives: Useful Reagents in Immunodiagnostic Techniques, Anal. Bichem., 162, 89-101, (1987).

E. Ullman et al., Fluorescent Excitation Transfer Immunoassay, A General Method for Determination of Antigens, J. Bio. Chem., 251(14), 4172-4178, (1976).

I. Hemmilia, Fluoroimmunoassays and Immunofluorometric Assays, Clin. Chem., 31(3), 359-70, (1985).

Mikaela Nichkova, Competitive Quenching Fluorescence Immunoassay for Chlorophenols Based on Laser-Induced Fluorescence Detection in Microdroplets, Analytical Chemistry, American Chemical Society, US, vol. 75, No. 1, Jan. 1, 2023, pp. 83-90.

Na Young Ji, Development of a fluorescent microsphere immunoassay for cystatin B (CSTB) in serum of patients with hepatocellular carcinoma, Clinical Chemistry and Laboratory Medicine, De Gruyter, De, vol. 49, No. 1, Jan. 1, 2011, pp. 151-155.

Supplementary Partial European Search Report, May 22, 2024.

Kobayashi, Y. et al., Fluorescence Quenching Immunoassay of Serum Cortisol, Steroids, Jan. 10, 2003, pp. 177-183, vol. 36, No. 2.

Wei, A. P. et al., Use of Synthetic Peptides as Tracer Antigens in Fluorescence Polarization Immunoassays of High Molecular Weight Analytes, Analytical Chemistry, Dec. 1, 1993, pp. 3372-3377, vol. 65, No. 23.

Ji, N. Y. et al., Development of a Fluorescent Microsphere Immunoassay for Cystatin B (CSTB) in serum of patients with hepatocellular carcinoma. Clin Chem Lab Med, Oct. 20, 2010, pp. 151-155, vol. 49, No. 1.

Tianjin Yian Biotechnology Co Ltd, CN110596396A English Translation, 0Protein detection method, test strip and kit, Jul. 19, 2022, page one.

Slade, Daniel J. et al., Chemical and biological methods to detect posttranslational modifications of arginine, Biopolymers, Feb. 2014, pp. 133-143, vol. 101, No. 2.

\* cited by examiner

FIG. 12.
12A
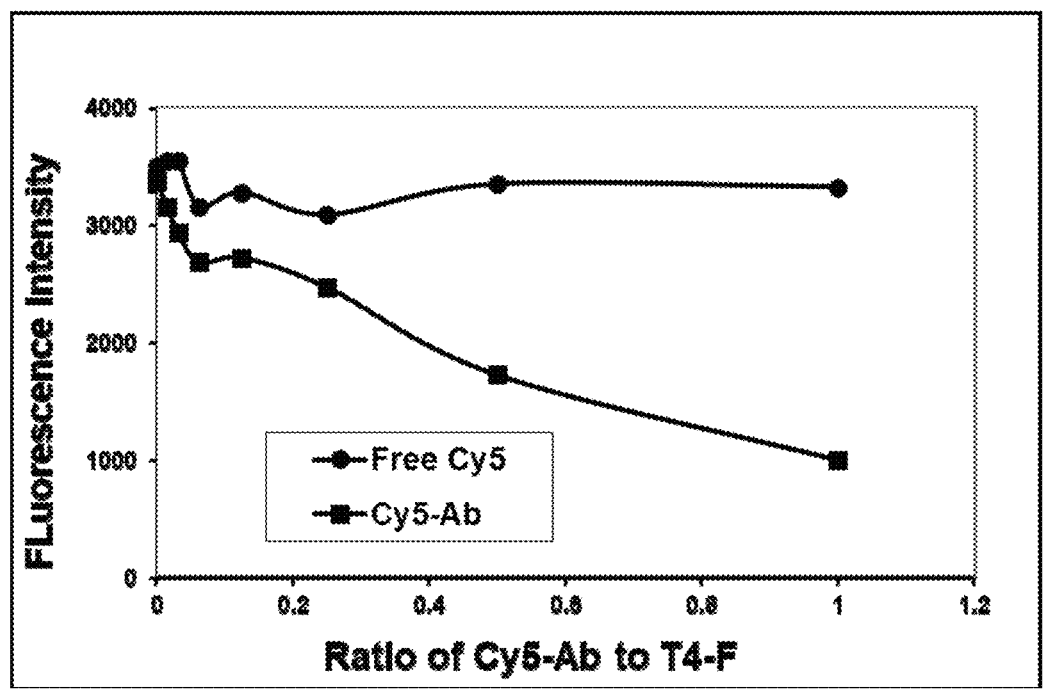
12B
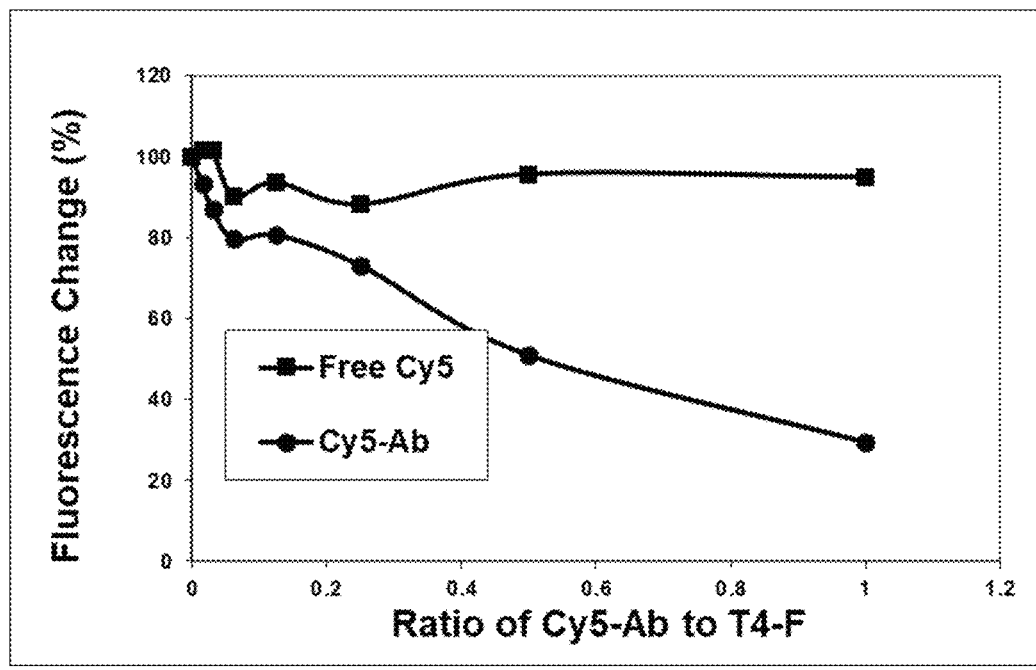

FIG. 13.
13A
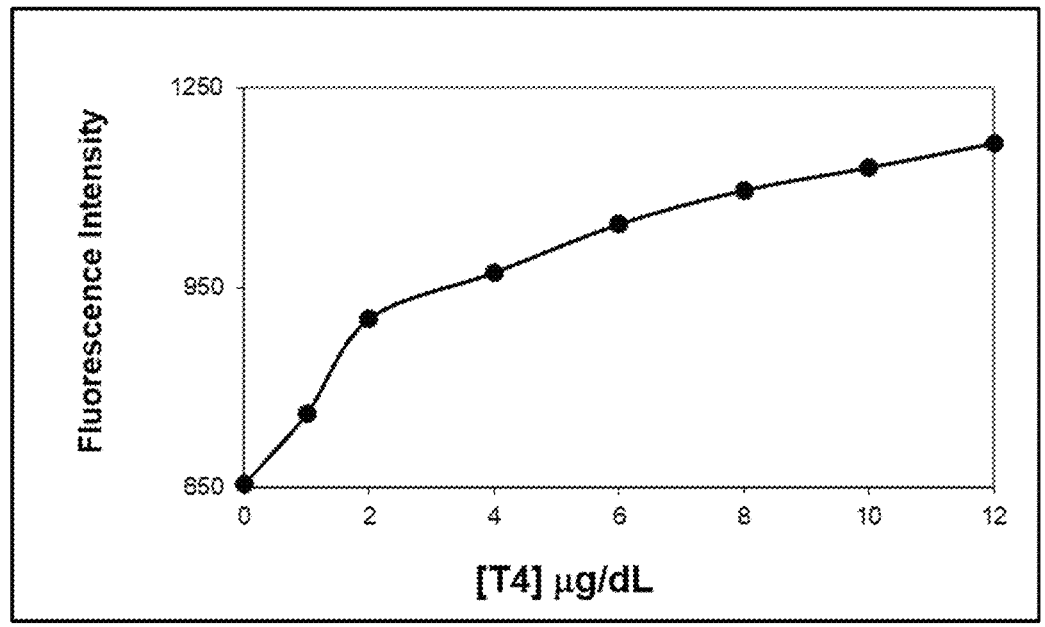
13B
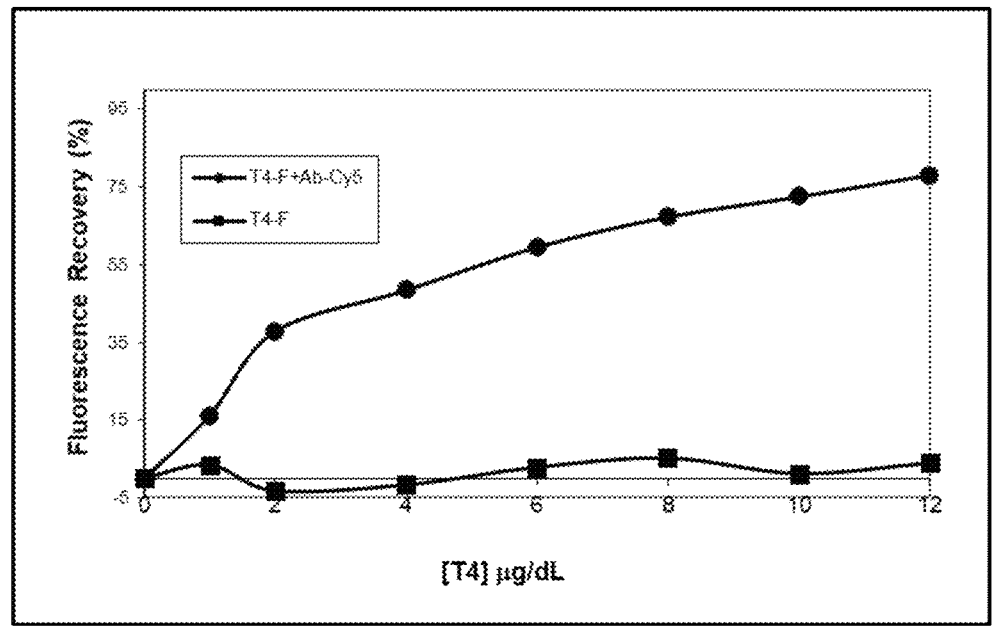

FLUORESCENCE QUENCHING IMMUNOASSAY

CROSS-REFERENCE TO RELATED APPLICATIONS

This Application claims the benefit of the filing date of U.S. Provisional Application Nos. 63/011,403 and 63/152,365, filed on Apr. 17, 2020 and Feb. 23, 2021, respectively, the contents of which are incorporated herein by reference in their entirety.

BACKGROUND OF THE INVENTION

The invention relates to a fluorescence quenching immunoassay for determining the concentration of an analyte in a sample. The invention also relates to a new class of fluorescein derivatives that can be employed as tracers in the immunoassay.

DESCRIPTION OF RELATED ART

Immunoassay is a technique for measuring the presence or concentration of a substance in a test sample, typically a solution, that frequently contains a complex mixture of substances. Typically, the test sample is a biological fluid, such as serum or urine. Immunoassay is based on the unique ability of an antibody, or other protein, to bind with high specificity to one or a very limited group of molecules. A molecule that binds to an antibody is called an antigen. Immunoassays can be carried out to measure the presence or concentration of either the antigen or the antibody (i.e., either the antigen or the antibody can be the analyte). In either case, the specificity of the assay depends on the degree to which the analyte is able to bind to its specific binding partner to the exclusion of other substances that might be present in the sample being analyzed. In addition to the need for specificity, a binding partner must be selected that has a sufficiently high affinity for the analyte to permit an accurate measurement.

A requirement of immunoassays is a means to produce a measurable signal in response to a specific binding event. This can be accomplished by measuring a change in some physical characteristic, such as light scattering or refractive index, that occurs when the analyte is bound to its binding partner. Most immunoassays depend on the use of a binding partner that is associated with a detectable label. A binding partner associated with a detectable label is often referred to as a tracer. A large variety of detectable labels have been used, including radioactive elements (used in radioimmunoassay); enzymes; fluorescent, phosphorescent, and chemiluminescent dyes; latex and magnetic particles; dye crystalites; gold, silver, and selenium colloidal particles; metal chelates;

coenzymes; electroactive groups; oligonucleotides, stable radicals, and others. Such detectable labels permit detection and quantitation of binding events either after separating free and bound tracer or by designing the system in such a way that a binding event effects a change in the signal produced by the tracer.

Immunoassays requiring a separation step, often called separation immunoassays or heterogeneous immunoassays, frequently require multiple steps, for example, careful washing of a surface to separate tracer that is bound to its binding partner from unbound tracer. Immunoassays in which a signal is affected by binding can often be run without a separation step. Such assays can frequently be carried out by simply mixing the reagents and sample and making a physical measurement. Such assays are called homogenous immunoassays and are easier to perform than heterogenous immunoassays.

Regardless of the method used, interpretation of the signal produced in an immunoassay requires reference to a standard that mimics the characteristics of the sample medium. For qualitative assays the standards may consist of a reference sample with no analyte and a positive sample having the lowest concentration of the analyte that is considered detectable. Quantitative assays require additional standards with known analyte concentrations. Comparison of the assay response of a test sample to the assay responses produced by the standards makes it possible to interpret the signal strength in terms of the presence or concentration of the analyte in the sample.

An immunoassay can be competitive or non-competitive. In a competitive immunoassay, the antibodies in a sample compete with a tracer (i.e., an antibody linked to a detectable label) to bind with an antigen. The amount of tracer bound to the antibody is then measured. In a competitive immunoassay, the amount of tracer bound to the antibody is inversely related to the concentration of antibodies in the sample. This is because when there are higher amounts of antibodies in the sample more antigen binds to the antibodies in the sample and less antigen is available to bind to the tracer.

In noncompetitive immunoassays, an antigen in the sample is specifically bound to an antibody, or an antibody in the sample is specifically bound to an antigen. The amount of antigen or antibody is then measured. Unlike the competitive immunoassay, in the noncompetitive immunoassay the response is directly proportional to the concentration of the antigen in the sample. This is because the detectable label on the second antibody will not be bound if the antigen is not present in the sample.

Fluorescence polarization has been used as a detection technique to determine the concentration of, for example, an antibody or antigen in a sample. Fluorescence polarization techniques are based on the principle that a compound containing a group that fluoresces (i.e., a fluorescent tracer) when excited by linearly polarized light will emit fluorescence having a degree of polarization inversely related to its rate of rotation. Therefore, when a fluorescent antigen that is bound to an antibody is excited with linearly polarized light, the emitted light remains highly polarized because the fluorescent antigen-antibody complex, because of its size, is constrained from rotating between the time light is absorbed and emitted. When unbound fluorescent antigen (i.e., unbound to the antibody) is excited by linearly polarized light, its rotation is much faster than rotation of the corresponding fluorescent antigen-antibody complex and the unbound fluorescent antigen molecules are more randomly oriented, therefore, the emitted light is depolarized. Fluorescence polarization provides a quantitative means for measuring the amount of fluorescent antigen-antibody complex produced in an immunoassay.

Fluorescence quenching techniques also involve using a fluorescent tracer, but are based on the principle that fluorescence of a fluorescent antigen is quenched when the fluorescent antigen is bound to an antibody. Therefore, when a fluorescent antigen that is bound to an antibody is excited with light, the intensity of the emitted light is reduced compared to the intensity of emitted light from unbound fluorescent antigen. Thus, fluorescence quenching also provides a quantitative means for measuring the amount of fluorescent antigen-antibody complex produced in an immunoassay. In a typical assay, a test sample containing an antibody whose concentration is to be determined is mixed with a fluorescent antigen, the resulting mixture excited with light, and the intensity of the emitted light measured. The antibody present in the sample bind to the fluorescent antigen. The decrease in intensity of the emitted light of the mixture compared to a control (with no antibody) is inversely proportional to the concentration of antigen in the sample.

In another fluorescence quenching assay, a test sample containing an antigen whose concentration is to be determined is combined with a mixture of a fluorescent antigen and an antibody specific for the antigen portion of the fluorescent antigen. The antigens present in the test sample and the fluorescent antigen compete for the limited number of antibodies. A higher the concentration of antigen in the test sample, leads to more of the antibodies being bound to antigen from the test sample and less being bound to fluorescent antigen (i.e., leads to more unbound fluorescent antigen). By maintaining constant the concentration of the fluorescent antigen and the antibody, the ratio of sample antigen-antibody complex to fluorescent antigen-antibody complex is directly proportional to the amount of antigen present in the sample. Similarly, the amount of unbound fluorescent antigen is directly proportional to the amount of antigen present in the sample. Therefore, by exciting the mixture with light and measuring the intensity of the emitted light, one is able to quantitatively determine the amount of antigen in the sample. The concentration of antigen in the test sample is directly proportional to the intensity of the emitted light.

These techniques are not limited to antibody-antigen binding partners. Similar assays can be performed using a protein (which is not an antibody) to determine the presence or concentration of a substrate that specifically binds to the protein. The tracer in these assays can be, for example, a detectable label linked to the protein or a detectable label linked to a molecule that binds to the protein.

Immunoassays are advantageous over other analytical methods for measuring the presence or concentration of a substance in a test sample, such as, for example, gas chromatography (GC) and high-performance liquid chromatography (HPLC), because immunoassays avoid the extractions and other complex sample work-up procedures and lengthy assay times that are often associated with these other analytical methods.

There remains a need in the art, however, for immunoassays that exhibit higher sensitivity, are simpler to perform, and less expensive to perform.

Citation of any reference in this application is not to be construed that such reference is prior art to the present application.

These and other features and advantages of the present invention will become apparent from the remainder of the disclosure, in particular the following detailed description of the preferred embodiments, all of which illustrate by way of example the principles of the invention.

SUMMARY OF THE INVENTION

The invention is directed to methods for determining the presence of or the amount of an analyte in a sample. The methods involve:

(i) providing a sample suspected of containing an analyte;
(ii) contacting the sample with a fluorescent tracer and a binding partner to provide an assay composition; wherein the binding partner is specific for the analyte and the fluorescent tracer;
(iii) irradiating the assay composition with light at a first wavelength, wherein the light at the first wavelength is not linearly polarized; and
(iv) measuring the intensity of light emitted at a second wavelength, wherein the intensity of the light emitted at the second wavelength is proportional to the concentration of the analyte in the sample.

The method can be performed in solution or as a dry slide assay. In one embodiment, the analyte is SDMA. In one embodiment, the method does not involve a separation step.

The invention also encompasses fluorescent tracers that can be used in the methods of the invention. In one embodiment, the fluorescent tracer is selected from the group consisting of:

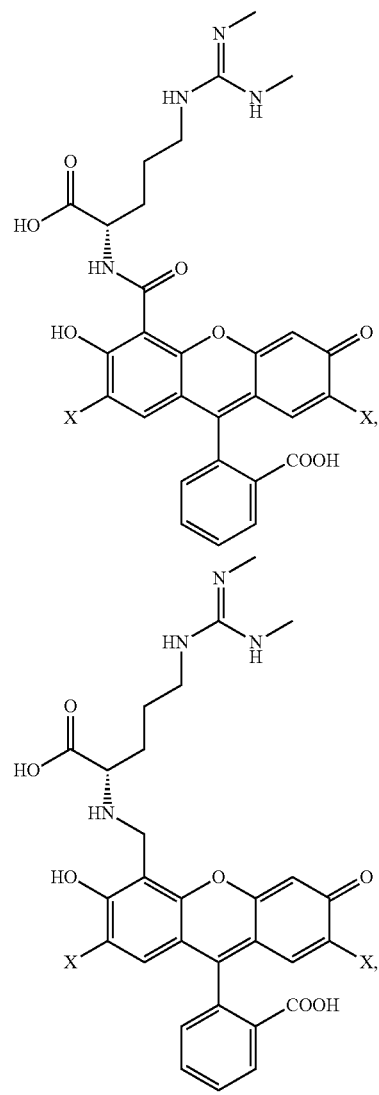

-continued

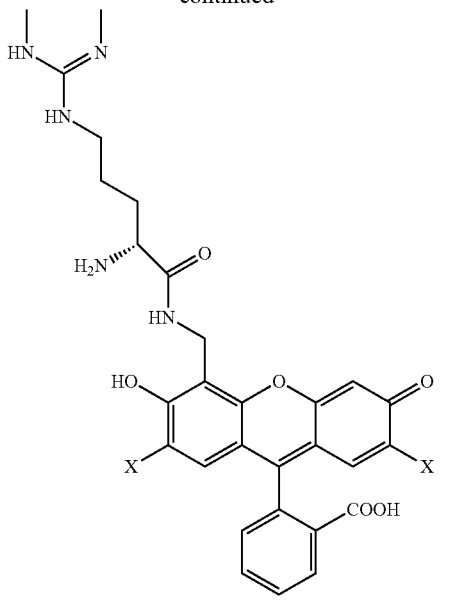

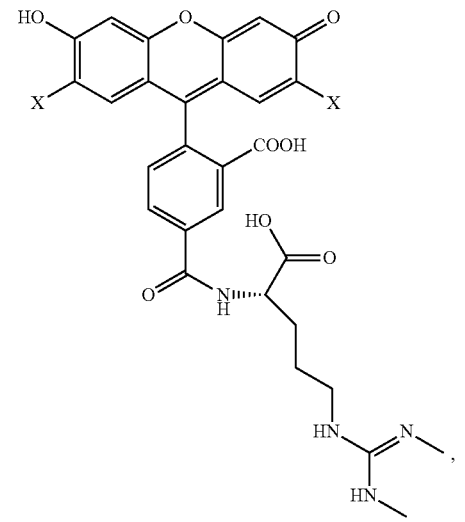

, and

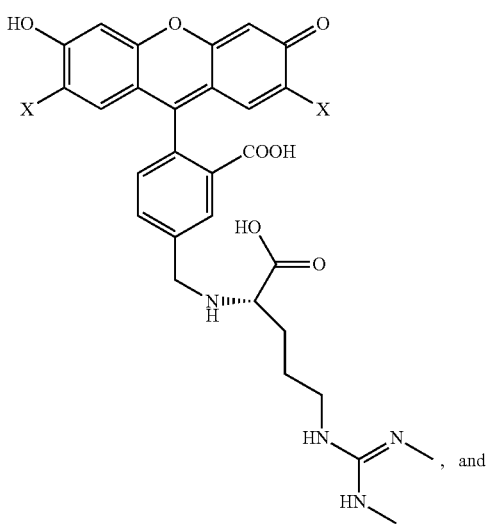

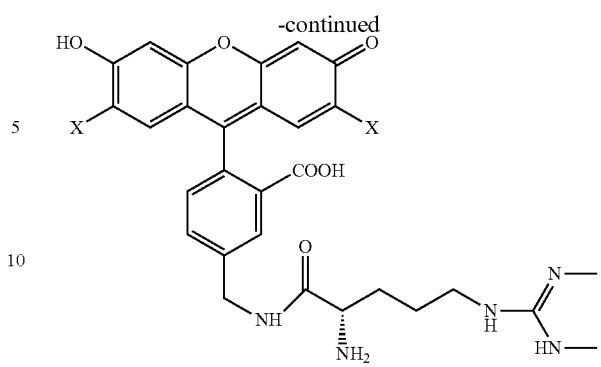

wherein X=—H,—F, —CH$_3$, —OCH$_3$, —Cl, —OH, —NO$_2$, —CN, —COOH, or —SO$_3$H.

The invention also encompasses a slide that can be used in the methods.

The invention also encompasses derivatized fluorescein molecules that are useful as intermediates for synthesizing the substituted fluorescent tracers that can be used in the methods of the invention.

BRIEF DESCRIPTION OF THE DRAWINGS

FIG. 12A is a plot of fluorescent intensity of solutions containing T4-5 and Ab-Cy5 as a function of the ratio of T4-5 to Ab-Cy5 as described in Example 22. FIG. 12B is a plot of percentage change in fluorescence of solutions containing T4-5 and Ab-Cy5 as a function of the ratio of T4-5 to Ab-Cy5 as described in Example 23.

FIG. 13A is a plot of fluorescent intensity of a solution of T4-F and Ab-Cy5 to which T4 has been added vs the T4 concentration as described in Example 23. FIG. 13B is a plot of percentage fluorescence recovery of T4-F and Ab-Cy5 to which T4 has been added vs the T4 concentration as described in Example 23.

FIGS. 18 A, B, and C depict the structure of various embodiments of the slide used in the dry slide assay method described herein.

FIGS. 18 A, B, and C depicts the structure of various embodiments of the slide used in the dry slide assay method described herein.

FIGS. 19 A and B depicts illustrative embodiments of the slide used in the dry slide assay method described herein.

DETAILED DESCRIPTION OF THE INVENTION

Figure 1:
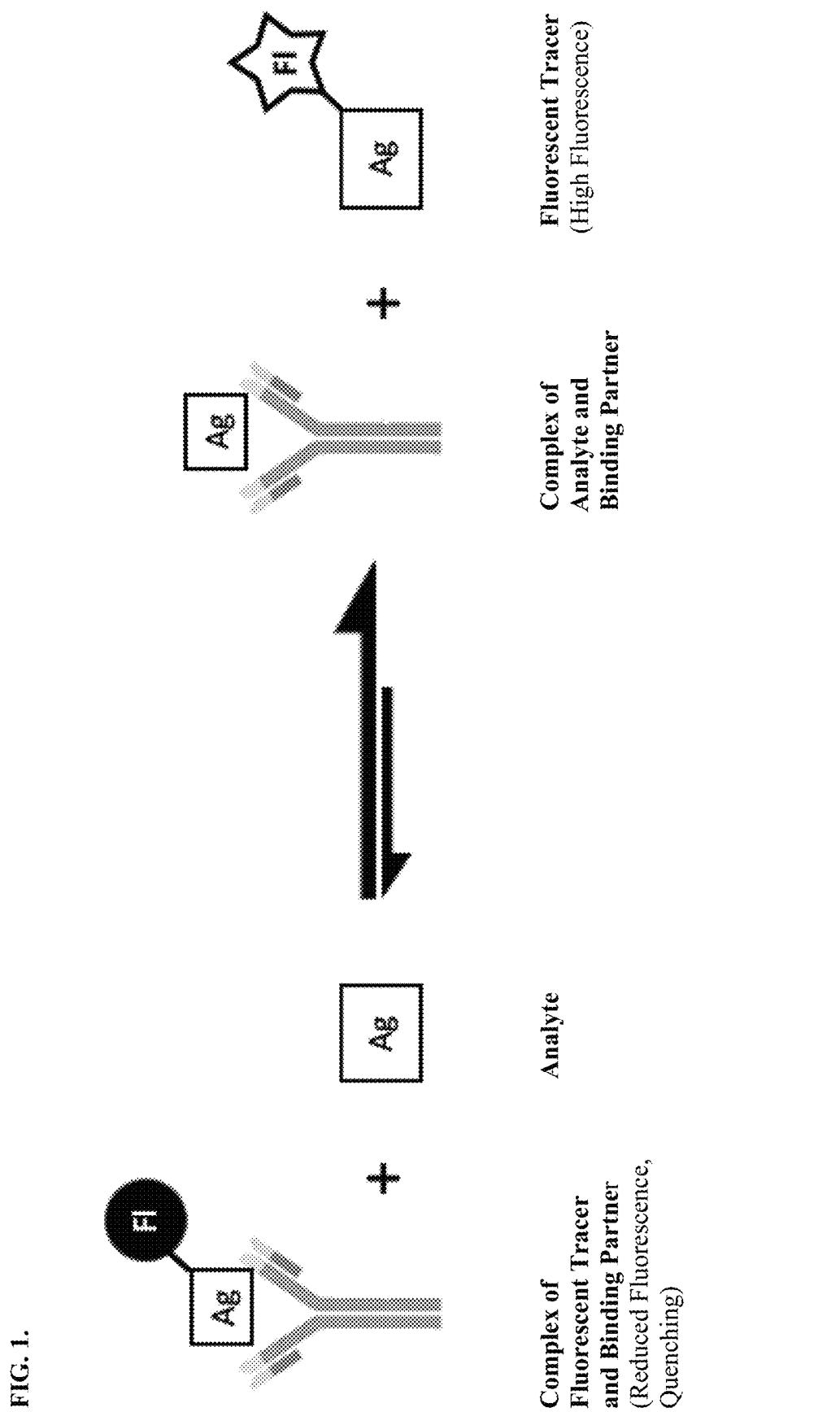
FIG. 1 is a schematic depicting the general principle of the method.

The invention is directed to methods for determining the presence of or the amount of an analyte in a sample.

The invention also encompasses a slide that can be used in the method.

The invention also encompasses substituted fluorescent tracers that can be used in the methods of the invention.

The invention also encompasses derivatized fluorescein molecules that are useful as intermediates for synthesizing the substituted fluorescent tracers that can be used in the methods of the invention.

1. Definitions

The term "analyte," as that term is used herein, refers to a molecule (e.g., antibody or antigen) that is present in a sample, such as a biological fluid, whose presence or concentration in the sample is intended to be determined and which binds to (i.e., forms a complex with) a binding partner (e.g., antigen or antibody). An analyte may be, for example, a protein, a glycoprotein, a saccharide, a polysaccharide, an amino acid, a substituted amino acid, a methylated amino acid, a hormone, an antibiotic, a nucleic acid, a metabolite, or a derivative of any of the foregoing.

A "complex," as that term is used herein, is a species formed by an association of two or more molecular entities (which can be ionic or uncharged) that does not involve a covalent bond between the entities. Examples of a complex are the association of an antibody with an antigen (or antigen derivative) and the association of a peptide with a receptor.

The term "hapten," as that term is used herein, is a molecule that does not induce antibody formation when injected into an animal but can be linked to a carrier protein to provide an antigen (immunogen) that elicits an immune response when injected into an animal that results in the formation of antibodies. The resulting antibodies may be isolated by known antibody isolation techniques. The hapten binds to the resulting antibody.

The term "antigen," as used herein, has its art recognized meaning, i.e., a substance that when introduced into the body stimulates the production of an antibody.

The term "antibody," as used herein, has its art recognized meaning, i.e., a protein produced because of the introduction of an antigen into a body. An antibody may be produced in vivo, in vitro, recombinantly or synthetically. The term "antibody" as used herein, includes a polyclonal antibody, a monoclonal antibody, a single chain antibody (scFv), or an antigen binding fragment of an antibody. Antigen-binding fragments of antibodies are a portion of an intact antibody comprising the antigen binding site or variable region of an intact antibody, wherein the portion is free of the constant heavy chain domains of the Fc region of the intact antibody. Examples of antigen binding antibody fragments include Fab, Fab', Fab'-SH, F(ab')$_2$ and F$_v$ fragments. An antibody can be any antibody class, including for example, IgG, IgM, IgA, IgD and IgE.

The terms "mAb" or "Mab," as used herein, are abbreviations for monoclonal antibody.

The phrase "binding partner," as that phrase is used herein, means a molecule that binds a second molecule with specificity. For example, the second molecule can be an antigen/antibody and the "binding partner" can be an antibody/antigen. Similarly, the second molecule can be a substrate for a receptor and the "binding partner" can be the receptor or the second molecule can be the receptor and the "binding partner" can be the substrate. In addition, the binding partner can be an aptamer. The binding partner can be a lectin and the second molecule can be a carbohydrate. The second molecule can be an analyte.

The phrases "with specificity," "specifically binds," "binds the analyte with specificity," "specific for the analyte," and similar phrases, as used herein, have their art-recognized meaning, i.e., that the binding partner recognizes and binds to an analyte (or a class of analytes) with greater affinity than it binds to other non-specific molecules. For example, an antibody raised against an antigen that binds the antigen more efficiently than other non-specific molecules can be described as specifically binding to the antigen. Binding specificity can be tested using methodology known in the art such as, for example, an enzyme-linked immunosorbant assay (ELISA), a radioimmunoassay (MA), or a western blot assay. A non-specific molecule is a molecule that binds a binding partner with less than 25%, preferably less than 10%, more preferably less than 5%, and most preferably less than 1% of the reactivity exhibited between that binding partner and its corresponding analyte.

The term "analyte-conjugate," as used herein, refers to a molecule (e.g., antigen or antibody) that is recognized by and binds to a binding partner (e.g., antibody or antigen) that is linked to a second molecule. A characteristic of the analyte-conjugate is that it possesses sufficient structural similarly to the analyte of interest so that it will be recognized by and bind to the binding partner for the analyte.

For example, if the analyte is an antigen, a substantial portion of the analyte-conjugate will have substantially the same structural, spatial, and polar arrangement as the antigen so as to define one or more determinant or epitopic sites (hereinafter referred to as an "epitopic moiety") so that the analyte-conjugate is capable of competing with the antigen for the binding site(s) of an antibody. For the most part, the analyte-conjugate will have the same or substantially the same structure and charge distribution (spatial and polar arrangement) for a significant portion of its molecular surface as the analyte being assayed for in a sample.

The analyte-conjugate can be an epitopic moiety that is linked to a detectable label (i.e., the second molecular moiety is a detectable label) so as to provide a "tracer."

The analyte-conjugate can be a hapten linked to a detectable label so as to provide a tracer. In other words, the epitopic moiety that is linked to the detectable label so as to provide the tracer is a moiety of a hapten, i.e., a moiety of the hapten that was used to develop an immune response. Functional groups on the hapten may be chemically modified to link the hapten to the detectable label.

The analyte-conjugate can be a binding protein, such as an antibody, that is linked to a detectable label, so as to provide a tracer.

A "tracer," as that term is used herein, is an analyte-conjugate that includes a detectable label.

Fluorescein is a molecule having the following structure:

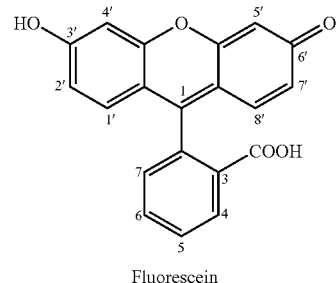

Fluorescein

It will be appreciated that fluorescein can exist in an open form and a closed form, with the open form existing as a pair of rotamers, as illustrated below:

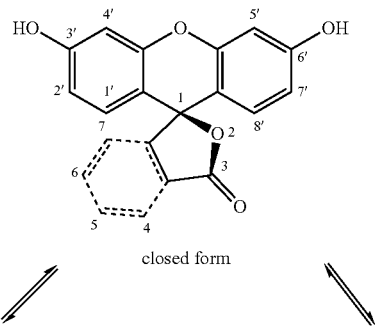

closed form

-continued

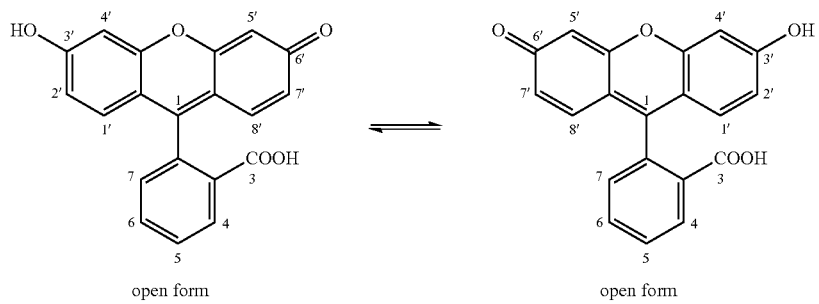

open form        open form

The term fluorescein, as used herein, includes the open form and the closed form and both rotamers of the open form. The term fluorescein, as used herein, also includes ionic and/or salt forms. The numbering of the carbon atoms of the fluorescein molecule varies in the art, depending upon whether the open or closed form of the molecule is considered. Accordingly, the literature concerning fluorescein and derivatives of fluorescein is not uniform as to carbon atom numbering. The numbering indicated above is used for the purposes of the present disclosure.

The term "fluorescent tracer," as that term is used herein, means an analyte-conjugate, wherein an epitopic moiety is linked to a molecule that fluoresces either directly or with a linking group. In an embodiment, the epitopic moiety is linked to a molecule derived from fluorescein. Preferably, the epitopic moiety is linked to fluorescein or difluorofluorescein.

The phrase "epitopic moiety," as used herein, means the portion of an analyte that has the structural, spatial, and polar arrangement so as to define one or more determinant or epitopic sites of the analyte so that the analyte is capable of being recognized by and specifically bind to its binding partner. The phrase "epitopic moiety," as used herein, means an epitopic moiety or a molecular entity that includes the epitopic moiety.

In one embodiment, the fluorescent tracer is:

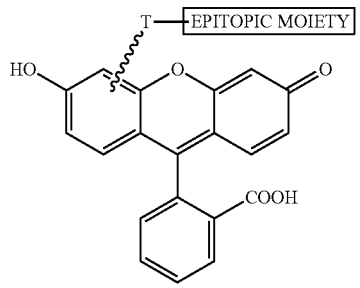

wherein T is a bond or a divalent radical (i.e., linking group) that links the epitopic moiety to the fluorescein molecule and the squiggled line shows that the T-epitopic moiety can replace any hydrogen bonded to a carbon of the fluorescein molecule.

The term "quencher," as used herein, means a moiety that when linked to a binding partner reduces the intensity of the light emitted by a fluorescent tracer that is complexed to the binding partner, compared to the intensity of the light emitted by the fluorescent tracer when it is complexed to the same binding partner but not linked to the quencher, in a fluorescence quenching immunoassay.

The term "about," as used herein means±10%, preferably±5%, more preferably,±2%, and most preferably±1%.

The phrase "substantially free of," as used herein means less than 10%, preferably less than 5%, more preferably less than 2%, and most preferably less than 1%.

The phrase "proportional to," as used herein, means that there is a correspondence or relationship between a measured value and the amount of something. For example, the phrase "the intensity of the light emitted at the second wavelength is proportional to the concentration of the analyte in the sample" means that the intensity of light emitted at a second wavelength corresponds to the concentration of an analyte in a sample. The measured value and the amount may be linearly related.

The term "macromolecule," as used herein means a compound having a molecular weight of greater than about 500 daltons. In one embodiment, the molecular weight is greater than about 2,200 daltons. In one embodiment, the molecular weight is greater than about 5,500 daltons. In one embodiment, the molecular weight is greater than about 11,000 daltons. The molecular weight of the macromolecule is typically less than about 200 kilodaltons. In one embodiment, the macromolecule is a polypeptide wherein the amino acid length is greater than about 3 amino acids. In one embodiment, the macromolecule is a polypeptide wherein the amino acid length is greater than about 5 amino acids. In one embodiment, the macromolecule is a polypeptide wherein the amino acid length is greater than about 10 amino acids. In one embodiment, the macromolecule is a polypeptide wherein the amino acid length is greater than about 20 amino acids. In one embodiment, the macromolecule is a polypeptide wherein the amino acid length is greater than about 50 amino acids. In one embodiment, the macromolecule is a polypeptide wherein the amino acid length is greater than about 100 amino acids. In one embodiment, the macromolecule is a polypeptide wherein the amino acid length is greater than about 200 amino acids. In one embodiment, the macromolecule is a polypeptide wherein the amino acid length is greater than about 300 amino acids. In one embodiment, the macromolecule is a polypeptide wherein the amino acid length is greater than about 400 amino acids. In one embodiment, the macromolecule is a polypeptide wherein the amino acid length is greater than about 500 amino acids. In one embodiment, the macromolecule is a polypeptide wherein the amino acid length is greater than about 600 amino acids. In one embodiment, the macromolecule is a polypeptide wherein the amino acid length is greater than about 700 amino acids. In one embodiment, the macromolecule is a polypeptide wherein the amino acid length is greater than about 800 amino acids. When the macromolecule is a polypeptide, the amino acid length is typically less than about 1000 amino acids. The polypeptide may be glycosylated. The polypeptide may be an antibody. In other embodiments, the macromolecule may be a carbohydrate, a polysaccharide, a lipid or a nucleic acid.

The term "SDMA" means symmetrical dimethylarginine, also known as free SDMA, and derivatives thereof. Examples of derivatives of SDMA include alkylated SDMA and acylated SDMA. Certain antibodies specific for SDMA are described in U.S. Pat. No. 9,970,927.

2. Description of the Method

The method of the invention comprises:
(i) providing a sample suspected of containing an analyte;
(ii) contacting the sample with a fluorescent tracer and a binding partner to provide an assay composition;
wherein the binding partner is specific for the analyte and the fluorescent tracer;
(iii) irradiating the assay composition with light at a first wavelength, wherein the light at the first wavelength is not linearly polarized; and
(iv) measuring the intensity of light emitted at a second wavelength,
wherein the intensity of the light emitted at the second wavelength is proportional to the concentration of the analyte in the sample.

In another embodiment of the invention, the method comprises:
(i) providing a sample suspected of containing an analyte;
(ii) contacting the sample with a fluorescent tracer and a binding partner to provide an assay composition;
wherein the binding partner is specific for the analyte and the fluorescent tracer;
(iii) irradiating the assay composition with light at a first wavelength, wherein the light at the first wavelength is linearly polarized; and
(iv) measuring the intensity of light emitted at a second wavelength,
wherein the intensity of the light emitted at the second wavelength is proportional to the concentration of the analyte in the sample.

Thus, in one embodiment, the light at the first wavelength is not linearly polarized and, in another embodiment, the light at the first wavelength is linearly polarized.

In one embodiment, there is a linear relationship between the intensity of the light emitted at the second wavelength and the concentration of the analyte in the sample.

Without wishing to be bound by theory, the basis for the method is that the fluorescence of the fluorescent tracer is quenched when the tracer is bound to the binding partner. Therefore, if the fluorescent tracer is bound to the binding partner when it is excited with the light of a first wavelength, the intensity of the light emitted at the second wavelength is reduced (quenched) compared to the intensity that would be emitted if the tracer was not bound to the binding partner. The analyte present in the sample and the fluorescent tracer compete for a limited number of binding sites on the binding partner resulting in the formation of an analyte-binding partner complex and a tracer-binding partner complex. The higher the concentration of the analyte in the sample, the fewer fluorescent tracer molecules that can bind to the binding partner and, therefore, the more fluorescent tracer molecules that will be unbound. Therefore, the intensity of light emitted at the second wavelength is directly proportional to the amount of analyte in the sample. This general principle is depicted in FIG. 1. The affinity of the binding partner for the analyte and the affinity of the binding partner for the fluorescent tracer may be different.

In one embodiment, the analyte is an antigen, the fluorescent tracer is an analyte-conjugate comprising an epitopic moiety of the antigen linked to a fluorescent label, and the binding partner is an antibody to the antigen.

In one embodiment, the fluorescent tracer is selected from the group consisting of a 4'-substituted fluorescent tracer, a 4'-substituted fluorescent tracer derivative, a 5-substituted fluorescent tracer, and a 5-substituted fluorescent tracer derivative.

In one embodiment, the fluorescent tracer is a 4'-substituted fluorescent tracer.

In one embodiment, the fluorescent tracer is a 4'-substituted fluorescent tracer derivative.

Preferably, the fluorescent tracer is a 4'-substituted fluorescent tracer or a 4'-substituted fluorescent tracer derivative, most preferably the fluorescent tracer is a 4'-substituted fluorescent tracer.

In one embodiment, the 4'-substituted fluorescent tracer is structure A1.

In one embodiment, the 4'-substituted fluorescent tracer is structure A2.

In one embodiment, the 4'-substituted fluorescent tracer is structure A3.

In one embodiment, the fluorescent tracer is a 5-substituted fluorescent tracer.

In one embodiment, the fluorescent tracer is a 5-substituted fluorescent tracer derivative.

In one embodiment, the 5-substituted fluorescent tracer is structure A4.

In one embodiment, the 5-substituted fluorescent tracer is structure A5.

In one embodiment, the 5-substituted fluorescent tracer is structure A6.

In one embodiment, the tracer is a 4'-substituted fluorescein tracer or 4'-substituted fluorescein tracer derivative having the following structure:

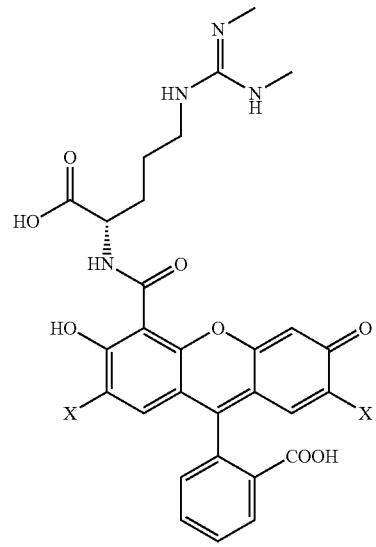

wherein X is selected from the group consisting of —H, —F, —CH$_3$, —OCH$_3$, —Cl, —OH, —NO$_2$, —CN, —COOH, and —SO$_3$H.

In one embodiment, the tracer is a 4'-substituted fluorescein tracer or 4'-substituted fluorescein tracer derivative having the following structure:

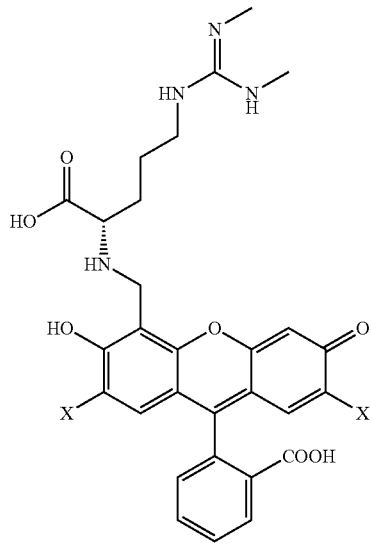

wherein X is selected from the group consisting of —H, —F, —CH₃, —OCH₃, —Cl, —OH, —NO₂, —CN, —COOH, and —SO₃H.

In one embodiment, the tracer is a 4-substituted fluorescein tracer or 4-substituted fluorescein tracer derivative having the following structure:

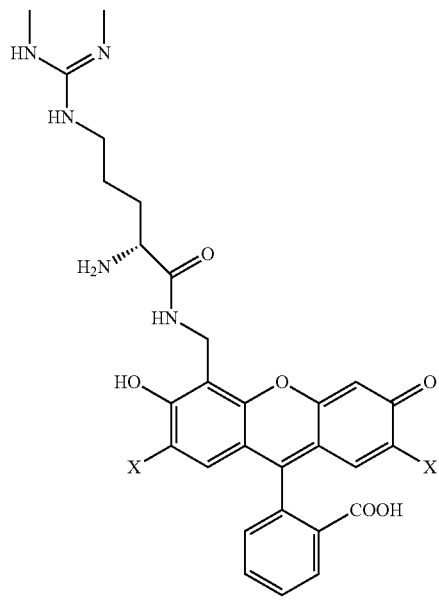

wherein X is selected from the group consisting of —H, —F, —CH₃, —OCH₃, —Cl, —OH, —NO₂, —CN, —COOH, and —SO₃H.

In one embodiment, the tracer is a 5-substituted fluorescein tracer or 5-substituted fluorescein tracer derivative having the following structure:

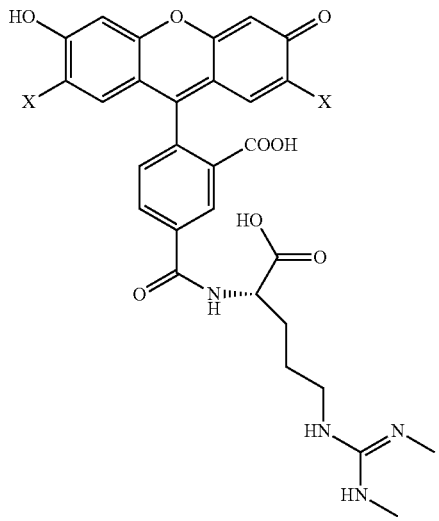

wherein X is selected from the group consisting of —H, —F, —CH₃, —OCH₃, —Cl, —OH, —NO₂, —CN, —COOH, and —SO₃H.

In one embodiment, the tracer is a 5-substituted fluorescein tracer or 5-substituted fluorescein tracer derivative having the following structure:

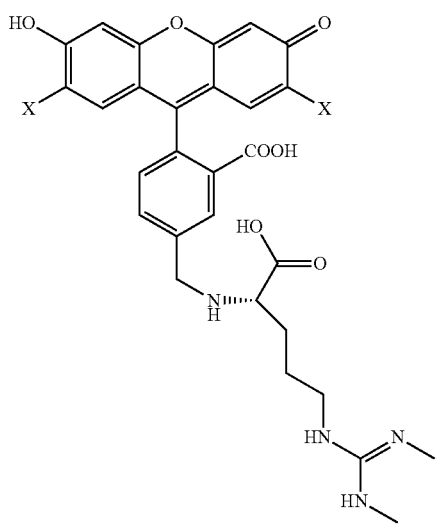

wherein X is selected from the group consisting of —H, —F, —CH₃, —OCH₃, —Cl, —OH, —NO₂, —CN, —COOH, and —SO₃H.

In one embodiment, the tracer is a 5-substituted fluorescein tracer or 5-substituted fluorescein tracer derivative having the following structure:

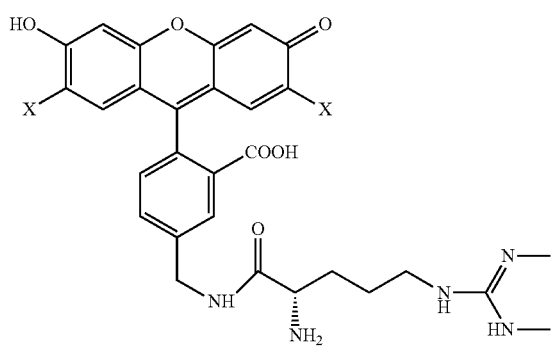

wherein X is selected from the group consisting of —H, —F, —CH$_3$, —OCH$_3$, —Cl, —OH, —NO$_2$, —CN, —COOH, and —SO$_3$H.

The molecular weight of the analyte can vary over a wide range. Typically, the molecular weight of the analyte is greater than 50 Daltons. For analytes that are small molecules, the molecular weight of the analyte is typically between about 50 and about 4,000 Daltons, preferably about 100 to about 2,000 Daltons. When the analyte is a larger molecule, such as a protein, the molecular weight can be greater than 2,000 Daltons. When the analyte is a larger molecule, such as a protein, the molecular weight can even be greater than 4,000 Daltons.

The method of the invention can be used to assay for a wide variety of analytes. Illustrative analytes include, but are not limited to, small molecules (e.g., symmetrical dimethyl arginine (SDMA), aymmetrical dimethyl arginine (ADMA), mono methylarginine (MMA), melamine, antibiotics, T4, β-lactam antibiotics (such as penicillin), sulfa drugs, cephalosporins, and steroids (e.g., progesterone and cortisol)) and macromolecules such as proteins (e.g., cystatin-B) and antibodies.

In one embodiment, the analyte is SDMA.
In one embodiment, the analyte is melamine.
In one embodiment, the analyte is T4.
In one embodiment, the analyte is cortisol. In another embodiment, the analyte is a bile acid.
In one embodiment, the analyte is progesterone.
In one embodiment, the analyte is cystatin-B. In particular embodiments, the analyte is canine or feline cystatin-B. In one embodiment, the analyte is NT-proBNP. In particular embodiments, the analyte is canine or feline NT-proBNP.
In one embodiment, the analyte is an antibiotic.
Illustrative antibiotics include, but are not limited to, amoxicillin, ampicillin, cefacetrile, cefquinome, cefazolin, cefoperazone, ceftiofur, cephalexin, cefalonium, cloxacillin, desacetyl cephapirin, dicloxacillin, nafcillin, oxacillin, cephapirin, desfuroylceftiofur, cefuroxime, and penicillin.
In one embodiment, the analyte is one or more antibiotics selected from the group consisting of the antibiotics that must be tested for in milk as required by the European Union.
In one embodiment, the analyte is one or more antibiotics selected from the group consisting of penicillin G (benzylpenicillin), ampicillin, amoxicillin, oxacillin, cloxacillin, dicloxacillin, nafcillin, cephapirin, desacetylcephapirin, ceftiofur, desfuroylceftiofur, cefquinome, cefalonium, cefazolin, cefacetrile, cephalexin, cefuroxime, and cefoperazone
In one embodiment, the analyte is one or more antibiotics selected from the group consisting of the antibiotics that must be tested for in milk as required by the United States Food and Drug Administration.
In one embodiment, the analyte is one or more antibiotics selected from the group consisting of penicillin G (benzylpenicillin), ampicillin, amoxicillin, cloxacillin, cephapirin, ceftiofur, and desfuroylceftiofur.
In one embodiment, the analyte is a macromolecule. In one embodiment, the macromolecule is a polypeptide.
In one embodiment, the assay composition is a solution.
In one embodiment, the assay composition is an aqueous solution.

The sample is typically a liquid and is commonly a biological sample such as, but not limited to, urine, serum, milk, saliva, plasma, whole blood, sweat, tears, and spinal fluid. Although the sample is typically a liquid, solid samples may also be used in the methods of the invention. Solid materials include, but are not limited to, fecal samples and solid tissue samples, extracts of the solid material, and dried liquid samples. In one embodiment, the solid sample is dissolved in or suspended in a liquid.

In one embodiment, the sample is an aqueous solution.
In one embodiment the sample is urine.
In one embodiment, the sample is serum.
In one embodiment, the sample is milk.
In one embodiment, the sample is saliva.
In one embodiment, the sample is plasma.
In one embodiment, the sample is whole blood.
In one embodiment, the sample is sweat.
In one embodiment, the sample is tears.
In one embodiment, the sample is spinal fluid.
In one embodiment, the sample is a fecal sample or fecal extract.

Typically, the sample size ranges from about 1 µL to about 5 mL. In one embodiment, the sample size is preferably about 2 µL to about 20 µL, more preferably about 2 µL to about 15 µL, and most preferably about 2 µL to about 10 µL. In one embodiment, the sample size ranges from about 50 µL to about 200 µL. In one embodiment, the sample size is about 75 µL to about 150 µL. In one embodiment, the sample size is about 100 µL.

The concentration of the analyte in the assay solution can vary over a wide range. Generally, the concentration of the analyte in the assay solution ranges from about 0.1 nM to about 1,000 nM, and typically is about 10 nm to about 100 nM. One will readily understand that more concentrated samples can simply be diluted with an appropriate diluent to provide a diluted sample having a concentration that is suitable for the assay. The method of the invention is extremely sensitive and for some analytes can be used to detect the analyte at a concentration as low as 4 ppb.

The concentration of the binding partner in the assay solution typically ranges from about 0.1 nM to about 2,000 nM. In one embodiment, the concentration of the binding partner in the assay solution ranges from about 1 nM to about 1,000 nM. In one embodiment, the concentration of the binding partner in the assay solution ranges from about 5 nM to about 500 nM. In one embodiment, the concentration of the binding partner in the assay solution ranges from about 10 nM to about 200 nM.

In various embodiments, the binding partner is linked to a solid support. Examples of solid supports include, but are not limited to, a reaction vessel, a particle, a microparticle, a microbead, a bar coded bead, a magnetic particle, or a magnetic bar coded bead.

The concentration of the fluorescent tracer in the assay solution typically ranges from about 0.1 to about 1,000 nM. In one embodiment, the concentration of the fluorescent tracer in the assay solution ranges from about 1 nM to about 500 nM. In one embodiment, the concentration of the fluorescent tracer in the assay solution ranges from about 10 nM to about 200 nM.

Typically, the ratio of the binding partner to the fluorescent tracer in the assay solution ranges from about 0.05 to about 10. In one embodiment, the ratio of the binding partner to the fluorescent tracer in the assay solution ranges from about 0.1 to about 8. In one embodiment, the ratio of the binding partner to the fluorescent tracer in the assay solution ranges from about 0.5 to about 5. One will understand, however, that the accuracy of the assay will depend on having the proper ratios for the binding partner to the tracer and for the binding partner to the analyte. Suitable ratios depend on the affinity of the analyte (and tracer) for the binding partner. One of ordinary skill in the art will readily be able to determine what are suitable ratios.

In one embodiment, the ratio of the binding partner to the fluorescent tracer is about 1:1. In one embodiment, the binding partner and the tracer are provided as a complex wherein the ratio of the binding partner to the fluorescent tracer in the complex is about 1:1. In one embodiment, the complex is provided as a solid. For example, the binding partner and the fluorescent tracer are combined in an aqueous solvent to provide an aqueous solution of the complex and the water removed from the solution by lyophilization so as to provide the complex as a solid.

Typically, the assay is conducted by intermixing the sample with the binding partner and fluorescent tracer that have previously been combined together. Typically, about 25 ul of a solution of the binding partner is combined with about 25 ul of a solution of the fluorescent tracer and the resulting solution then added to about 50 ul of a solution of the sample suspected of containing an analyte so as to provide the assay composition. The volumes of the solution of the binding partner, the solution of the fluorescent tracer, and the sample solution, however, can vary over a wide range. The assay may also be conducted by intermixing the fluorescent tracer with the binding partner and the sample that have previously been combined together. The assay may further be conducted by intermixing binding partner with the fluorescent tracer and the sample that have previously been combined together.

In one embodiment, the sample and the fluorescent tracer and binding partner are intermixed by gentle swirling or shaking to make the assay composition as a solution. When the sample, the fluorescent tracer, and binding partner are intermixed, the resulting assay solution typically has to equilibrate for only a short period of time before the assay solution is irradiated with the light of a first wavelength. Generally, it is necessary to equilibrate the assay solution for less than 1 minute. In most cases it is necessary to equilibrate the assay solution for less than 15 seconds.

The first wavelength and the second wavelength depend on the excitation and emission spectra of the fluorescent tracer. One of ordinary skill in the art will readily be able to determine what is a suitable first wavelength and a suitable second wavelength. The term first wavelength, as used herein, can encompass a range of wavelengths. Similarly, the term second wavelength, as used herein, can encompass a range of wavelengths. Typically, the first wavelength and the second wavelength are each between about 200 nm and about 900 nm. In one embodiment, the first wavelength ($\lambda$) is about 490 nm and the second wavelength ($\lambda_{em}$) is about 520 nm.

In one embodiment the sample is milk. In one embodiment, the sample is milk wherein the milk has been contacted with riboflavin binding protein (commercially available from Sigma Aldrich, St. Louis, MO). Without wishing to be bound by theory, it is believed that treating the milk with riboflavin binding protein reduces the auto-fluorescence that is associated with milk samples. Without wishing to be bound by theory, it is believed that the auto-fluorescence observed with milk samples is caused by riboflavin in the milk and that the riboflavin binding protein, by binding to riboflavin, reduces the auto-fluorescence. Reducing the auto-fluorescence advantageously provides a more accurate measurement of the light emitted at the second wavelength. Typically, the riboflavin binding protein is added to the milk in an amount sufficient to provide a concentration of the riboflavin binding protein in the assay solution of greater than about 100 µL/mL, preferably from about 100 µL/mL to about 300 µL/mL.

In one embodiment, the sample is milk and the milk is irradiated with light at a first wavelength on a first side of the sample and the intensity of the light emitted at the second wavelength is measured from a second side of the sample that is different from the first side.

In one embodiment, the sample is milk and the milk is irradiated with light at a first wavelength on one side of the sample and the intensity of the light emitted at the second wavelength is measured from the opposite side of the sample.

In one embodiment, the sample is milk and the milk is irradiated with light at a first wavelength on one side of the sample and the intensity of the light emitted at the second wavelength is measured from the same side of the sample.

When the sample is milk, the milk can be whole milk (raw milk) or skimmed milk (i.e., milk from which fat has been removed). When the sample is milk, there is no requirement of a pre-treatment step to remove cream from the milk, for example, by centrifugation.

In one embodiment, the sample is milk and the analyte is melamine.

In one embodiment, the sample is milk and the analyte is an antibiotic. Illustrative antibiotics include, but are not limited to, β-lactam antibiotics (such as penicillin), cephalosporins, sulfa drugs, fluoroquinolones, chloramphenicol, and fluoramphenicol.

In one embodiment, the sample is milk and the analyte is one or more antibiotics selected from the group consisting of the antibiotics that must be tested for in milk as required by the European Union.

In one embodiment, the antibiotic is selected from the group consisting of penicillin G (benzylpenicillin), ampicillin, amoxicillin, oxacillin, cloxacillin, dicloxacillin, nafcillin, cephapirin, desacetylcephapirin, ceftiofur, desfuroylceftiofur, cefquinome, cefalonium, cefazolin, cefacetrile, cephalexin, cefuroxime, and cefoperazone.

In one embodiment, the sample is milk and the analyte is one or more antibiotics selected from the group consisting of the antibiotics that must be tested for in milk as required by the United States Food and Drug Administration.

In one embodiment, the sample is milk and the analyte is one or more antibiotics selected from the group consisting of Penicillin G (benzylpenicillin), ampicillin, amoxicillin, cloxacillin, cephapirin, ceftiofur, and desfuroylceftiofur.

Suitable instrumentation that can be used to conduct the assay includes any commercially available fluorescent spectrometer, such as the Fluoromax+spectrometer (commercially available from Horiba Instruments Inc. of Japan) and the Synergy 4 Microplate Reader (commercially available from Biotek Instruments Inc. of Winooski, VT).

The method involves only one-step (i.e., combining the sample with the fluorescent tracer and the binding partner) and, advantageously, does not require any separation steps (i.e., steps to separate tracer that is bound to its binding partner from unbound tracer), such as washing steps.

3. Dry Slide Assay Method

In one embodiment, the method involves determining the presence or amount of an analyte in a sample on a dry slide, also referred to herein as a "slide." The method involves simply applying a sample to the slide, irradiating the slide with light of the first wavelength, and measuring the intensity of the light emitted at the second wavelength. The invention also encompasses the slide used in the method. The slide comprises 2 or more layers.

Figure 18A:
FIG. 18A depicts an embodiment having a support layer and an indicator layer.

The general structure of the slide is depicted in FIG. 18A. The slide comprises a support layer upon which is applied an indicator layer.

The support layer is a solid that provides support for the slide. The support layer is optically clear to the first wavelength and the second wavelength, i.e., it does not substantially absorb light at the first and second wavelengths. Preferably, the support layer is water-insoluble and water-impermeable. Preferably, the support layer is mechanically and thermally stable and scratch resistant. The support layer can be any suitable polymer that meets these criteria.

Illustrative support layers include, but are not limited to, glass, polystyrene, polyesters, polycarbonates, cellulose derivatives (such as cellulose acetate), polyethylene terephthalate, and mixtures thereof.

In one embodiment, the support layer is a polyethylene terephthalate layer.

In one embodiment, the support layer is a polyester layer. In one embodiment, the support layer is a polyester commercially available under the tradename Melinex® (commercially available from Tekra, a division of EIS, Inc. of Berlin, WI). In one embodiment, the support layer is a polyester commercially available under the tradename ESTAR™ (commercially available from the Eastman Kodak Company of Rochester, NY).

The thickness of the support layer typically ranges from about 15 µm to about 200 µm, preferably about 50 µm to about 150 µm, and more preferably about 70 µm to about 130 µm. In one embodiment, the thickness of the support layer is about 125 µm. In one embodiment, the thickness of the support layer is about 75 µm.

The indicator layer comprises the fluorescent tracer and the binding partner dispersed in a polymer. The fluorescent tracer and the binding partner may be present as a complex.

In one embodiment, the fluorescent tracer and the binding partner are combined in a liquid, the liquid removed to provide a solid, and the resulting solid dispersed or dissolved in the polymer which is used to provide the indicator layer. In one embodiment, the fluorescent tracer and the binding partner are combined in water, the water removed by lyophilization, and the resulting solid lyophilate dissolved or dispersed in the polymer to provide the indicator layer. In one embodiment, the fluorescent tracer and the binding partner are provided as a pre-formed complex.

In one embodiment, the indicator layer is obtained by dissolving or suspending the fluorescent tracer and the binding partner (preferably as a preformed complex) and the polymer in a solvent to provide a coating liquid, the coating liquid coated on the support layer to provide a wet indicator layer, and the solvent then removed to provide a dry indicator layer with the fluorescent tracer and the binding partner dispersed in the polymer. Preferably, the solvent is an aqueous solvent.

The thickness of the wet indicator layer typically ranges from about 30 µm to about 200 µm, preferably about 50 µm to about 150 µm, and more preferably about 80 µm to about 120 µm. When dry, the thickness of the indicator layer typically ranges from about 15 µm to about 100 µm, preferably about 10 to about 75 µm, more preferably about 20 µm to about 60 µm. In one embodiment the thickness of the dry indicator layer is from about 30 µm to about 40 µm. In one embodiment the thickness of the dry indicator layer is about 50 µm. The thickness of the indicator layer depends in part on the sample volume. For example, when the sample is a very dilute solution of the analyte, the assay will require a larger sample volume and a thicker indicator layer will be preferred so as to accommodate the larger sample volume.

In one embodiment, the binding partner is an antibody. The concentration of the fluorescent tracer and the antibody in the wet indicator layer typically ranges from about $4 \times 10^{-6}$% by wt. to about $4 \times 10^{-2}$% by wt. and about $4 \times 10^{-4}$% by wt. to about 4% by wt. of the layer, respectively. In one embodiment, the concentration of the fluorescent tracer and the antibody in the wet indicator layer ranges from about $8 \times 10^{-6}$% by wt. to about $2 \times 10^{-2}$% by wt. and about $8 \times 10^{-4}$% by wt. to about 2% by wt. of the layer, respectively. In one embodiment, the concentration of the fluorescent tracer and the antibody in the wet indicator layer ranges from about $1.6 \times 10^{-5}$% by wt. to about $1 \times 10^{-2}$% by wt. and about $1.6 \times 10^{-3}$% by wt. to about 1% by wt. of the layer, respectively. In one embodiment, the concentration of the fluorescent tracer and the antibody in the wet indicator layer ranges from about $4 \times 10^{-5}$% by wt. to about $4 \times 10^{-3}$% by wt. and about $4 \times 10^{-3}$% by wt. to about $4 \times 10^{-1}$% by wt. of the layer, respectively. The concentration of the fluorescent tracer and the antibody in the dry indicator layer typically ranges from about $1 \times 10^{-5}$% by wt. to about $1 \times 10^{-1}$% by wt. and about $1 \times 10^{-1}$% by wt. to about 1% by wt. of the layer, respectively. In one embodiment, the concentration of the fluorescent tracer and the antibody in the dry indicator layer ranges from about $2 \times 10^{-5}$% by wt. to about $5 \times 10^{-2}$% by wt. and about $2 \times 10^{-4}$% by wt. to about $5 \times 10^{-1}$% by wt. of the layer, respectively. In one embodiment, the concentration of the fluorescent tracer and the antibody in the dry indicator layer ranges from about $4 \times 10^{-5}$% by wt. to about $2.5 \times 10^{-2}$% by wt. and about $4 \times 10^{-4}$% by wt. to $2.55 \times 10^{-1}$% by wt. of the layer, respectively. In one embodiment, the concentration of the fluorescent tracer and the antibody in the dry indicator layer ranges from about $1 \times 10^{-4}$% by wt. to about $1 \times 10^{-2}$% by wt. and about $1 \times 10^{-3}$% by wt. to $1 \times 10^{-1}$% by wt. of the layer, respectively.

The indicator layer is water permeable. Suitable polymers for the indicator layer include, but are not limited to, cellulose and cellulose derivatives (e.g., hydroxypropyl cellulose, methyl cellulose, and hydroxypropyl methylcellulose), polysaccharides (such as dextran, gum arabic, agarose, and pullulan), gelatin and gelatin derivatives, polyvinyl alcohol, polyvinyl pyrrolidone, acrylamide polymers, polyurethane, alginate, xantham, and mixtures thereof.

In one embodiment, the indicator layer includes a polysaccharide. In one embodiment the indicator layer includes a linear polyglucan. In one embodiment, the polysaccharide comprises maltotriose units. In a preferred embodiment, the indicator layer includes pullulan. Without wishing to be bound by theory, it is believed that the polysaccharide acts as a binder that provides stability and integrity to the indicator layer.

The polysaccharide is typically present in the wet indicator layer in an amount ranging from about 0.5% by wt. to about 40% by wt., preferably about 1% by wt. to about 30% by wt., more preferably about 5% by wt. to about 20% by wt., and most preferably about 6% by wt. to about 15% by wt. of the wet layer. In the dry indicator layer, the polysaccharide is typically present in an amount ranging from about 1% by wt. to about 60% by wt., preferably about 5% by wt. to about 50% by wt., more preferably about 10% by wt. to about 40% by wt., and most preferably about 20% by wt. to about 35% by wt. of the dry layer.

Preferably, the indicator layer includes pullulan. In one embodiment, the indicator layer comprises pullulan, cellulose, hydroxypropyl cellulose, and mixtures thereof.

In one embodiment, the indicator layer comprises pullulan, cellulose, a surfactant, a buffer, and the fluorescent tracer and the binding partner.

Pullulan is a polysaccharide polymer consisting of maltotriose units having the structure:

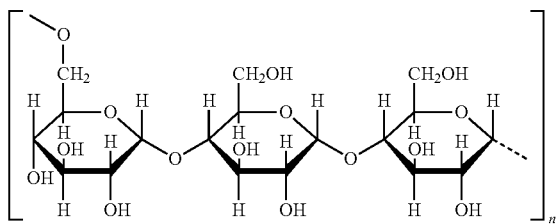

The pullulan is typically present in the wet indicator layer in an amount ranging from about 0.5% by wt. to about 40% by wt., preferably about 1% by wt. to about 30% by wt., more preferably about 5% by wt. to about 20% by wt., and most preferably about 6% by wt. to about 15% by wt. of the wet layer. In the dry indicator layer, the pullulan is typically present in an amount ranging from about 1% by wt. to about 60% by wt., preferably about 5% by wt. to about 50% by wt., more preferably about 10% by wt. to about 40% by wt., and most preferably about 20% by wt. to about 35% by wt. of the dry layer.

Without wishing to be bound by theory, it is believed that the pullulan acts as a binder that provides stability to the indicator layer and, advantageously, does not result in degradation of the complex of the fluorescent tracer and the binding partner, the fluorescent tracer, or the binding partner. Pullulan is a particularly advantageous polymer for forming the indicator layer because it is water soluble and therefore allows the indicator layer to be formed using a solution that is predominately aqueous, with minimal amounts of organic solvents (e.g., ethanol), which can lead to degradation of the fluorescent tracer and/or the binding partner. Pullulan stabilizes biological reagents, such as proteins. In one embodiment, the pullulan has a molecular weight of about 25 kDa.

The surfactant is optional. Preferably, the indicator layer includes a surfactant. Preferably the surfactant is a non-ionic surfactant. Illustrative surfactants include, but are not limited to, Igepal (commercially available from Sigma Aldrich of St. Louis, MO) or Merpol A (commercially available from Stepan Company of Northfield, IL). The surfactant, is typically present in the wet indicator layer an amount ranging from about 0.05% by wt. to about 2.0% by wt., preferably about 0.1% by wt. to about 1.0% by wt., more preferably about 0.2% by wt. to about 0.6%, and most preferably about 0.3% by wt. to about 0.5% by wt. of the layer. In the dry indicator layer, the surfactant is typically present an amount ranging from about 0.1% by wt. to about 4.0% by wt., preferably about 0.2% by wt. to about 3.0% by wt., more preferably about 0.4% by wt. to about 2.5%, and most preferably about 0.5% by wt. to about 2.0% by wt. of the layer. Without wishing to be bound by theory, it is believed that the surfactant provides better wetting of the indicator layer so as to provide a more uniform layer.

Illustrative buffers include, but are not limited to, phosphate buffered saline (PBS) and 4-(2-hydroxyethyl)-1-piperazineethanesulfonic acid (HEPES). The buffer is typically present in the wet indicator layer in an amount ranging from about 10 mM to about 300 mM, preferably about 25 mM to about 250 mM, more preferably about 50 mM to about 200 mM, and most preferably about 75 mM to about 175 mM. Preferably, the buffer is a buffer that provides a pH value of an aqueous solution of between about 4.5 to about 9.5, more preferably about 5 to about 9, and most preferably about 6 to about 8.5. In one embodiment, the buffer is a buffer that provides a pH value of an aqueous solution of about 8.

Cellulose is typically present in the wet indicator layer an amount ranging from about 2% by wt. to about 40% by wt., preferably about 5% by wt. to about 35% by wt., more preferably about 10% by wt. to about 30% by wt., and most preferably about 15% by wt. to about 25% by wt. of the layer. In the dry indicator layer, the cellulose is typically present in an amount ranging from about 30% by wt. to about 90% by wt., preferably about 40% by wt. to about 85% by wt., more preferably about 45% by wt. to about 85% by wt., and most preferably about 50% by wt. to about 75% by wt. of the dry layer. In one embodiment the cellulose is microcrystalline cellulose having a molecular weight of about 350 kDa. Preferably, the particle size of the cellulose ranges from about 5 μm to about 30 μm, preferably about 10 μm to about 25 μm. In one embodiment, the particle size of the cellulose is about 20 μm. Without wishing to be bound by theory, it is believed that the amount and particle size of the cellulose polymer is important for maximizing sensitivity of the method.

The indicator layer may further contain hydroxypropyl cellulose (HPC). The HPC, when present, is typically present in the wet layer in an amount ranging from about 2% by wt. to about 10% by wt., preferably, about 3% by wt. to about 7.5% by wt., and more preferably about 5% by wt. of the wet layer. Without wishing to be bound by theory, it is believed that HPC increases the viscosity of the wet layer so as to improve spreading of the layer. It is also believed that HPC improves the integrity of the indicator layer.

In one embodiment, the indicator layer was formed by applying a solution/suspension containing about 18% cellulose by wt., about 9% pullulan by wt., about 0.4% Merpol A by wt., about 52% of an aqueous solution of HEPES (250 mM in deionized water, pH 8) by wt., about 20% by wt. of a solution of antibody conjugated to a quencher (2.31 mg/mL in 250 mM HEPES buffer, pH 8) and about 1.5% by wt. of a solution of fluorescent tracer (0.25 mg/mL in deionized water) to a support layer and removing solvent from the solution/suspension. The resulting dry indicator layer contains about 57.0% by wt. of cellulose, about 28.5% by wt. of pullulan, about 1.2% by wt. of Merpol A, about 0.14% by wt. of the antibody conjugated to a quencher, about $1.1 \times 10^{-3}$% by wt of the fluorescent tracer, and about 13.2% by wt. of HEPES buffer. In one embodiment, the fluorescent tracer has the structure A3, the antibody is an antibody to SDMA, and the quencher is BHQ10. Antibodies to SDMA are described in, for example, U.S. Pat. No. 8,481,690.

The solution/suspension used to form the indicator layer may further contain a preservative in an amount suitable to prevent bacterial growth in the solution/suspension. In one embodiment, the preservative is Proclin™ 300 (MilliporeSigma, Burlington, MA) at a concentration of 0.05% by wt., in the solution/suspension. One of skill in the art will readily be able to identify other suitable preservatives.

The indicator layer is typically prepared by combining the components, in a solvent, preferably an aqueous solvent, and allowing them to mix. The order of addition is not particularly important. Generally, after each component is added the resulting solution/suspension is mixed. Typically, the final solution is mixed for about ½ hour before being coated onto the support layer. The solution is then applied to the support layer and the solvent removed so as to provide the indicator layer on top of the support layer. The fluorescent tracer and the binding partner can be added to the solution individually or as a preformed complex of the fluorescent tracer and the binding partner. Preferably, a preformed complex of the fluorescent tracer and the binding partner is added to the solution.

In one embodiment, the slide further comprises a spreading layer. The spreading layer is coated on top of the indicator layer. The spreading layer is water permeable. The spreading layer is water permeable and is isotropically porous, i.e., it is porous within every direction within the layer.

In one embodiment, the slide further comprises a filtering layer. The filtering layer is coated on top of the indicator layer.

Figure 18B:
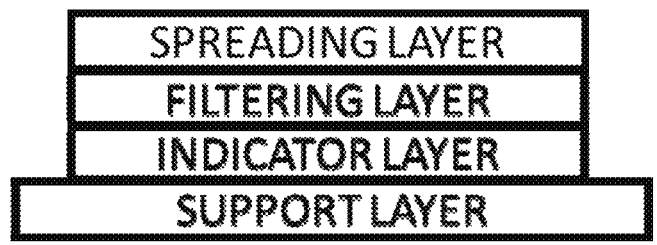
FIG. 18B depicts an embodiment having a support layer, an indicator layer, a filtering layer, and a spreading layer.

In one embodiment, the slide further comprises a spreading layer and a filtering layer. When the slide further comprises a spreading layer and a filtering layer, the filtering layer is coated on top of the indicator layer and the spreading layer is then coated on top of the filtering layer. The general structure of a slide further comprising a spreading layer and a filtering layer is depicted in FIG. 18B.

The spreading layer and the filtering layer are provided in a manner similar to how the indicator layer is provided, i.e., the components of the layer are combined in a solvent with mixing to provide a solution/suspension, the solution/suspension applied to the appropriate layer of the slide, and the solvent removed so as to provide the spreading layer or filtering layer on top of the appropriate layer.

The thickness of the wet spreading layer typically ranges from about 100 μm to about 500 μm, preferably about 150 μm to about 450 μm, more preferably about 200 μm to about 400 μm, and most preferably about 250 μm to about 350 μm. When dry, the thickness of the spreading layer typically ranges from about 25 μm to about 250 μm, preferably about 50 μm to about 200 μm, and more preferably about 75 μm to about 150 μm. The thickness of the spreading layer depends in part on the sample volume. For example, when the sample is a very dilute solution of the analyte, the assay will require a larger sample volume and a thicker spreading layer will be preferred so as to accommodate the larger sample volume.

The spreading layer is a typically a mixture of cellulose in a hydrophilic polymer matrix. Suitable hydrophilic polymers include, but are not limited to, polyacrylic acid, polyvinylpyrrolidone, polythylene glycol, polyethylene oxide, polyvinyl alcohol, polyacrylamides, and polethylenimines. The spreading layer advantageously spreads and disperses the liquid sample evenly over the slide.

The amount of cellulose in the wet spreading layer typically ranges from about 1% by wt. to about 20% by wt., preferably 5% by wt. to about 15% by wt., and more preferably about 10% by wt. of the layer. When dry, the amount of cellulose in the wet spreading layer typically ranges from about 50% by wt. to about 98% by wt., preferably about 60% by wt. to about 95% by wt., and more preferably about 70% by wt. to about 90% by wt. of the layer. In one embodiment, the spreading layer is 100% cellulose. In one embodiment, the cellulose has a particle size of about 300 μm.

The spreading layer may include polyvinylpyrrolidone (PVP). The amount of PVP by weight in the wet spreading layer typically ranges from about 0.5% by wt. to about 10% by wt., preferably about 1% by wt. to about 5% by wt., more preferably about 1.5% by wt. to about 3% by wt. of the layer. In one embodiment, the amount of PVP in the wet spreading layer is about 2% by wt. The amount of PVP by weight in the dry spreading layer typically ranges from about 1% by wt. to about 30% by wt., preferably about 5% by wt. to about 25% by wt., more preferably about 10% by wt. to about 20% by wt. of the layer. In one embodiment, the amount of PVP in the dry spreading layer is about 17% by wt.

The spreading layer may include tetramethylammonium hydroxide (TMAH) or other suitable base. The TMAH may serve to adjust the pH of the spreading layer. Without wishing to be bound by theory, it is believed that TMAH increases the ability of the spreading layer to absorb and spread the sample rapidly across the whole slide. The amount of TMAH by weight in the wet spreading layer typically ranges from about 0.01% by wt. to about 0.5% by wt., preferably about 0.025% by wt. to about 0.25% by wt. In one embodiment, the amount of TMAH in the wet spreading layer is about 0.05% by wt. The amount of TMAH by weight in the dry spreading layer typically ranges from about 0.08% by wt. to about 4% by wt., preferably about 0.2% by wt. to about 2% by wt., more preferably about 10% by wt. In one embodiment, the amount of TMAH in the dry spreading layer is about 0.4% by wt.

In one embodiment, the spreading layer is formed by applying a solution/suspension containing about 10% by wt. of cellulose, about 2% by wt. of polyvinylpyrrolidone (PVP), about 68% by wt. of water, about 20% by wt. of ethanol, about 0.06% by wt. of polyacrylic acid (PAA), and about 0.05% by wt. of tetramethylammonium hydroxide (TMAH) and removing solvent from the solution/suspension. The resulting dry spreading layer contains about 82.6% by wt. of cellulose, about 16.5% by wt. of PVP, about 0.5% by wt. of PAA, and about 0.4% by wt. of TMAH.

The filtering layer binds to compounds present in the sample other than the analyte that could potentially interfere with the assay and prevents these other compounds from diffusing into the indicator layer.

The thickness of the wet filtering layer typically ranges from about 50 μm to about 250 μm, preferably about 75 μm to about 225 μm, and more preferably about 100 μm to about 200 μm. When dry, the thickness of the filtering layer typically ranges from about 5 μm to about 50 μm, preferably about 7 μm to about 40 μm, and more preferably about 10 μm to about 30 μm. The thickness of the filtering layer depends in part on the sample volume. For example, when the sample is a very dilute solution of the analyte, the assay will require a larger sample volume and a thicker filtering layer will be preferred so as to accommodate the larger sample volume.

The filtering layer typically comprises a polyurethane in combination with another hydrophylic polymer(s) that retains moisture. In one embodiment, the filtering layer comprises polyurethane and cellulose. A suitable polyurethane is HydroMed D4 (commercially available from AdvanSource Biomaterials Corp of Wilmington, MA). In one embodiment, the polyurethane is a mixture of low viscosity HydroMed D4 and high viscosity HydroMed D4. In one embodiment, the polyurethane is a mixture of about equal amounts of low viscosity HydroMed D4 and high viscosity HydroMed D4.

The amount of polyurethane in the wet filtering layer typically ranges from about 2% by wt. to about 40% by wt., preferably about 5% by wt. to about 30% by wt., and more preferably about 10% by wt. to about 20% by wt. of the layer. In one embodiment, the amount of polyurethane in the wet filtering layer is about 15% by wt. of the layer. When dry, the amount of polyurethane in the filtering layer typically ranges from about 40% by wt. to about 95% by wt., preferably about 50% by wt. to about 80% by wt., more preferably about 55% by wt. to about 75% by wt. of the layer. In one embodiment, the amount of polyurethane in the dry filtering layer is about 65% by wt. of the layer.

The amount of cellulose in the wet filtering layer typically ranges from about 2% by wt. to about 60% by wt., preferably about 4% by wt. to about 50% by wt., and more preferably about 6% by wt. to about 40% by wt. of the layer. In one embodiment, the amount of cellulose in the wet filtering layer is about 8% by wt. When dry, the amount of cellulose in the filtering layer typically ranges from about 10% by wt. to about 60% by wt., preferably about 20% by wt. to about 50% by wt., and more preferably about 25% by wt. to about 45% by wt. of the layer. In one embodiment, the amount of cellulose in the dry filtering layer is about 35% by wt. of the layer.

FIG. 24 depicts the result of an assay (using a slide with a filtering layer containing about 20% by wt. of cellulose, about 42% by wt. of titanium dioxide, and about 38% by wt. of HydroMed D4, as described below) to determine the concentration of SDMA in a sample containing a fixed amount of SDMA (μg/dL), wherein the sample includes various concentrations of compounds that could potentially interfere with the assay (i.e., interferents). The interferents are (A) hemolysis (0 to 500 mg/dL), (B) bilirubin (0 to 30 mg/dL), (C) intralipid (0 to 1000 mg/dL) and (D) whole blood (0 to 10%). The experiment is described in Example 39.

In one embodiment, the filtering layer further comprises titanium oxide (TiO2). Typically, the titanium dioxide is present in the wet filtering layer in an amount ranging from about 2% by wt. to about 30% by wt., preferably about 5% by wt. to about 20% by wt., and more preferably about 10% by wt. to about 20% by wt. of the layer. In one embodiment, the titanium oxide is present in the wet filtering layer in an amount of about 14% by wt. of the layer. Typically, the titanium dioxide is present in the dry filtering layer in an amount ranging from about 20% by wt. to about 60% by wt., preferably about 25% by wt. to about 55% by wt., and more preferably about 30% by wt. to about 50% by wt. of the layer. In one embodiment, the titanium oxide is present in the wet filtering layer in an amount of about 42% by wt. of the layer.

The average particle size of the titanium oxide particles is typically less than about 10 μm and preferably less than about 5 μm. In one embodiment, the average particle size of the titanium oxide particles is about 0.35 μm.

A filtering layer comprising titanium oxide is particularly advantageous when the slide includes a carbon black layer, as described below, because the carbon black layer absorbs scattered light. The titanium oxide layer advantageously reflects the light away from the carbon black layer and back towards the detector, so as to prevent the carbon black layer from absorbing the scattered light, resulting in improved sensitivity.

In one embodiment, the filtering layer is formed by applying a solution/suspension containing about 7% by wt. of cellulose, about 14% by wt. of titanium dioxide, and about 79% by wt. of a D4 hydrogel solution (containing about 16% by wt. of a mixture of equal amounts of low viscosity HydroMed D4 and high viscosity HydroMed D4, about 90% by wt. of ethanol, and about 10% by wt. of water) and removing solvent from the solution/suspension. The resulting dry filtering layer contains about 20% by wt. of cellulose, about 42% by wt. of titanium dioxide, and about 38% by wt. of HydroMed D4.

Figure 18C:
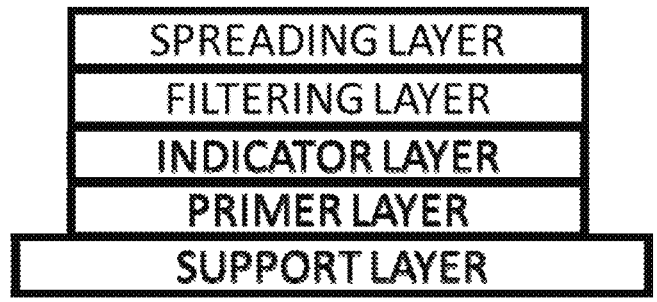
FIG. 18C depicts an embodiment having a support layer, a primer layer, an indicator layer, a filtering layer, and a spreading layer.

In one embodiment, the slide further comprises a primer layer. The primer layer is layered on top of the support layer and is positioned between the support layer and the indicator layer. The general structure of a slide further comprising a spreading layer, a filtering layer, and a primer layer, in addition to the support layer and the indicator layer, is depicted in FIG. 18C.

The primer layer advantageously facilitates coating of the indicator layer on top of the support layer. Without wishing to be bound by theory, it is believed that the support layer is hydrophobic and the indicator layer is hydrophilic so that they are not particularly compatible. The primer layer overcomes this incompatibility. The primer layer preferably comprises polyurethane, such as HydroMed D4. In one embodiment, the polyurethane is a mixture of low viscosity HydroMed D4 and high viscosity HydroMed D4. In one embodiment, the polyurethane is a mixture of about equal amounts of low viscosity HydroMed D4 and high viscosity HydroMed D4.

The thickness of the wet primer layer typically ranges from about 5 μm to about 60 μm, preferably about 10 μm to about 55 μm, and more preferably about 20 μm to about 50 μm. In one embodiment, the wet thickness of the primer layer is about 40 μm. When dry, the thickness of the primer layer typically ranges from about 1 μm to about 20 μm, preferably about 1.5 to about 15 μm, and more preferably about 2 μm to about 10 μm. In one embodiment, the dry thickness of the primer layer is about 4 μm.

In one embodiment, the primer layer is formed by by applying a solution/suspension containing about 10% by wt. of a mixture of equal amounts of low viscosity HydroMed D4 and high viscosity HydroMed D4 in a solvent of about 90% by wt. of ethanol and about 10% by wt. of water and removing solvent from the solution/suspension. The resulting dry primer layer contains about 100% by wt. of HydroMed D4.

In one embodiment, the slide further comprises a carbon black layer. The carbon black layer is coated on top of the filter layer and positioned between the filter layer and the spreading layer. The carbon black layer acts as an optical barrier to advantageously filter stray light from the environment that interferes with the measurement of the emitted light of the second wavelength. The carbon black layer also functions to bind compounds present in the sample other than the analyte that could potentially interfere with the assay and prevents these other compounds from diffusing into the indicator layer. Thus, a function of the carbon black layer is similar to the function of the filtering layer.

The carbon black can be replaced with, or used in combination with, other materials to filter stray light. Illustrative other materials include, but are not limited to black latex beads, black silica beads, activated charcoal, $C_{60}$, graphene, or other colored materials such as red latex beads.

The carbon black layer comprises carbon black dispersed in a polymer. Suitable polymers for the carbon black layer include, but are not limited to, polyurethane (such as HydroMed D4), polyethylene oxide, silicones, polyvinyl alcohol, and polyacrylamides. In one embodiment, the polymer is HydroMed D4.

The amount of carbon black in the wet carbon black layer typically ranges from about 1% by wt. to about 20% by wt., preferably about 1.5% by wt. to about 15% by wt., more preferably about 2% by wt. to about 10% by wt. of the layer. In one embodiment, the amount of carbon black in the wet carbon black layer is about 5% by wt. of the layer. When dry, the amount of carbon black in the carbon black layer typically ranges from about 10% by wt. to about 40% by wt., preferably about 15% by wt. to about 35% by wt., more preferably about 20% by wt. to about 30% by wt. of the layer. In one embodiment, the amount of carbon black in the wet carbon black layer is about 25% by wt. of the layer.

The thickness of the wet carbon black layer typically ranges from about 50 µm to about 300 µm, preferably about 75 µm to about 250 µm, and more preferably about 100 µm to about 200 µm. In one embodiment, the thickness of the wet carbon black is about 140 µm. When dry, the thickness of the carbon black layer typically ranges from about 5 µm to about 30 µm, preferably about 7.5 µm to about 25 µm, and more preferably about 10 µm to about 20 µm. In one embodiment, the thickness of the wet carbon black is about 14 µm.

In one embodiment, the carbon black layer is formed by by applying a solution/suspension containing about 4.7% by wt. of carbon black, about 95.3% by wt. of a D4 hydrogel solution (containing about 16% by wt. of a mixture of equal amounts of low viscosity HydroMed D4 and high viscosity HydroMed D4, about 90% by wt. of ethanol, and about 10% by wt. of water) and removing solvent from the solution/suspension. The resulting dry carbon black layer contains about 24% by wt. of carbon black and about 76% by wt. of HydroMed D4.

As noted above, when the slide includes a carbon black layer the slide preferably also includes titanium oxide in the filtering layer.

Alternatively, when the slide includes a carbon black layer, rather than the slide including titanium oxide in the filtering layer, the slide can include a separate titanium oxide layer positioned between the indicator layer and the filtering layer or between the filtering layer and the carbon black layer. When the slide includes a separate titanium oxide layer, the thickness of the wet titanium oxide layer typically ranges from about 50 µm to about 250 µm, preferably about 75 µm to about 225 µm, and more preferably about 100 µm to about 200 µm. When dry, the thickness of the titanium dioxide layer typically ranges from about 5 µm to about 50 µm, preferably about 7 µm to about 40 µm, and more preferably about 10 µm to about 30 µm.

The titanium oxide layer comprises titanium oxide dispersed in a polymer. Suitable polymers for the titanium oxide layer include, but are not limited to, polyurethane polymer (e.g., HydroMed D4), polyethylene oxide, silicones, polyvinyl alcohol, and polyacrylamides. In one embodiment, the titanium oxide is dispersed in a polyurethane polymer, such as HydroMed D4. In one embodiment, the polyurethane is a mixture of low viscosity HydroMed D4 and high viscosity HydroMed D4. In one embodiment, the polyurethane is a mixture of about equal amounts of low viscosity HydroMed D4 and high viscosity HydroMed D4.

When the slide includes a separate titanium oxide layer, the titanium dioxide is typically present in the wet titanium dioxide layer in an amount ranging from about 2% by wt. to about 30% by wt., preferably about 5% by wt. to about 25% by wt., and more preferably about 10% by wt. to about 20% by wt. of the layer. In one embodiment, the titanium oxide is present in the wet layer in an amount of about 14% by wt. of the layer. Typically, the titanium dioxide is present in the dry layer in an amount ranging from about 20% by wt. to about 60% by wt., preferably about 25% by wt. to about 55% by wt., and more preferably about 30% by wt. to about 50% by wt. of the layer. In one embodiment, the titanium oxide is present in the dry layer in an amount of about 42% by wt. of the layer.

The average particle size of the titanium oxide particles is typically less than about 20 µm, preferably less than about 15 µm, more preferably less than about 10 µm, and most preferably less than about 5 µm.

The titanium oxide can be replaced with, or used in combination with, other reflective materials. Illustrative other reflective materials include, but are not limited to barium sulfate, zinc oxide, clay, and aluminum silicate. In one embodiment, the reflective material is fully or partially metal-coated particles. Suitable metals include, but are not limited, to aluminum, gold, nickel or silver. Silver is a preferred coating. These particles can be used alone or in combination with other light reflective materials such as $TiO_2$. The particles (i.e., the core that is coated) can be a variety of materials, including, but not limited to, solid and hollow glass, poly(methyl methacrylate) (PMMA), and silica. Suitable metal-coated particles are commercially available, e.g., from Cospheric LLC (Santa Barbara, California, USA). Preferred particles are silver-coated silica microspheres, for example from Cospheric LLC.

In another embodiment, the slide does not include a separate carbon black layer. Rather, the carbon black is included in the spreading layer. The amount of carbon black included in the spreading layer is similar to the amount of carbon black that is included in a separate carbon black layer.

The slides are prepared by starting with the support layer and sequentially coating each layer upon the support layer. The components of each layer are dissolved or suspended in a suitable solvent to provide a solution or suspension, the resulting solution or suspension is then applied to the previous layer to provide the desired wet layer, and the solvent removed so as to provide the desired dry layer. Preferably, the solution is an aqueous solution. Any method of coating can be used to provide each layer of the slide at the desired thickness. Suitable coating techniques are described in "Liquid Film Coating: Scientific principles and their technological implications," Ed. Stephan F. Kistler and Peter M. Schweizer, First Ed., 01997 Springer Science+Business Media Dordrecht.

Typically, the thickness of the slide does not exceed about 300 µm, preferably the thickness of the slide does not exceed about 250 µm, and more preferably the thickness of the slide does not exceed about 200 µm. In one embodiment, the thickness of the slide is about 185 µm.

FIG. 19 depicts illustrative embodiments of the slides.

Figure 19A:
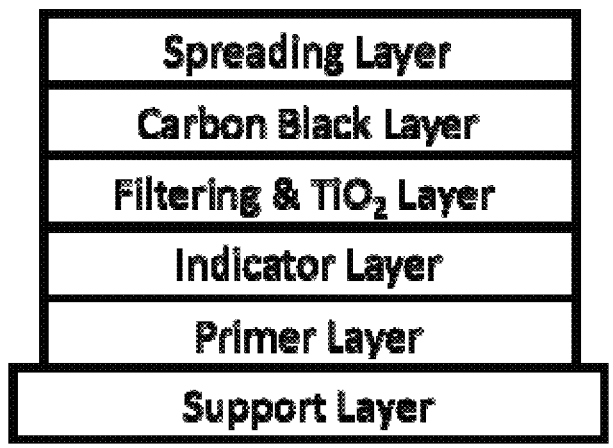
FIG. 19A depicts an embodiment having a support layer, a primer layer, an indicator layer, a filtering and titanium dioxide layer, a carbon black layer, and a spreading layer.

FIG. 19A depicts an embodiment wherein a Melinex support layer is sequentially coated with a primer layer, an indicator layer, a filtering layer that also includes titanium oxide, a carbon black layer, and a spreading layer. In one embodiment, as depicted in FIG. 19A, the spreading layer is formed by applying an aqueous ethanol solution/suspension containing about 10% by wt. cellulose, about 2% by wt. polyvinylpyrrolidone (PVP), about 0.1% by wt. tetramethylammonium hydroxide (TMAH), about 0.01% by wt. polyacrylic acid (PAA), and about 68% by wt. water, and 20% by wt. ethanol and then removing water and ethanol from the solution/suspension. The wet spreading layer has a thickness of about 310 μm. The resulting dry spreading layer contains about 82.6% by wt. of cellulose, about 16.5% by wt. of PVP, about 0.42% by wt. TMAH, and about 0.46% by wt. of PAA. The dry spreading layer has a thickness of about 100 μm.

The carbon black layer is formed by applying an aqueous solution/suspension containing about 95% by wt. of a D4 hydrogel solution (containing about 16% by wt. of a mixture of equal amounts of low viscosity HydroMed D4 and high viscosity HydroMed D4 dissolved/suspended in a solvent of about 90% by wt. of ethanol and about 10% by wt. of water) and about 5% by wt. of carbon black and removing solvent from the solution/suspension. The wet carbon black layer has a thickness of about 140 μm. The resulting dry carbon black layer contains about 76.3% by wt. HydroMed D4 and 23.7% by wt. of carbon black. The dry carbon black layer has a thickness of about 14 μm.

The filtering layer is formed by applying a solution/suspension containing about 79% by wt. of a D4 hydrogel solution (containing about 16% by wt. of a mixture of equal amounts of low viscosity HydroMed D4 and high viscosity HydroMed D4 dissolved/suspended in a solvent of about 90% by wt. of ethanol and about 10% by wt. of water), about 7% by wt. of cellulose, and about 14% by wt. of titanium oxide and removing solvent from the solution/suspension. The wet filtering layer has a thickness of about 130 μm. The resulting dry filtering layer contains about 37.9% by wt. of HydroMed D4, about 20.0% by wt. of cellulose, and about 42.1% by wt. titanium oxide. The dry filtering layer has a thickness of about 20 μm.

The indicator layer is formed by applying an aqueous solution/suspension containing about 18.7% by wt. of cellulose, about 9.3% by wt. of pullulan, about 0.4% by wt. of Merpol A, about 4.3% by wt. HEPES buffer (added as 52% by wt. of a 250 mM aqueous solution), about $4.0 \times 10^{-4}$% by wt. of the fluorescent tracer, and about 0.04% by wt. of the antibody conjugated to a quencher and removing solvent from the solution/suspension. The wet indicator layer has a thickness of about 93 μm. The resulting dry indicator layer contains about 57.0% by wt. of cellulose, about 28.5% by wt. of pullulan, about 1.2% by wt. of Merpol A, about 13.2% by wt. of HEPES buffer, about 0.14% by wt. of the antibody conjugated to a quencher, and about $1.1 \times 10^{-3}$% by wt. of the fluorescent tracer. The dry indicator layer has a thickness of about 30-40 μm. In one embodiment, the fluorescent tracer is A4 and the antibody is an antibody for SDMA that has been conjugated to BHQ10 and obtained by combining A4 with 20 eq. of BHQ10.

The primer layer is formed by applying an aqueous solution/suspension containing about 10% by wt. of a D4 hydrogel (containing equal amounts of low viscosity HydroMed D4 and high viscosity HydroMed D4) dissolved/suspended in a solvent of about 90% by wt. of ethanol and about 10% by wt. of water. The wet primer layer has a thickness of about 40 μm. The dry primer layer is 100% by wt. HydroMed D4. The dry primer layer has a thickness of about 4 μm.

Figure 19B:
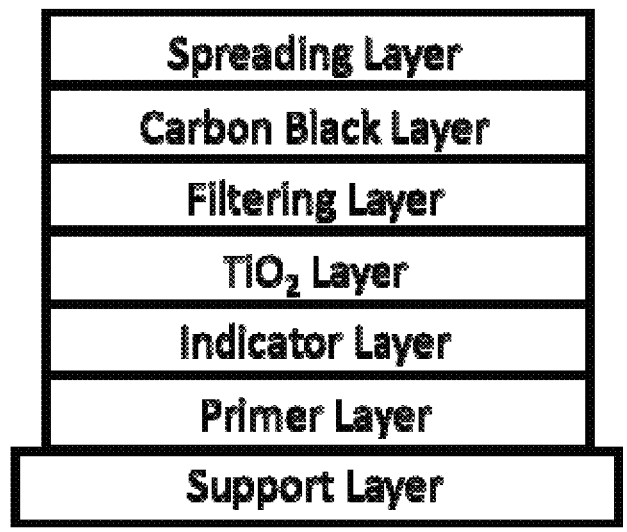
FIG. 19B depicts an embodiment having a support layer, a primer layer, an indicator layer, a titanium dioxide layer, a filtering layer, a carbon black layer, and a spreading layer.

FIG. 19B depicts an embodiment wherein a Melinex support layer is sequentially coated with a primer layer, an indicator layer, a titanium oxide-containing layer, a filtering layer, a carbon black layer, and a spreading layer. In one embodiment, as depicted in FIG. 19B, the spreading layer is formed by applying an aqueous solution/suspension containing about 10% by wt. of cellulose, about 1% by wt. of PVP, about 1% by wt. of TMAH, about 0.01% by wt. of PAA, and about 88% by wt. of water and removing water from the solution/suspension. The wet spreading layer has a thickness of about 350 μm. The resulting dry spreading layer contains about 83.2% by wt. of cellulose, about 8.3% by wt. of PVP, about 8.3% by wt. TMAH, and about 0.1% by wt. of PAA.

The carbon black layer is formed by applying a solution/suspension containing about 95% by wt. of a 10% solution of HydroMed D4 (in 90% by wt. water and 10% by wt. ethanol) and about 5% by wt. of carbon black and removing solvent from the solution/suspension. The wet carbon black layer has a thickness of about 250 μm. The resulting dry carbon black layer contains about 65.5% by wt. HydroMed D4 and 34.5% by wt. of carbon black.

The filtering layer is formed by applying an aqueous solution/suspension containing about 95% by wt. of a 10% solution of HydroMed D4 (in 90% by wt. water and 10% by wt. ethanol) and about 5% by wt. of cellulose and removing solvent from the solution/suspension. The wet filtering layer has a thickness of about 250 μm. The resulting dry filtering layer contains about 65.5% by wt. HydroMed D4 and about 34.5% by wt. of cellulose.

The titanium oxide-containing layer is formed by applying an aqueous solution/suspension containing about 95% by wt. of a 9.13% solution of HydroMed D4 (in 90% by wt. water and 10% by wt. ethanol) and about 5% by wt. of titanium oxide and removing solvent from the solution/suspension. The wet titanium oxide-containing layer has a thickness of about 100 μm. The resulting dry titanium oxide-containing layer contains about 63.5% by wt. of HydroMed D4 and about 36.5% by wt. of titanium oxide.

The indicator layer was formed by applying an aqueous solution/suspension containing about 14% by wt. of cellulose, about 14% by wt. of pullulan, about 0.1% by wt. Igepal CA-630, about 58% by wt. of an aqueous PBS solution (100 mM), and about 14.5% by wt. of a complex between a fluorescent tracer and its binding partner and removing solvent from the solution/suspension. The wet indicator layer has a thickness of about 100 μm. The resulting dry indicator layer contains about 32.8% by wt. of cellulose, about 32.8% by wt. of pullulan, about 0.2% by wt. of Igepal CA-630, about 34.0% by wt. of the complex, and phosphate buffer. In one embodiment, the complex is a complex of A4 with an antibody for SDMA that has been conjugated with BHQ10 and obtained by combining the antibody with 4 eq. of BHQ10.

The thickness of the wet primer layer is about 35 μm. The dry primer layer is 100% HydroMed D4.

Figure 20:
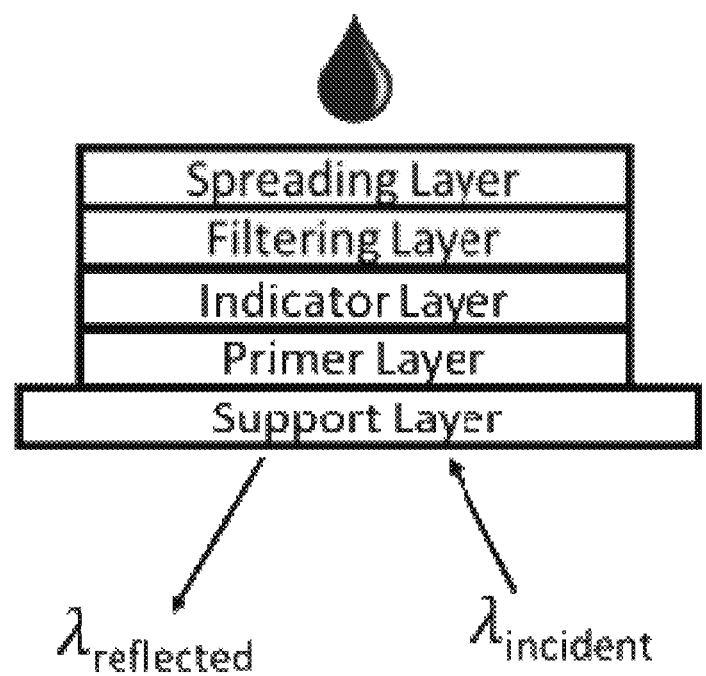
FIG. 20 is an illustration depicting how the dry slide assay method described herein is performed using the dry slide depicted in FIG. 18C.

The assay is performed by simply adding the sample containing the analyte of interest to the top of the slide (i.e., the layer of the slide farthest from the support layer), irradiating the slide with light of the first wavelength from the bottom of the slide (i.e., the layer of the slide with the support layer), and measuring the intensity of the light emitted at the second wavelength from the bottom of the slide. FIG. 20 depicts the assay method using the slide depicted in FIG. 18C.

Typically, the sample is added to the top of the slide as a liquid containing the analyte dissolved therein. Typically, the sample size ranges from about 0.5 μL to about 30 μL. In one embodiment, the sample size ranges from about 1 μL to about 20 μL. In one embodiment, the sample size ranges from about 2 μL to about 15 μL. In one embodiment, the sample size ranges from about 3 μL to about 12 μL.

In one embodiment, the slide further includes a "pop-off" layer. The pop-off layer includes a reagent that frees the analyte when the analyte is complexed with another molecule, such as a binding protein. Analytes (e.g., cortisol) are often complexed to a binding protein (e.g., cortisol binding protein). The pop-off layer includes a reagent that frees the analyte from the binding protein. In one embodiment, the reagent that that frees the analyte from the binding protein is sarkosyl. The structure of sarkosyl is:

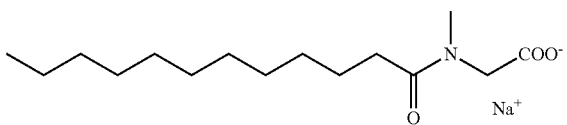

Sarkosyl is particularly useful when the analyte is cortisol. Other reagents that potentially can be used to free cortisol from cortisol binding protein include prednisolone, prednisone, 11-deoxycorticosterone, cortisone, and 11-deoxycortisol. In another embodiment, the reagent that frees the analyte from the binding protein is Docusate (Dioctyl Sodium Sulfosuccinate). Sarkosyl is preferred when the analyte is cortisol.

In one embodiment, the slide does not include an additional pop-off layer but includes the reagent that frees the analyte from the binding protein in one or more of the layers already present on the slide, for example in the spreading layer, the filtering layer, and/or the indicator layer.

Illustrative examples of slide configurations that include a reagent that frees the analyte from the binding protein are described below. These embodiments are particularly useful when the analyte is cortisol.

Figure 57:
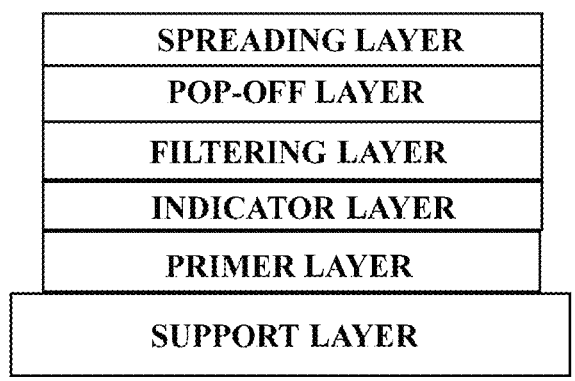
FIG. 57 depicts an illustrative embodiment of the slide used in the dry slide assay method described herein.

In one embodiment, depicted in FIG. 57, a support layer (e.g., Melinex) is sequentially coated with a primer layer, an indicator layer (including the fluorescent tracer and the binding partner), a filtering layer (optionally including titanium dioxide or other reflective material), a pop-off layer, and a spreading layer.

In one embodiment, the primer layer is formed by applying a solution/suspension containing about 9-10% HydroMed D4 (commercially available from AdvanSource Biomaterials Corp of Wilmington, MA) to the support layer and removing the solvent from the solution/suspension; the indicator layer is formed by applying a solution/suspension containing about 12% polyvinylpyrrolidone, about 6% cellulose, about 1% Tween-20, and the fluorescent tracer and the binding partner to the primer layer and removing the solvent from the solution/suspension; the filtering layer is formed by applying a solution/suspension containing about 10% HydroMed D4, about 10% TiO$_2$, and about 5% cellulose to the detection layer and removing the solvent from the solution/suspension; the pop-off layer is formed by applying a solution/suspension containing about 12% pullulan, about 6% cellulose, about 1% of the reagent that frees the analyte from the binding protein, and about 1% Merpol A to the filtering layer and removing the solvent from the solution/suspension; and the spreading layer is formed by applying a solution/suspension containing suitable components for a spreading layer to the pop-off layer and removing the solvent from the solution/suspension.

In one embodiment, the reagent that frees the analyte from the binding protein is sarkosyl. In one embodiment, the analyte is cortisol, the binding partner is an antibody against cortisol, and the reagent that frees the analyte from the binding protein is sarkosyl.

Figure 58:
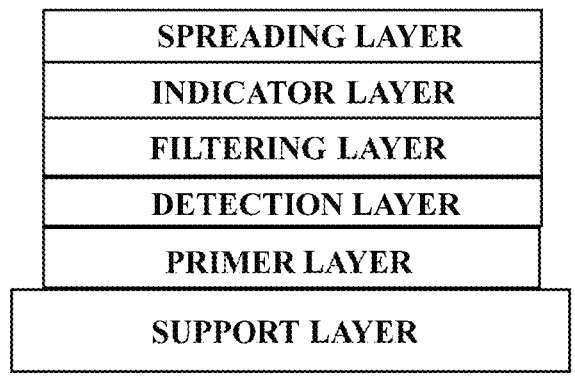
FIG. 58 depicts an illustrative embodiment of the slide used in the dry slide assay method described herein.

In one embodiment, depicted in FIG. 58, a support layer (e.g., Melinex) is sequentially coated with a primer layer, a detection layer, a filtering layer (optionally including titanium dioxide or other reflective material), an indicator layer, and a spreading layer. In this embodiment, the spreading layer includes a reagent that frees the analyte from the binding protein.

In one embodiment, the primer layer is formed by applying a solution/suspension containing about 9-10% HydroMed D4 (commercially available from AdvanSource Biomaterials Corp of Wilmington, MA) to the support layer and removing the solvent from the solution/suspension; the detection layer is formed by applying a solution/suspension containing about 12% polyvinylpyrrolidone, about 6% cellulose, and about 1% Tween-20 to the primer layer and removing the solvent from the solution/suspension; the filtering layer is formed by applying a solution/suspension containing about 10% HydroMed D4, about 10% TiO$_2$, and about 5% cellulose to the detection layer and removing the solvent from the solution/suspension; the indicator layer is formed by applying a solution/suspension containing about 12% pullulan, about 6% cellulose, about 1% Tween-20, and the fluorescent tracer and the binding partner to the filtering layer and removing the solvent from the solution/suspension; and the spreading layer is formed by applying a solution/suspension containing about 1% of the reagent that frees the analyte from the binding protein, about 1% Merpol A, and suitable components of a spreading layer to the indicator layer and removing the solvent from the solution/suspension.

In one embodiment, the reagent that frees the analyte from the binding protein is sarkosyl. In one embodiment, the analyte is cortisol, the binding partner is an antibody against cortisol, and the reagent that frees the analyte from the binding protein is sarkosyl.

In another embodiment, depicted in FIG. 58, the indicator layer includes a reagent that frees the analyte from the binding protein.

In one embodiment, the primer layer is formed by applying a solution/suspension containing about 9-10% HydroMed D4 to the support layer and removing the solvent from the solution/suspension; the detection layer is formed by applying a solution/suspension containing about 12% polyvinylpyrrolidone, about 6% cellulose, and about 1% Tween-20 to the primer layer and removing the solvent from the solution/suspension; the filtering layer is formed by applying a solution/suspension containing about 10% HydroMed D4, about 10% TiO$_2$, and about 5% cellulose to the detection layer and removing the solvent from the solution/suspension; the indicator layer is formed by applying a solution/suspension containing about 12% pullulan, about 6% cellulose, about 1% sarkosyl, about 1% Merpol A, and the fluorescent tracer and the binding partner to the filtering layer and removing the solvent from the solution/suspension; and the spreading layer is formed by applying a solution/suspension containing suitable components of a spreading layer to the indicator layer and removing the solvent from the solution/suspension.

In one embodiment, the reagent that frees the analyte from the binding protein is sarkosyl. In one embodiment, the analyte is cortisol, the binding partner is an antibody against cortisol, and the reagent that frees the analyte from the binding protein is sarkosyl.

In another embodiment, depicted in FIG. 58, the reagent that frees the analyte from the binding protein is included in both the spreading layer and the detection layer. In one embodiment, the primer layer is formed by applying a solution/suspension containing about 9-10% HydroMed D4 to the support layer and removing the solvent from the solution/suspension; the detection layer is formed by applying a solution/suspension containing about 12% polyvinylpyrrolidone, about 6% cellulose, and about 1% Tween-20 to the primer layer and removing the solvent from the solution/suspension; the filtering layer is formed by applying a solution/suspension containing about 10% HydroMed D4, about 10% TiO$_2$, and about 5% cellulose to the detection layer and removing the solvent from the solution/suspension; the indicator layer is formed by applying a solution/suspension containing about 12% pullulan, about 6% cellulose, about 0.5% sarkosyl, about 0.5% Merpol A, and the fluorescent tracer and the binding partner to the filtering layer and removing the solvent from the solution/suspension; and the spreading layer is formed by applying a solution/suspension containing suitable components of a spreading layer, about 0.5% sarkosyl, and about 0.5% Merpol A to the indicator layer and removing the solvent from the solution/suspension.

In one embodiment, the reagent that frees the analyte from the binding protein is sarkosyl. In one embodiment, the analyte is cortisol, the binding partner is an antibody against cortisol, and the reagent that frees the analyte from the binding protein is sarkosyl.

In further embodiments, the primer layer and the detection layer are combined. The combined primer/detection layer is formed by applying a solution/suspension containing about 9-10% HydroMed D4 and about 10% cellulose to the support layer and removing the solvent from the solution/suspension. In one embodiment, the primer and detection layers of the slide shown in FIG. 58 are combined.

In some embodiments, one or more of the layers may comprise glass beads. To form a layer that contains glass beads, the solution/suspension used to form that layer contains about 6% glass beads. In preferred embodiments, the glass beads are included in the indicator layer and/or the filtering layer.

One or more of the layers may comprise Merpol A. The addition of Merpol A is preferred when the reagent that frees the analyte is sarkosyl. When sarkosyl is used as the reagent that frees the analyte, Merpol A is preferably included in at least the layer that contains sarkosyl.

The sample can be any of the samples described above including, but not limited to, urine, serum, milk, saliva, plasma, whole blood, sweat, tears, feces, and spinal fluid.

The analyte can be any of the analytes described above including, but not limited to SDMA, melamine, antibiotics, T4, β-lactam antibiotics (such as penicillin), sulfa drugs, cephalosporins, progesterone, cortisol, bile acids, proteins, NT-proBNP, and cystatin-B.

In one embodiment, the dry slide is part of a device wherein the liquid sample containing the analyte of interest is applied to an aperture on the device and the liquid then conveyed to the dry slide via a capillary transport zone. Illustrative examples of such a device are described in U.S. Pat. Nos. 4,323,536 and 5,726,010. The slide may be part of a device wherein the slide is disposed within an opening or cavity defined by a frame, housing or case. In one embodiment, the slide is disposed within a housing or case as disclosed in U.S. Pat. No. 9,933,428. Other examples of dry slide devices comprising a housing or case are Catalyst® slides, for example the Catalyst® Fructosamine slide or the Catalyst® Total T4 (TT4) slide (commercially available from IDEXX Laboratories, Inc. of Westbrook, ME).

In one embodiment, the assay is performed using a dry chemistry analytical instrument, for example, a Catalyst One® or a Catalyst Dx® analyzer (commercially available from IDEXX Laboratories, Inc. of Westbrook, ME).

4. Fluorescent Tracers

Any molecule that fluoresces and can be linked to a T-epitopic moiety can be used so as to provide a fluorescent tracer. Examples of suitable molecules that fluoresce include, but are not limited to, fluorescein, coumarin, and rhodamine dyes.

In one embodiment, the fluorescent tracer has a T-epitopic moiety linked to a fluorescein molecule. Preferably, the T-epitopic moiety is linked to the 4'-position or the 5-position of the fluorescein molecule. More preferably, the T-epitopic moiety is linked to the 4'-position of the fluorescein molecule.

Specifically, the invention contemplates 4'-substituted fluorescein tracers, i.e., a fluorescent tracer wherein the T-epitopic moiety is attached to the 4'-position of the fluorescein molecule. The general structure of a 4'-substituted fluorescein tracer is:

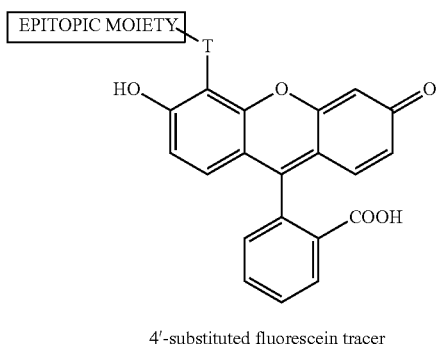

4'-substituted fluorescein tracer wherein T is a bond or a linking group.

The invention also contemplates 4'-substituted fluorescein tracer derivatives. The phrase "4'-substituted fluorescein tracer derivatives," as used herein, means a 4'-substituted fluorescein tracer molecule wherein one or more of the hydrogen atoms that are bonded to a carbon of the fluorescein core structure are replaced with another functional group. In one embodiment, one or more of the hydrogen atoms that are bonded to a carbon of the fluorescein core structure are replaced with an electron donating group such as, but not limited to, —CH$_3$, —OCH$_3$, and —OH. In one embodiment, one or more of the hydrogen atoms that are bonded to a carbon of the fluorescein core structure are replaced with an electron withdrawing group such as, but not limited to,—F, —NO$_2$, —CN, —COOH, —SO$_3$H, and —Cl. In one embodiment, the functional group replaces a hydrogen at the 2' -and/or 7'- position(s) of the fluorescein molecule.

An illustrative 4'-substituted fluorescein tracer derivative is:

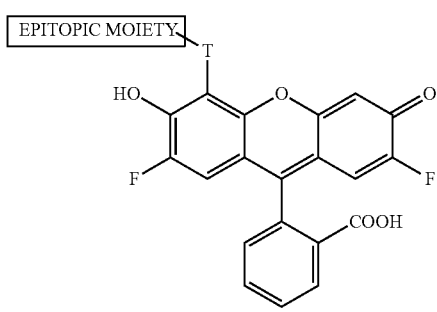

The invention also contemplates 5-substituted fluorescein tracers, i.e., fluorescein tracers wherein the T-epitopic moiety is attached to the 5-position of the fluorescein molecule. The general structure of a 5-substituted fluorescein tracer is:

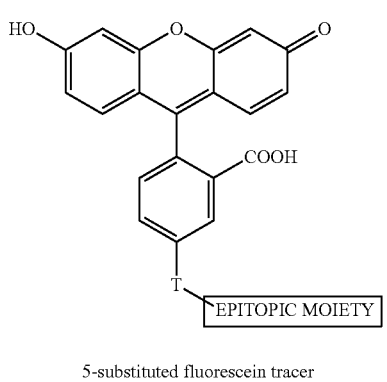

5-substituted fluorescein tracer wherein T is a bond or a linking group.

The invention also contemplates 5-substituted fluorescein tracer derivatives. The phrase "5-substituted fluorescein tracer derivatives," as used herein, means a 5-substituted fluorescein tracer molecule wherein one or more of the hydrogen atoms that are bonded to a carbon of the fluorescein core structure are replaced with another functional group. In one embodiment, one or more of the hydrogen atoms that are bonded to a carbon of the fluorescein core structure are replaced with an electron donating group such as, but not limited to, —$CH_3$, —$OCH_3$, and —OH. In one embodiment, one or more of the hydrogen atoms that are bonded to a carbon of the fluorescein core structure are replaced with an electron withdrawing group such as, but not limited to, —F, —$NO_2$, —CN, —COOH, —$SO_3H$, and —Cl. In one embodiment, the functional group replaces a hydrogen at the 2'- and/or 7'-position(s) of the fluorescein molecule.

An illustrative 5-substituted fluorescein tracer derivative is:

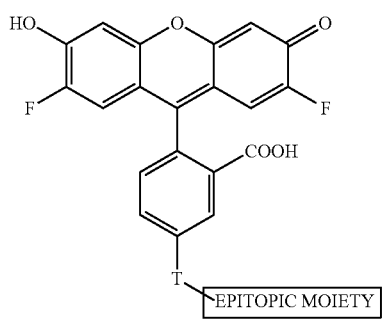

The epitopic moiety can be directly bound to the fluorescein core structure or can be separated from the fluorescein core structure by a linker T. Generally, the epitopic moiety is separated from the fluorescein core structure by a linker. Generally, the linker is less than 8 atoms in length, preferably less than 6 atoms in length, more preferably less than 4 atoms in length, and most preferably less than 2 atoms in length. In one embodiment the linker is 1 atom in length.

In one embodiment, the fluorescent tracer has a T-epitopic moiety linked to a coumarin molecule.

Illustrative linkers include, but are not limited to, —$CH_2$—, —C(O)—, —$CH_2$—NH—$CH_2$—$CH_2$—, —NH—$CH_2$—$CH_2$—, —$CH_2$—NH—C(O)—$CH_2CH_2$—C(O)—, —NH—, —$CH_2$—NH—, —$CH_2N(CH_3)$—, and —NH—C(O)—$CH_2CH_2$—C(O)—.

In one embodiment, the 4'-substituted fluorescein tracer is obtained by functionalizing the 4' position of fluorescein with an aldehyde group which can then be reacted with a functional group on the epitopic moiety (such as an amine) to provide a 4'-substituted fluorescein tracer wherein the linking group is a —$CH_2$—moiety, as illustrated below:

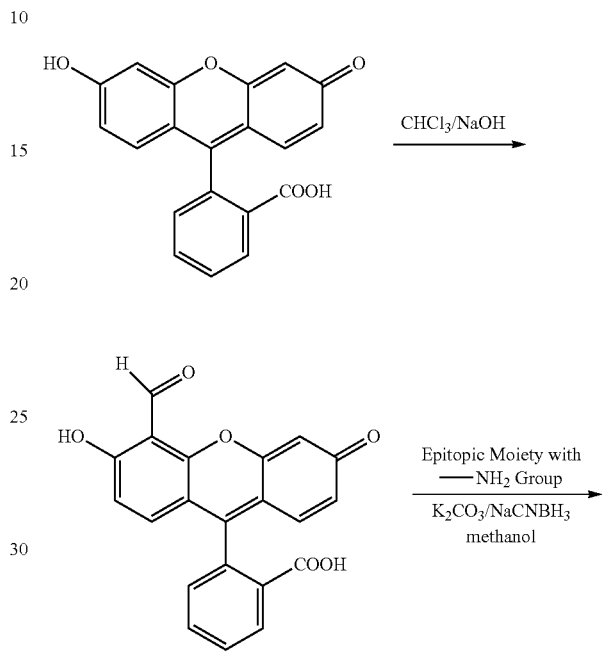

Figure 2:
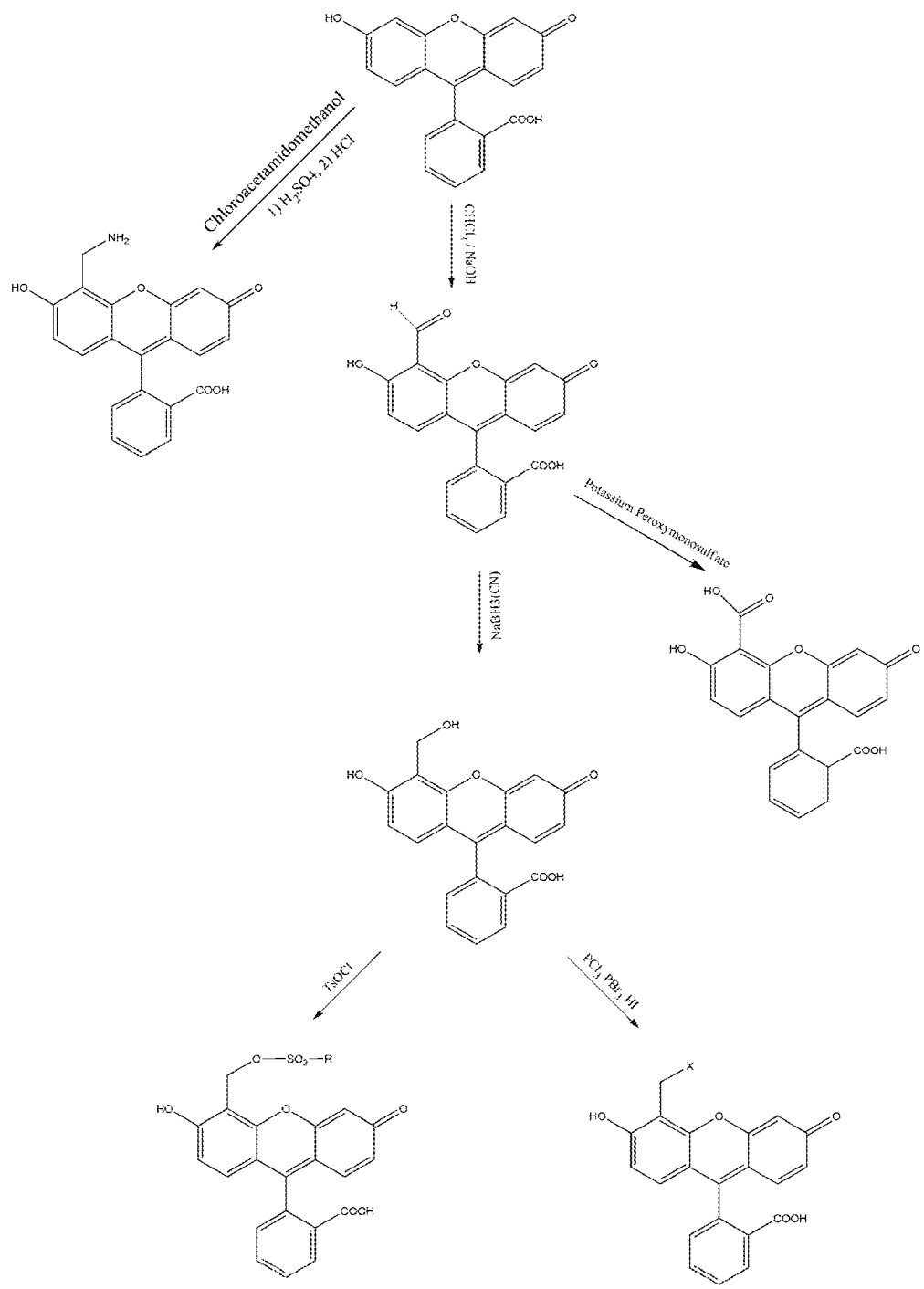
FIG. 2 is a schematic depicting synthetic schemes for functionalizing the 4'-position of a fluorescein molecule.

In another embodiment, the aldehyde group is converted to another functional group, using chemistry well-known to those skilled in the art, as illustrated in FIG. 2, and the resulting 4'-substituted fluorescein molecule then reacted with a functional group on the epitopic moiety, such as an amine or carboxylic acid group, using chemistry known to those in the art, to provide the 4'-substituted fluorescein tracer.

In another embodiment, the aldehyde is converted to a carboxylic acid, the resulting carboxylic acid reacted with N-hydroxysuccinimide, and the resulting N-hydroxysuccinimide ester then reacted with a functional group on the epitopic moiety (such as an amine) to provide a 4'-substituted fluorescein tracer wherein the linking group is a —C(O)-moiety, as illustrated below:

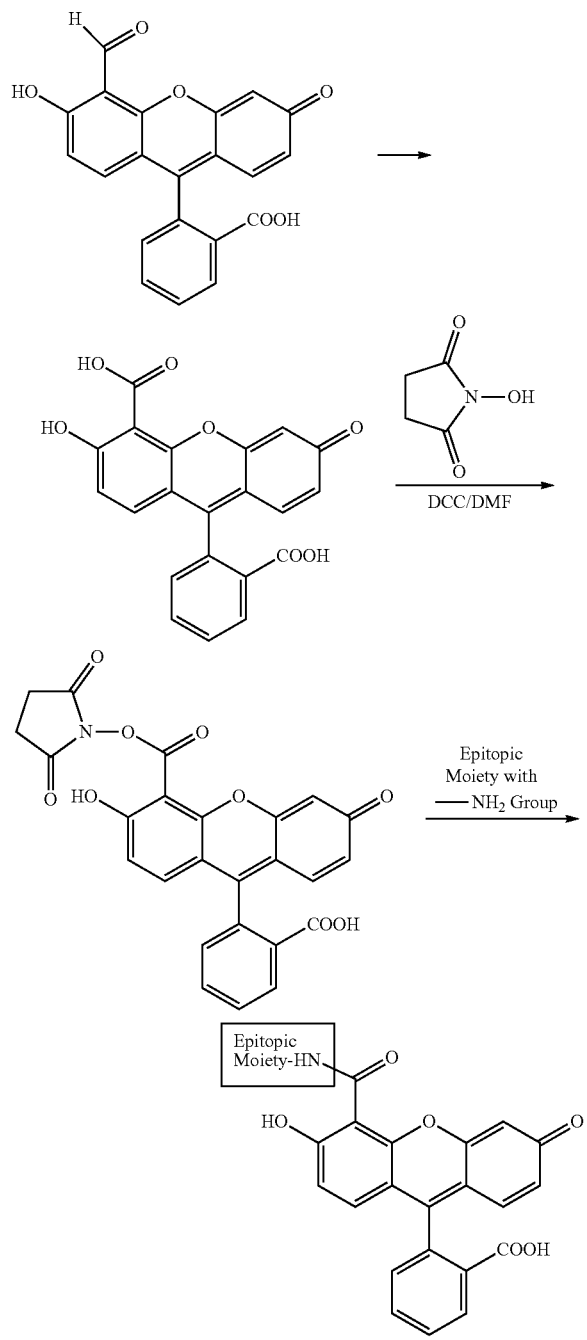

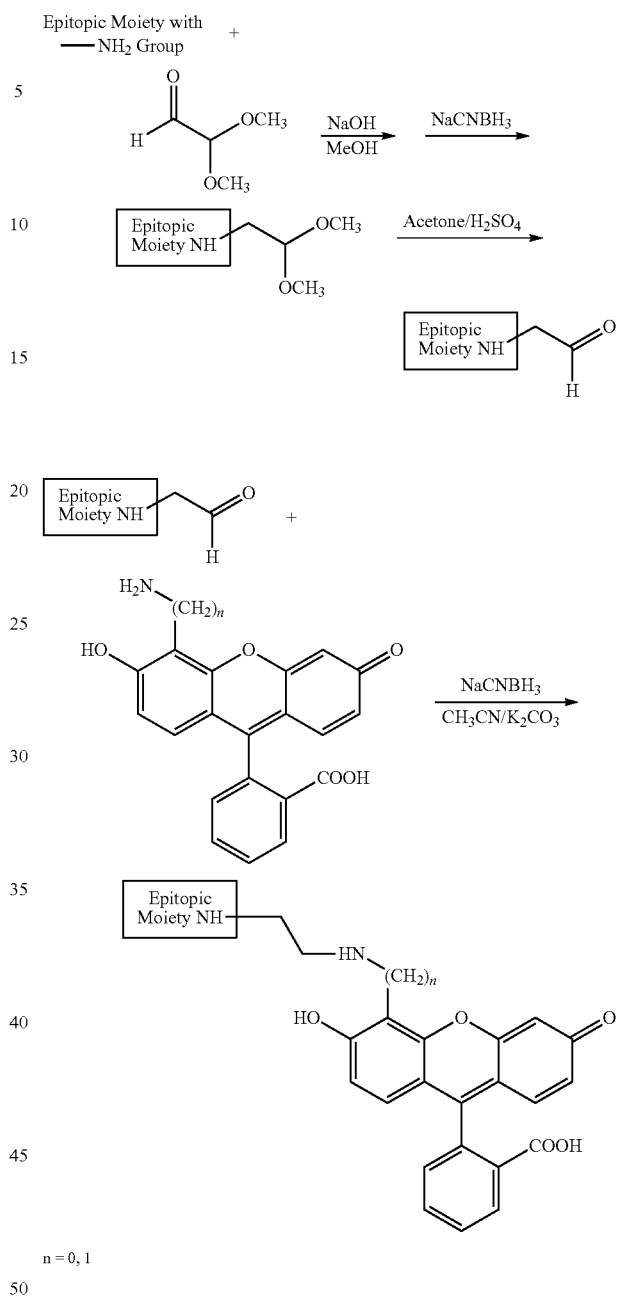

Suitable reagents for converting an aldehyde to a carboxylic acid include, but are not limited to, potassium permanganate and sodium dichromate.

In another embodiment, an amine group on the epitopic moiety is reacted with 2,2-dimethoxyacetaldehyde to provide an acetal derivatized epitopic moiety, the acetal group of the acetal derivatized epitopic moiety is converted to the aldehyde, and the resulting aldehyde derivatized epitopic moiety then condensed with a fluorescein derivative wherein the 4'-position is substituted with a —CH₂—NH₂-group or an —NH₂ group to provide a 4'-substituted fluorescein tracer wherein the linking group is a —CH₂NHCH₂CH₂— or a —NHCH₂CH₂-moiety, as illustrated below:

A fluorescein molecule that is substituted at the 4'-position with an —NH₂ group can be prepared by first protecting the carboxylic acid group at the 3-position (for example, as an ester) of fluorescein that is substituted at the 4'-position with an aldehyde group (prepared as described in Example 1), converting the aldehyde group to a carboxylic acid, to provide a fluorescein with a carboxylic acid group at the 4'-position and a protected carboxylic acid at the 3-position. The carboxylic acid at the 4-position is then converted to an acid chloride (e.g., by reaction with thionyl chloride), the acid chloride reacted with ammonia to provide the amide, and the amide reacted with Br₂/NaOH to provide the amine (i.e., Hoffman bromamide degradation). The acid protecting group is then removed. The general reaction scheme is depicted below.

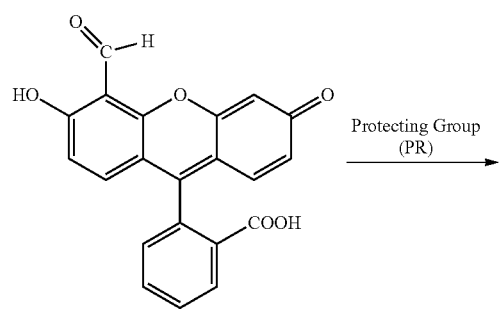
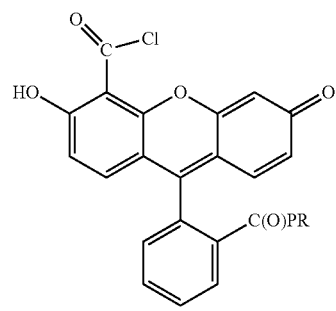
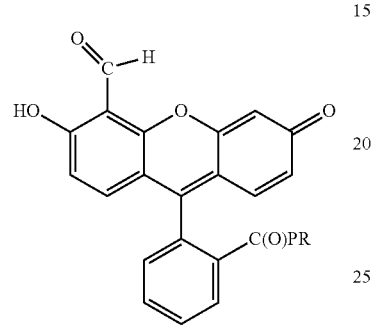
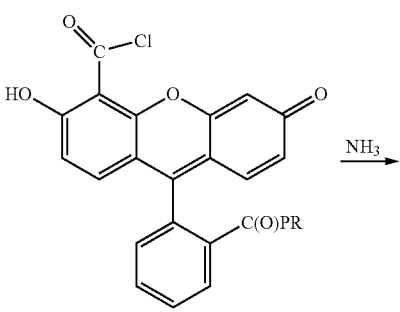
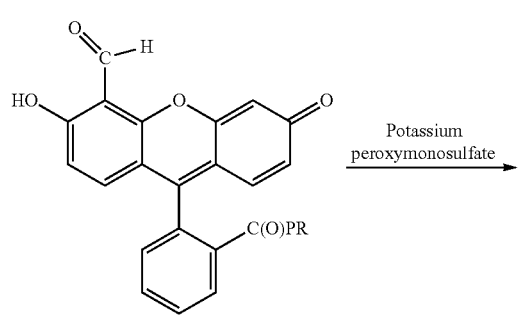
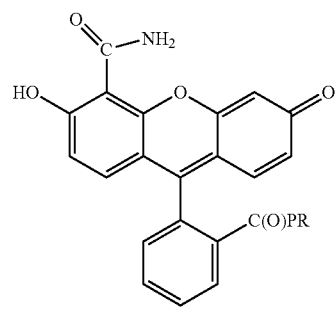
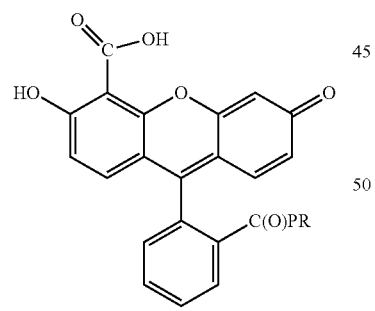
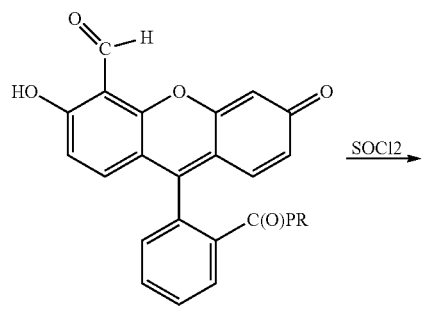

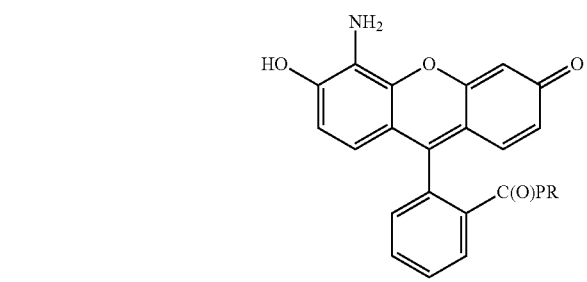

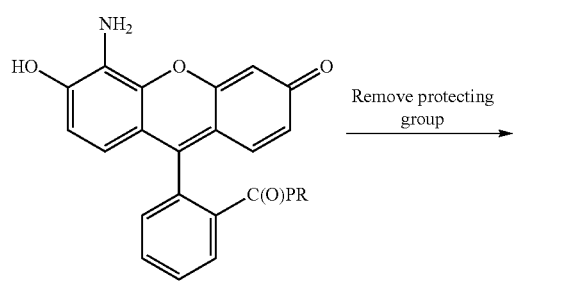

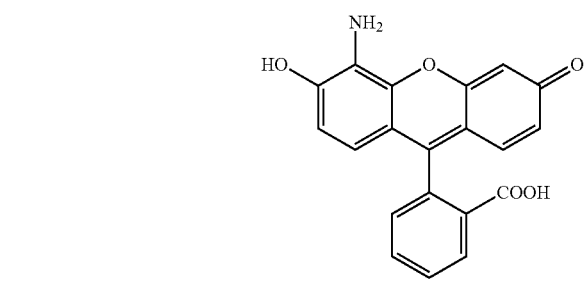

In another embodiment, an amine group on the epitopic molecule is reacted with succinic anhydride (dihydrofuran-2,5-dione) to provide a —C(O)—CH₂CH₂C(O)OH derivatized epitopic moiety, the derivatized epitopic moiety then reacted with N-hydroxysuccinimide to provide an anhydride, and the anhydride then reacted with a fluorescein derivative wherein the 4'-position is substituted with a —CH₂—NH₂-group or an —NH₂ group to provide a 4'-substituted fluorescein tracer wherein the linking group is a —CH₂NHC(O)CH₂CH₂C(O)— or —NHC(O)CH₂CH₂C(O)—, as illustrated below:

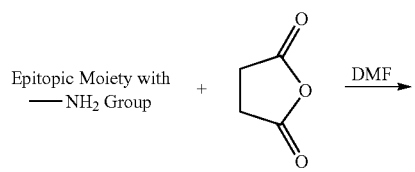

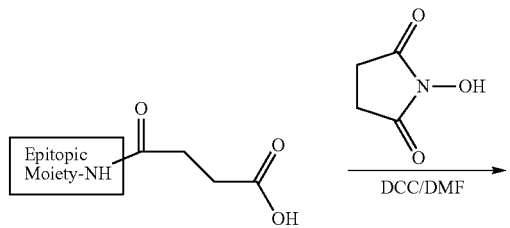

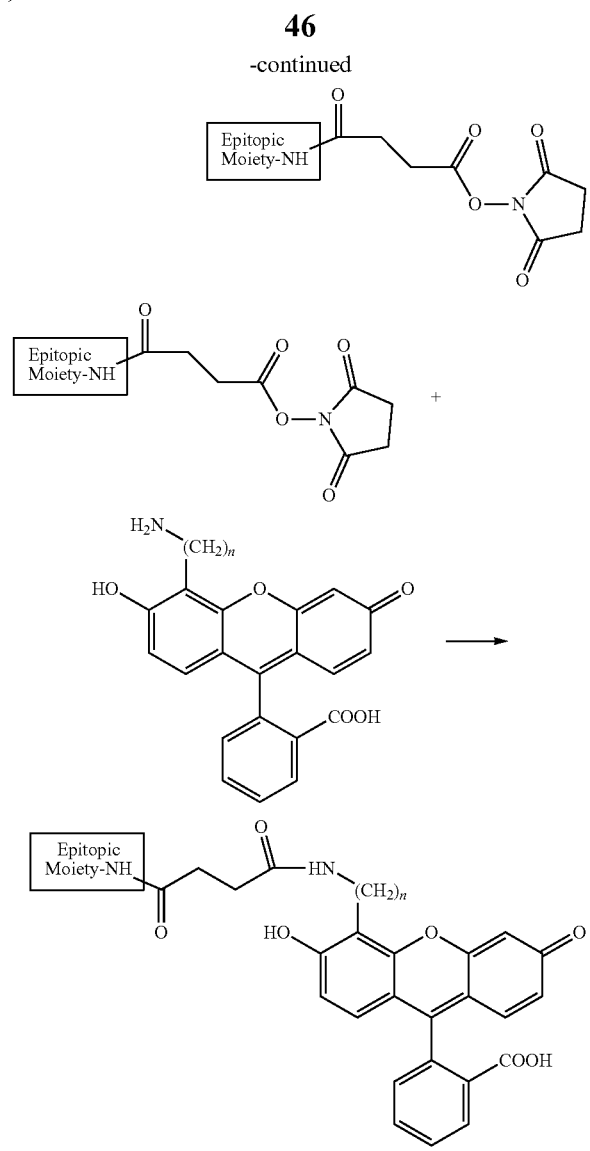

n = 0, 1

In another embodiment, an acid group on the epitopic molecule is reacted with N-hydroxysuccinimide to provide an anhydride, and the anhydride then reacted with a fluorescein derivative wherein the 4'-position is substituted with a —CH₂—NH₂-group (commercially available from AAT Bioquest of Sunyvale, CA) or an —NH₂ group to provide a 4'-substituted fluorescent tracer wherein the linking group is a —CH₂—NH₂-group or an —NH₂ group, as illustrated below:

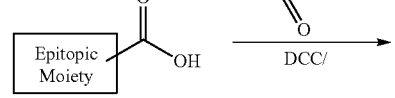

-continued

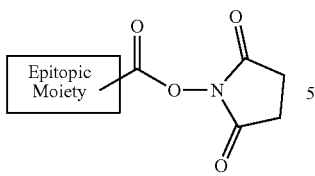

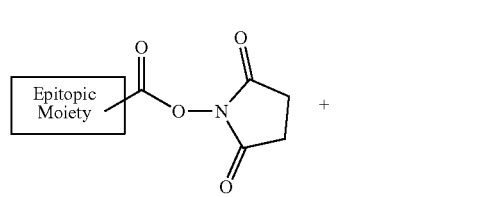

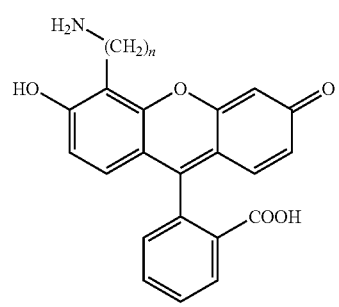

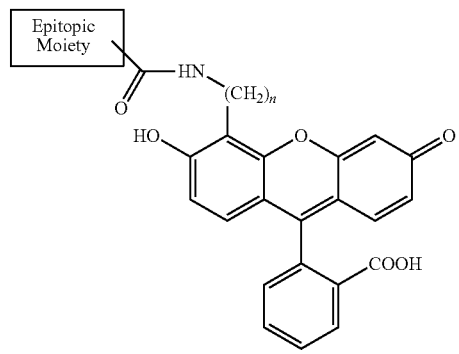

n = 0, 1

It is understood that, when synthesizing a 4'-substituted fluorescein tracer, conventional protecting groups may be necessary to prevent certain functional groups from undergoing undesired reactions. The choice of a suitable protecting group for a particular functional group as well as suitable conditions for protection and deprotection are known in the art. For example, numerous protecting groups, and their introduction and removal, are described in T. W. Greene and P. G. M. Wuts, *Protecting Groups in Organic Synthesis*, 2$^{nd}$ ed., Wiley, New York, 1991, and references cited therein.

Similar chemistry can be used to obtain 4'-substituted fluorescein tracer derivatives.

In one embodiment, the epitopic molecule with an —NH2 group is symmetrical dimethyl arginine (SDMA). The structure of SDMA is:

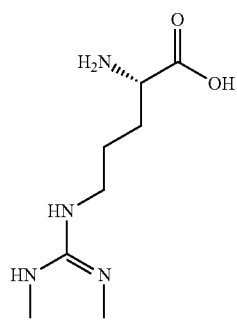

In one embodiment, the invention is directed to a 4'-substituted fluorescein tracer or 4'-substituted fluorescein tracer derivative having the following structure:

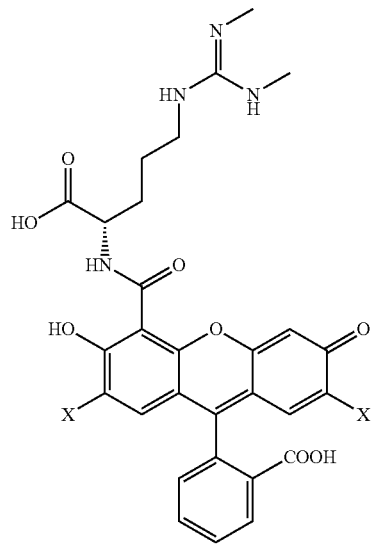

wherein X is selected from the group consisting of —H, —F, —CH$_3$, —OCH$_3$, —Cl, —OH, —NO$_2$, —CN, —COOH, and —SO$_3$H.

In one embodiment, the invention is directed to a complex comprising a 4'-substituted fluorescein tracer or 4'-substituted fluorescein tracer derivative selected from the above-identified structures and an antibody against SDMA. In one embodiment, the antibody is conjugated to a quencher.

In one embodiment, the invention is directed to a 4'-substituted fluorescein tracer or 4'-substituted fluorescein tracer derivative having the following structure:

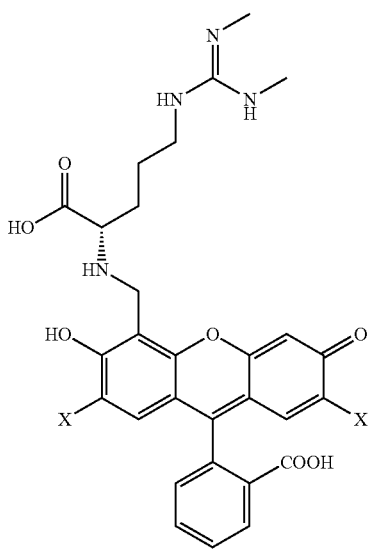

wherein X is selected from the group consisting of —H, —F, —CH₃, —OCH₃, —Cl, —OH, —NO₂, —CN, —COOH, and —SO₃H.

In one embodiment, the invention is directed to a complex comprising a 4'-substituted fluorescein tracer or 4'-substituted fluorescein tracer derivative selected from the above-identified structures and an antibody against SDMA. In one embodiment, the antibody is conjugated to a quencher.

In one embodiment, the invention is directed to a 4'-substituted fluorescein tracer or 4'-substituted fluorescein tracer derivative having the following structure:

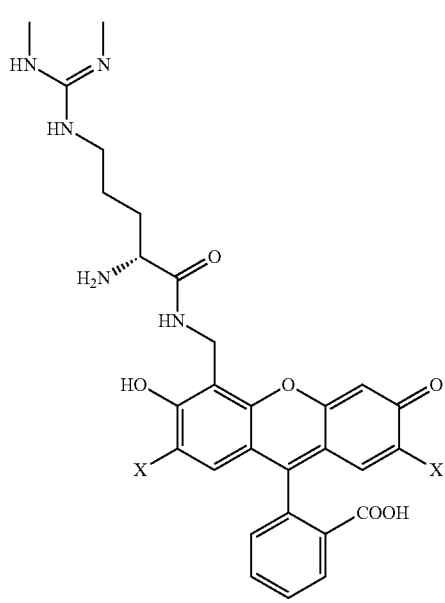

wherein X is selected from the group consisting of —H, —F, —CH₃, —OCH₃, —Cl, —OH, —NO₂, —CN, —COOH, and —SO₃H.

In one embodiment, the invention is directed to a complex comprising a 4'-substituted fluorescein tracer or 4'-substituted fluorescein tracer derivative selected from the above-identified structures and an antibody against SDMA. In one embodiment, the antibody is conjugated to a quencher.

In one embodiment, the invention is directed to a 4'-substituted fluorescein tracer having the following structure:

Structure A1

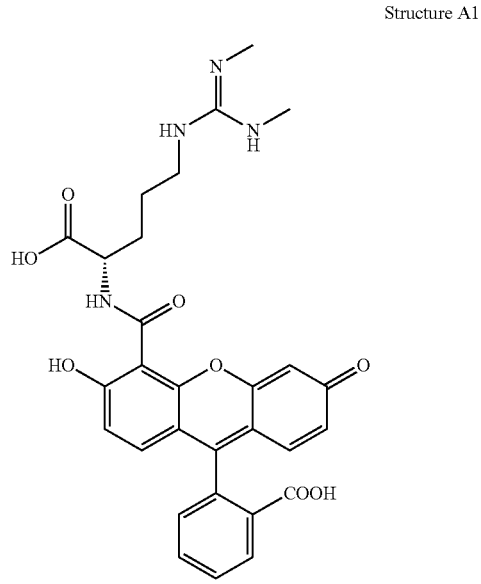 [SMILES: C/N=C(\NC)NCCC[C@H](NC(=O)c1c(O)ccc2c(-c3ccccc3C(=O)O)c3ccc(=O)cc-3oc12)C(=O)O]

In one embodiment, the invention is directed to a 4'-substituted fluorescein tracer having the following structure:

Structure A2

In one embodiment, the invention is directed to a 4'-substituted fluorescein tracer having the following structure:

Structure A3

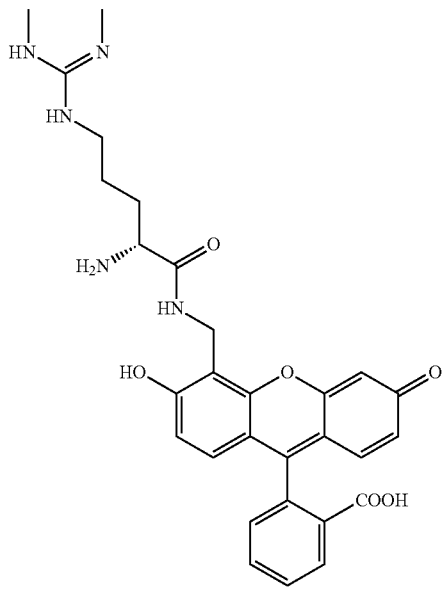

In one embodiment, the invention is directed to a complex comprising the 4'-substituted tracer of structure A1 and an antibody against SDMA. In one embodiment, the antibody is conjugated to a quencher.

In one embodiment, the invention is directed to a complex comprising the 4'-substituted tracer of structure A2 and an antibody against SDMA. In one embodiment, the antibody is conjugated to a quencher.

In one embodiment, the invention is directed to a complex comprising the 4'-substituted tracer of structure A3 and an antibody against SDMA. In one embodiment, the antibody is conjugated to a quencher.

Similarly, the 5-substituted fluorescein tracers are obtained by functionalizing the 5-position of fluorescein with an aldehyde group which can then be reacted with a functional group on the epitopic moiety (such as an amine) to provide a 5-substituted fluorescein tracer wherein the linking group is a —CH$_2$-moiety, as illustrated below:

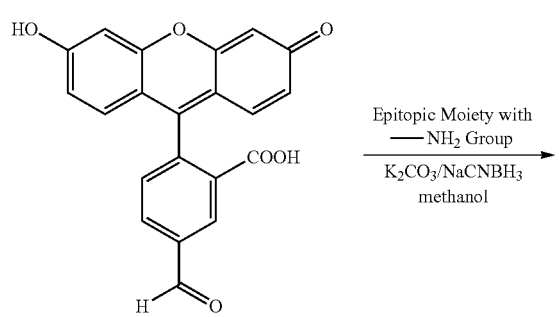

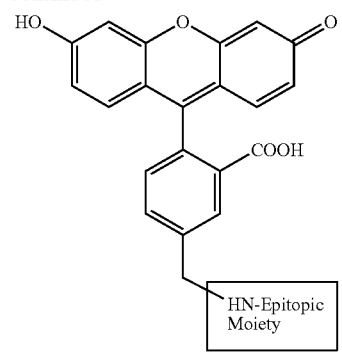

Fluorescein functionalized at the 5-position with an aldehyde group can be obtained by reducing the carboxylic acid group of a fluorescein molecule substituted at the 5-position with a carboxylic acid group to an alcohol (—CH$_2$OH) and then oxidizing the resulting alcohol to the aldehyde. Fluorescein functionalized at the 5-position with a carboxylic acid group is commercially available from Thermo Scientific of Waltham, MA In one embodiment, the invention is directed to a 5-substituted fluorescein tracer or 5-substituted fluorescein tracer derivative having the following structure:

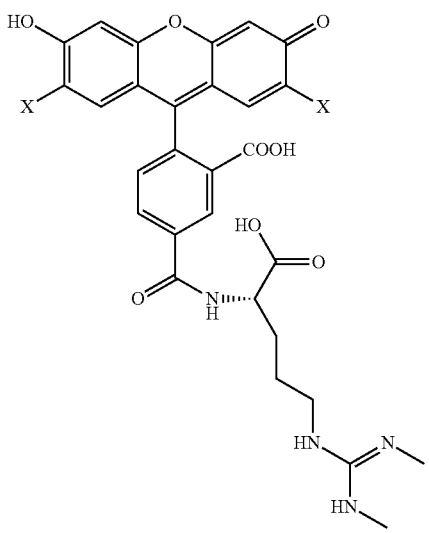

wherein X is selected from the group consisting of —H, —F, —CH$_3$, —OCH$_3$, —Cl, —OH, —NO$_2$, —CN, —COOH, and —SO$_3$H.

In one embodiment, the invention is directed to a complex comprising a 5-substituted fluorescein tracer or 5-substituted fluorescein tracer derivative selected from the above-identified structures and an antibody against SDMA. In one embodiment, the antibody is conjugated to a quencher.

In one embodiment, the invention is directed to a 5-substituted fluorescein tracer or 5-substituted fluorescein tracer derivative having the following structure:

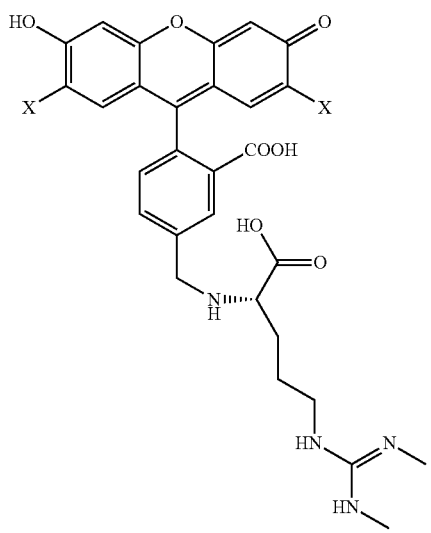

wherein X is selected from the group consisting of —H, —F, —CH₃, —OCH₃, —Cl, —OH, —NO₂, —CN, —COOH, and —SO₃H.

In one embodiment, the invention is directed to a complex comprising a 5-substituted fluorescein tracer or 5-substituted fluorescein tracer derivative selected from the above-identified structures and an antibody against SDMA. In one embodiment, the antibody is conjugated to a quencher.

In one embodiment, the invention is directed to a 5-substituted fluorescein tracer or 5-substituted fluorescein tracer derivative having the following structure:

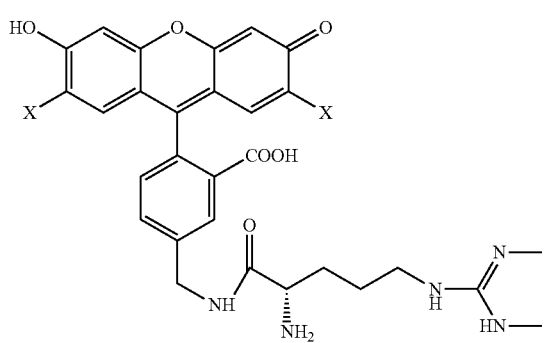

wherein X is selected from the group consisting of —H, —F, —CH₃, —OCH₃, —Cl, —OH, —NO₂, —CN, —COOH, and —SO₃H.

In one embodiment, the invention is directed to a complex comprising a 5-substituted fluorescein tracer or 5-substituted fluorescein tracer derivative selected from the above-identified structures and an antibody against SDMA. In one embodiment, the antibody is conjugated to a quencher.

In one embodiment, the invention is directed to a 5-substituted fluorescein tracer of structure A4.

Structure A4

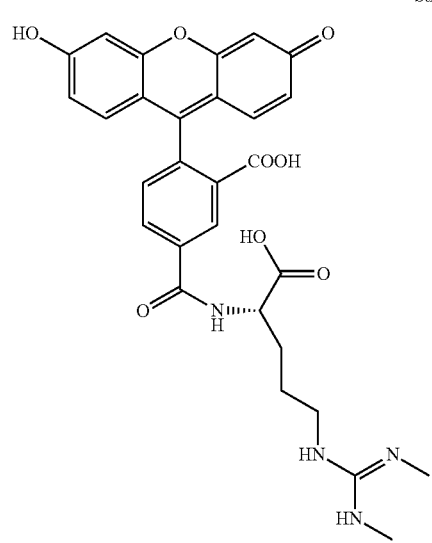

In one embodiment, the invention is directed to a 5-substituted fluorescein tracer of structure A5.

Structure A5

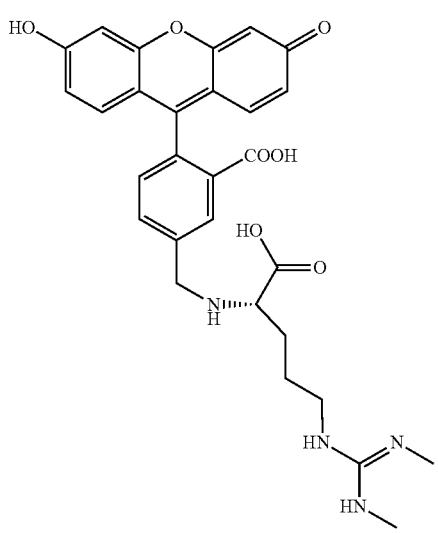

In one embodiment, the invention is directed to a 5-substituted fluorescein tracer of structure A6:

Structure A6

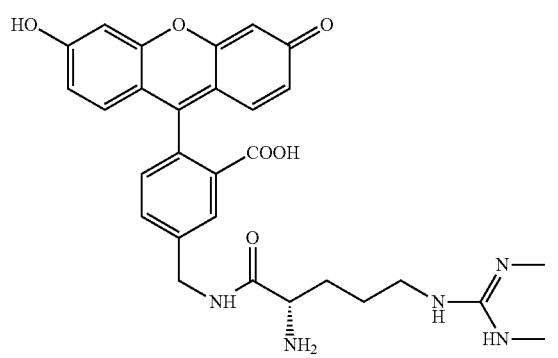

In one embodiment, the invention is directed to a complex comprising the 5-substituted fluorescein tracer of structure A4 and an antibody against SDMA. In one embodiment, the antibody is conjugated to a quencher.

In one embodiment, the invention is directed to a complex comprising the 5-substituted fluorescein tracer of structure A5 and an antibody against SDMA. In one embodiment, the antibody is conjugated to a quencher.

In one embodiment, the invention is directed to a complex comprising the 5-substituted fluorescein tracer of structure A6 and an antibody against SDMA. In one embodiment, the antibody is conjugated to a quencher.

Illustrative 4'-substituted fluorescein tracers that can be used in an assay for melamine are:

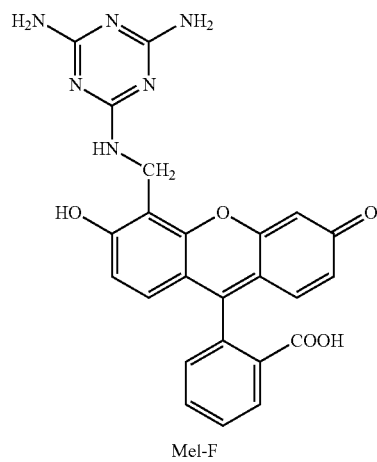

Mel-F

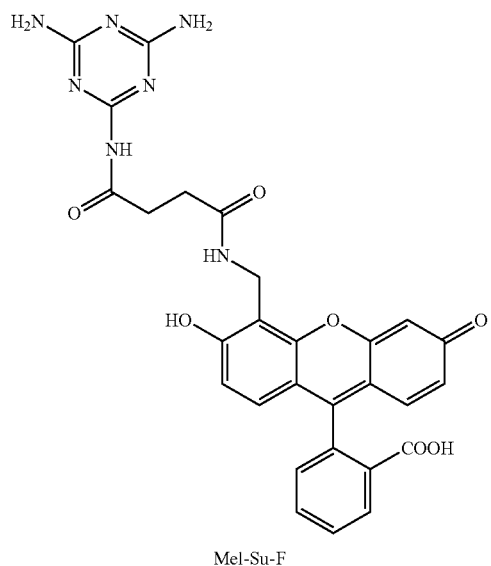

Mel-Su-F

In one embodiment, the invention is directed to a complex comprising Mel-F or Mel-Su-F and an antibody against melamine. In one embodiment, the antibody is conjugated to a quencher.

An illustrative 4'-substituted fluorescein tracers that can be used in an assay for biotin is:

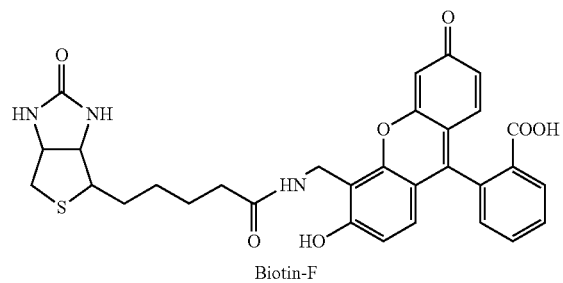 [SMILES: O=C(CCCCC1SCC2NC(=O)NC21)NCc1c(O)ccc2c(-c3ccccc3C(=O)O)c3ccc(=O)cc-3oc12]

Biotin-F

In one embodiment, the invention is directed to a complex comprising Biotin-F and an antibody against biotin. In one embodiment, the antibody is conjugated to a quencher.

Illustrative 4'-substituted fluorescein tracers that can be used in an assay for thyroxine are:

T2-F

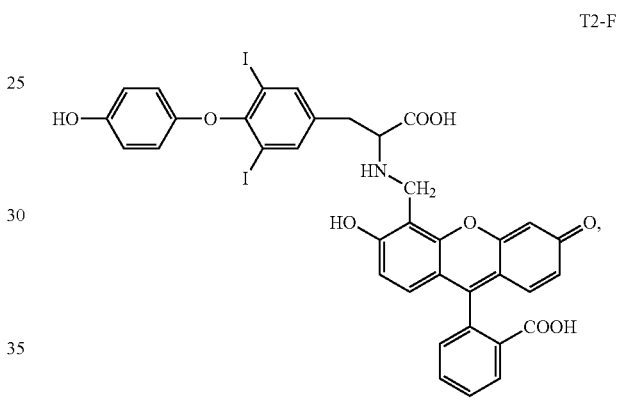

T3-F

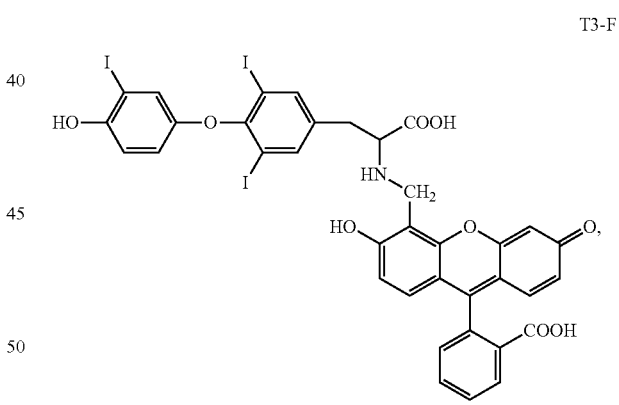

T4-F

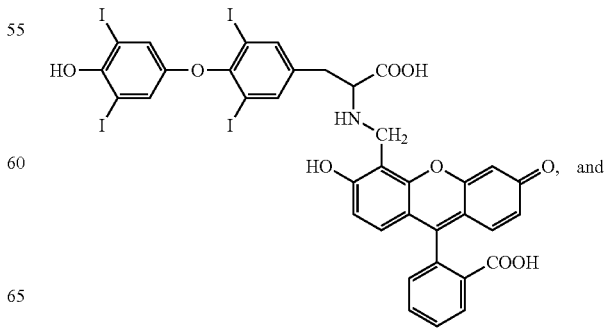

and

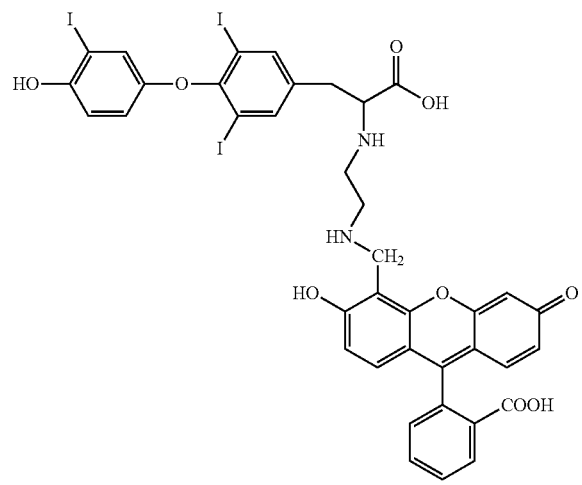

T3-E-F

In one embodiment, the invention is directed to a complex comprising T2-F, T3-F, T4-F, or T3-E-F and an antibody against thyronine. In one embodiment, the antibody is conjugated to a quencher.

An illustrative 4'-substituted fluorescein tracer that can be used in an assay for amoxicillin is:

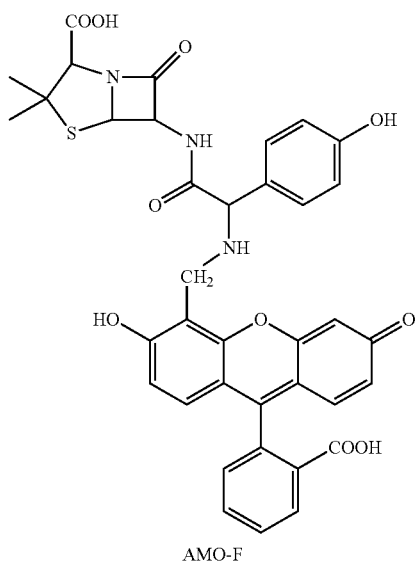

AMO-F

In one embodiment, the invention is directed to a complex comprising AMO-F and an antibody against amoxicillin. In one embodiment, the antibody is conjugated to a quencher.

An illustrative 4'-substituted fluorescein tracer that can be used in an assay for ampicillin is:

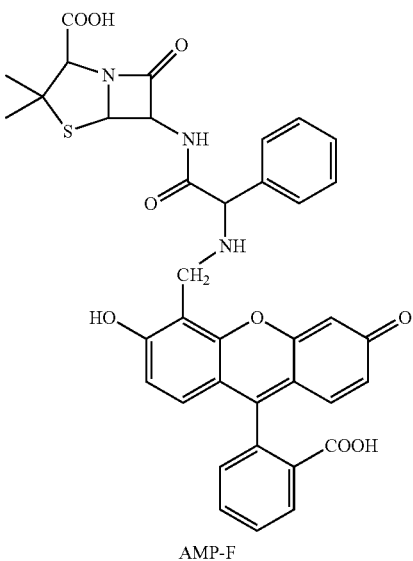

AMP-F

In one embodiment, the invention is directed to a complex comprising AMP-F and an antibody against ampicillin. In one embodiment, the antibody is conjugated to a quencher.

An illustrative 4'-substituted fluorescein tracer that can be used in an assay for cefotaxime is:

CEF-F

In one embodiment, the invention is directed to a complex comprising CEF-F and an antibody against cefotaxime. In one embodiment, the antibody is conjugated to a quencher.

Illustrative 4'-substituted fluorescein tracers that can be used in an assay for sulfadimethoxine are:

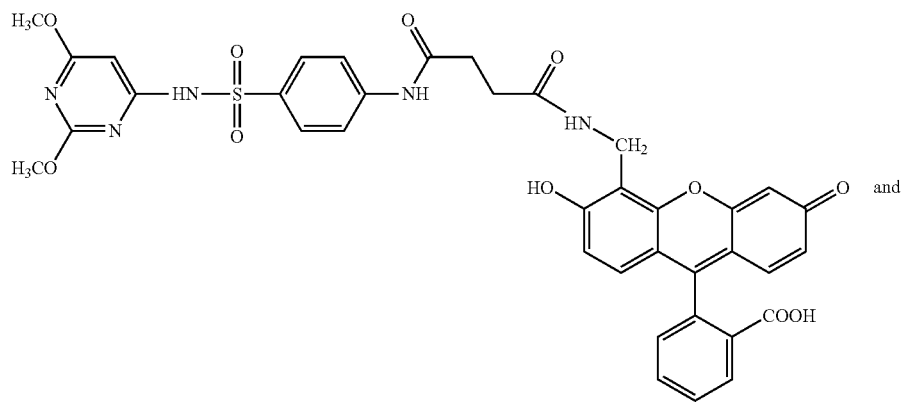

SDM-Su-F

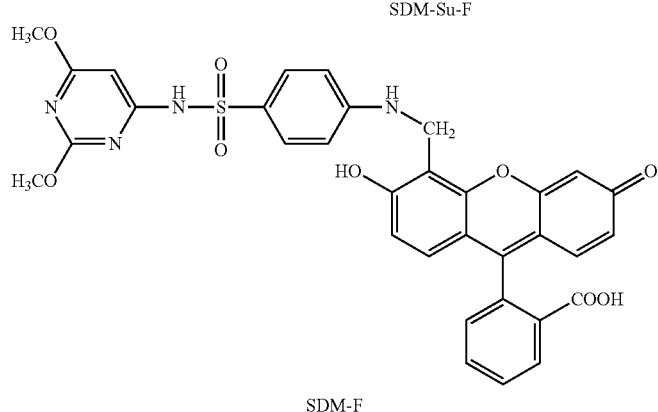

SDM-F

In one embodiment, the invention is directed to a complex comprising SDM-Su-F or SDM-F and an antibody against sulfadimethoxine. In one embodiment, the antibody is conjugated to a quencher.

An illustrative 4'-substituted fluorescein tracer that can be used in an assay for cortisol is:

In one embodiment, the invention is directed to a complex comprising Cortisol-4-Fl and an antibody against cortisol. In one embodiment, the antibody is conjugated to a quencher.

An illustrative 4'-substituted fluorescein tracer that can be used in an assay for progesterone is:

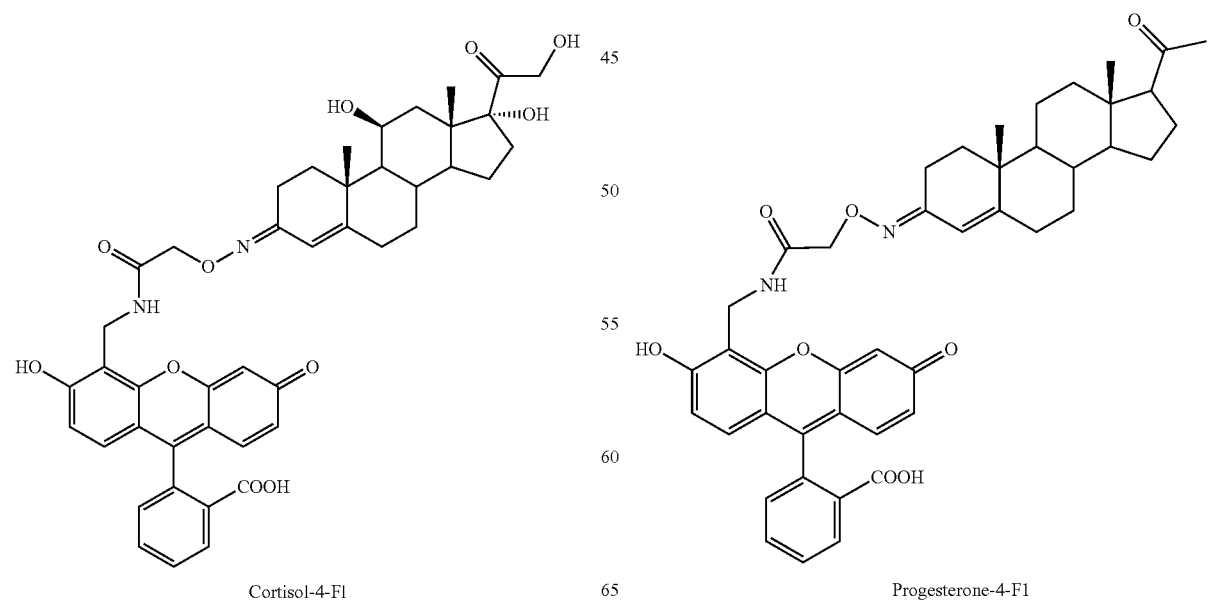

Cortisol-4-Fl

Progesterone-4-Fl

Progesterone-4-Fl

In one embodiment, the invention is directed to a complex comprising Progesterone-4-Fl and an antibody against progesterone. In one embodiment, the antibody is conjugated to a quencher.

An illustrative 4'-substituted fluorescein tracer that can be used in an assay for bile acids is:

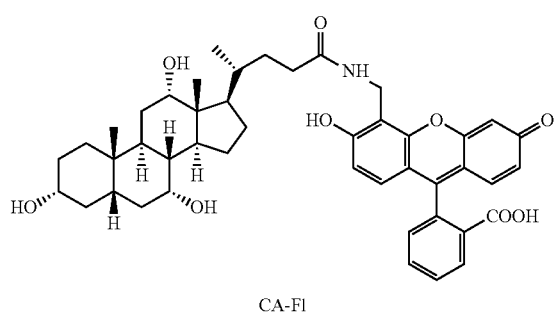

CA-Fl

In one embodiment, the invention is directed to a complex comprising CA-Fl and an antibody against bile acids. In one embodiment, the antibody is conjugated to a quencher.

Illustrative bile acids include, but are not limited to, cholic acid and taurocholic acid.

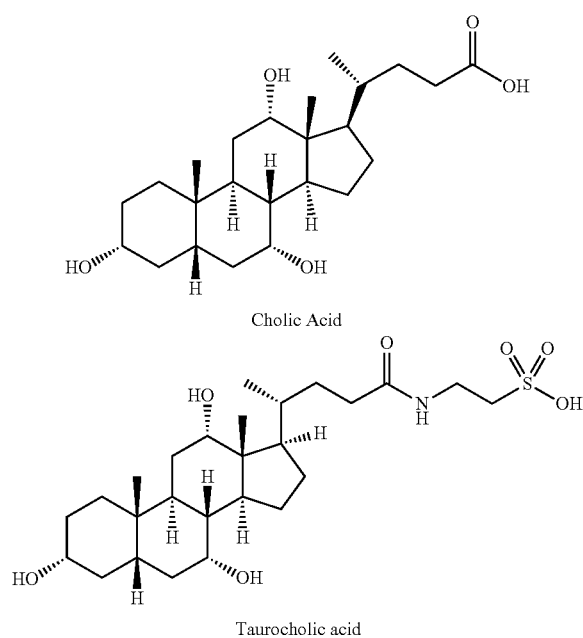

Cholic Acid

Taurocholic acid

In one embodiment, the molecule that fluoresces is a fluorescein that is functionalized at both the 4'- and 5'-position, for example, with an aldehyde group, a —COOH group, or a —CH$_2$NH$_2$ group, as depicted below:

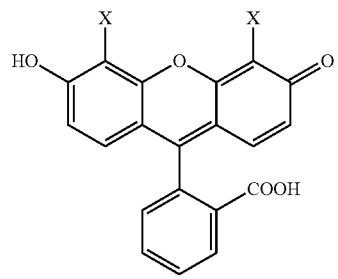

wherein X is —C(O)H, —COOH, or —CH$_2$NH$_2$. The T-epitopic moiety can be attached to the fluorescein core structure at either the 4'-position, the 5'-position, or both the 4'- and 5'-positons. The T-epitopic moiety can be attached to the fluorescein core structure using the chemistry described above.

In one embodiment, the invention is directed to a complex comprising AMO-F, AMP-F, or CEF-F and penicillin binding protein. In one embodiment, the penicillin binding protein is conjugated to a quencher.

5. The Binding Partner

The binding partner that is specific for the analyte and the fluorescent tracer can be, for example, an antibody. Antibodies can be obtained by developing an immune response in an animal to the analyte using art recognized techniques. Typically, a hapten (which has an epitopic moiety in common with the analyte of interest) is conjugated to a carrier protein, such as bovine serum albumin, to provide an immunogen (antigen) that is administered to an animal, such as a rabbit, mouse, or sheep, by a series of injections and then the resulting antibodies isolated using conventional techniques. Other illustrative protein carriers that can be used to form the immunogen include, but are not limited to, keyhole limpet hemocyanin, egg ovalbumin, bovine gamma-globulin, and thyroxine-binding globulin. Alternatively, the antigen can be formed by conjugating the hapten to a synthetic or natural polymeric material that contains a functional group that is reactive with the hapten.

The binding partner can also be a protein that is not an antibody. Proteins can be isolated by conventional techniques. The analyte is a substrate that is specific for the protein. For example, the analyte can be selected from the group consisting of penicillin, estradiol, and progesterone and the binding partner can be selected from the group consisting of penicillin binding protein, estradiol binding protein, and progesterone binding protein, respectively.

In one embodiment, the binding partner is linked to a magnetic bar coded bead.

In one embodiment, the binding partner is conjugated to a quencher. Without wishing to be bound by theory, it is believed that when the fluorescent tracer is bound to the binding partner and the binding partner is conjugated to a quencher and the fluorescent tracer is excited by being irradiated with light of a first wavelength, energy is transferred from the fluorescent tracer to the quencher and the quencher then loses the energy thermally or by emitting light at a wavelength other than the second wavelength. Thus, the quencher provides for a greater decrease in the fluorescence intensity than would be observed if the binding partner were not conjugated to the quencher.

Figure 23:
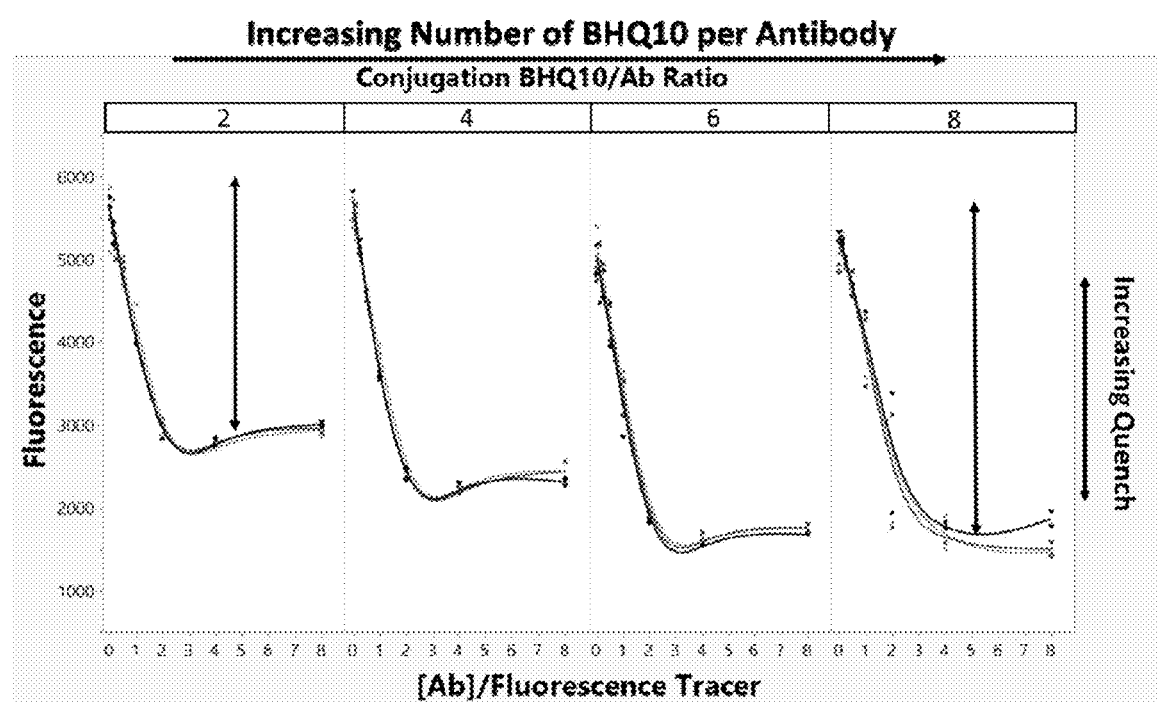
FIG. 23 depicts the decrease in fluorescence when the fluorescent tracer A3 forms a complex with an antibody to SDMA as a function of equivalents of BHQ10 quencher conjugated to the antibody.
Figure 24A:
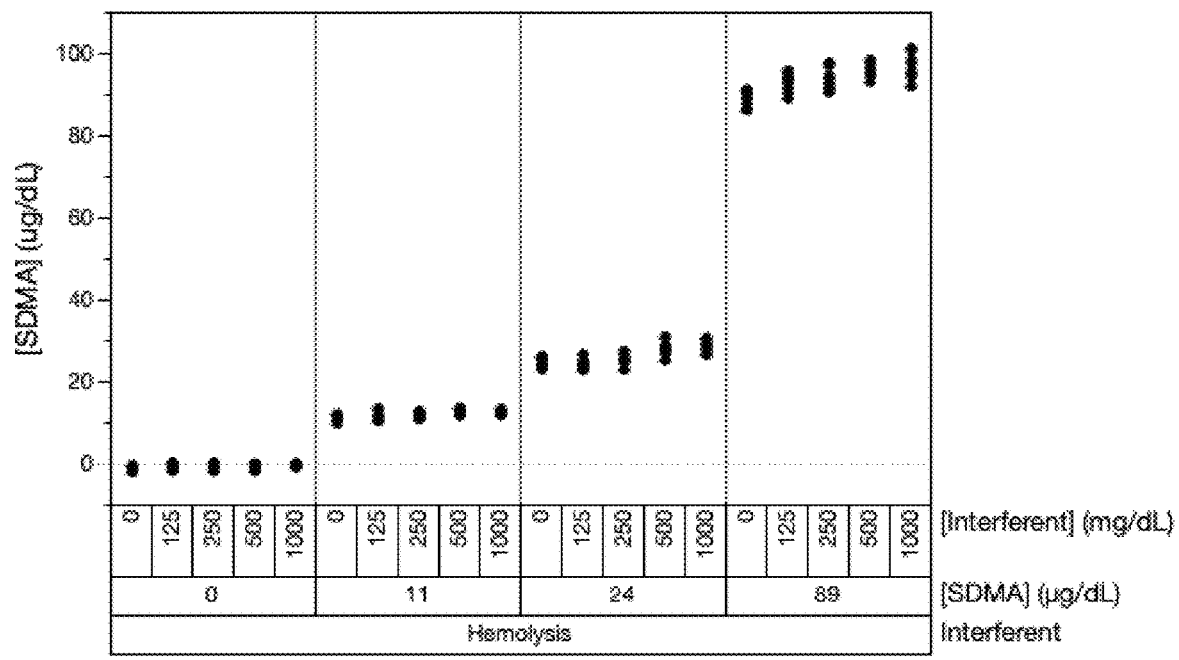
FIGS. 24 A, B, C, and D depicts the result of an assay (using a slide with a filtering layer) to determine the concentration of SDMA in a sample containing a fixed amount of SDMA (µg/dL), wherein the sample includes various concentrations of compounds that could potentially interfere with the assay (i.e., interferents). The interferents are (FIG. A) hemolysis (0 to 500 mg/dL), (FIG. B) bilirubin (0 to 30 mg/dL), (FIG. C) intralipid (0 to 1000 mg/dL) and (FIG. D) whole blood (0 to 10%).
Figure 24B:
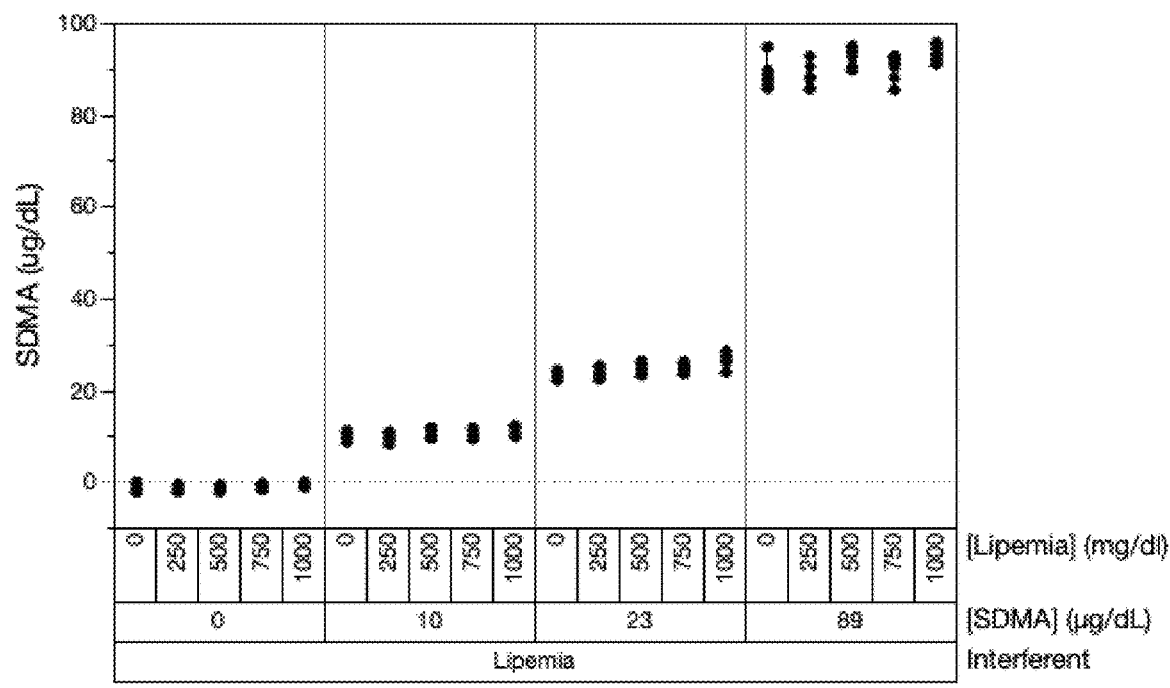
Figure 24C:
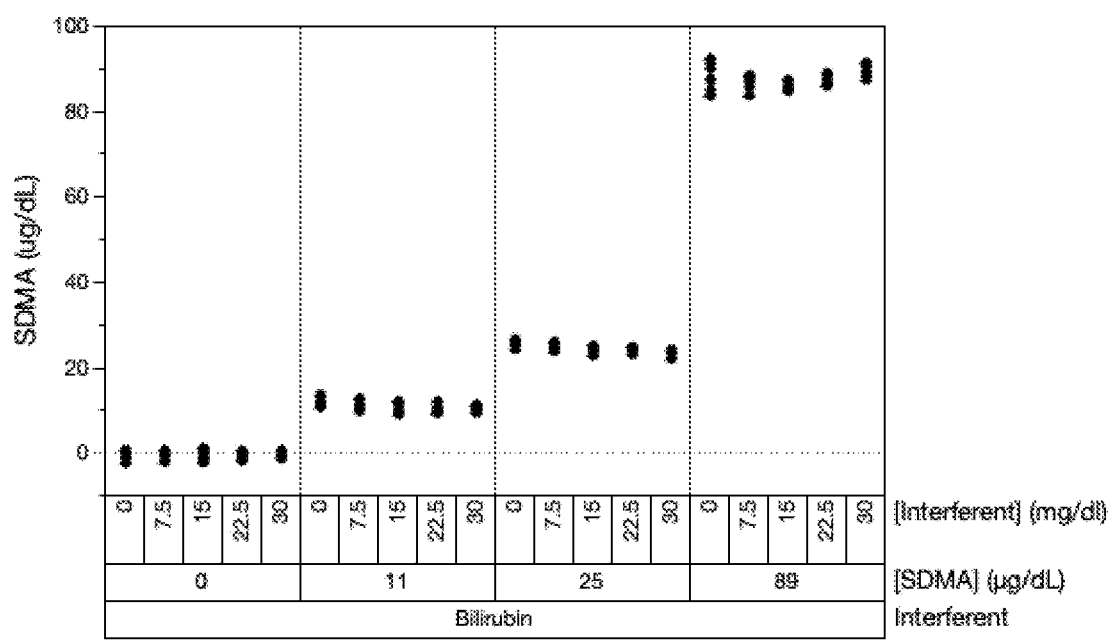
Figure 24D:
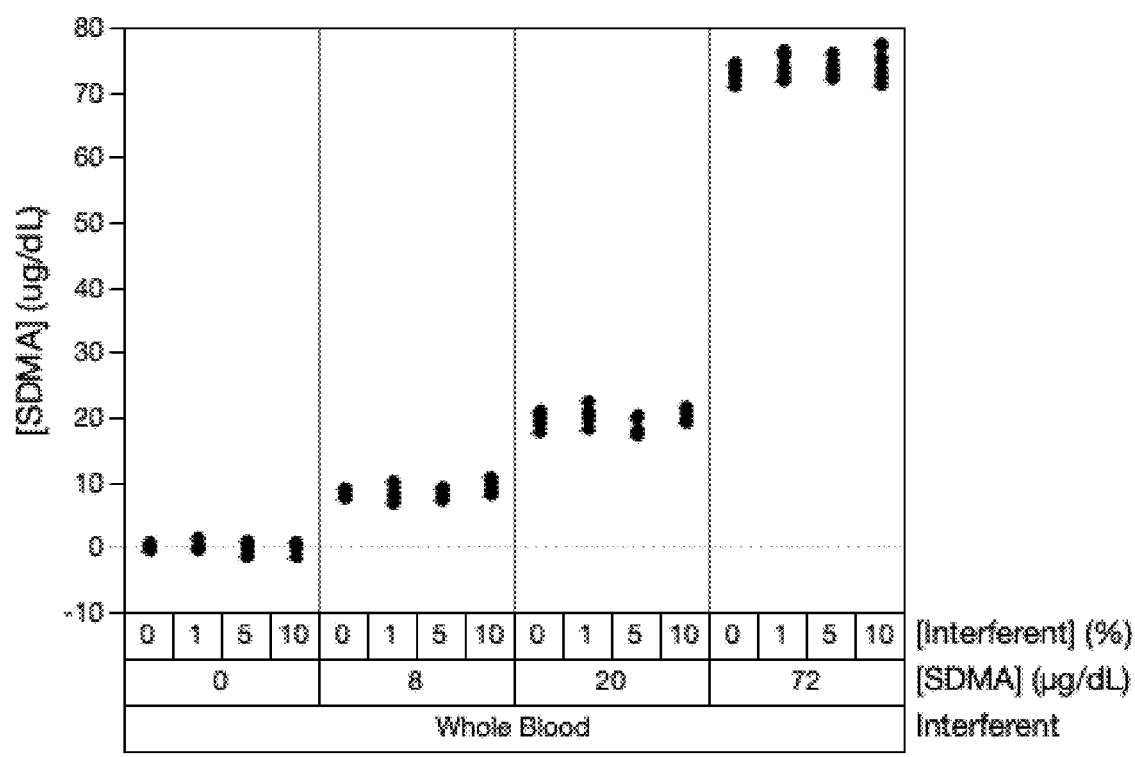

The decrease in fluorescence of a fluorescent tracer when it forms a complex with a binding partner that is conjugated to a quencher is a function of the equivalents of quencher molecules that are conjugated to the binding partner. The more quencher molecules conjugated to the binding partner, the greater the decrease in fluorescence. This is depicted in FIG. 23 as a plot of fluorescence vs. ratio of antibody: fluorescent tracer for antibody that is conjugated to 2, 4, 6, and 8 BHQ10 quencher molecules. FIG. 23 shows that, when the fluorescent tracer A3 forms a complex with an antibody to SDMA, there is a decrease in fluorescence and the maximum decrease in fluorescence is proportional to the equivalents of quencher molecules (BHQ10) conjugated to the antibody. FIG. 23 shows that when the antibody is conjugated to 2 equivalents of BHQ10 the maximum decrease in fluorescence is about 50% and when the antibody is conjugated to 8 equivalents of BHQ10, the maximum decrease in fluorescence is about 70%.

Suitable quenchers that can be bound to the binding partner include, but are not limited to, those illustrated below:

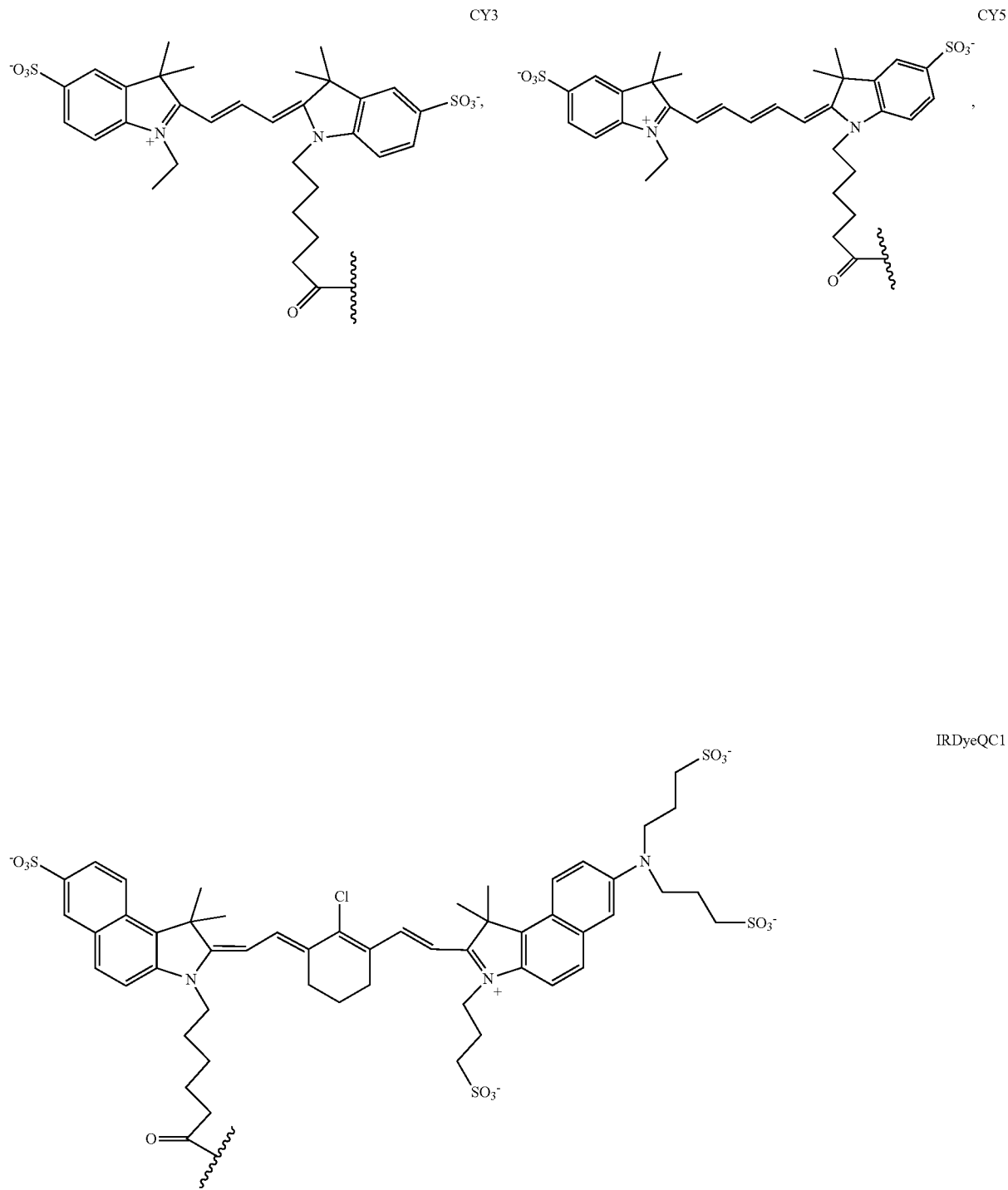

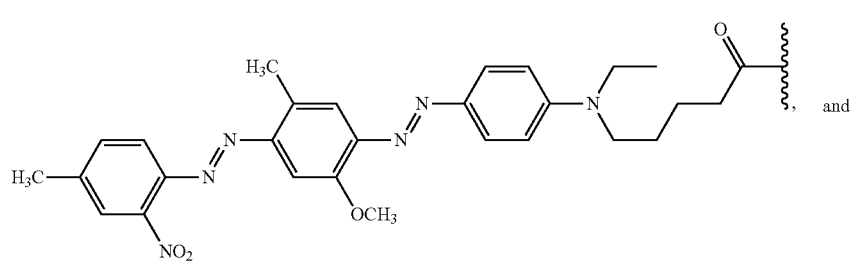

BHQ1 and

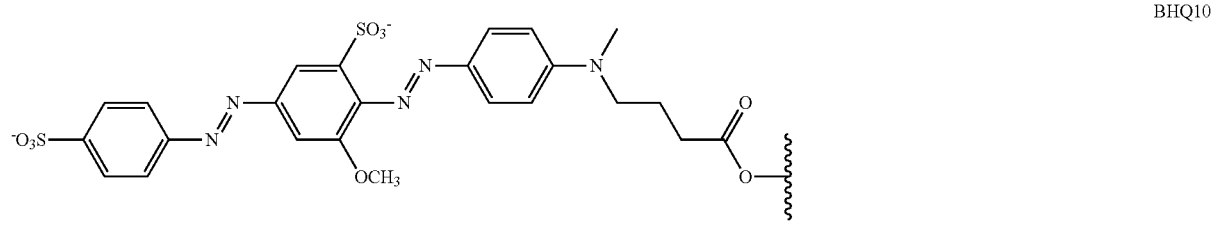

BHQ10 wherein counterions are not depicted in the above-structures and wherein the binding partner is linked to the quencher at the ⌇.

Additional suitable quenchers include, but are not limited to, DABCYL and DABCYL-Plus™ (commercially available from AnaSpec Inc. of Freemont, CA); Procion® MX-5B, Reactive Red 4, and Reactive Red 120 (commercially available from Sigma Aldrich of St. Louis, MO); DylightQ543 (commercially available from Thermo Scientific of Waltham, MA); TIDE QUENCHER™ 2WS (commercially available from AAT Bioquest of Sunyvale, CA); PADA (pyridine-2-azo-p-dimethylaniline) (commercially available from TCI America of Cambridge, MA); QSY™ quenchers (including QSY 7, QSY 9, and QSY 21, commercially available from Thermo Fisher Scientific of Waltham, MA); QXL™ Quenchers (including QXL 490, QXL 570, QXL 610, and QXL 670, commercially available from AnaSpec, Inc. of Fremont, CA); Iowa Black® quenchers (including Iowa Black FQ and Iowa Black RQ, commercially available from Integrated DNA Technologies, Inc. of Coralville, IA); and julolidine derivatives (including BlackBerry® Quencher 650, commercially available from Berry & Associates, Inc. of Dexter, MI).

The binding partner-quencher conjugates are made using commercially available reagents. For example, the binding partner bound to Cy3 and Cy5 are prepared by reacting the binding partner with:

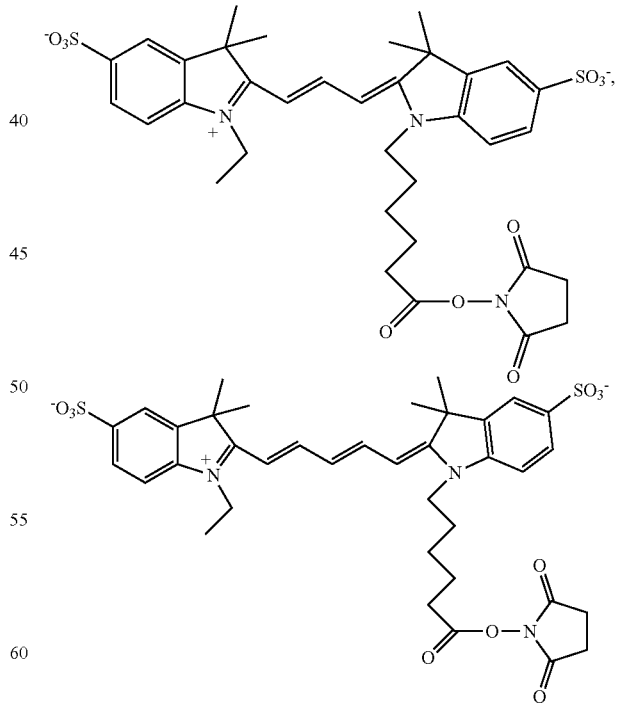

(without depicting counterions), respectively, which are commercially available from GE Healthcare of Chicago, IL; the binding partner bound to IRDyeQC1 is prepared by reacting the binding partner with:

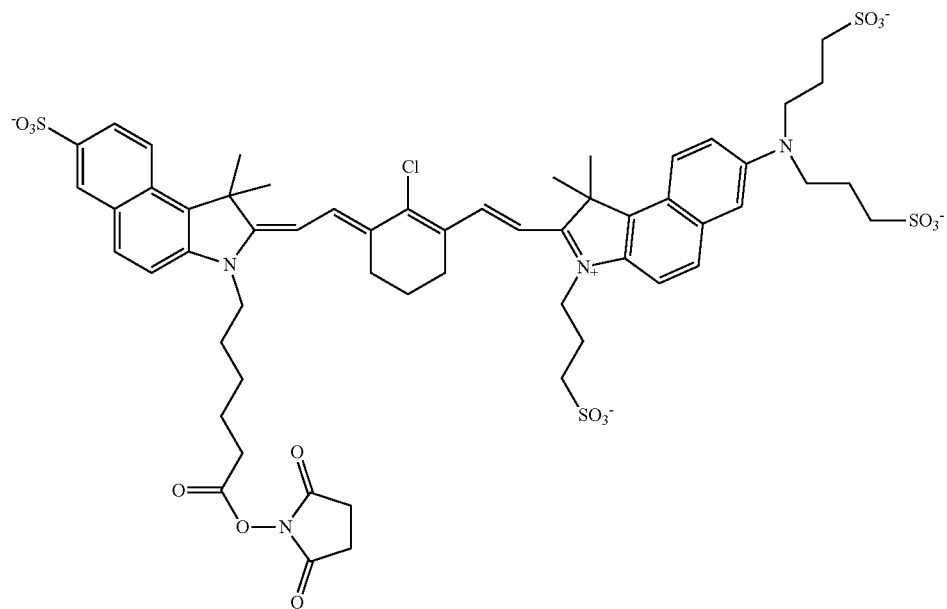

(without depicting counterions), which is commercially available from Li-Cor Biosciences of Lincoln, NB; the binding partner bound to BHQ1 is prepared by reacting the binding partner with:

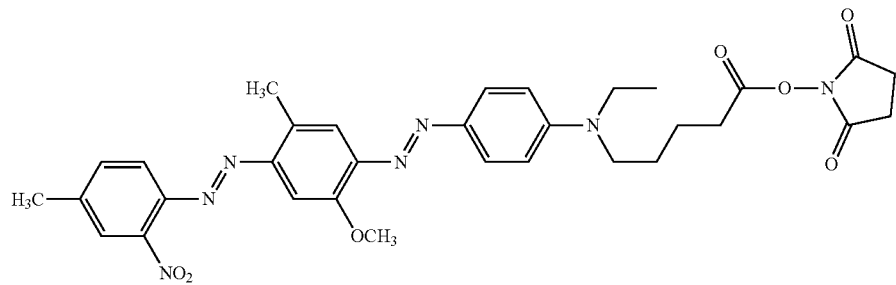 [SMILES: CCN(CCCCC(=O)ON1C(=O)CCC1=O)c1ccc(/N=N/c2cc(C)c(/N=N/c3ccc(C)cc3[N+](=O)[O-])cc2OC)cc1]

(without depicting counterions), which is commercially available from LGC Biosearch Technologies of Petaluma, CA; and the binding partner for BHQ10 is prepared by reacting the binding partner with:

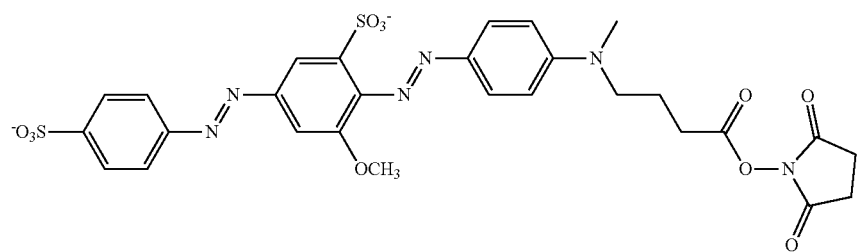

(without depicting counterions), which is commercially available from LGC Biosearch Technologies of Petaluma, CA The binding partner is conjugated to the quencher by reacting the binding partner with the N-hydroxysuccinimide esters following the directions of the supplier. Alternatively, the N-hydroxysuccinimide ester can be prepared from the corresponding carboxylic acid.

The ratio of N-hydroxysuccinimide ester to binding partner typically ranges from about 1 to about 30, preferably about 1 to about 20, and more preferably from about 1 to about 12. The ratio will vary depending on the choice of the fluorescent molecule used to make the fluorescent tracer, the quencher, the analyte, and the binding partner. Preferred ratios are determined by measuring the quench in fluorescence of different concentrations of each of these molecules.

Without wishing to be bound by theory, it is believed that the N-hydroxysuccinimide ester acylates one or more groups on the binding partner, such as amine groups, to provide a structure such as depicted below for the quencher CY3:

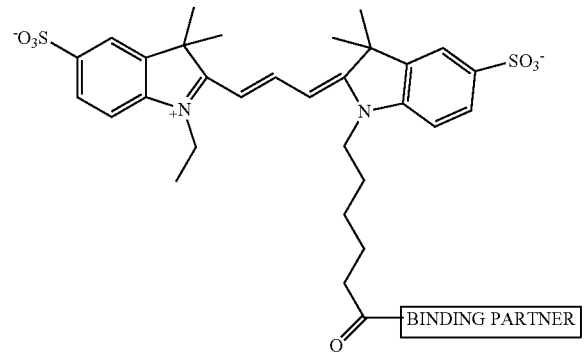

Preferably the quencher is CY3, CY5, BHQ1, or BHQ10. More preferably, the quencher is BHQ10.

The quencher is selected such that light emitted from the fluorescent tracer is able to excite the quencher or be absorbed by the quencher. The quencher is selected such that the wavelength of the light emitted by the quencher does not substantially overlap with the wavelength of the irradiating light.

In one embodiment, the analyte is an antigen, the fluorescent tracer is an analyte-conjugate comprising an epitopic moiety of the antigen linked to a fluorescent label, and the binding partner is an antibody to the antigen.

In one embodiment, the analyte is SDMA, the fluorescent tracer is an analyte-conjugate comprising an epitopic moiety of SDMA, and the binding partner is an antibody to SDMA that is conjugated to BHQ10. Preferably, the ratio of BHQ10 to the antibody is 20:1. In one embodiment, the ratio of BHQ10 to the antibody is 12:1.

In one embodiment, the analyte is SDMA; the fluorescent tracer is selected from the group consisting of A1, A2, A3, A4, A5, and A6; and the binding partner is an antibody to SDMA that is conjugated to BHQ10. In one embodiment, the analyte is SDMA; the fluorescent tracer is selected from the group consisting of A1, A2, and A3; and the binding partner is an antibody to SDMA that is conjugated to BHQ10. In one embodiment, the analyte is SDMA, the fluorescent tracer is A3; and the binding partner is an antibody to SDMA that is conjugated to BHQ10.

6. Illustrative Embodiments of the Fluorescence Quenching Assay wherein the Analyte is a Macromolecule In one embodiment, the analyte is a macromolecule, such as a protein. An illustrative protein is cystatin.

In one embodiment, the analyte is cystatin-B (i.e., Cys-B or CysB); the fluorescent tracer is a fluorescent moiety attached to CysB; and the binding partner is an anti-cystatin-B antibody (i.e., anti-Cys-B or anti-CysB antibody) that is conjugated to one or more quenchers.

In one embodiment, the fluorescent tracer is CysB conjugated to fluorescein through one or more lysine residues. To provide the fluorescent tracer conjugated to fluorescein through one or more lysine residues, CysB is reacted with various equivalents of fluorescein-NHS (the N-hydroxysuccinimide ester of fluorescein (i.e., 5-(and 6-) carboxyfluorescein, succinimidyl ester) commercially available from Sigma Aldrich of St. Louis, MO) to provide CysB-Fl conjugated to FL through lysine residues. Without wishing to be bound by theory, it is believed that the fluorescein-NHS reacts with lysine residues on the CysB to provide the CysB-FL conjugated to FL through lysine residues. Typically, the CysB-FL conjugated to FL through lysine residues is obtained by reacting CysB with between 1 and 4 equivalents of fluorescein-NHS. In one embodiment, the CysB-Fl conjugated to FL through lysine residues is obtained by reacting CysB with 2 equivalents of fluorescein-NHS. In one embodiment, the CysB conjugated to FL through lysine residues is obtained by reacting CysB with 4 equivalents of fluorescein-NHS.

In one embodiment, the fluorescent tracer is CysB conjugated to fluorescein through one or more cysteine residues. To provide the fluorescent tracer conjugated to fluorescein through one or more cysteine residues, CysB is reacted with various equivalents of fluroescein-5-maleimide (commercially available from Sigma Aldrich of St. Louis, MO). Without wishing to be bound by theory, it is believed that the fluroescein-5-maleimide reacts with cysteine residues on the CysB to provide the CysB-FL conjugated to fluorescein through cysteine residues. Typically, the CysB conjugated to FL through cysteine residues is obtained by reacting CysB with between 1 and 4 equivalents of fluroescein-5-maleimide. In one embodiment, the CysB-FL conjugated through cysteine residues is obtained by reacting CysB with 2 equivalents of fluroescein-5-maleimide.

In one embodiment, the fluorescent tracer is CysB-Peptide 9 conjugated to fluorescein, i.e., CysB-Peptide 9-FL. CysB-Peptide 9-FL is obtained by reacting CysB-Peptide 9 with fluorescein-NHS. Without wishing to be bound by theory, it is believed that the fluorescein-NHS reacts with lysine residues on the CysB-Peptide 9 to provide the CysB-Peptide 9-FL. Typically, CysB-Peptide 9-FL is obtained by reacting CysB-Peptide 9 with between 1 and 4 equivalents of fluorescein-NHS. In one embodiment, the CysB-Peptide 9-FL is obtained by reacting CysB-Peptide 9 with 4 equivalents of fluorescein-NHS.

In one embodiment, the binding partner is an anti-cystatin-B antibody (i.e., anti-CysB antibody) that is conjugated to one or more BHQ10 molecules i.e., anti-CysB-BHQ. The anti-CysB-BHQ can be obtained by reacting anti-CysB antibody with BHQ10-NHS (the N-hydroxysuccinimide ester of BHQ10, commercially available from LGC Biosearch Technologies of Petaluma, CA). Without wishing to be bound by theory, it is believed that the BHQ10-NHS reacts with lysine residues on the anti-CysB antibody to provide the anti-CysB-BHQ. Typically, anti-CysB-BHQ is obtained by reacting CysB with between 1 and 16 equivalents of BHQ10-NHS. Illustrative examples of CysB antibodies include, but are not limited to, 3H4-anti-cystatin-B antibody, Ra355 Polyclonal-anti-CysB antibody, and 7C2-Anti-CysB antibody (Each of these antibodies was custom made; the Ra355 is a rabbit polyclonal anti-CysB antibody that was raised by SDIX, Newark, Delaware 19702 and the 3H4-anti-cystatin-B antibody and the 7C2-Anti-CysB antibody are mouse monoclonal anti-CysB antibodies that were raised by Immunoprecise Antibodies LLC, Vancouver BC, Canada). In one embodiment, anti-CysB-BHQ is obtained by reacting 3H4-anti-cystatin-B antibody with 2 equivalents of BHQ10-NHS. In one embodiment, anti-CysB-BHQ is obtained by reacting 3H4-anti-cystatin-B antibody with 4 equivalents of BHQ10-NHS. In one embodiment, anti-CysB-BHQ is obtained by reacting Ra355 Polyclonal-anti-CysB antibody with 4 equivalents of BHQ10-NHS. In one embodiment, anti-CysB-BHQ is obtained by reacting 7C2-Anti-CysB antibody with 4 equivalents of BHQ10-NHS.

In one embodiment, the binding partner is an anti-CysB antibody that is conjugated to one or more boron-dipyrromethene (BODIPY) molecules, i.e., anti-CysB-BODIPY. Anti-CysB-BODIPY can be obtained by reacting anti-CysB antibody with BODIPY-NHS (the N-hydroxysuccinimide ester of BODIPY, commercially available from Thermo Scientific of Waltham, MA). Typically, anti-CysB-BODIPY is obtained by reacting CysB with between 1 and 4 equivalents of BODIPY-NHS. In one embodiment, anti-CysB-BODIPY is obtained by reacting 3H4-anti-cystatin-B antibody with 2 equivalents of BODIPY-NHS. In one embodiment, anti-CysB-BODIPY is obtained by reacting 3H4-anti-cystatin-B antibody with 4 equivalents of BODIPY-NHS. Preferably, anti-CysB-BODIPY is obtained by reacting 3H4-anti-CysB antibody with 4 equivalents of BODIPY-NHS.

In one embodiment, the analyte is CysB; the fluorescent tracer is a fluorescent moiety attached to an anti-CysB antibody; and the binding partner is CysB that is conjugated to one or more quenchers.

In one embodiment, the fluorescent tracer is an anti-CysB antibody that has been reacted with various equivalents of fluorescein-NHS to provide anti-CysB-FL. Without wishing to be bound by theory, it is believed that the fluorescein-NHS reacts with lysine residues on the anti-CysB antibody to provide the anti-CysB-FL. Typically, the anti-CysB-FL is obtained by reacting anti-CysB antibody with between 1 and 4 equivalents of fluorescein-NHS. In one embodiment, the anti-CysB-FL is obtained by reacting 3H4-anti-CysB antibody with fluorescein-NHS. Illustrative examples of CysB antibodies include, but are not limited to, 3H4-anti-cystatin-B antibody, Ra355 Polyclonal-anti-CysB antibody, and 7C2-Anti-CysB antibody. In one embodiment, the anti-CysB-FL is obtained by reacting 3H4-anti-CysB antibody with 2 equivalents of fluorescein-NHS. Preferably, the anti-CysB-FL is obtained by reacting 3H4-anti-CysB antibody with 2 equivalents of fluorescein-NHS. In one embodiment, the anti-CysB-FL is obtained by reacting 3H4-anti-CysB antibody with 4 equivalents of fluorescein-NHS. In one embodiment, the anti-CysB-FL is obtained by reacting Ra355 polyclonal-anti-CysB antibody with 2 equivalents of fluorescein-NHS. In one embodiment, the anti-CysB-FL is obtained by reacting 7C2-anti-CysB antibody with 2 equivalents of fluorescein-NHS.

In one embodiment, the fluorescent tracer is an anti-CysB antibody that has been reacted with various equivalents of fluorescein aldehyde, i.e., fluorescein that is functionalized at the 4' position with an aldehyde group, to provide anti-CysB-FL conjugated to fluorescein aldehyde, i.e., anti-CysB-FL-Ald. Without wishing to be bound by theory, it is believed that the fluorescein aldehyde reacts with lysine residues on the anti-CysB antibody to provide the anti-CysB-FL-Ald. In one embodiment, the anti-CysB-FL-Ald is obtained by reacting 3H4-anti-CysB antibody with 2 equivalents of fluorescein aldehyde. Preferably, the anti-CysB-FL-Ald is obtained by reacting 3H4-anti-CysB antibody with 2 equivalents of fluorescein aldehyde.

In one embodiment, the binding partner is CysB that is conjugated to one or more BHQ10 molecules i.e., CysB-BHQ. The CysB-BHQ can be obtained by reacting CysB with BHQ10-NHS. Without wishing to be bound by theory, it is believed that the BHQ10-NHS reacts with lysine residues on the CysB to provide the CysB-BHQ. Typically, CysB-BHQ is obtained by reacting CysB with between 1 and 16 equivalents of BHQ10-NHS. In one embodiment, CysB-BHQ is obtained by reacting CysB with 4 equivalents of BHQ10-NHS. In one embodiment, CysB-BHQ is obtained by reacting CysB with 8 equivalents of BHQ10-NHS. Preferably, CysB-BHQ is obtained by reacting CysB with 8 equivalents of BHQ10-NHS. In one embodiment, CysB-BHQ is obtained by reacting CysB with 12 equivalents of BHQ10-NHS.

In one embodiment, the analyte is a polypeptide and the fluorescent tracer is a molecule that fluoresces linked to a peptide chain with an amino acid length shorter than the amino acid length of the polypeptide. In one embodiment, the peptide chain has an amino acid length of less than 20 amino acids. In one embodiment, the peptide chain has an amino acid length of less than 15 amino acids. In one embodiment, the peptide chain has an amino acid length of less than 10 amino acids. In one embodiment, the peptide chain has an amino acid length of less than 7 amino acids. In one embodiment, the polypeptide is a macromolecule (e.g., a protein). In one embodiment, the amino acid sequence of the peptide chain corresponds to the amino acid sequence of the epitopic moiety on the polypeptide.

In one embodiment, the analyte is a macromolecule, such as a protein; the fluorescent tracer is a fluorescent moiety attached to an amino acid chain with an amino acid length shorter than the amino acid length of the protein. The amino acid sequence of the amino acid chain corresponds to the amino acid sequence of the epitope on the protein that is responsible for complexing with the binding partner. In one embodiment, the binding partner is conjugated to a quencher An advantage of linking the fluorescent moiety to an amino acid chain with an amino acid length shorter than the amino acid length of the protein, rather than linking the fluorescent tracer to the complete protein, is that it assures that the distance between the molecule that fluoresces and the quencher is sufficiently close for there to be efficient quenching. When the fluorescent tracer is attached to the complete protein, only the epitopic site on the complete protein interacts with the binding partner. Therefore, if the fluorescent moiety on the protein is not near the epitopic site, the separation between the fluorescent moiety on the protein and the quencher on the binding partner when they form a complex could be too large for there to be effective quenching. Linking the fluorescent moiety to an amino acid chain with an amino acid length shorter than the amino acid length of the protein, minimizes this problem.

In one embodiment, the amino acid sequence (i.e., a polypeptide having the amino acid sequence) is attached to the 5-position of fluorescein. In one embodiment, the amino acid sequence is attached to the 5-position of fluorescein with a linker. In one embodiment, the linker is —NH—C(O)—.

In one embodiment, the amino acid sequence is attached to the 4'-position of fluorescein. In one embodiment, the amino acid sequence is attached to the 4'-position of fluorescein with a linker. In one embodiment, the linker is —CH$_2$—.

As an example, the analyte is canine CysB; the fluorescent tracer is a fluorescent moiety attached to an amino acid sequence of between 5 and 15 amino acids, preferably between 5 and 10 amino acids; and the binding partner is an anti-cystatin-B antibody (i.e., anti-Cys-B or anti-CysB antibody) that is optionally conjugated to one or more quenchers.

In one embodiment, the fluorescent moiety is attached to the amino acid sequence (i.e., is attached to a polypeptide having the amino acid sequence) QTNKAKHDELAYF (P9) [SEQ ID NO: 2]. In one embodiment, the amino acid sequence is attached to the 5-position of fluorescein. In one embodiment, the amino acid sequence is attached to the 5-position of fluorescein with a linker. In one embodiment, the linker is —NH—C(O)—. In one embodiment, the amino acid sequence is attached to the 4'-position of fluorescein. In one embodiment, the amino acid sequence is attached to the 4'-position of fluorescein with a linker. In one embodiment, the linker is —CH$_2$—.

In one embodiment, the fluorescent moiety is attached to the amino acid sequence: YQTNKAKHDELAYF (P14) [SEQ ID NO: 3]. In one embodiment, the amino acid sequence is attached to the 5-position of fluorescein. In one embodiment, the amino acid sequence is attached to the 5-position of fluorescein with a linker. In one embodiment, the linker is —NH—C(O)—. In one embodiment, the amino acid sequence is attached to the 4'-position of fluorescein. In one embodiment, the amino acid sequence is attached to the 4'-position of fluorescein with a linker, the linker is —CH$_2$—.

In one embodiment, the fluorescent moiety is attached to the amino acid sequence: GHDELAYF (P7) [SEQ ID NO: 4]. In one embodiment, the amino acid sequence is attached to the 5-position of fluorescein. In one embodiment, the amino acid sequence is attached to the 5-position of fluorescein with a linker. In one embodiment, the linker is —NH—C(O)—. In one embodiment, the amino acid sequence is attached to the 4'-position of fluorescein. In one embodiment, the amino acid sequence is attached to the 4'-position of fluorescein with a linker. In one embodiment, the linker is —CH$_2$—.

In one embodiment, the fluorescent moiety is attached to the amino acid sequence: GDELAYF (P6) [SEQ ID NO: 5]. In one embodiment, the amino acid sequence is attached to the 5-position of fluorescein. In one embodiment, the amino acid sequence is attached to the 5-position of fluorescein with a linker. In one embodiment, the linker is —NH—C(O)—. In one embodiment, the amino acid sequence is attached to the 4'-position of fluorescein. In one embodiment, the amino acid sequence is attached to the 4'-position of fluorescein with a linker. In one embodiment, the linker is —CH$_2$—.

In one embodiment, the fluorescent moiety is attached to the amino acid sequence: GELAYF (P5) [SEQ ID NO: 6]. In one embodiment, the amino acid sequence is attached to the 5-position of fluorescein. In one embodiment, the amino acid sequence is attached to the 5-position of fluorescein with a linker. In one embodiment, the linker is —NH—C(O)—. In one embodiment, the amino acid sequence is attached to the 4'-position of fluorescein. In one embodiment, the amino acid sequence is attached to the 4'-position of fluorescein with a linker. In one embodiment, the linker is —CH$_2$—.

In one embodiment, the fluorescent moiety is attached to the amino acid sequence: GLAYF (P4) [SEQ ID NO: 7]. In one embodiment, the amino acid sequence is attached to the 5-position of fluorescein. In one embodiment, the amino acid sequence is attached to the 5-position of fluorescein with a linker. In one embodiment, the linker is —NH—C(O)—. In one embodiment, the amino acid sequence is attached to the 4'-position of fluorescein. In one embodiment, the amino acid sequence is attached to the 4'-position of fluorescein with a linker. In one embodiment, the linker is —CH$_2$—.

In one embodiment, the fluorescent moiety is attached to the amino acid sequence: MMCGAPSASQPATADTQAIADQVKAQLEERENKKYTTFKAVTFRSQVVAGTPYFIKVQVDDDEFVHLRVFQSLPHENKPLALSSYQTNKAKHDELAYF [SEQ ID NO: 1]. In one embodiment, the amino acid sequence is attached to the 5-position of fluorescein. In one embodiment, the amino acid sequence is attached to the 5-position of fluorescein with a linker. In one embodiment, the linker is —NH—C(O)—. In one embodiment, the amino acid sequence is attached to the 4'-position of fluorescein. In one embodiment, the amino acid sequence is attached to the 4'-position of fluorescein with a linker. In one embodiment, the linker is —CH$_2$—.

As another example, the analyte is canine NT-proBNP (NT-Pro-B-type natriuretic protein); the fluorescent tracer is a fluorescent moiety attached to an amino acid sequence of between 5 and 15 amino acids, preferably between 5 and 10 amino acids; and the binding partner is an anti-NT-proBNP Mab that is optionally conjugated to one or more quenchers.

In one embodiment, the fluorescent moiety is attached to the amino acid sequence: AEQLALEPLHRS (P1) [SEQ ID NO: 8]. In one embodiment, the amino acid sequence is attached to the 5-position of fluorescein. In one embodiment, the amino acid sequence is attached to the 5-position of fluorescein with a linker. In one embodiment, the linker is —NH—C(O)—. In one embodiment, the amino acid sequence is attached to the 4'-position of fluorescein. In one embodiment, the amino acid sequence is attached to the 4'-position of fluorescein with a linker. In one embodiment, the linker is —CH$_2$—.

In one embodiment, the fluorescent moiety is attached to the amino acid sequence: AEQLAL (P2) [SEQ ID NO: 9]. In one embodiment, the amino acid sequence is attached to the 5-position of fluorescein. In one embodiment, the amino acid sequence is attached to the 5-position of fluorescein with a linker. In one embodiment, the linker is —NH—C(O)—. In one embodiment, the amino acid sequence is attached to the 4'-position of fluorescein. In one embodiment, the amino acid sequence is attached to the 4'-position of fluorescein with a linker. In one embodiment, the linker is —CH$_2$—.

In one embodiment, the fluorescent moiety is attached to the amino acid sequence: EPLHRS (P3) [SEQ ID NO: 10]. In one embodiment, the amino acid sequence is attached to the 5-position of fluorescein. In one embodiment, the amino acid sequence is attached to the 5-position of fluorescein with a linker. In one embodiment, the linker is —NH—C(O)—. In one embodiment, the amino acid sequence is attached to the 4'-position of fluorescein. In one embodiment, the amino acid sequence is attached to the 4'-position of fluorescein with a linker. In one embodiment, the linker is —CH$_2$—.

In one embodiment, the fluorescent moiety is attached to the amino acid sequence: LALEPL (P4) [SEQ ID NO: 11]. In one embodiment, the amino acid sequence is attached to the 5-position of fluorescein. In one embodiment, the amino acid sequence is attached to the 5-position of fluorescein with a linker. In one embodiment, the linker is —NH—C(O)—. In one embodiment, the amino acid sequence is attached to the 4'-position of fluorescein. In one embodiment, the amino acid sequence is attached to the 4'-position of fluorescein with a linker. In one embodiment, the linker is —CH$_2$—.

In one embodiment, the fluorescent moiety is attached to the amino acid sequence: AEQLALE (P5) [SEQ ID NO: 12]. In one embodiment, the amino acid sequence is attached to the 5-position of fluorescein. In one embodiment, the amino acid sequence is attached to the 5-position of fluorescein with a linker. In one embodiment, the linker is —NH—C(O)—. In one embodiment, the amino acid sequence is attached to the 4'-position of fluorescein. In one embodiment, the amino acid sequence is attached to the 4'-position of fluorescein with a linker. In one embodiment, the linker is —CH$_2$—.

In one embodiment, the fluorescent moiety is attached to the amino acid sequence: LEPLHRS (P6) [SEQ ID NO: 13]. In one embodiment, the amino acid sequence is attached to the 5-position of fluorescein. In one embodiment, the amino acid sequence is attached to the 5-position of fluorescein with a linker. In one embodiment, the linker is —NH—C(O)—. In one embodiment, the amino acid sequence is attached to the 4'-position of fluorescein. In one embodiment, the amino acid sequence is attached to the 4'-position of fluorescein with a linker. In one embodiment, the linker is —CH$_2$—.

In one embodiment, the fluorescent moiety is attached to the amino acid sequence: GRSPASEASEASEASGLWAVQ [SEQ ID NO: 15]. In one embodiment, the amino acid sequence is attached to the 5-position of fluorescein. In one embodiment, the amino acid sequence is attached to the 5-position of fluorescein with a linker. In one embodiment, the linker is —NH—C(O)—. In one embodiment, the amino acid sequence is attached to the 4'-position of fluorescein. In one embodiment, the amino acid sequence is attached to the 4'-position of fluorescein with a linker. In one embodiment, the linker is —CH$_2$—.

In one embodiment, the fluorescent moiety is attached to the amino acid sequence: SHSPAEAPEAGGTPRGV-LAPHDSVLQ [SEQ ID NO: 16]. In one embodiment, the amino acid sequence is attached to the 5-position of fluorescein. In one embodiment, the amino acid sequence is attached to the 5-position of fluorescein with a linker. In one embodiment, the linker is —NH—C(O)—. In one embodiment, the amino acid sequence is attached to the 4'-position of fluorescein. In one embodiment, the amino acid sequence is attached to the 4'-position of fluorescein with a linker. In one embodiment, the linker is —CH$_2$—.

In one embodiment, the fluorescent moiety is attached to the amino acid sequence: HPLGGRSPASEASEASEASGL-WAVQELLGRLKDAVSELQAEQLALEPLHRSHS-PAEAPEAG GTPRGVLAPHDSVLQALR [SEQ ID NO: 14]. In one embodiment, the amino acid sequence is attached to the 5-position of fluorescein. In one embodiment, the amino acid sequence is attached to the 5-position of fluorescein with a linker. In one embodiment, the linker is —NH—C(O)—. In one embodiment, the amino acid sequence is attached to the 4'-position of fluorescein. In one embodiment, the amino acid sequence is attached to the 4'-position of fluorescein with a linker. In one embodiment, the linker is —CH$_2$—.

The fluorescent moiety may be attached to any of the polypeptides disclosed in U.S. Pat. Nos. 8,628,973; 8,778,699; 9,605,068; 9,005,984; and 10,725,052 which are incorporated herein by reference in their entirety. Each resulting polypeptide tracer may be used in the methods of the invention in conjunction with a binding partner chosen from any of the corresponding antibodies disclosed in U.S. Pat. Nos. 8,628,973; 8,778,699; 9,605,068; 9,005,984; and 10,725,052.

EXAMPLES

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims. Such variations of the invention, including the substitution of all equivalents now known or later developed, which would be within the purview of those skilled in the art, and changes in formulation or minor changes in experimental design, are to be considered to fall within the scope of the invention incorporated herein.

Example 1

Preparation of Fluorescein Aldehyde

Fluorescein aldehyde was prepared as depicted in the reaction scheme provided below:

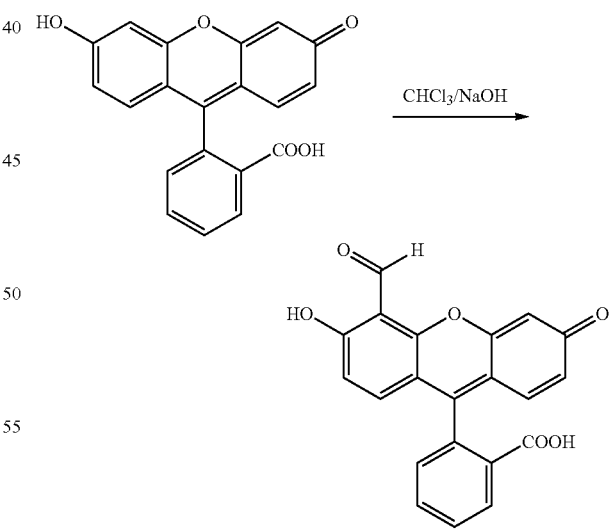

Fluorescein (4 g, 12 mmol, commercially available from Sigma Aldrich of St. Louis, MO) was dissolved in 40 mL sodium hydroxide solution (1M) and then heated to 70° C. To the warmed solution was added chloroform (8 mL, 45 mmol) in a drop wise manner and the resulting mixture maintained at the same temperature for 3 hours. After cooling to room temperature, the reaction mixture was poured into 250 mL of a 1M HCl solution to provide a precipitate. The precipitate was collected by filtration, washed several times with water, dried, and protected from light.

The resulting crude product was then purified by column chromatography using a silica gel column (2.5 cm×30 cm) eluted with dichloromethane/acetonitrile (15:1). Fractions containing fluorescein aldehyde were identified using an LC/MS equipped with a C18 reverse phase column that was eluted with a gradient of 40% to 80% acetonitrile in water containing 1% acetic acid. Fractions containing fluorescein aldehyde were combined, the solvent removed under reduced pressure, and the resulting residue dried under high vacuum to provide 0.28 g of light yellow crystals. Mass spectrum m/z=361.1(M+H)$^+$.

Example 2

Preparation of Melamine-Fluorescein (Mel-F)

Mel-F was prepared as depicted in the reaction scheme provided below:

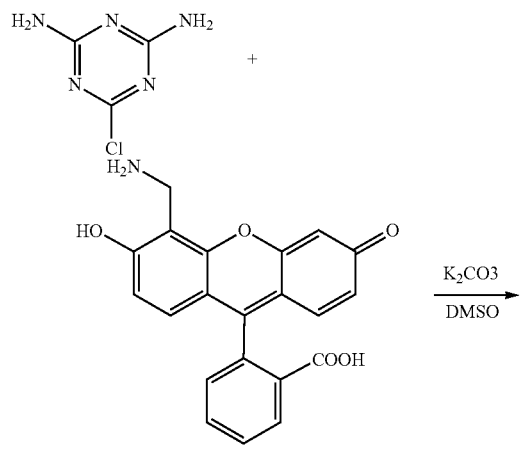

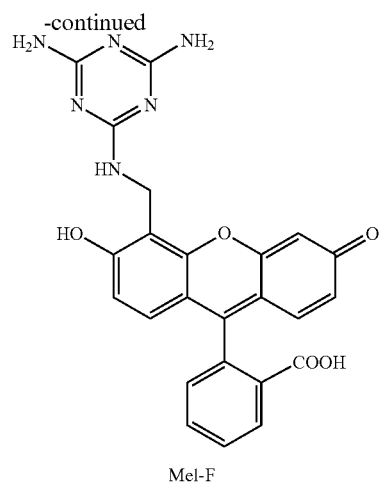

Mel-F 2-chloro-4, 6-diamino-1,3,5-triazine (4.5 mg, 0.03 mmol, commercially available from Sigma Aldrich of St. Louis, MO) and 4'-aminomethyl fluorescein (7.9 mg, 0.02 mmol, commercially available from AAT Bioquest of Sunyvale, CA) were dissolved in anhydrous dimethyl sulfoxide (DMSO) (1 mL). To the resulting solution was added anhydrous potassium carbonate (5.5 mg, 0.04 mmol), the solution heated to 95° C., and the solution allowed to stir overnight at this temperature. The solvent was then removed under reduced pressure and the resulting residue dissolved in 30% aqueous acetonitrile containing 0.1% trifluoroacetic acid (TFA). The resulting solution was purified by column chromatography using a C18 reverse phase column (10 g) eluted with aqueous acetonitrile solutions containing 0.1% TFA. A gradient of 30% acetonitrile to 60% acetonitrile was used for the gradient. The fractions containing pure Mel-F were combined and lyophilized to provide Mel-F as a yellow powder. Mass spectrum m/z=471.7 (M+H)$^+$.

Example 3

Preparation of Melamine-Succinic-Fluorescein (Mel-Su-F)

Mel-Su-F was prepared as depicted in the reaction scheme provided below:

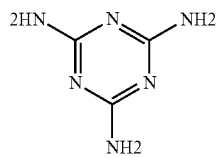

Mel

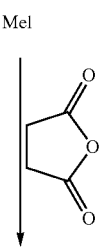

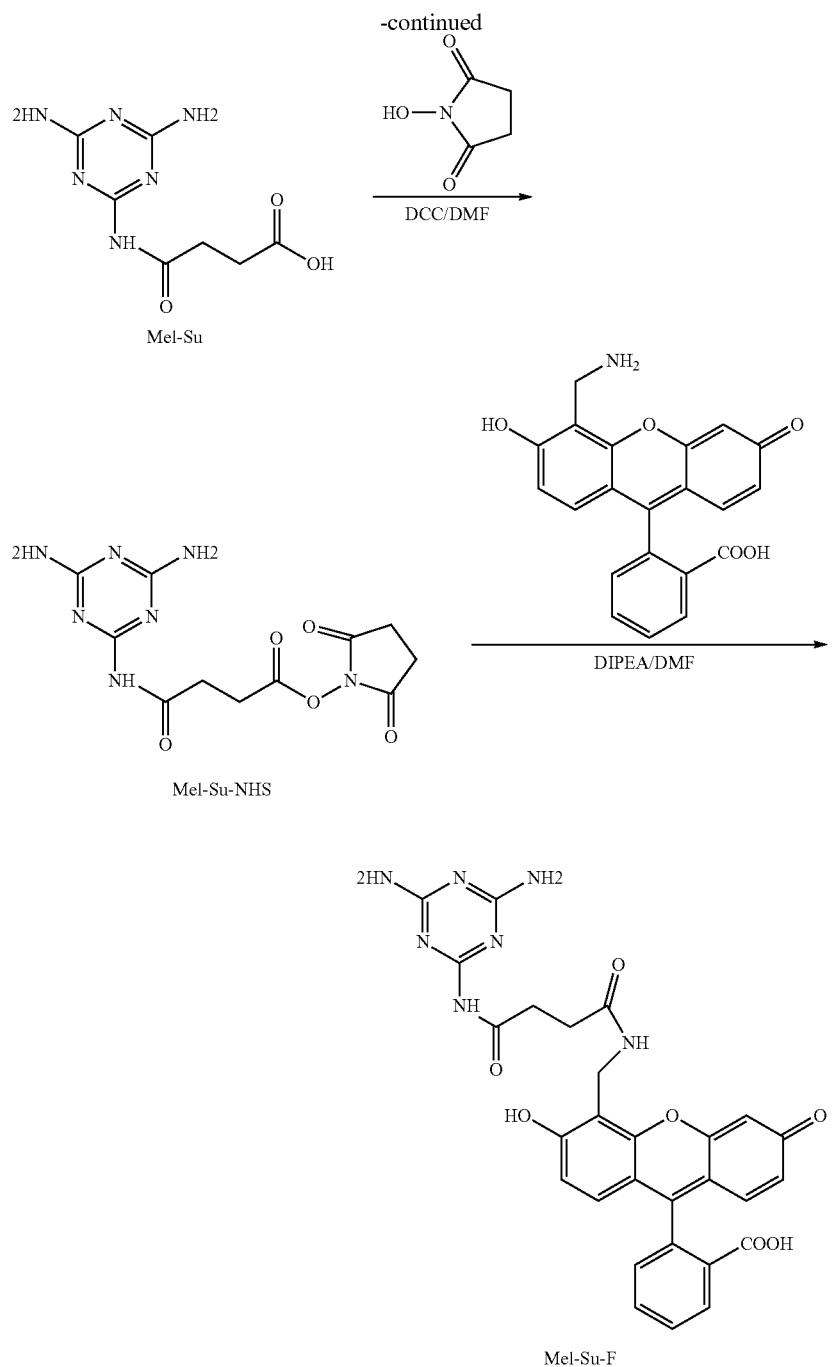

Melamine (416 mg, 3.3 mmol, commercially available from Sigma Aldrich of St. Louis, MO) and succinic anhydride (0.5 g, 5.0 mmol) were dissolved in anhydrous dimethyl formamide (DMF) (8 mL). The resulting solution was heated to 100° C. and allowed to stir overnight at this temperature. The solvent was then removed under reduced pressure to provide the melamine-succinic acid derivative (Mel-Su).

Mel-Su (270 mg, 1.2 mmol), N',N'-dicyclohexylcarbodiimide (268 mg, 1.3 mmol), and N-hydroxysuccinimide (0.15 g, 1.30 mmol) were dissolved in anhydrous dimethyl sulfoxide (DMSO) (5 mL) and the resulting solution stirred at room temperature overnight. The solvents were then removed under reduced pressure to provide (Mel-Su-NHS) that was used without further purification.

Mel-Su-NHS (8 mg, 0.025 mmol) and 4'-aminomethylfluorescein (10 mg, 0.025 mmol, commercially available from AAT Bioquest of Sunyvale, CA) was dissolved in anhydrous DMF (0.5 mL). To the resulting DMF solution was added N'N'-diisopropylethylamine (DIPEA) (10 μL), the solution stirred at room temperature for 2 hours, and the solvents removed under high vacuum to provide a residue. The resulting residue was purified by column chromatography using a C18 reverse phase column (10 g) eluted with a gradient of 40% to 60% acetonitrile to provide Mel-Su-F. Mass spectrum m/z=570.2 (M+H)$^+$.

Example 4

Preparation of Biotin-Fluorescein (Biotin-F)

Biotin-F was prepared as depicted in the reaction scheme provided below:

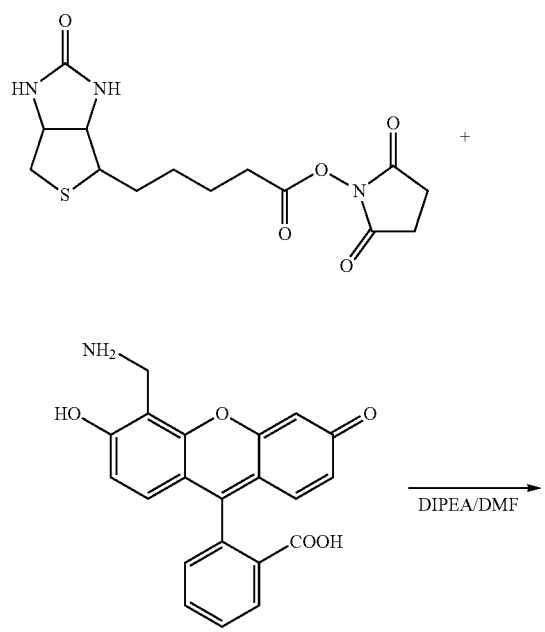

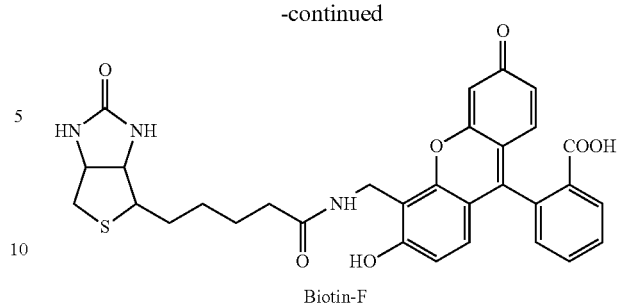

Biotin-F

4'-aminomethyl fluorescein (3 mg, 7.54 µmol, commercially available from AAT Bioquest of Sunyvale, CA) and N-hydroxysuccinimido biotin (2.5 mg, 7.54 µmol, commercially available from Thermo Scientific of Waltham, MA) were dissolved in anhydrous DMF (0.5 mL). To the DMF solution was added N,N,-diisopropylethylamine (4 µL) and the resulting solution allowed to stir at room temperature for two hours. The solution was then diluted with 40% acetonitrile in water containing 0.1% formic acid and purified by column chromatography using a C18 reverse phase column (1 g) eluted with a mobile phase of 40% acetonitrile in water containing 0.1% formic acid to provide 3 mg of Biotin-F as yellow solid (yield: 68%). Mass spectrum m/z=588.4 $(M+H)^+$.

Example 5

Preparation of Sulfadimethoxine-Succinic-Fluorescein (SDM-Su-F)

SDM-Su-F was prepared as depicted in the reaction scheme provided below:

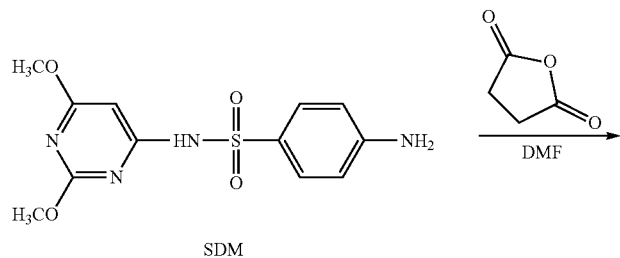

SDM

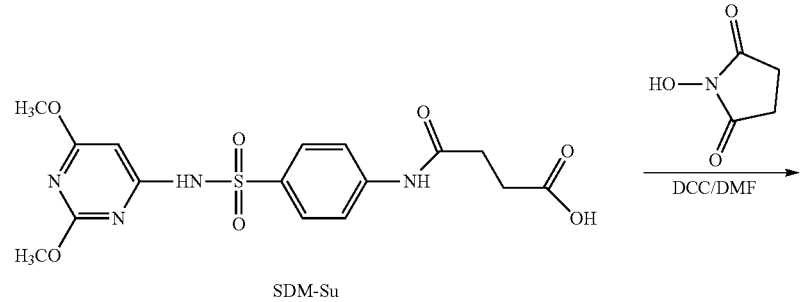

SDM-Su

-continued

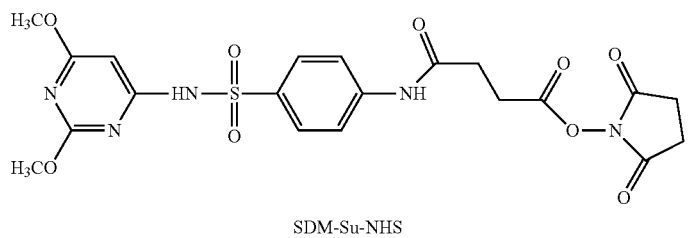
SDM-Su-NHS

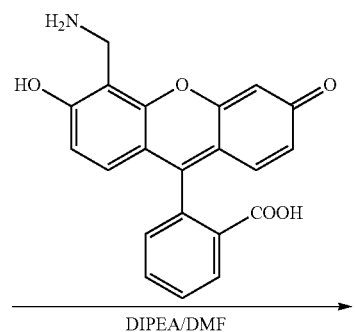

DIPEA/DMF

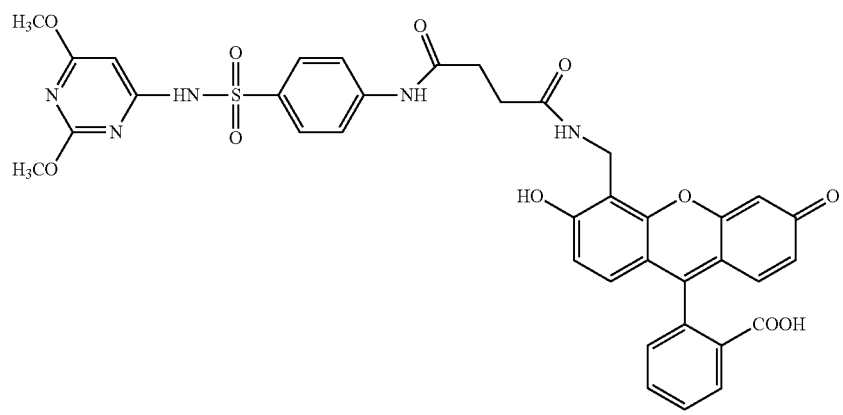
SDM-Su-F

Sulfadimethoxine (SDM, 1.0 g, 3.2 mmol, commercially available from Sigma Aldrich of St. Louis, MO) and succinic anhydride (0.49 g, 4.9 mmol) were dissolved in anhydrous DMF (6 mL). The resulting solution was heated to 100° C. and maintained at this temperature for 2 hour after which the solvent was removed under reduced pressure to provide a residue. The resulting residue was recrystallized from ethanol: water (1:1) to provide 1 g of SDM-Succinic acid (SDM-Su).

SDM-Su (0.51 g, 1.24 mmol), N'N'-dicyclohexylcarbodiimide (0.28 mL, 1.36 mmol) and N-hydroxysuccinimide (0.15 g, 1.30 mmol) were combined and dissolved in anhydrous DMF (5 mL) under an argon atmosphere. The resulting solution was stirred at room temperature overnight. The solvent was then removed under reduced pressure and the resulting product (SDM-Su-NHS) used without further purification.

SDM-Su-NHS (15.2 mg, 0.03 mmol) and 4'-aminomethyl-fluorescein (8 mg, 0.02 mmol, commercially available from AAT Bioquest of Sunyvale, CA) were dissolved in anhydrous DMF (0.5 mL). To the DMF solution was added N'N'-diisopropylethylamine (7 μL, 0.04 mmol) and the solution stirred at room temperature for 2 hours. The solvent was then removed under high vacuum to provide a residue. The resulting residue was purified by column chromatography using a C18 reverse phase column (10 g) eluted with 40% acetonitrile to provide SDM-Su-F as a yellow powder. Mass spectrum m/z=754.8 (M+H)$^+$.

Example 6

Preparation of T3-Ethyl-Fluorescein (T3-E-F)

T3-E-F was prepared as depicted in the reaction scheme provided below:

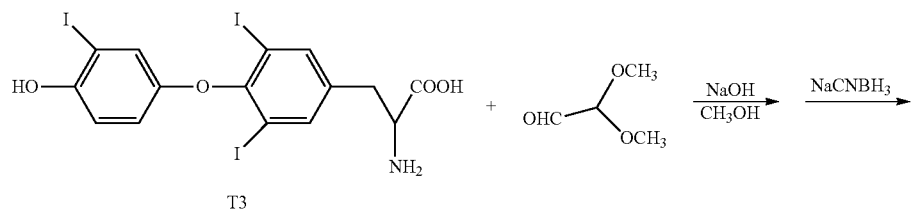

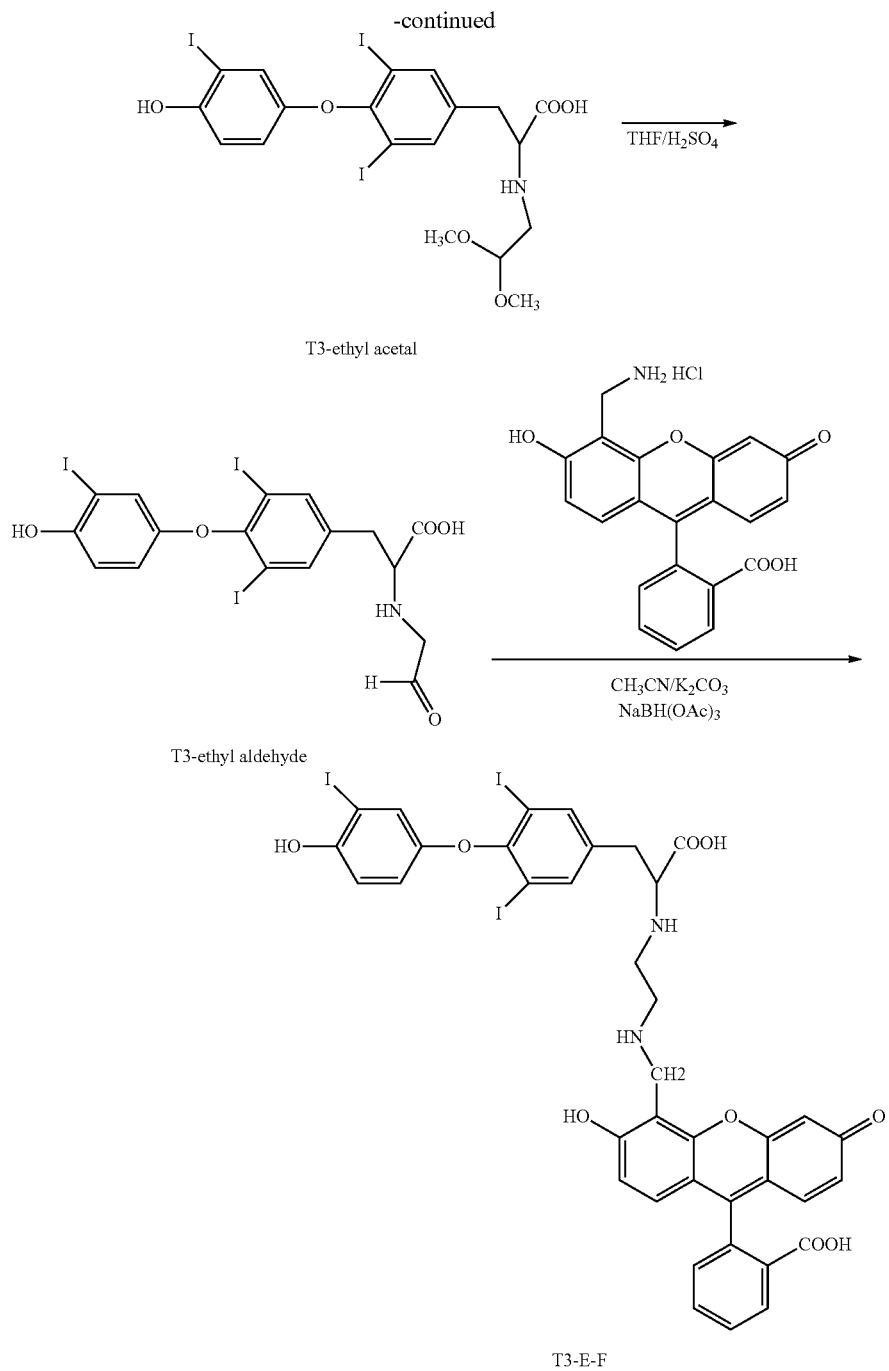

T3-Ethyl Acetal

Triiodothyronine (100 mg, 0.154 mmol, commercially available from Sigma Aldrich of St. Louis, MO) was dissolved in methanol (5 mL). To the methanol solution was then added sodium hydroxide (45 µL. 10 M) and dimethoxyacetal aldehyde (230 mL, 60% aqueous solution, 1.5 mmol) and the solution kept at room temperature for 30 min. Sodium cyanoborohydride (50 mg, 0.77 mmol) was then added and the resulting reaction mixture allowed to stir for 2 hours. Sodium hydroxide (0.1 mL, 1 M) was then added and the resulting reaction mixture allowed to stir for another 2 hours. 1 M HCl was then added to the reaction mixture to precipitate T3-ethyl acetal (100 mg), mass spectrum m/z=740.3 (M+H)$^+$, which was used without further purification.

T3-Ethyl Aldehyde

The T3-ethyl acetal was hydrolyzed overnight in tetrahydrofuran and sulfuric acid (THF/H$_2$SO$_4$). The solvent was then removed under reduced pressure to provide a residue. The resulting residue was dissolved in 20% aqueous acetonitrile containing 1% acetic acid and purified by column chromatography using a C18 reverse phase column (5 g) that was eluted with a gradient of 20% to 50% acetonitrile in water. The fractions containing T3-ethyl-aldehyde were combined and lyophilized to provide a white powder.

T3-E-F

T3-ethyl aldehyde (3 mg, 0.0042 mmol) and 4'-aminomethyl fluorescein (0.9 mg, 0.002 mmol, commercially available from AAT Bioquest of Sunyvale, CA) were dissolved in THF (1 mL) and acetic acid (12 µL) and sodium triacetoxyborohydride (NaBH(OAc)$_3$) (2 mg) was added. The resulting solution was stirred at room temperature overnight. The following day the solvents were removed under reduced pressure and the resulting residue purified by column chromatography using a C18 reverse phase column eluted with a gradient of 20% to 60% acetonitrile in water to provide T3-E-F. Mass spectrum m/z=1039.4 (M+H)$^+$.

Example 7

Preparation of Sulfadimethoxine-Fluorescein (SDM-F)

SDM-F was prepared as depicted in the reaction scheme provided below:

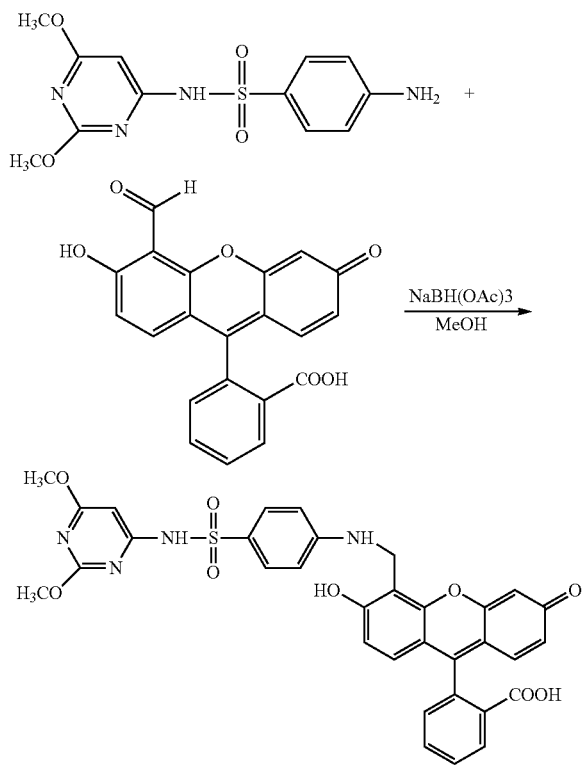

Sulfadimethoxine (8.6 mg, 0.028 mmol, commercially available from Sigma Aldrich of St. Louis, MO) and fluorescein aldehyde (8 mg, 0.022 mmol) were dissolved in methanol (2 mL). Sodium triacetoxyborohydride (15 mg, 0.15 mmol) and acetic acid (4 µL) were added and the resulting solution stirred at room temperature overnight. The reaction solution was then diluted with 40% acetonitrile in water containing 0.1% trifluoroacetic acid (TFA) and purified by column chromatography using a C18 reverse phase column (5 g) eluted with a gradient of 40% to 60% acetonitrile in water containing 0.1% TFA. The fractions containing SDM-F product were combined and lyophilized to provide 1 mg of SDM-F as a yellow powder. Mass spectrum m/z=623.7 (M+H)$^+$.

Example 8

Preparation of T3-F

T3-F was prepared as depicted in the reaction scheme provided below:

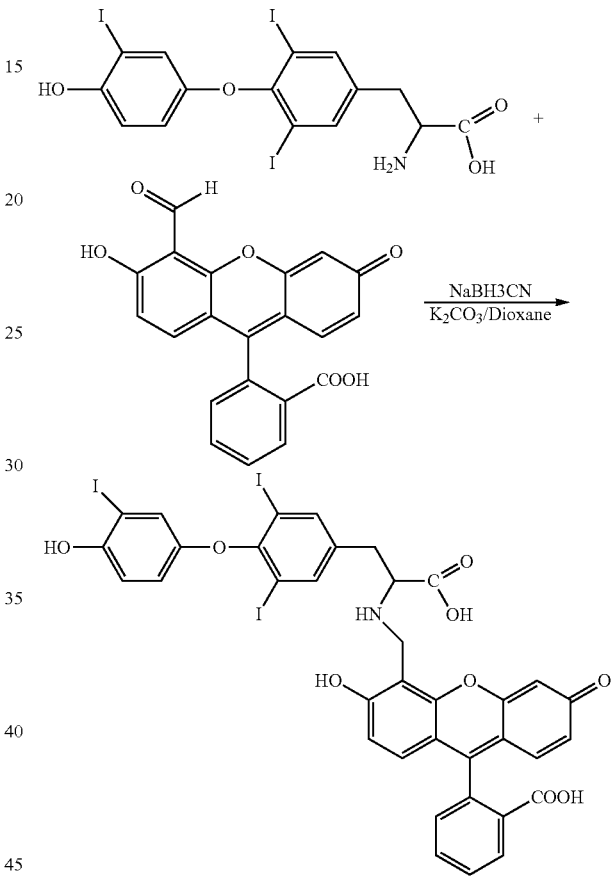

In a 100 mL flask containing a mixture of 40 ml sodium bicarbonate buffer (100 mM at pH 8.0) and 20 mL dioxane was added fluorescein aldehyde (180 mg, 0.5 mmol) and triiodothyroxine (390 mg, 0.6 mmol, commercially available from Sigma Aldrich of St. Louis, MO) and the resulting solution allowed to stir at room temperature for 1 hour. Sodium cyanoborohydride (400 mg, 5 mmol) was then added to the solution and the resulting mixture stirred overnight at room temperature in the dark. The pH of the resulting mixture was then adjusted to pH 5.0 using 1M HCl and the solvents removed by lyophilization.

A flash column having a diameter of 38 mm and a length of 200 mm was prepared using 100 g of C18 reverse phase silica. The column was equilibrated using at least three column volumes of 30% acetonitrile in water containing 0.1% acetic acid. The crude T3-F product was then dissolved in 30% acetonitrile in water containing 0.1% acetic acid, applied to the column, and the column eluted with 30% acetonitrile in water containing 0.1% acetic acid. The eluted fractions were monitored for the presence of T3-F using HPLC (a 4.6 mm x 100 mm XTerrao C18 reverse phase column) equipped with a UV detector operated at 220 nm. The fractions containing T3-F were combined. The combined fractions exhibit a purity of over 95% based on HPLC analysis using UV detection at 220 nm. The combined fractions were lyophilized to provide 350 mg of product. Mass spectrum m/z=996.6(M+H)⁺. The overall yield was about 50%.

T2-F and T4-F were prepared using a similar method. The products were characterized by their mass spectrum. T2-F, m/z=869.8 (M+H)⁺ and T4-F, m/z=1122.1 (M+H)⁺.

Example 9

Preparation of Amoxicillin-Fluorescein (AMO-F)

AMO-F was prepared as depicted in the reaction scheme provided below:

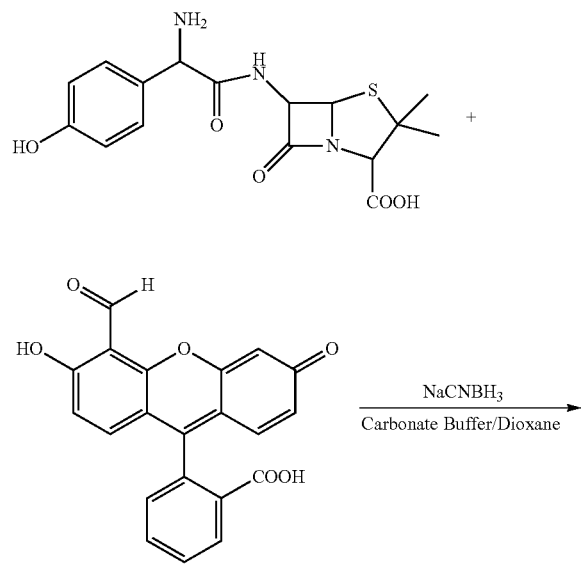

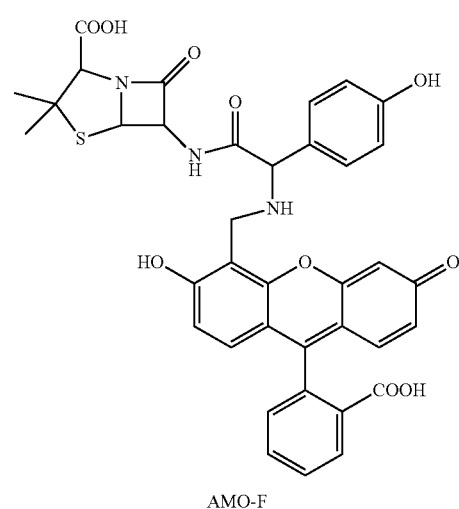

AMO-F

In a 100 mL flask containing a mixture of 40 ml sodium bicarbonate buffer (100 mM at pH 8.0) and 20 ml dioxane was added fluorescein aldehyde (360 mg, 1 mmol) and amoxicillin (547 mg, 1.5 mmol, commercially available from Sigma Aldrich of St. Louis, MO) and the resulting solution cooled to 4° C. using an ice bath and stirred for 40 min. Sodium cyanoborohydride (314 mg, 5 mmol) was then added and the reaction mixture allowed to stir at 4° C. in the dark. After about 2 hours, another portion of sodium cyanoborohydride (125 mg, 2 mmol) was added and the reaction mixture allowed to stir at 4° C. in the dark. The reaction mixture was monitored using HPLC. When the reaction was completed (as indicated by at least 90% product formation), the pH of the reaction mixture was adjusted to a pH to 5.5 with 1 M HCl and the solvents then removed by lyophilization to provide a crude product. One third of the crude product was dissolved in 50 mL of 30% acetonitrile in water containing 0.1% acetic acid to provide a clear yellow solution having a pH of 5.4 and the resulting solution was purified by column chromatography using a C18 reverse phase column eluted with a mobile phase of 30% acetonitrile in water containing 0.1% acetic acid. The fractions containing AMO-F were combined. The combined fractions were analyzed by HPLC equipped with a UV detector operated at 220 nm and showed a purity of over 95% based on absorption at 220 nm. The combined fractions were then lyophilized to provide 61 mg of product. The overall yield of product was about 42%. Mass spectrum m/z=710.1795 (M+H)⁺.

Ampicillin-Fluorescein (AMP-F) was prepared using a similar method. Mass spectrum m/z=694.2 (M+H)⁺.

Example 10

Preparation of AMO-FITC

AMO-FITC was prepared as depicted in the reaction scheme provided below:

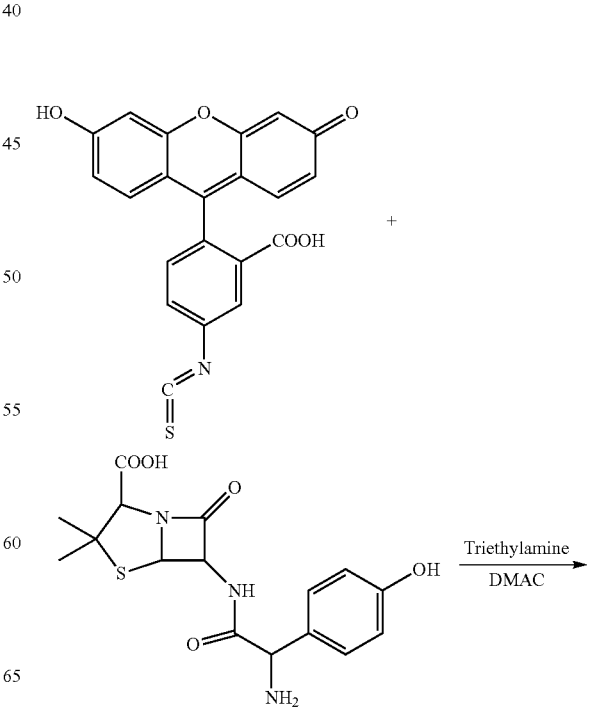

-continued

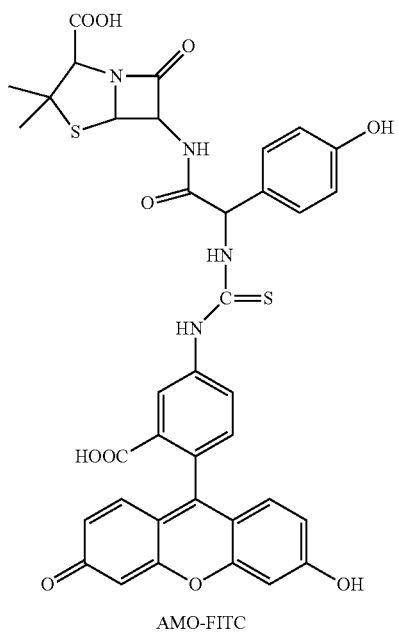

AMO-FITC

Amoxicillin (9.4 mg, 0.026 mmol, commercially available from Sigma), fluorescein isothiocyanate (FITC) (10 mg, 0.026 mmol, commercially available from Thermo Scientific of Waltham, MA), and triethylamine (5.6 μL, 0.75 mmol) were dissolved in DMF (1 mL) and the resulting solution allowed to stir overnight at room temperature. The solution was then diluted with 30% acetonitrile in water containing 0.1% acetic acid and applied to a C18 reverse phase column. The column was eluted with a gradient of 30% to 50% acetonitrile in water containing 0.1% acetic acid. The fractions containing AMO-FITC were combined and the combined fractions lyophilized to provide a yellow powder. Mass spectrum m/z=755.2 (M+H)$^+$.

Example 11

Preparation of Cefotaxime-Fluorescein (CEF-F)

CEF-F was prepared as depicted in the reaction scheme provided below:

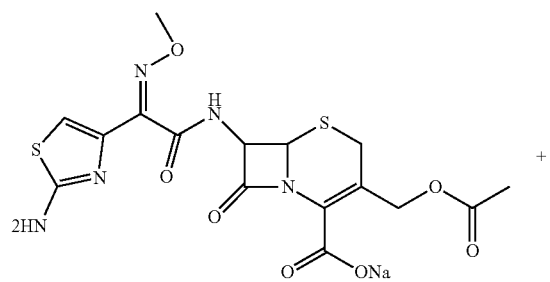

-continued

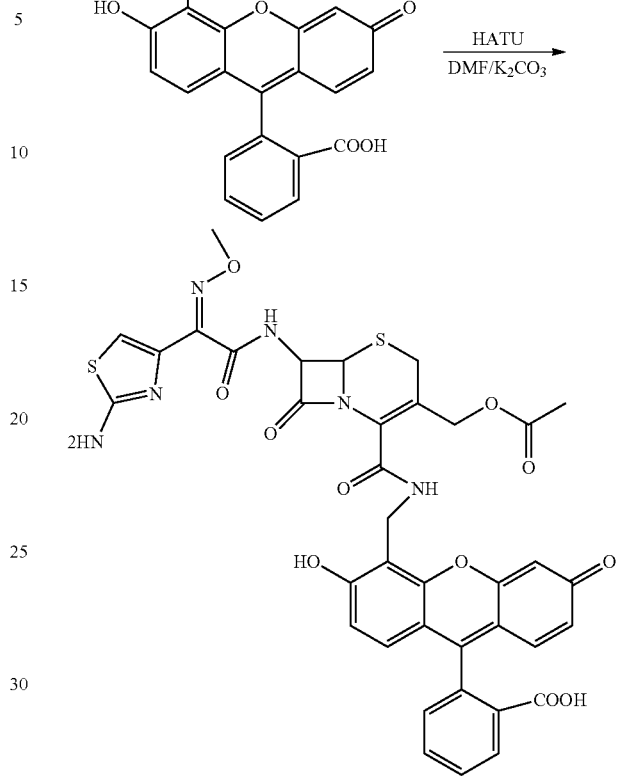

Cefotaxime acid (63 mg, 0.138 mmol, commercially available from LIT Laboratories Inc. of St. Paul, MN), 4'-aminomethyl fluorescein (50 mg, 0.126 mmol, commercially available from AAT Bioquest of Sunyvale, CA), and anhydrous potassium carbonate (52 mg, 0.378 mmol) were dissolved in anhydrous DMF (10 mL) and the resulting solution was stirred at room temperature for 10 min. 2-(1H-7-Azabenzotriazol-1-yl)-1,1,3,3-tetramethylaminium hexafluorophosphate (HATU) (53 mg, 0.15 mmol) was added to the solution and the resulting mixture allowed to stir for 6 hours at room temperature. The solvents were then removed under reduced pressure to provide a residue. The residue was then dissolved in 30% acetonitrile in water containing 0.1% acetic acid and the resulting solution applied to a C18 reverse phase column (100 g) that was eluted with a gradient of 40% to 50% acetonitrile in water containing 0.1% acetic acid. The fractions containing CEF-F product were combined and lyophilized to provide 105 mg of product. Mass spectrum m/z=799.1477 (M+H)$^+$.

Example 12

Preparation of CY3-, CY5-, IRDyeQC1, and BHQ1-Labelled Anti-T4-Mab

Monoclonal anti-T4 antibody (Anti-T4-Mab) (4 mg, commercially available from Meridian Life Sciences Inc. (Biodesign) of Memphis, TN) in PBS (1 mL) was mixed with 0.5 mg of Cy3-NHS (i.e., the N-hydroxysuccinimide ester of Cy3, commercially available from GE Healthcare of Chicago, IL), Cy5-NHS (the N-hydroxysuccinimide ester of Cy5, commercially available from GE Healthcare of Chicago, IL), IRDyeQC1-NHS (the N-hydroxysuccinimide ester of IRDyeQC1, commercially available from Li-Cor Biosciences of Lincoln, NE), or BHQ1-NHS (the N-hydroxysuccinimide ester of BHQ1, commercially available from LGC Biossearch Technologies of Petaluma, CA) in DMSO (0.25 mL) to provide a solution. The resulting solution was stirred overnight at 4° C. The quencher-labeled antibody was then purified by column chromatography using a Sephadex G-25 column eluted with a PBS mobile phase. The protein concentration was determined using a BCA kit (commercially available from Thermo Scientific of Waltham, MA).

Example 13

Preparation of T3-FITC

T3-FITC was prepared as depicted in the reaction scheme provided below:

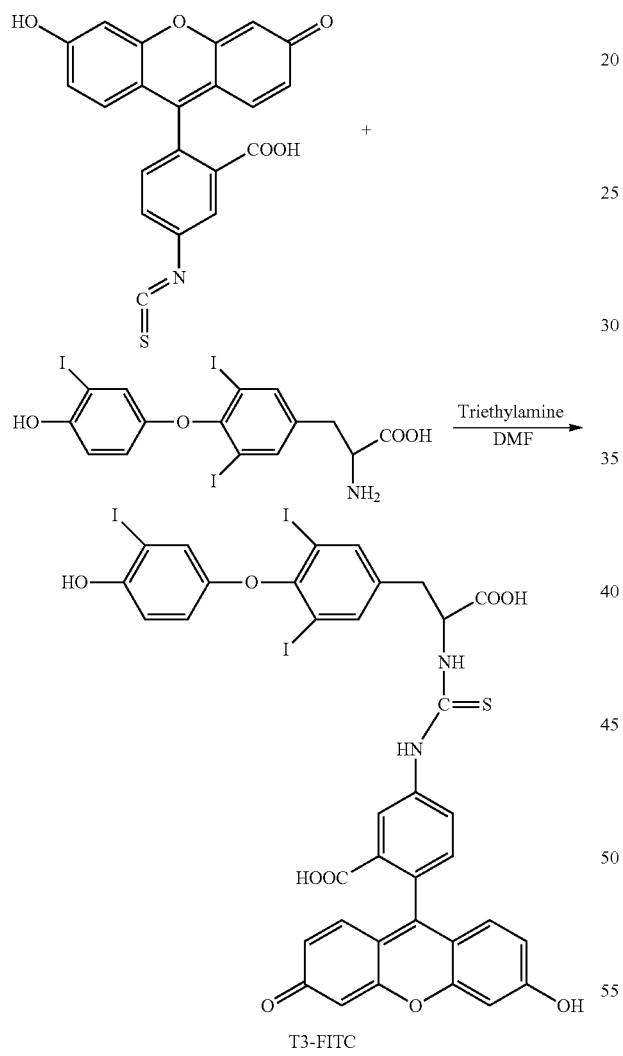

T3-FITC

Triiodothyroxine (16.7 mg, 0.025 mmol), fluorescein isothiocyanate (FITC, 10 mg, 0.026 mmol, commercially available from Thermo Scientific of Waltham, MA), and triethylamine (5.6 µL, 0.75 mmol) were dissolved in DMF (1 mL) and the resulting solution allowed to stir overnight at room temperature. The solution was then diluted with 30% acetonitrile in water containing 0.1% acetic acid and the resulting solution purified by column chromatography using a C18 reverse phase column eluted with a gradient of 30% to 70% acetonitrile in water containing 0.1% acetic acid. The fractions containing T3-FITC were combined and lyophilized to provide a yellow powder. Mass spectrum m/z=1040.8295 (M+H)$^+$.

Example 14

Preparation of Melamine-ED-F and Melamine-OG

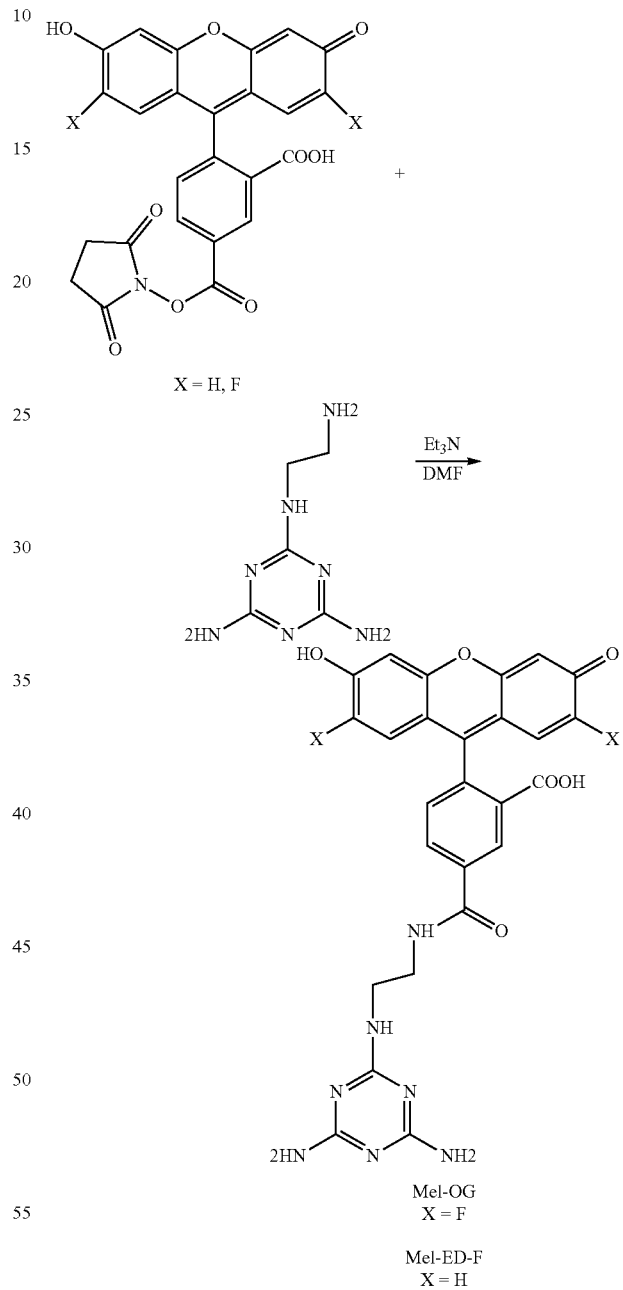

Mel-OG
X = F

Mel-ED-F
X = H 2-chloro-4, 6-diamino-1,3,5-triazine (36 mg, 0.24 mmol, commercially available from Sigma Aldrich of St. Louis, MO) and ethylenediamine (30 mg, 0.5 mmol) were dissolved in anhydrous DMSO (2 mL), anhydrous potassium carbonate (82 mg, 0.6 mmol) was added, and the resulting suspension was heated to 95° C. and kept under an argon atmosphere at that temperature for overnight. The solvent was then removed under reduced pressure to provide a residue. The resulting residue was purified by column chromatography using a C18 reverse phase column (10 g) eluted with 50% acetonitrile in water to provide melamine-ethylamine.

Melamine-ethylamine (0.5 mg, 0.003 mmol) and Oregon Green-NHS ester (1 mg, 0.002 mmol, commercially available from Invitrogen Life Technologies of Carlsbad, CA) or 5-carboxyfluorescein succinimidyl ester (1 mg, 0.002 mmol, commercially available from Thermo Scientific of Waltham, MA) was dissolved in DMF (0.5 mL) containing triethylamine (8 μL) and incubated at room temperature for 6 hours. The resulting solution was diluted with 30% acetonitrile in water containing 1% acetic acid and purified by column chromatography using a C18 reverse phase column to provide melamine-ED-F or melamine-OG. Melamine-ED-F, m/z=528.2 (M+H)$^+$; Melamine-OG, m/z=564.1 (M+H)$^+$.

Example 15

Fluorescence of Mixtures of Various Fluorescent Tracers and Anti-Melamine Antibody Various substituted fluorescent tracers wherein melamine is conjugated to fluorescein were dissolved in DMSO (1 mM) and diluted in phosphate buffered saline (PBS) (pH=7.3) to provide a melamine tracer solution (1.2 μM). The following melamine tracers were used:

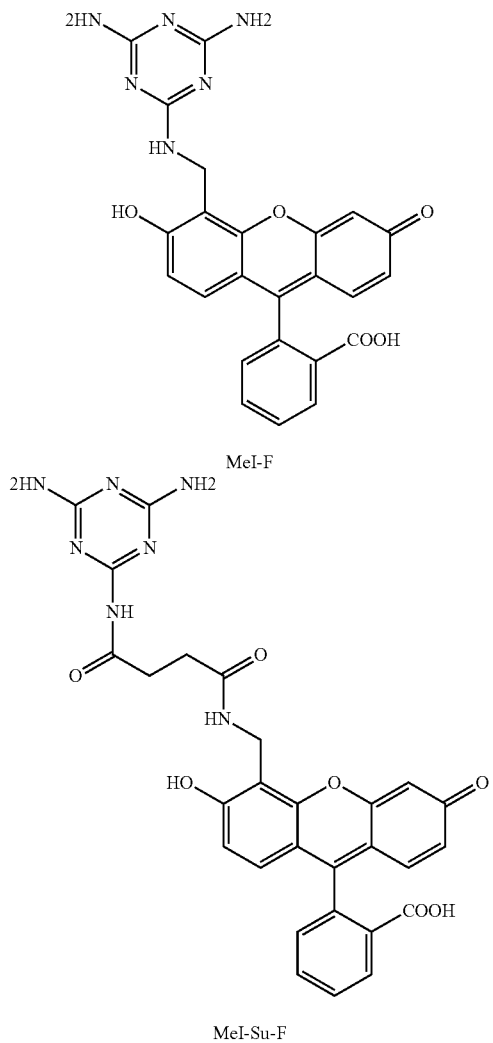

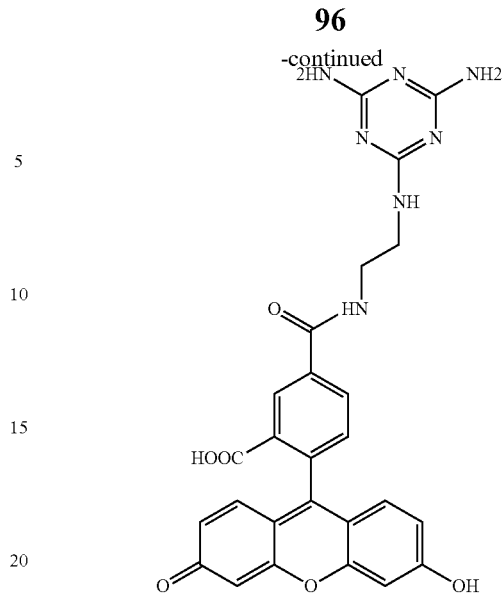

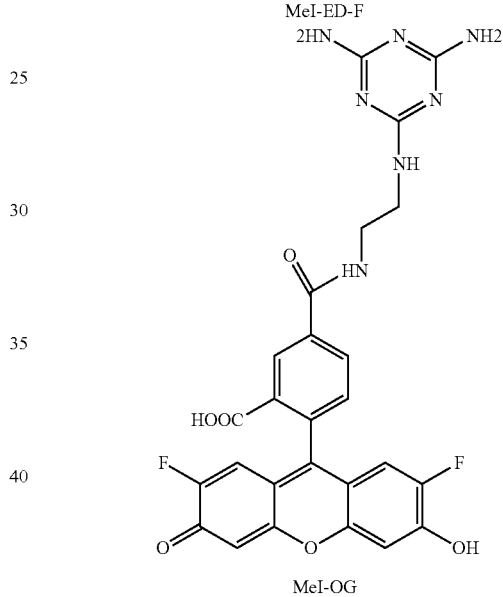

Polyclonal anti-melamine antibody (Anti-Mel-Ab, 4.65 mg/ml, commercially available from Meridian Life Sciences Inc. (Biodesign) of Memphis, TN) was diluted in PBS and serially diluted to provide Anti-Mel-Ab solutions having Anti-Mel-Ab concentrations ranging from 0 to 300 nM. The melamine tracer solutions (5 μL) were mixed with each Anti-Mel-Ab solution (195 μl) in a 96 well black assay plate with non-binding surface (commercially available from Corning Inc. of Corning, NY) to provide solutions having different molar ratios of the Anti-Mel-Ab to the melamine tracer. The concentration of the melamine tracer was 30 nM. The plate was gently shaken for 30 min at room temperature. The fluorescence intensities of each solution was then measured using a fluorescence plate reader (Synergy 4 Microplate Reader, commercially available from BioTek Instruments, Inc. of Winooski, VT) using an excitation wavelength of 490 nm and reading the emission at 520 nm. The results are shown in FIG. 3.

Figure 3:
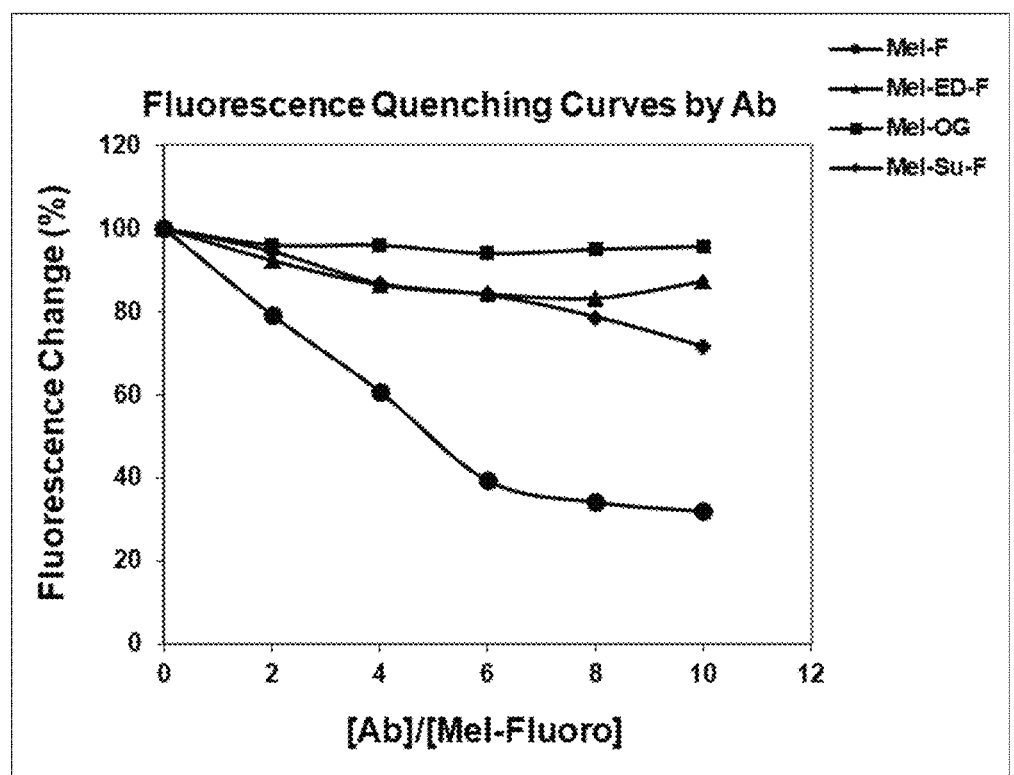
FIG. 3 is a plot of percent change in fluorescence as a function the ratio of [Anti-Mel-Ab]/[Mel-Tracer] for various Mel-Tracers as described in Example 15.

FIG. 3 shows that the different melamine-fluorescein conjugates quench fluorescence to a different extent and that the amount of quenching is a function of the molar ratio of Anti-Mel-Ab to the melamine tracer. The higher the ratio of Anti-Mel-Ab to the melamine tracer, the greater the amount of quenching. The results also demonstrate that, compared to the other melamine tracers, the 4'-substitued tracer (i.e., Mel-F) exhibited the highest degree of quenching and reached a saturation point when the molar ratio of Anti-Mel-Ab to the melamine tracer was 6:1. These results show that quenching efficiency (i.e., the percentage decrease in fluorescence at an fluorescent antibody: antigen ratio of 1:1 compared to fluorescence in the absence of the antibody) depends on the position where the ligand is attached to the fluorescein molecule with 4'-substituted tracers exhibiting better quenching efficiency that 5-substituted tracers. The results also demonstrate that quenching efficiency is higher when the linker is shorter.

Unless otherwise indicated, an excitation wavelength of 490 nm and reading the emission at 520 nm were used throughout the examples. Unless otherwise indicated, all results are the average of triplicate measurements.

Example 16

Figure 4:
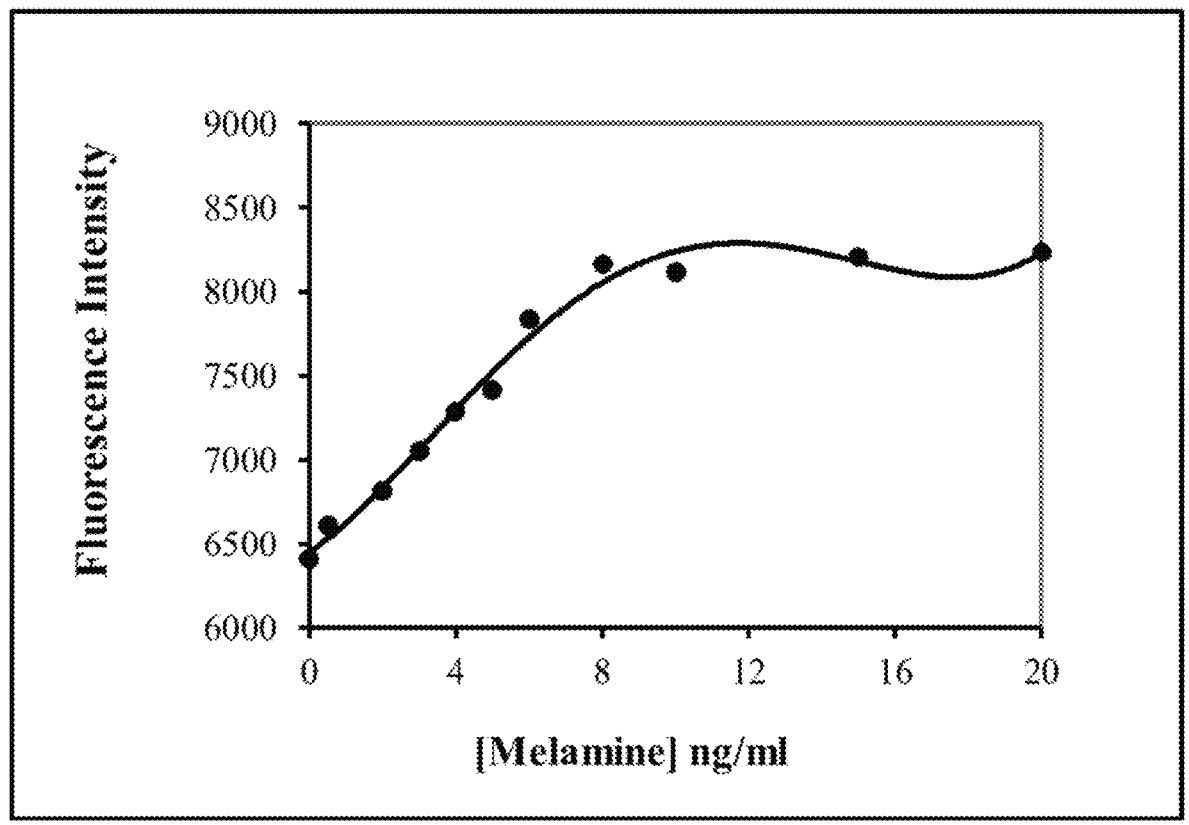
FIG. 4 is a plot of fluorescent intensity vs melamine concentration when melamine is added to a solution of Mel-F and Anti-Mel-Ab as described in Example 16.

Fluorescence of Solutions of Mel-F and Anti-Mel-Ab as a Function of Melamine Concentration Aliquots of Mel-F in PBS (1.2 µM, 54 µL) and Anti-Mel-Ab solution (6 µM, 5 µL) were added to a 96 well black assay plate and incubated for 30 min at room temperature with gentle shaking. Melamine standard solutions were prepared in PBS at concentrations ranging from 0 to 20 ng/ml. Each melamine standard solution was then added to a solution of Mel-F and Anti-Mel-Ab in the 96 well assay plate. The plate was then incubated for 1 hour at room temperature and the fluorescence intensities measured. The results are shown in FIG. 4 which depicts the recovery of fluorescence as a function of melamine concentration. In FIG. 4, the concentration of Mel-F is 30 nM and the concentration of Anti-Mel-Ab is 150 nM. The result indicate that a dynamic range of melamine is from about 0 to 8 ng/mL in PBS solution.

Example 17

Figure 5:
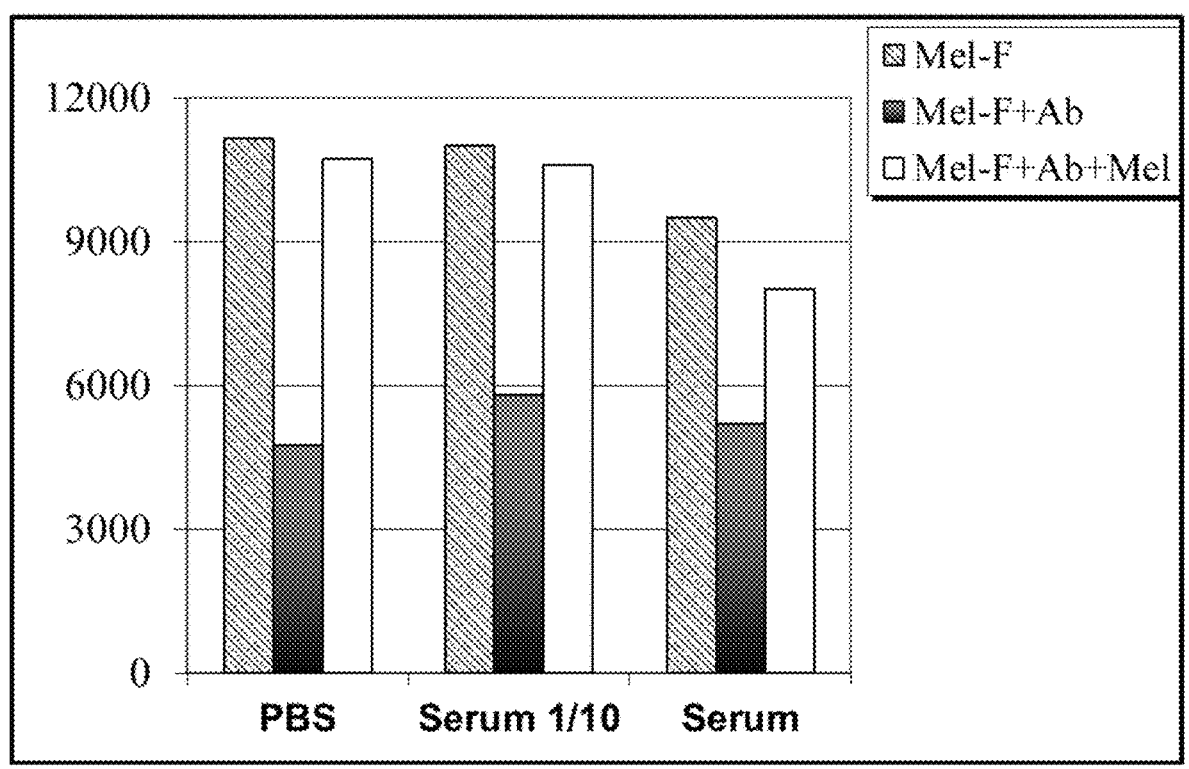
FIG. 5 is a plot of fluorescence intensity for solutions Mel-F, Mel-F+Anti-Mel-AB, and Mel-F+Anti-Mel-AB+Mel in various liquids as described in Example 17.

Fluorescence of Serum Solutions of Mel-F and Anti-Mel-Ab in the Presence of and Absence of Melamine Untreated canine serum was adjusted to a pH of 7.3 using a phosphate buffer and diluted 10 fold with PBS. To a solution of Mel-F in PBS (1 µM, 6 µL) and to a mixture of Mel-F in PBS (1 µM, 6 µL) and Anti-Mel-Ab (1 µM, 6 µL) in the absence of and in the presence of melamine (2 µM, 6 µL) was added PBS, serum, or diluted serum (i.e., serum diluted 1 in 10 with PBS) to provide a final volume of 200 µL. The resulting solutions were incubated at room temperature for 1 hour and the fluorescence intensities then measured. The results are shown in FIG. 5.

These results demonstrate that for each solution the fluorescence of Mel-F was quenched by the Anti-Mel-Ab to about one-half of the original value and that the fluorescence is recovered by adding melamine.

Example 18

Fluorescence of Milk Solutions of Anti-Mel-Ab and Mel-F in the Presence of Melamine Raw milk samples were diluted 10-fold with PBS. Melamine standard solutions in raw milk that had been diluted 10 fold with PBS, having a melamine concentration ranging from 0 to 250 nM, were prepared by serial dilution. To the wells of 96 well black assay plate was added Mel-F in PBS (2 µM, 5 µL) and Anti-Mel-Ab (10 µM, 5 µL). To each well was then added a melamine standard solution (190 µL), the plate was incubated for 1 hour at room temperature, and the fluorescence intensities recorded. The results are shown in FIG. 6.

Figure 6:
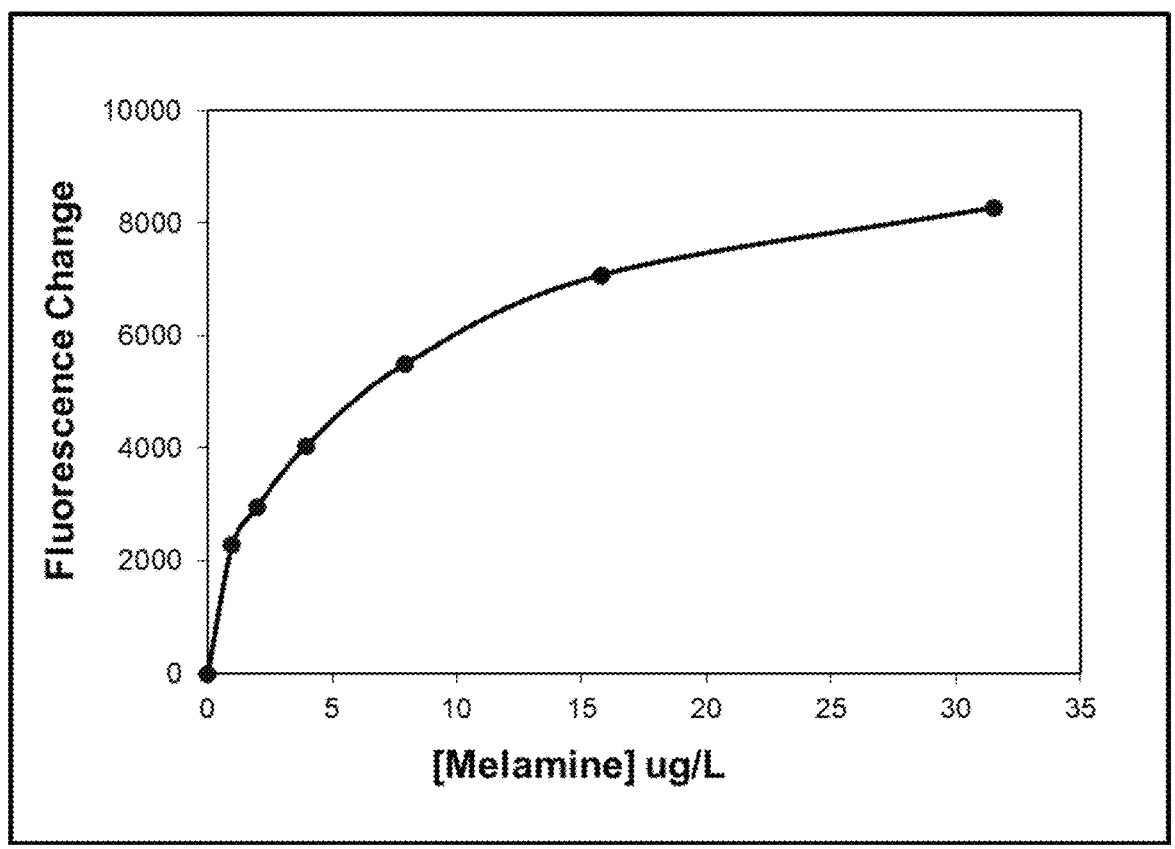
FIG. 6 is a plot of fluorescence of a mixture of Mel and Anti-Mel-Ab to which milk containing melamine has been added as a function of melamine concentration as described in Example 18.

FIG. 6 depicts the fluorescence intensity for solutions (10% raw milk in PBS) of Mel-F (50 nM) in the presence of Anti-Mel-Ab (250 nM) at various concentrations of melamine. The results show that the dynamic range for detecting melamine is from about 0 to 30 µg/L.

Example 19

Fluorescence of Solutions in the Presence of Biotin-F or Biotin-ED and Streptavidin Biotin-F or Biotin-ED (commercially available from Thermo Scientific of Waltham, MA) was dissolved in DMSO to provide a DMSO solution (8.5 µM). The structure of biotin ED is

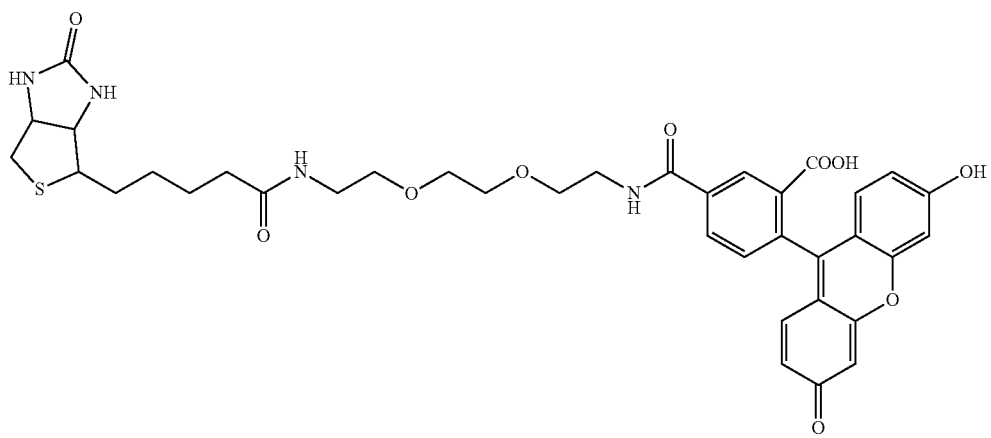

Biotin-ED

The DMSO solution was then diluted with PBS to provide a solution having a Biotin-F or Biotin-ED concentration of 100 nM. 20 µL aliquots of the resulting Biotin-F or Biotin-ED solution in PBS was then added to the wells of a 96 well black assay plate. Solutions of streptavidin in PBS having a streptavidin concentration ranging from 0 to 100 nM were prepared and added (180 µL) to the Biotin-F or Biotin-ED solution in the plate. The plate was incubated for 30 min at room temperature and the fluorescence intensities then recorded. The results are shown in FIG. 7, which shows the percentage change in fluorescence intensity as a function of the molar ratio of streptavidin to the tracer.

Figure 7:
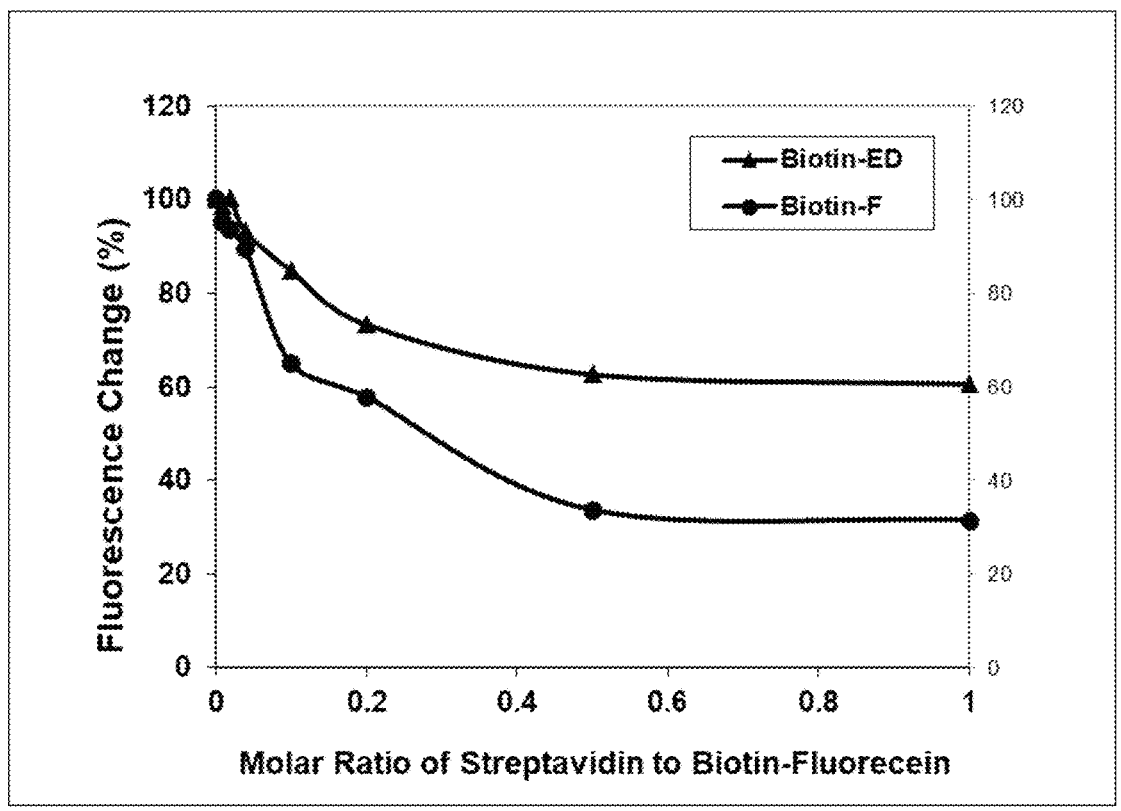
FIG. 7 is a plot of percentage change in fluorescence vs the molar ratio of streptavidin to tracer when streptavidin was added to a solution of Biotin-F and a solution of Bioten-ED as described in Example 19.

The results in FIG. 7 show that the fluorescence of biotin F is quenched more efficiently than the fluorescence of biotin ED. At the saturation point (1:1 molar ratio), the quenching efficiency of biotin-F is 70% higher than that of biotin-ED. The results show that the change in fluorescence for the 4'-substituted fluorescent tracer is greater than for the 5-substituted fluorescent tracer.

Example 20

Fluorescence of Solutions of T3-F and Anti-T4-Mab in the Presence of T4

A mixture of T3-F in PBS (1 µM, 6 µL) and anti-monoclonal anti-thyroxine antibody (anti-T4-Mab (commercially available from Biodesign Inc. of Denver, CO) (1 µM, 6 µL) in the absence of and the presence of L-thyroxine (T4, 2 µM, 6 µL, commercially available from Sigma Aldrich of St. Louis, MO) was added PBS to provide a final volume of 200 µL. The resulting solutions were incubated at room temperature for 1 hour and the fluorescence intensities then measured.

Similar solutions were prepared and the fluorescence measured except that the T3-F was replaced with T3-5-F, T3-E-F and T3-FITC.

The following procedure was used to synthesize T3-5-F:

Preparation of T3-5-Fluorescein (T3-5-F)

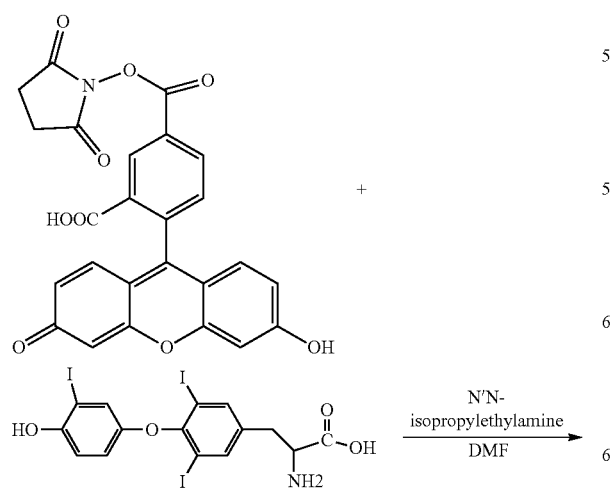

Triiodothyroxine (8.2 mg, 0.013 mmol), 5-carboxylfluorescein N-hydroxysuccinimide ("NETS") (5.9 mg, 0.013 mmol, commercially available from Thermo Scientific of Waltham, MA), and N'N-diisopropylethylamine (6.5 µL, 0.04 mmol) were dissolved in DMF (1 mL) and the resulting solution allowed to stir overnight at room temperature. The solution was purified by column chromatography using a C18 reverse phase column (5 g) eluted with 40% acetonitrile in water with 0.1% acetic acid to provide T3-5-F.

The structure for each tracer is depicted below:

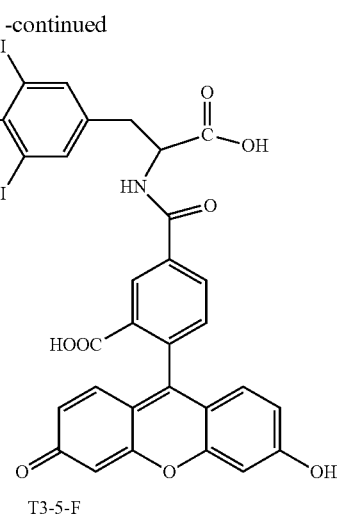

T3-5-F

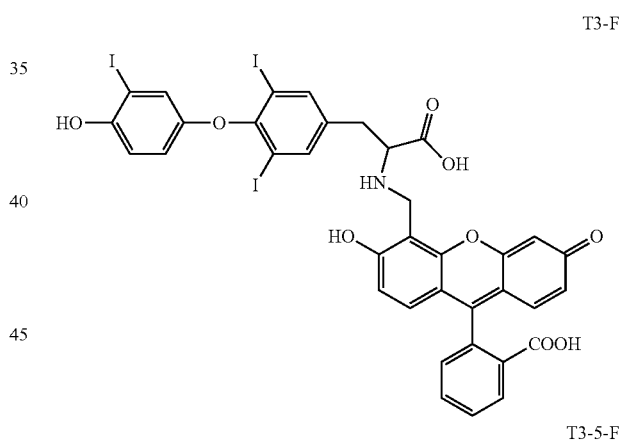

T3-F

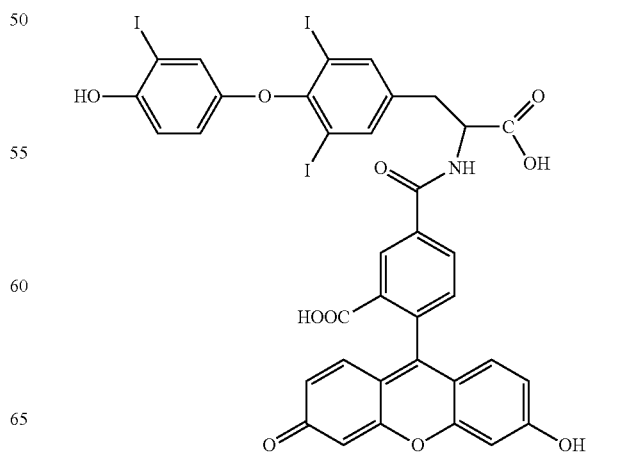

T3-5-F

-continued

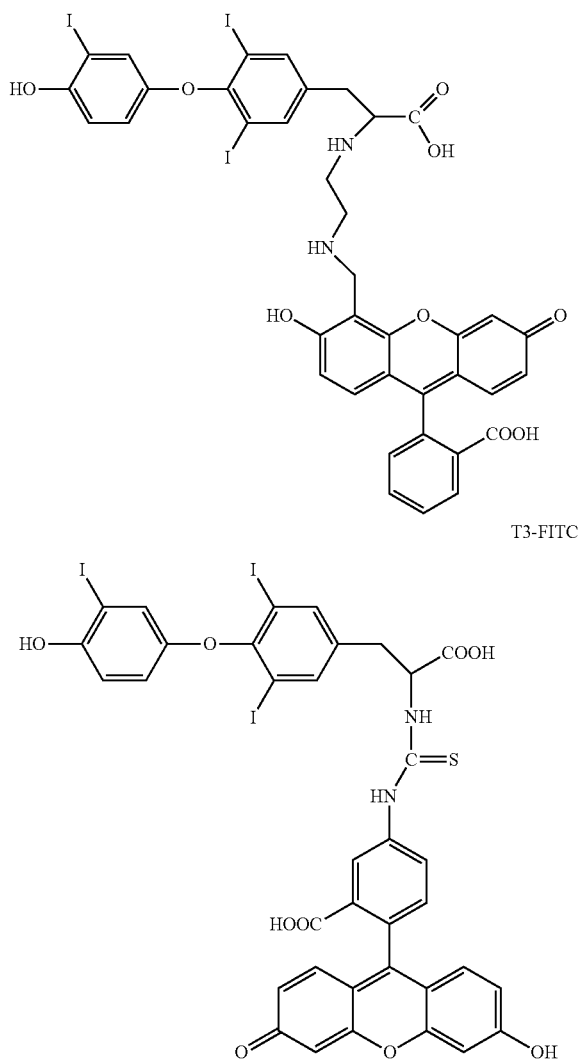

T3-E-F

T3-FITC

Figure 8:
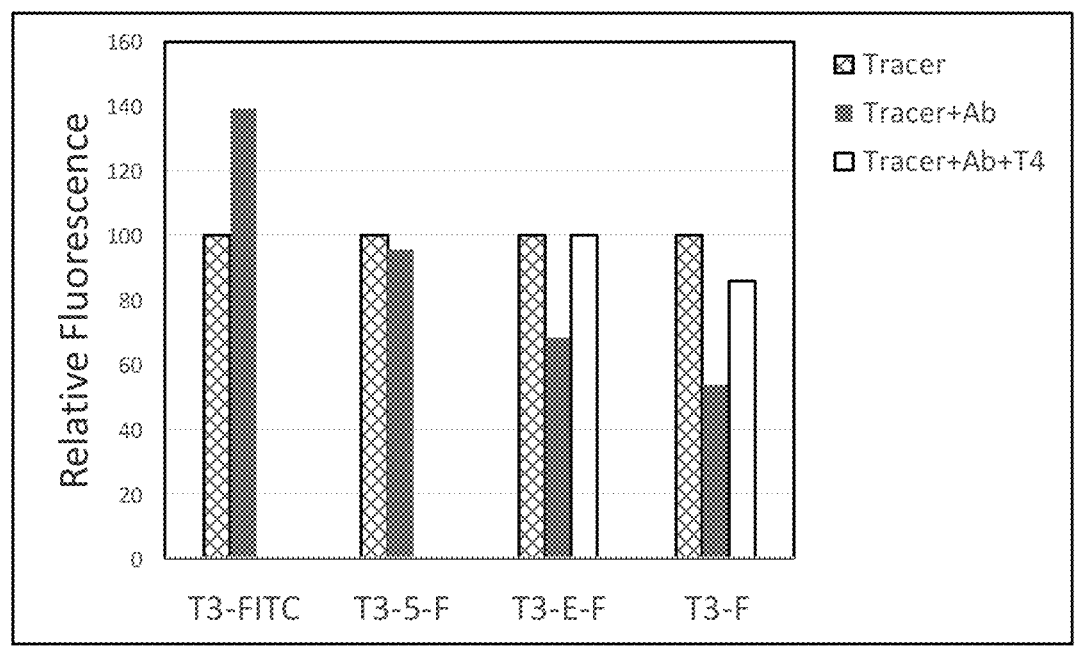
FIG. 8 is a plot of relative fluorescence of solutions of T3-F (conjugate only); T3-F and anti-T4-Mab (conjugate and monoclonal antibody); and T3-F, anti-T4-Mab (conjugate and monoclonal antibody), and T4 as described in Example 20.

The results are shown in FIG. 8. FIG. 8 shows that for both T3-FITC and T3-5-F fluorescence was not quenched by anti-T4-Mab. For T3-E-F and T3-F, fluorescence was quenched by anti-T4-Mab. This shows that quenching is more efficient for a 4'-substituted fluorescent tracer than a 5-substituted fluorescent tracer.

Figure 9:
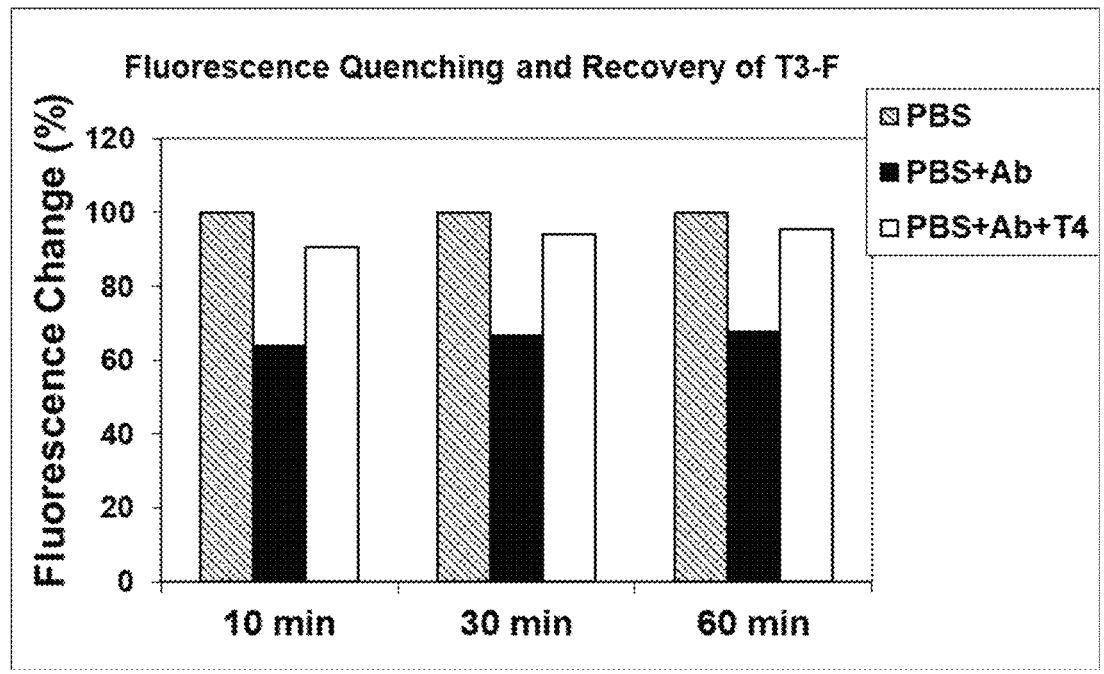
FIG. 9 is a plot of percentage change in fluorescence when T3-F is added to PBS and to PBS+anti-T4-Mab (i.e., AB) and recovery of quenching after addition of T4 (PBS+Ab+T4) as a function of time as described in Example 20.

FIG. 9 depicts the amount of quenching when T3-F is added to anti-T4-Mab and the recovery of quenching after addition of T4 as a function of time. The results show that a stable fluorescence signal is obtained within 10 minutes.

Example 21

T4 Dose Response in PBS

A mixture of T3-F in PBS (1.0 µM, 8 µL) and anti-T4-Mab in PBS (1 µM, 8 µL) were incubated at room temperature for 30 min in the wells of a 96 well black assay plate. A series of T4 standard solutions having T4 concentrations ranging from 0 to 32 µg/dL (184 µL) were then added to the mixtures of T3-F and anti-T4 Mab in PBS. The plate was then incubated for 30 min at room temperature and the fluorescence intensities recorded. The results are shown in FIG. 10.

Figure 10:
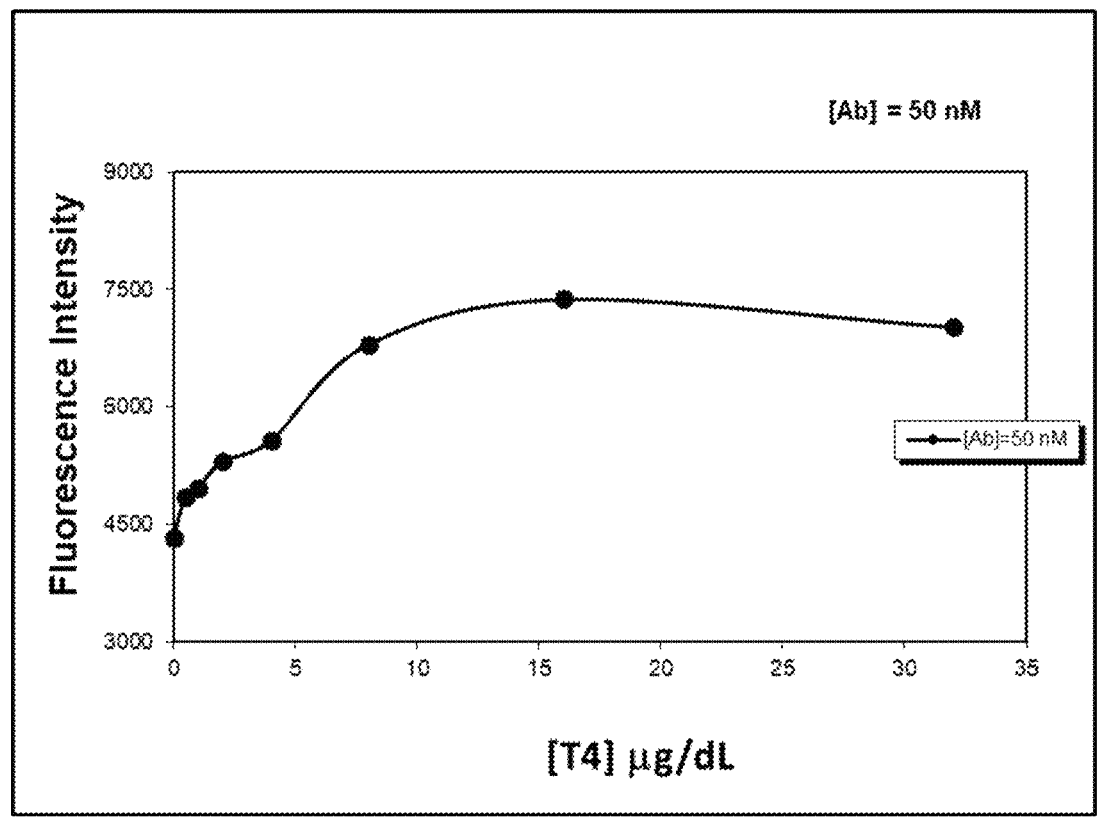
FIG. 10 is a plot of fluorescence intensity vs T4 concentration when various concentration of T4 were added to a solution of T3-F and anti-T4-Mab as described in Example 21.

FIG. 10 shows that when T4 is added to a solution of T3-F (50 nM) and anti-T4-Mab (50 nM) that fluorescence is recovered. The results show the dynamic range for T4 detection in PBS ranges from about 0 to 15 µg/dL.

Example 22

Fluorescence of Solutions of T3-F and Anti-T4-Mab in the Presence of T4 After Lyophilization T3-F (1.7 mg) was dissolved in 0.85 ml DMSO to provide a stock solution (2 mM). The T3-F stock solution was then diluted in PBS to provide a 1 µM working solution that was separated into two vials (1 mL each). To the first vial was added PBS (9 mL) and to the second vial was added PBS (8.9 mL) plus anti-T4 Mab (15 µM, 0.1 mL). The vials were mixed well and incubated for 30 min at room temperature. The fluorescence intensities for each solution (200 µL) was determined. Aliquots of each solution (200 µL) were then placed into wells of a 96 well black assay plate and lyophilized to dryness. To the dried residues was added 200 µL PBS, horse serum that had been treated with charcoal (i.e., the serum was "charcoal stripped" by dialyzing the serum in PBS buffer containing charcoal for at least three buffer changes to remove small molecules from the serum), or horse serum that had been treated with charcoal containing T4 (10 µg/dL) and the plate incubated for 30 min at room temperature. Fluorescence intensities were then recorded again. The results are shown in FIG. 11.

Figure 11:
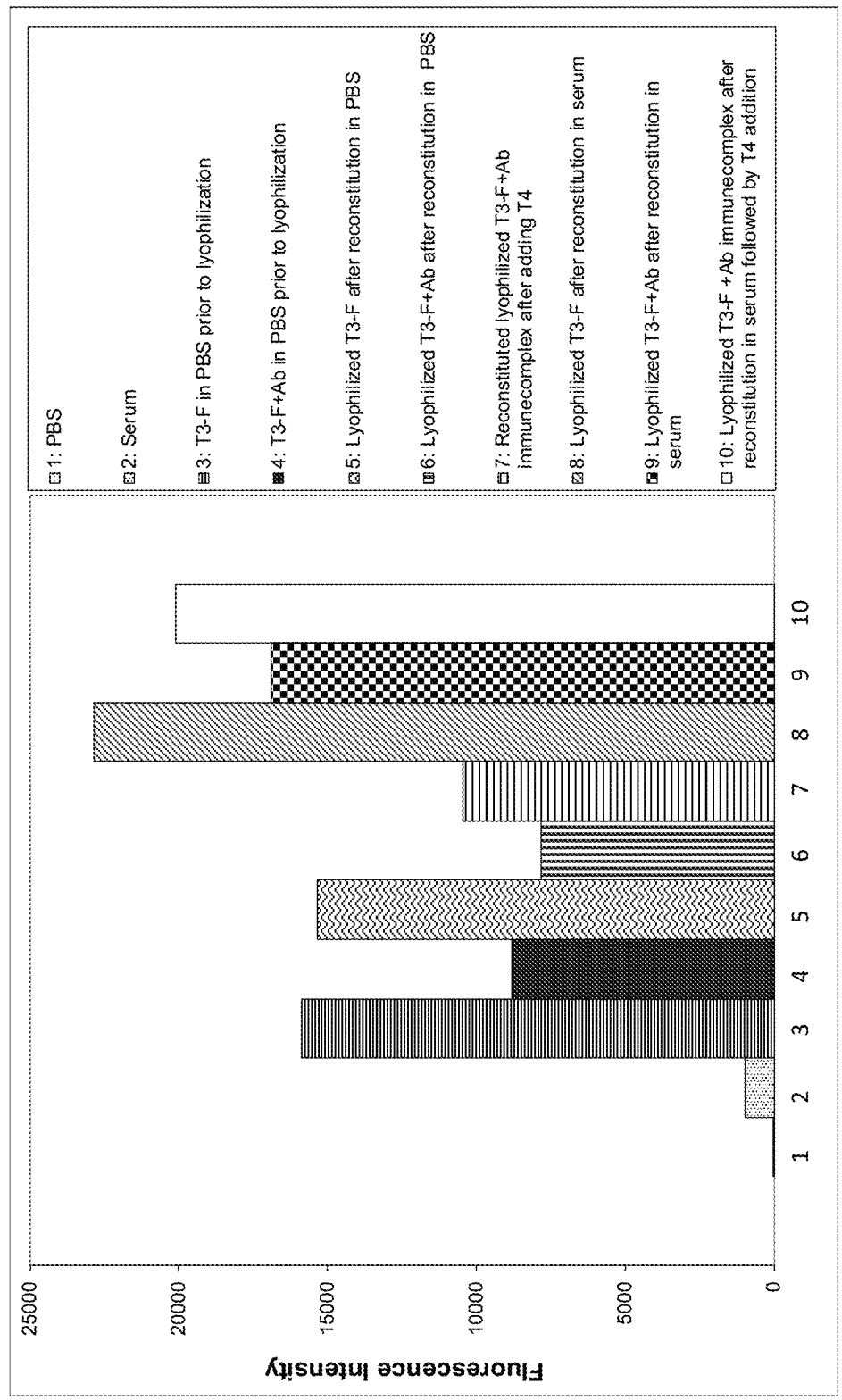
FIG. 11 is a plot of fluorescent intensity for various solutions of T3-F or T3-F and anti-T4-Mab before and after being lyophilized to dryness as described in Example 22.

FIG. 11 shows that the assay is effective even when the T3-F and/or the anti-T4-Mab has been lyophilized.

Example 23

Fluorescence of Mixtures of T4-F and Ab-Cy5 in the Presence of T4

T4-F was dissolved in DMSO (1 mM) and diluted with PBS to provide a stock solution (4 µM). A series of PBS solutions of Cy5 conjugated antibody (Ab-Cy5, made as in Example 12) having Ab-Cy5 concentrations ranging from 0 to 400 nM were prepared by serial dilution. In the wells of a 96 well black assay plate was combined T4-F in PBS (5 µL) and a serially diluted Ab-Cy5 solution (95 µL) and the plate shaken for 30 min at room temperature. Fluorescence intensities were measured using an excitation wavelength of 490 nm and an emission wavelength of 520 nm. FIGS. 12A and B shows that the fluorescence of T4-F is quenched in the presence of Ab-Cy5 (quenching efficiency about 70% at a ratio of T4-F: Ab-Cy5 of about 1:1). Cy5 alone (i.e., not conjugated to Anti-T4-Mab) did not quench fluorescence.

For experiments to demonstrate that fluorescence can be recovered in the presence of T4, aliquots of mixture of T4-F in PBS (5 µL, 4 µM) and Ab-Cy5 solution (5 µl, 8 µM) were added to the wells of a 96 well black assay plate. To each well was then added 90 µL of a T4 solution in PBS (0, 1, 2, 4, 6, 8, 10, 12 µg/dL). The resulting 100 µL solutions were incubated for 30 min and the fluorescence measured. The results are depicted in FIG. 13.

FIG. 13A shows that fluorescence increases when T4 is added to a solution of T4-F and Ab-Cy5 (Ab-Cy5: T4-F about 2:1) and that the increase in fluorescence is proportional to the amount of T4 that is added. The dynamic range is about 0 to 12 µg/dL. FIG. 13B depicts percentage fluorescence recovery as a function of T4-F concentration.

Example 24

Fluorescence of Mixtures of T3-F or T4-F and Ab-Cy3 in the Presence of T4

To horse serum that had been treated with charcoal (50 mL) was added 8-amino-napthalenesulfonic acid (ANS) to provide an ANS concentration of 0.5 mM and the pH adjusted to 7.3 with sodium hydroxide. A series of T4 standard solutions in PBS or serum were prepared having a concentration ranging from 0 to 64 µg/dL by serial dilution. In a 96 well black assay plate, each T4 standard (in PBS or serum, 80 µL) was added to a mixture of T3-F (or T4-F) in PBS (4 µM, 5 µL) and anti-T4-Mab conjugated to Cy3 (Ab-Cy3, prepared as described in Example 12) in PBS (4 µM, 5 µL). The resulting solutions were incubated at room temperature for 30 min and fluorescence intensities then measured. The results are shown in FIG. 14.

Figure 14A:
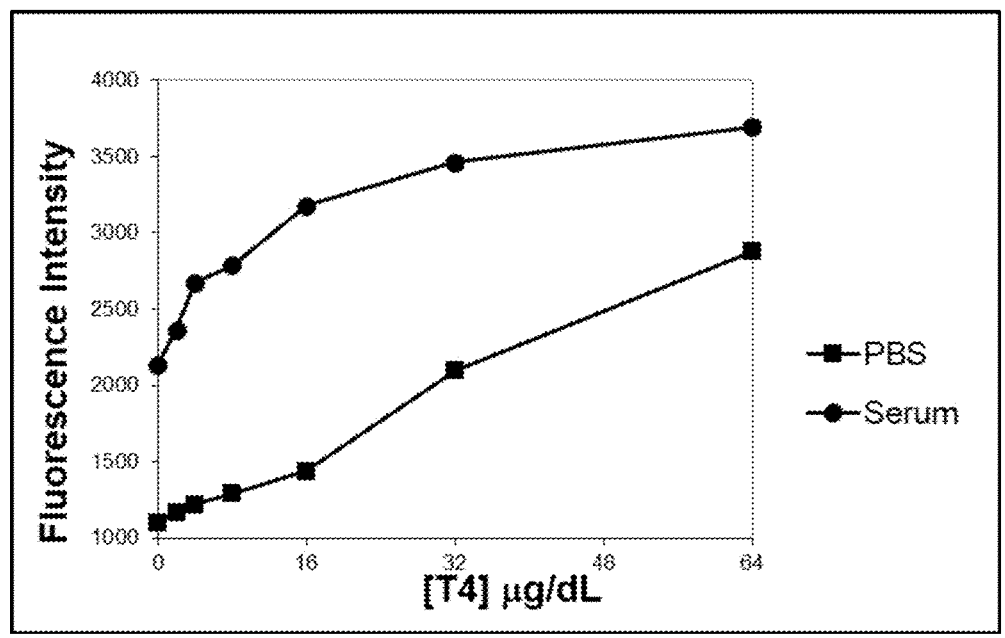
FIG. 14A is a plot of fluorescent intensity of various solutions containing T3-F and Ab-Cy3 to which T4 has been added vs the T4 concentration as described in Example 24.

FIG. 14A shows the fluorescence intensity as a function of T4 concentration when T4 is added to a solution of T3-F (200 nM) and Ab-Cy3 (200 nM) in PBS and in serum. The results show that the dynamic range for T4 detection in PBS and serum is from about 0 to 64 µg/L.

Figure 14B:
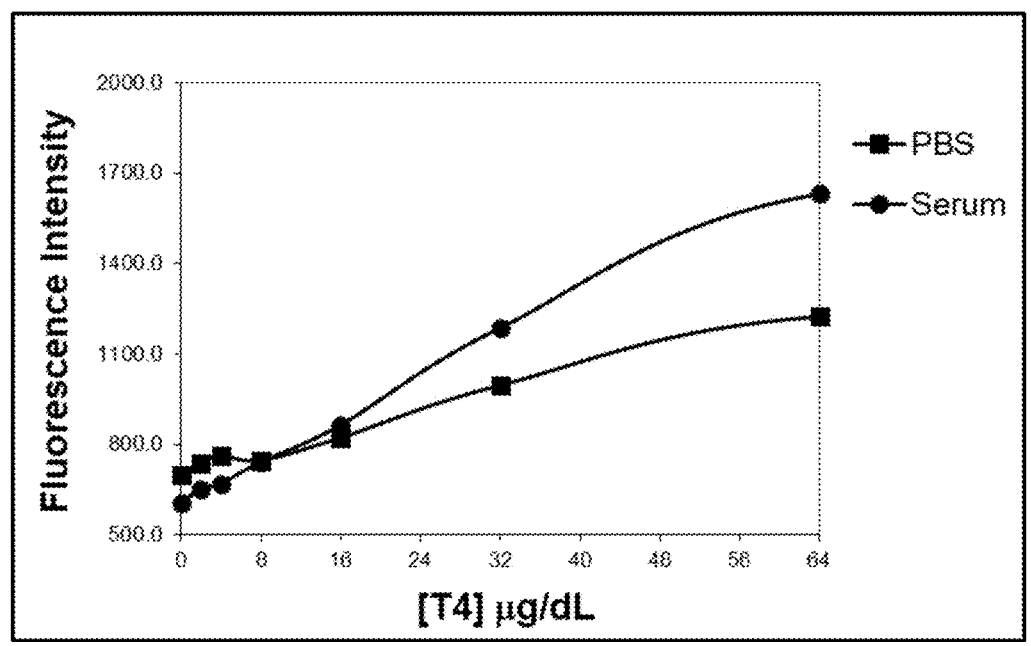
FIG. 14B is a plot of fluorescent intensity of various solutions containing T4-F and Ab-Cy3 to which T4 has been added vs the T4 concentration as described in Example 24.

FIG. 14B shows the fluorescence intensity as a function of T4 concentration when T4 is added to a solution of T4-F (200 nM) and Ab-Cy3 (200 nM) in PBS and in serum. The results show that the dynamic range for T4 detection in PBS and serum is from about 0 to 64 µg/L.

Figure 14C:
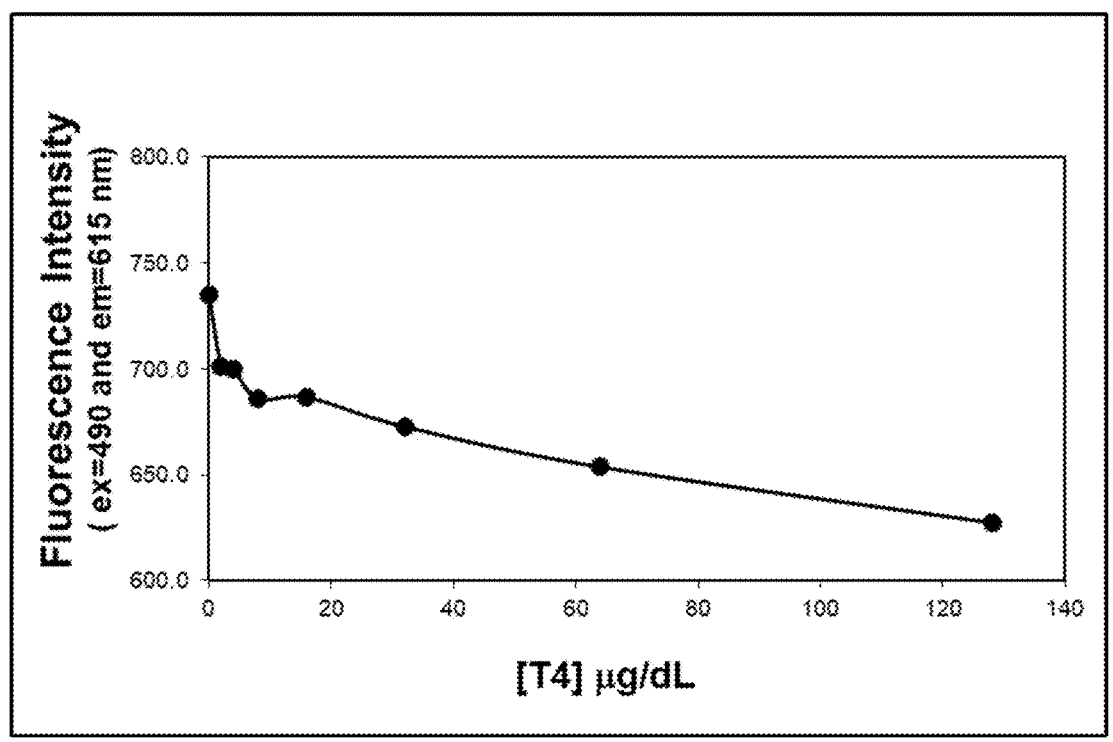
FIG. 14C is a plot of fluorescent intensity of various solutions containing T4-F and Ab-Cy3 to which T4 has been added vs the T4 concentration when the solution is excited at 490 nm and emission measured at 615 nm as described in Example 24.

FIG. 14C shows the fluorescence intensity as a function of T4 concentration when T4 is added to a solution of T4-F (200 nM) and Ab-Cy3 (200 nM) in PBS when the sample is excited at 490 nm and the emission measured at 615 nm. This decrease in emission is attributed to loss of the fluorescence resonance energy transfer (FRET). FRET involves energy transfer between a donor dye in an excited state, to an acceptor dye through nonradiative means. In this instance, excitation of the donor (T4-F) at 490 nm led to efficient energy transfer to the acceptor dye (Ab-Cy3), resulting in emission at 615 nm. The FRET process is highly distance dependent and only occurs when Ab-Cy3 is bound to T4-F. Upon addition of T4, dissociation of the Ab-Cy3 bound to T4-F leads to a decrease in FRET efficiency due to increased distance between the donor (T4-F) and acceptor (Ab-Cy3).

Example 25

Figure 15:
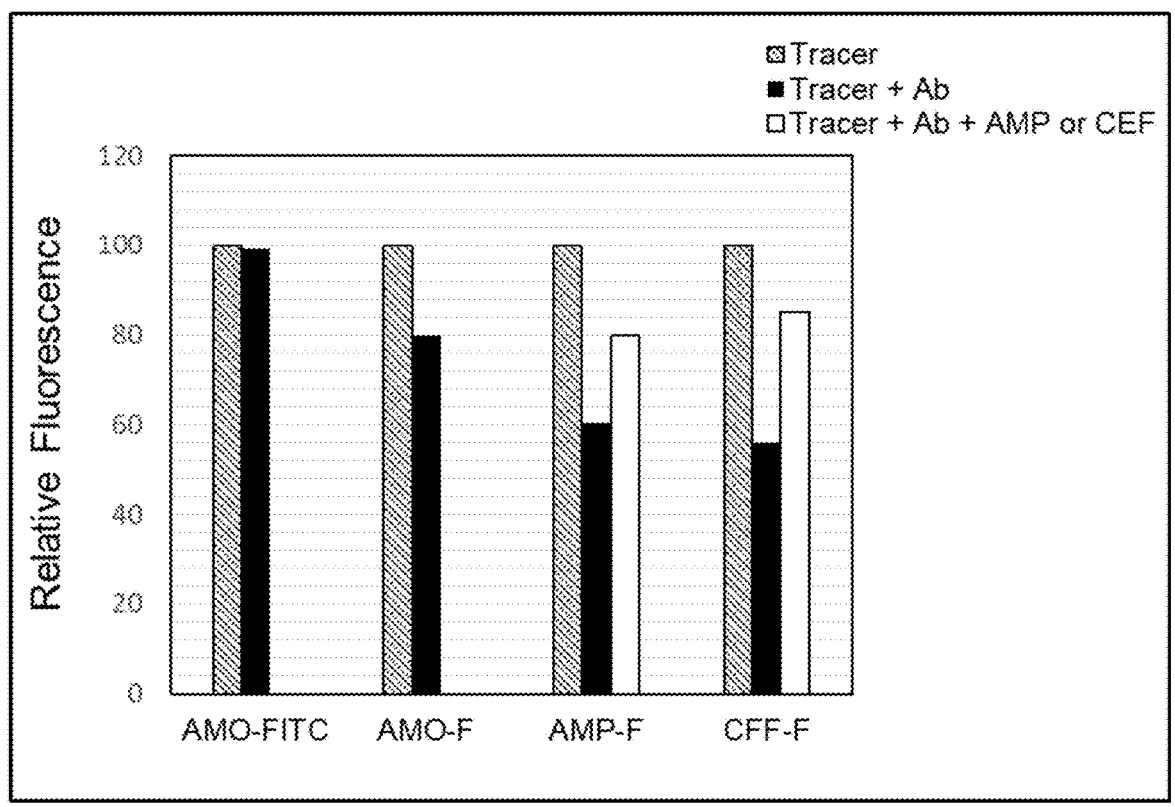
FIG. 15 is a plot of percentage change in fluorescence of solutions of various beta-lactam antibiotics linked to a fluorescent tracer; solutions of the tracers and an antibody (i.e., Ab); and solutions of the tracers, an antibody, and ampicillin or cefotaxime as described in Example 25.

Fluorescence of Mixtures of Beta Lactam Antibiotics Conjugated to Fluorescein and Antibody in the Presence of Free Antibiotic Beta lactam antibiotics conjugated to fluorescein (i.e., AMO-FITC, AMO-F, AMP-F, and CEF-F) in PBS (400 nM, 100 µL) were mixed with either anti-penicillin or anti-cefotaxime polyclonal antibody (400 nM, 100 µL, commercially available from Novus Biologicals, LLC of Centennial, CO) in the absence of and in the presence of free beta-lactam antibiotic (ampicillin (400 nM) was added to AMP-F and cefotaxime (400 nM) was added to CEF-F) in a 96 well black assay plate. The solutions had a concentration of tracer and antibody of 200 nM. The solutions were incubated at room temperature for 5 min and the fluorescence intensity measured. The results are shown in FIG. 15.

These results show that the fluorescence of AMO-FITC was not quenched by adding anti-penicillin antibody while the fluorescence of AMO-F and AMP-F were quenched by the same antibody. The results also show that adding ampicillin to the solution of anti-penicillin antibody and AMP-F causes the fluorescence intensity to increase (i.e., be recovered). Similarly, the fluorescence of CEF-F is quenched by anti-cefotaxime antibody and adding cefotaxime to the solution of anti-cefotaxime antibody and CEF-F causes the fluorescence intensity to increase (i.e., be recovered).

Example 26

Fluorescence of Mixtures of SDM-F or SDM-Su-F and Anti-Sulfadimethoxine

Figure 16:
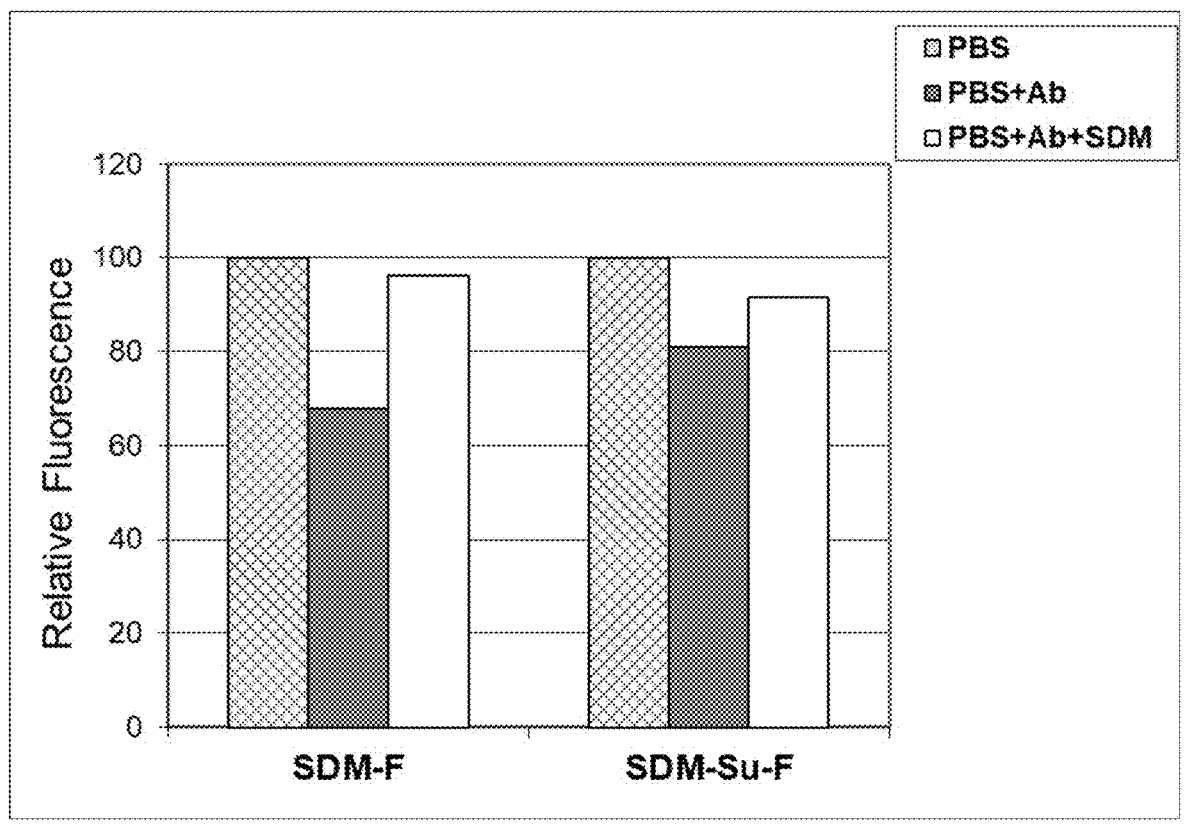
FIG. 16 is a plot of percentage relative fluorescence of solutions of SDM-F or SDM-Su-F; solutions SDM-F or SDM-Su-F and anti-sulfadimethoxine monoclonal antibody (Ab); and solutions of SDM-F or SDM-Su-F, Ab, and SDM as described in Example 26.

Monoclonal Antibody in the Presence of Sulfadimethoxine
SDM-F or SDM-Su-F in PBS (400 nM, 100 µL) was mixed with anti-sulfadimethoxine monoclonal antibody (400 nM, 100 µL, commercially available from Genway Biotech of San Diego, CA) in the absence of and the presence of sulfadimethoxine (SDM) (400 nM). The resulting solutions were incubated at room temperature for 5 min and the fluorescence intensity then measured. The results are shown in FIG. 16.

These results show that the fluorescence of SDM-F and SDM-Su-F are quenched when they are combined with anti-sulfadimethoxine monoclonal antibody. The greater amount of quenching for SDM-F compared to SDM-Su-F indicates that the length of the linker influences quenching. The results also show that adding SDM to the solution of anti-sulfadimethoxine-antibody and SDM-F or SDM-Su-F causes the fluorescence intensity to increase.

Example 27

Fluorescence Quenching of T3-F by Anti-T4-Mab

T3-F was dissolved in DMSO (1 mM) and diluted with PBS to provide a stock solution (4 µM). Monoclonal anti-T4 antibody (Anti-T4-Mab, commercially available from Meridian Life Sciences Inc. (Biodesign) of Memphis, TN) (4.65 mg/mL) was serially diluted in PBS buffer to provide solutions having an Anti-T4-Mab concentration ranging from 0 to 1000 nM. In a 96 well black assay plate containing the serially diluted Anti-T4-Mab solution (195 µL) was added the T3-F solution (5 µL), mixed well, incubated for 30 min and the fluorescence intensities recorded. The results are provided in FIG. 17.

Figure 17:
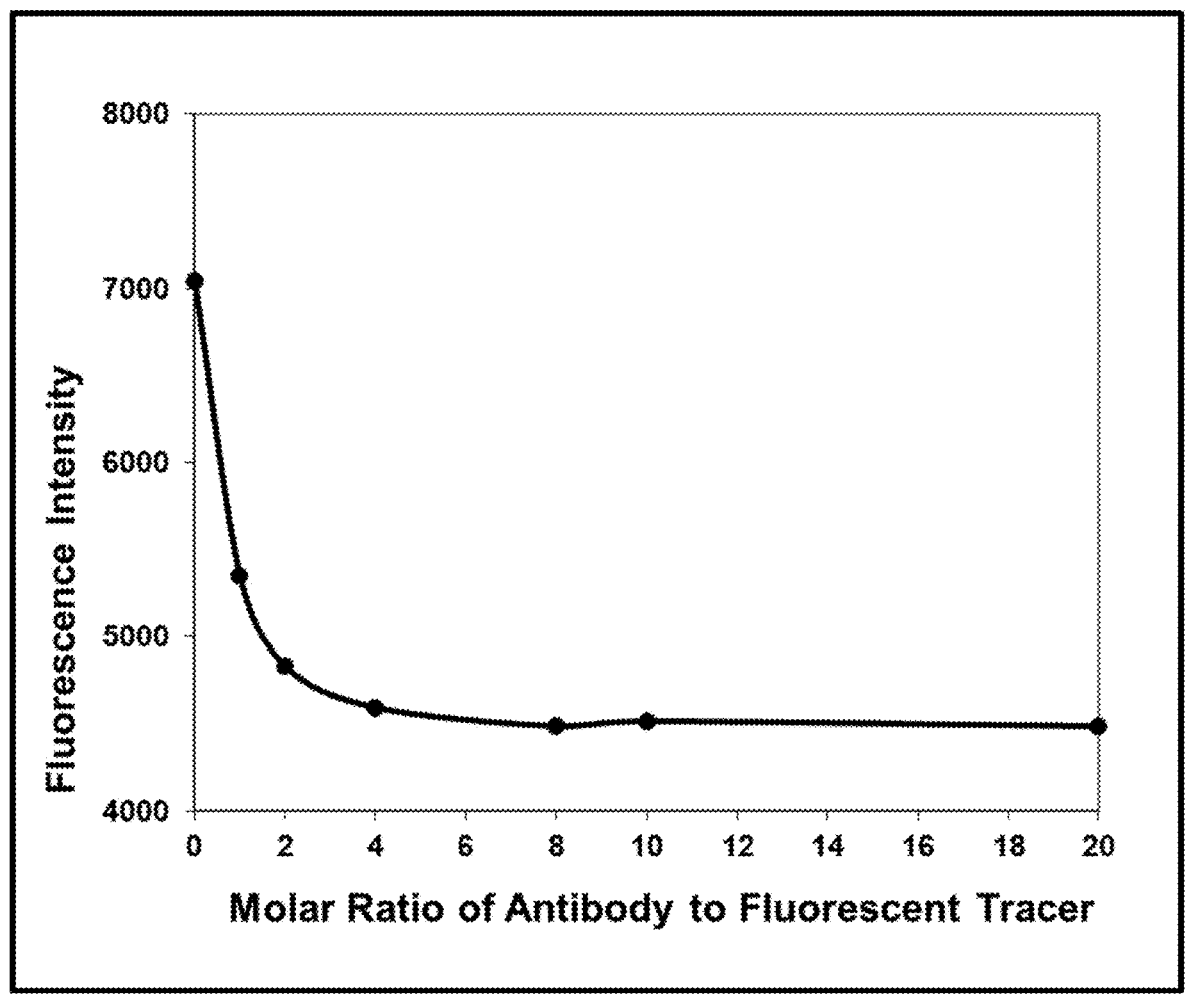
FIG. 17 is a plot of fluorescence intensity of various solutions of T3-F and monoclonal anti-T4-Mab vs molar ratio of monoclonal anti-T4-Mab to T3-F as described in Example 27.

FIG. 17 show that the fluorescence of T3-F is quenched in the presence of anti-T4-Mab. Maximum quenching is reached at a molar ratio of antibody to tracer of about 1:1. Increasing the ratio of anti-T4-Mab to tracer up to 20:1 showed no further increase in the amount of quenching.

In another experiment, tracer T2-F, T3-F, or T4-F was dissolved in DMSO to provide a DMSO solution at a tracer concentration of 1 mM. The DMSO solution was then diluted with phosphate buffered saline ("PBS") to provide a stock solution of each tracer at a concentration of 10 µM. Monoclonal anti-T4-Mab or anti-T4-Mab conjugated to a quencher (Cy3-Ab, IRdyeQC1-Ab, Cy5-Ab, BHQ1-Ab) were serially diluted in PBS to provide solutions having an Anti-T4-Mab or anti-T4-Mab conjugated to quencher at concentration ranging from 0 to 2 µM. In a 96 well black assay plate containing the serially diluted Anti-T4-Mab or anti-T4-Mab conjugated to quencher (95 µL) was added the tracer T2-F, T3-F, or T4-F solution (5 µL), mixed well, and incubated for 30 min and the fluorescence intensities then recorded at an excitation wavelength of 485 nm and an emission wavelength of 520 nm. The results of maximum percentage fluorescence quenching for different tracers and quencher-modified antibodies are provided in the following Table:

| Percentage of fluorescence quenching of fluorescein-Conjugates by anti-T4 antibody with and without labelling of Quenchers | | | | |
|---|---|---|---|---|
| Fluorescein-Conjugates | Cy3-Ab | IRdyeQC1-Ab | Cy5-Ab | BHQ1-Ab | Ab |
| T2-F | 58% | 8% | 16% | 11% | 22% |
| T3-F | 80% | 53% | 40% | 30% | 30% |
| T4-F | 82% | 78% | 31% | No | No |

The results show that Cy3-Ab quenched over 50% of fluorescence of all three fluorescein-conjugates (T2-F, T3-F, and T4-F), while IRdyeQC1-Ab quenched over 50% of fluorescence of T3-F and T4-F. These combinations of labeled antibodies and fluorescein-conjugates make them useful as reagents for a T4 assay. The data also showed T3-F is an optimal conjugate for T4 assay compared with T2-F and T4-F.

Example 28

Fluorescence Quenching of Cortisol-4-Fl and Cortisol-5-Fl with Cortisol Antibody Cortisol-4-Fl, i.e.:

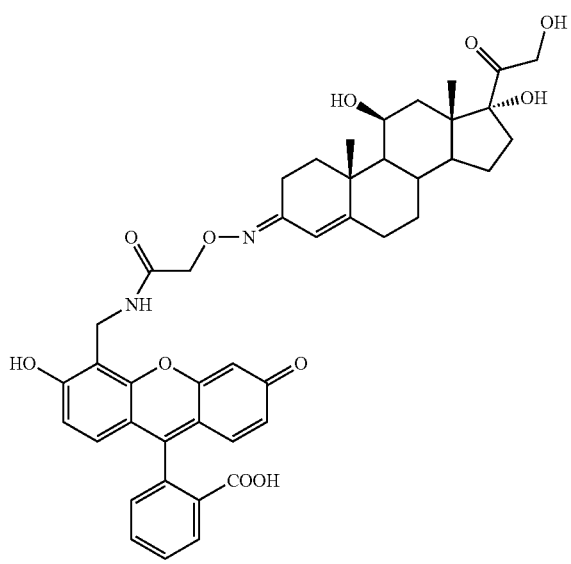 [SMILES: C[C@]12CC/C(=N\OCC(=O)NCc3c(O)ccc4c(-c5ccccc5C(=O)O)c5ccc(=O)cc-5oc34)C=C1CCC1C2[C@@H](O)C[C@@]2(C)C1CC[C@]2(O)C(=O)CO]

was prepared by dissolving hydrocortisone-3-(carboxymethyl) oxime, (30 mg, 0.069 mmol, commercially available from Sigma Aldrich of St. Louis, MO), 4'-aminomethyl fluorescein (25 mg, 0.063 mmol, commercially available from AAT Bioquest of Sunnyvale, CA), 1-[Bis(dimethylamino)methylene]-1H-1,2,3-triazolo[4,5-b]pyridinium 3-oxid hexafluorophosphate (HATU (2 9 mg, 0.075 mmol), commercially available from EMD Millipore of Burlington, MA), and N'N-diisopropylethylamine (24 mg, 0.189 mmol) in anhydrous dimethylformamide (DMF, 1.5 mL). The resulting mixture was stirred at room temperature for over 18 hrs and then diluted in 25 mL of 50% aqueous acetonitrile (with 0.1% acetic acid) and purified by column chromatography using a C18 reverse phase column (5 g) that was eluted with a gradient of 60% to 70% acetonitrile in water. The fractions containing cortisol-4-Fl were combined and lyophilized to provide a yellow solid product, confirmed by LCMS (M+1:779.4).

Cortisol-5-Fl, i.e.:

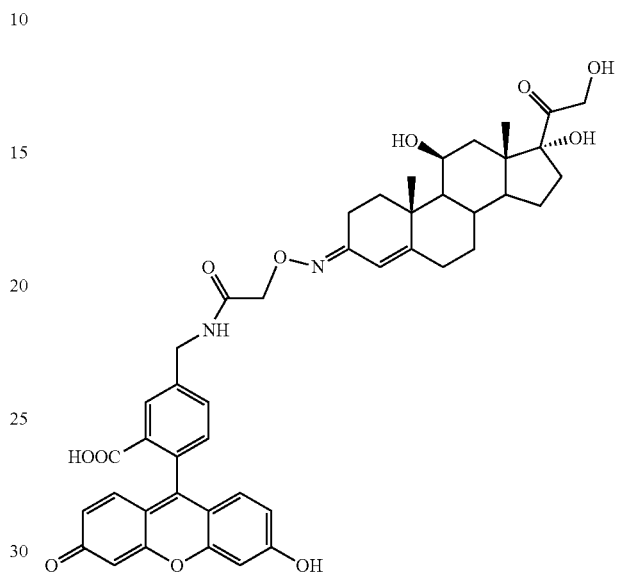

was prepared by dissolving hydrocortisone-3-(carboxymethyl) oxime, (12 mg, 0.028 mmol, commercially available from Sigma Aldrich of St. Louis, MO), 5-aminomethyl fluorescein (10 mg, 0.025 mmol, commercially available from Thermo Scientific of Waltham, MA), HATU (11 mg, 0.030 mmol, commercially available from EMD Millipore of Burlington, MA), and N'N-diisopropylethylamine (10 mg, 0.075 mmol) in anhydrous DMF (1.0 mL). The resulting mixture was stirred at room temperature for over 18 hrs and then diluted in 15 mL of 50% acetonitrile in water (with 0.1% acetic acid) and purified by column chromatography using a C18 reverse phase column (5 g) that was eluted with a gradient of 60% to 70% acetonitrile in water. The fractions containing cortisol-5-Fl were combined and lyophilized to provide a yellow solid product, confirmed by LCMS (M+1: 779.4).

Figure 21:
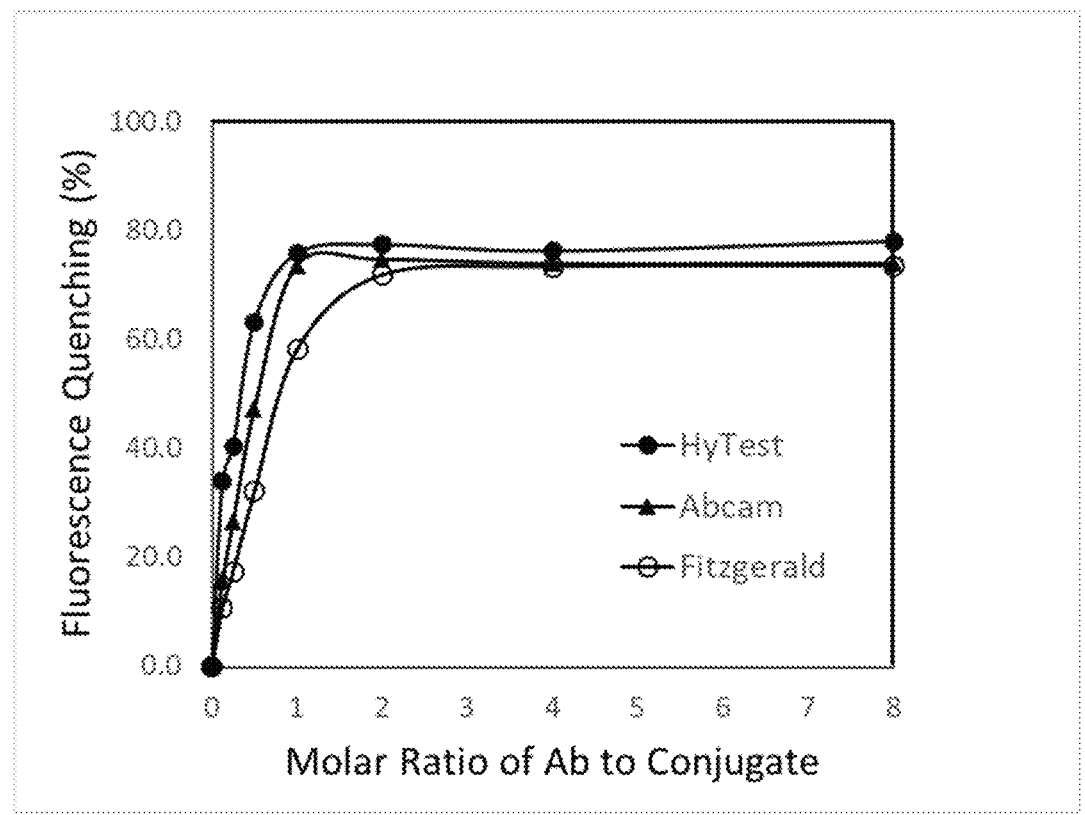
FIG. 21 is a plot of percent fluorescence quenching against the ratio of antibody:cortisol-4-Fl ratio as described in Example 28.

The cortisol-4-FL was combined with various equivalents of various a-cortisol antibodies commercially available from HyTest (of Turku, Finland), Abcam (of Cambridge, United Kingdom), and Bio-Connect BV (Fitzgerald Industries) (of the Netherlands). The fluorescence was measured as a function of the ratio of antibody (Ab) to cortisol-4-FL. The results are depicted in FIG. 21.

The results show that the fluorescence of cortisol-4-Fl is quenched when it forms a complex with the antibody. Maximum quenching is observed at a ratio of antibody/cortisol-4-Fl of about 1:1

Figure 22:
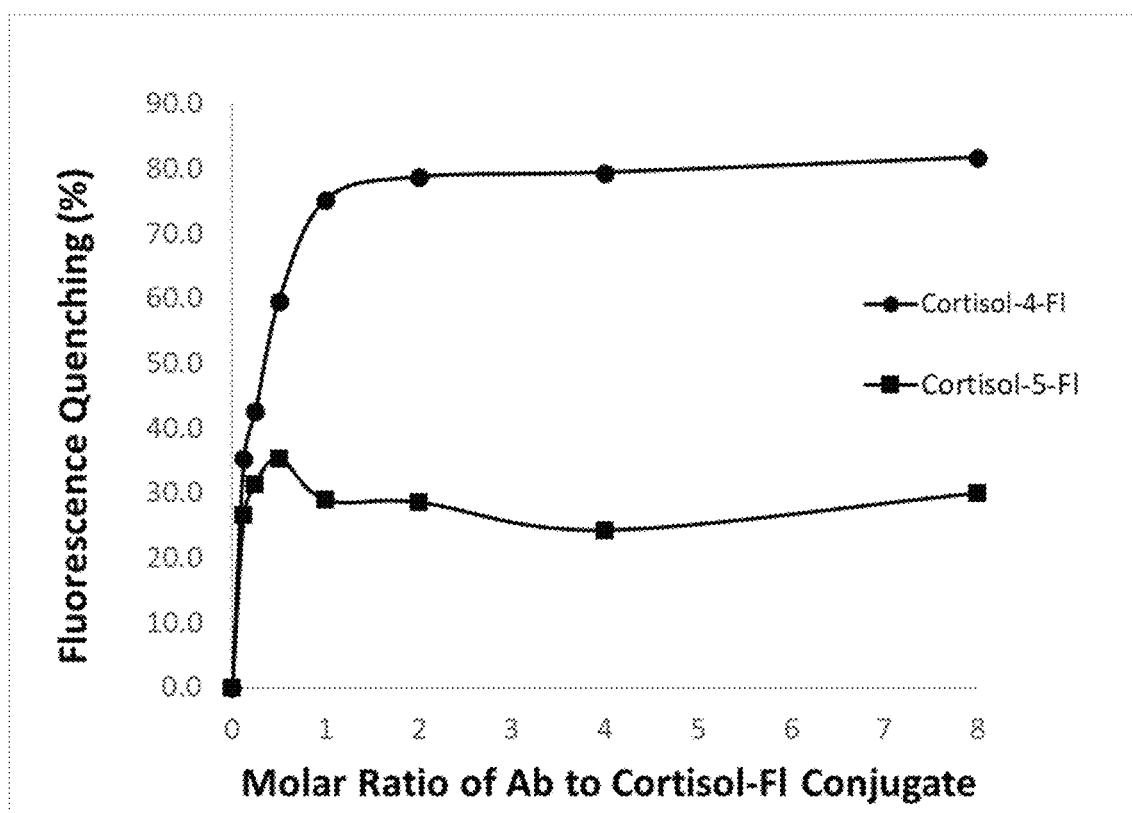
FIG. 22 is a plot of percent fluorescence quenching against the ratio of antibody:cortisol-4-Fl and against the ratio of antibody:cortisol-5-Fl and as described in Example 28.

FIG. 22 depicts the quench in fluorescence when cortisol-4-Fl and cortisol-5-Fl are combined with various equivalents of a-cortisol antibodies commercially available from HyTest (of Turku, Finland). The results show that the change in fluorescence for the 4'-substituted fluorescein tracer is greater than for the 5-substituted fluorescein tracer.

Example 29

Synthesis of 4'-Aminomethyl Difluoro-Fluorescein (4-AMDFF)

4-AMDFF, i.e.:

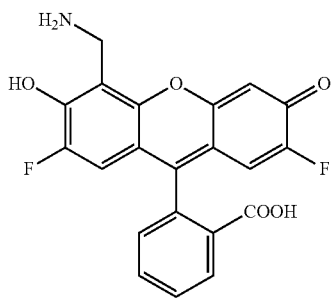 [SMILES: NCc1c(O)c(F)cc2c(-c3ccccc3C(=O)O)c3cc(F)c(=O)cc-3oc12]

was prepared according to the following synthetic scheme:

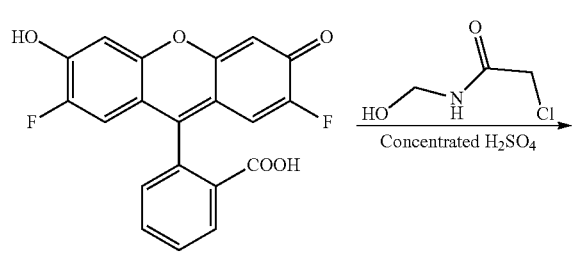

Chemical Formula: $C_{20}H_{10}F_2O_5$
Exact Mass: 368.05

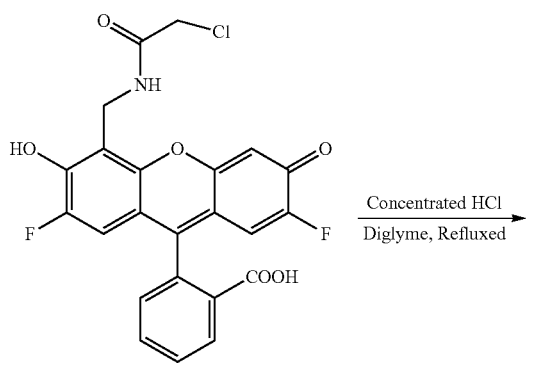

Chemical Formula: $C_{23}H_{14}ClF_2NO_6$
Exact Mass: 473.05

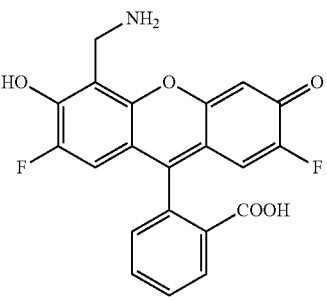

Chemical Formula: $C_{21}H_{13}F_2NO_5$
Exact Mass: 397.08

0.1 g of chloroacetamidomethanol (CLAM, 0.82 mmol) in concentrated sulfuric acid (1.5 mL) was added to a solution of 2',7'-difluorofluorescein (commercially from Chemodex Ltd. of Switzerland, 0.3 g, 0.82 mmol) in sulfuric acid (4 mL). After stirring protected from light for 18 h, the reaction mixture was poured over ice (25 mL) to form an orange colored precipitate. The orange precipitate was collected from the melted ice via filtration, washed with water, and dried to yield 0.3 g of product. The product was characterized by LCMS ([M+1]=474.5).

0.25 g of the above product was refluxed with concentrated HCl (3 mL) in diglyme (11 mL) for 20 h at about 160° C. After removing the solvent under reduced pressure, the residue was dissolved in DMF (2 mL) and purified using a reverse-phase chromatography system eluted with a water/acetonitrile gradient. The appropriate fractions were collected, evaporated to dryness under vacuum, and characterized by LCMS ([M+1]=398.4).

Example 30

Synthesis of 4'-Aminomethyl Dichloro-Fluorescein (4-AMDCF)

4-AMDCF, i.e.:

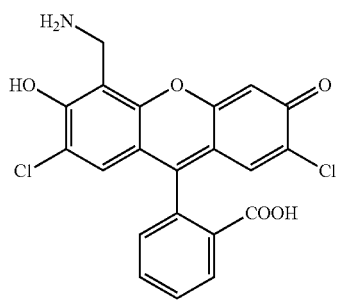 [SMILES: NCc1c(O)c(Cl)cc2c(-c3ccccc3C(=O)O)c3cc(Cl)c(=O)cc-3oc12]

was prepared according to the following synthetic scheme:

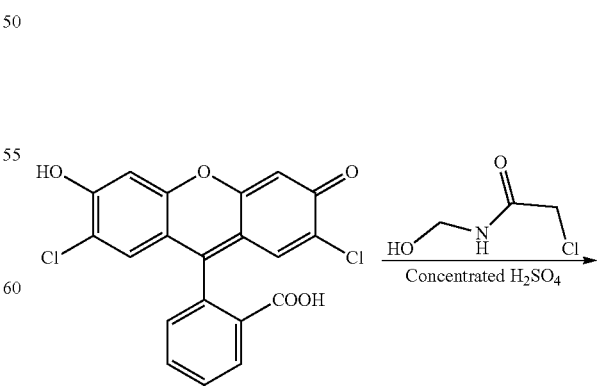

Chemical Formula: $C_{20}H_{10}Cl_2O_5$
Exact Mass: 399.99

-continued

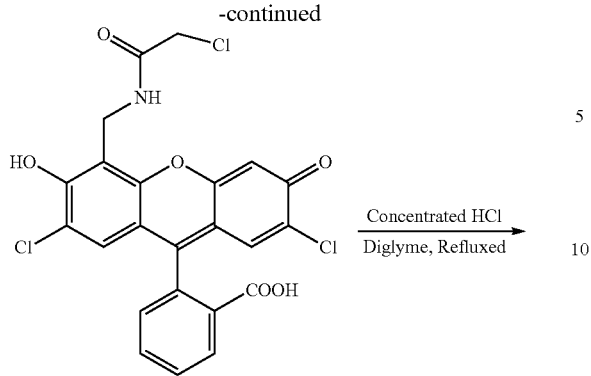

Chemical Formula: C₂₃H₁₄Cl₃NO₆
Exact Mass: 504.99

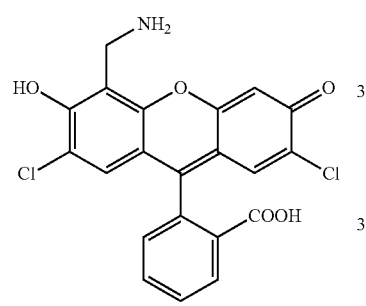

Chemical Formula: C₂₁H₁₃Cl₂NO₅
Exact Mass: 429.02

0.31 g of chloroacetamidomethanol (CLAM, 2.5 mmol) in concentrated sulfuric acid (4 mL) was added to a solution of 2',7'-dichlorofluorescein (commercially available from Sigma Aldrich of St. Louis, MO, 1 g, 2.5 mmol) in sulfuric acid (12 mL). After stirring protected from light for 18 h, the reaction mixture was poured over ice (100 mL) to form a orange colored precipitate. The orange precipitate was collected from the melted ice via filtration, washed with water, and dried to yield 1 g of product. The product was characterized by LCMS (>90% purity, [M+1]=505.8).

1.0 g of above product was refluxed with concentrated HCl (3 mL) in diglyme (11 mL) for 20 h at about 160° C. After removing the solvent under reduced pressure, the residue was dissolved in DMF (2 mL) and purified using a reverse-phase chromatography system eluted with a water/acetonitrile gradient. The appropriate fractions were collected, evaporated to dryness under vacuum, and characterized by LCMS ([M+1]=430.4).

Example 31

Synthesis of SDMA-DFF

SDMA-DFF, i.e.:

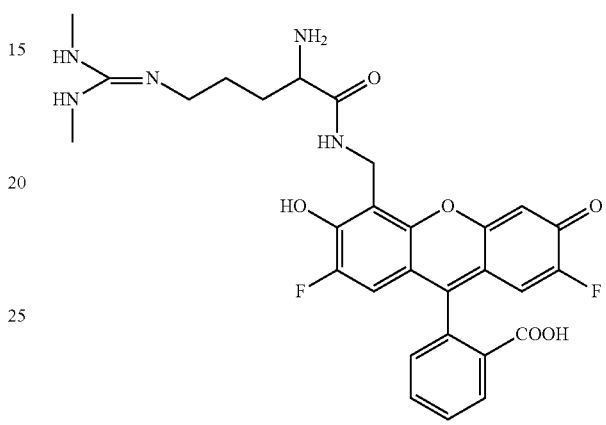

was prepared according to the following synthetic scheme:

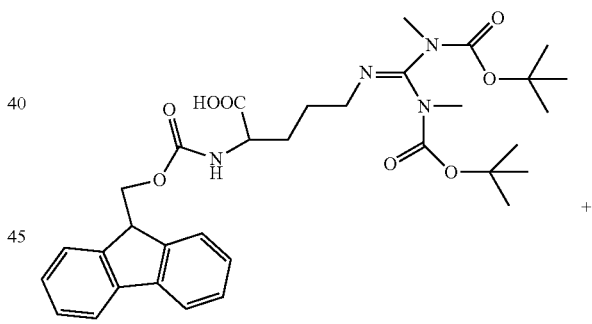

+

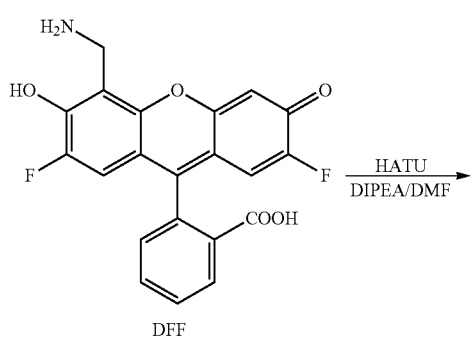

DFF $\xrightarrow{\text{HATU}}{\text{DIPEA/DMF}}$

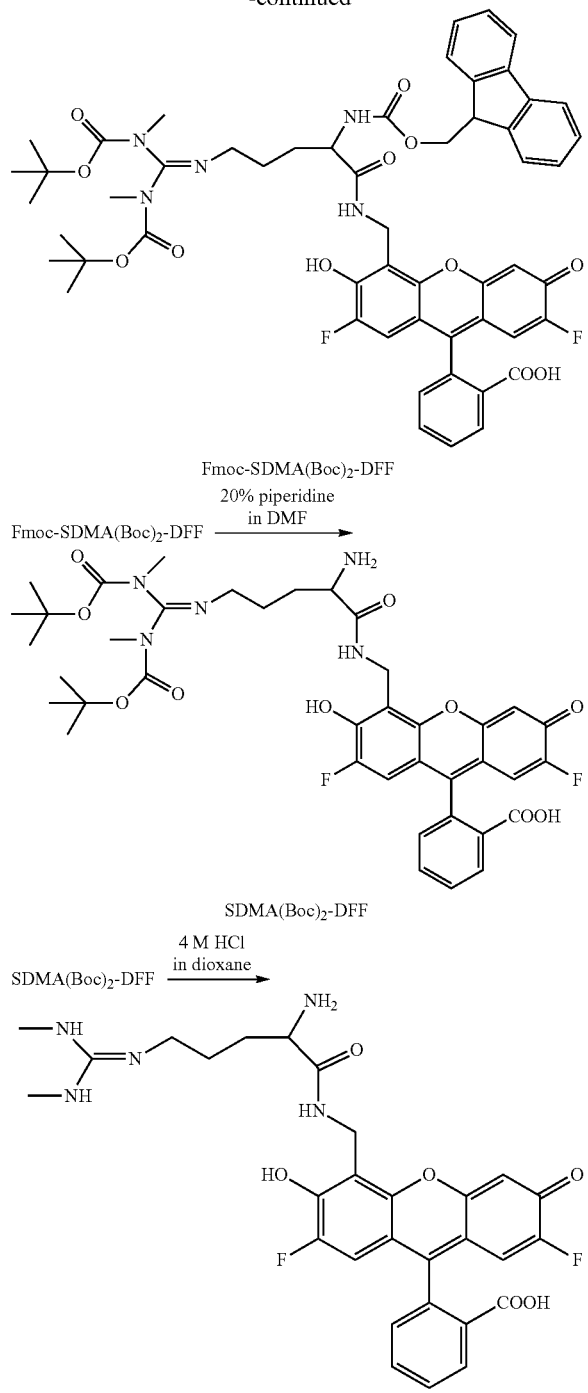

Synthesis of Fmoc-SDMA(Boc)2-DFF

To a 2 mL glass vial was added Fmoc-SDMA(Boc)₂—OH, (9.6 mg, 0.0148 mmol), 4'-aminomethyl 2',7'-difluorofluorescein (5.6 mg, 0.0141 mmol), HATU (6.2 mg, 0.0162 mmol), DIPEA (8.56 µL, 0.045 mmol), and anhydrous DMF (1.0 mL). The resulting reaction mixture was mixed well and stirred for 18 hrs at room temperature. The reaction mixture was loaded onto an automatic purification system equipped with a reverse phase column and eluted with a water/acetonitrile gradient (containing 0.1% formic acid). The appropriate fractions were collected and the solvent removed by evaporation to provide about 10 mg of the product as a red color powder. The product was characterized using LCMS ([M+1]=1004.6).

Synthesis of SDMA-DFF

To Fmoc-SDMA(Boc)2-DFF (10 mg, 0.01 mmol was added 5 mL of 20% piperidine in DMF and the resulting mixture stirred for 2 h at room temperature. The reaction mixture was then loaded onto an automatic purification system equipped with a reverse phase column and eluted with a water/acetonitrile gradient (containing 0.1% formic acid). The appropriate fractions were collected and the solvent removed by evaporation to provide a red solid. The red solid was combined with 1 mL of dioxane and 0.28 mL of 4 M HCl in dioxane, stirred overnight at room temperature, and the solvents removed by evaporation to provide the crude product. The crude product was dissolved in water and purified using an automatic purification system equipped with a reverse phase column and eluted with a water/acetonitrile gradient (containing 0.1% formic acid). The appropriate fractions were collected and the solvent removed by evaporation to provide yellow colored crystals that were characterized by LCMS ([M+1]=582.2).

Example 32

Synthesis of SDMA-DCF

SDMA-DCF, i.e.:

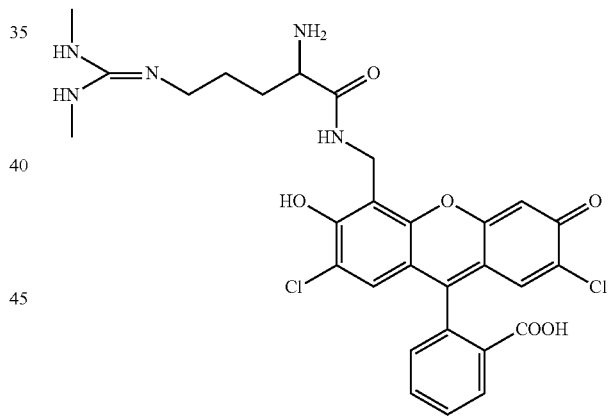

was prepared according to the following synthetic scheme:

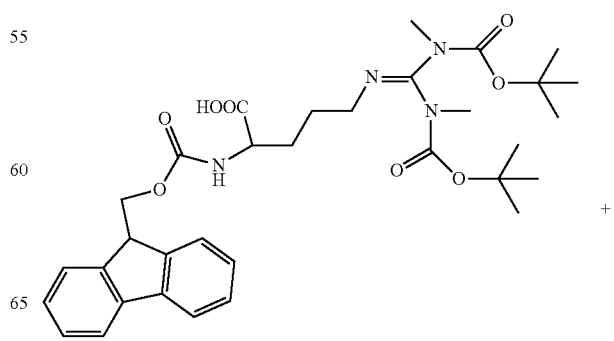

-continued

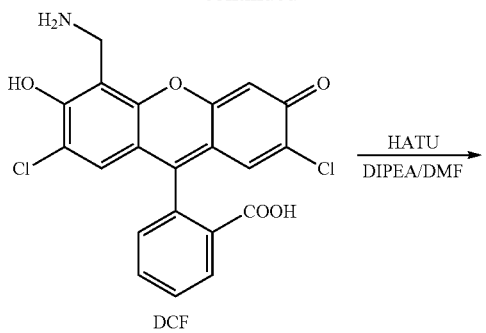

DCF

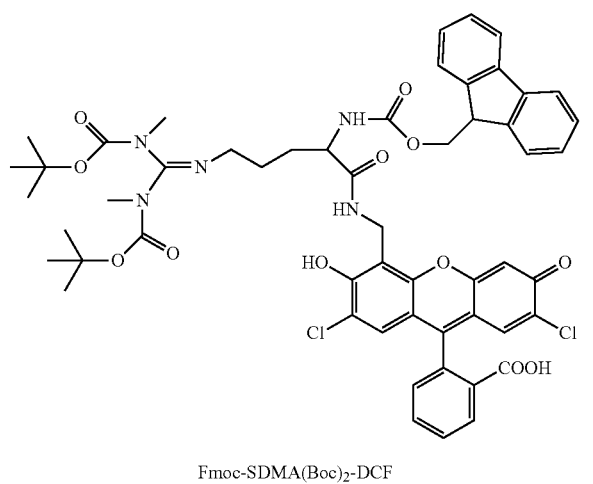

Fmoc-SDMA(Boc)₂-DCF

Fmoc-SDMA(Boc)₂-DCF  —20% piperidine in DMF→

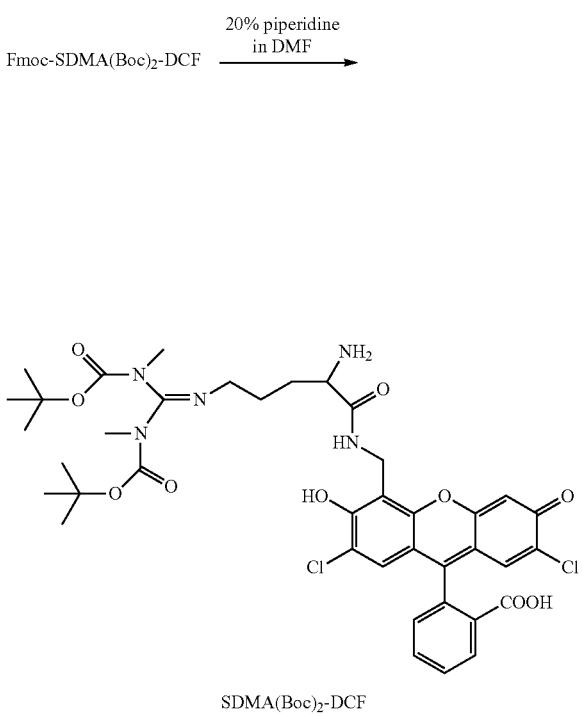

SDMA(Boc)₂-DCF

-continued

SDMA(Boc)₂-DCF  —4M HCl in dioxane→

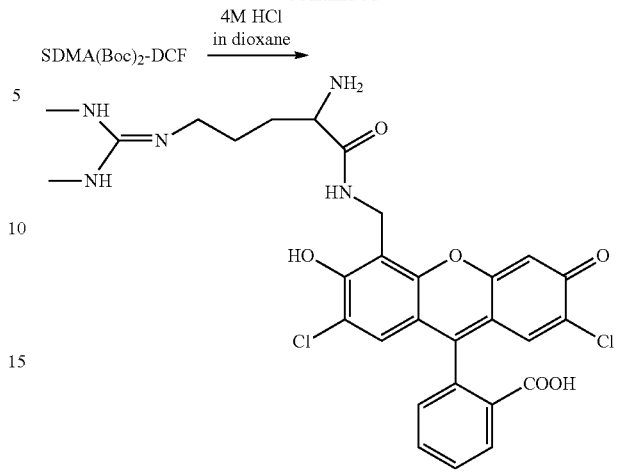

Synthesis of Fmoc-SDMA(Boc)₂-DCF

To a 2 mL glass vial was added Fmoc-SDMA(Boc)₂—OH, (20 mg, 0.0308 mmol), 4'-aminomethyl 2',7'-dichlorofluorescein (12.6 mg, 0.0294 mmol), HATU (13 mg, 0.034 mmol), DIPEA (17.8 µL, 0.088 mmol), and anhydrous DMF (1.0 mL). The resulting reaction mixture was mixed well and stirred for 18 hrs at room temperature. The reaction mixture was loaded onto an automatic purification system equipped with a reverse phase column and eluted with a water/acetonitrile gradient (containing 0.1% formic acid). The appropriate fractions were collected and the solvent removed by evaporation to provide about 25 mg of the product as a red color powder. The product was characterized using LCMS ([M+1]=1036.5).

Synthesis of SDMA-DCF

To Fmoc-SDMA(Boc)₂-DCF (15 mg, 0.0145 mmol) was added 5 mL of 20% piperidine in DMF and the resulting mixture stirred for 2 h at room temperature. The reaction mixture was loaded onto an automatic purification system equipped with a reverse phase column and eluted with a water/acetonitrile gradient (containing 0.1% formic acid). The appropriate fractions were collected and the solvent removed by evaporation to provide a red solid. The red solid was combined with 1 mL of dioxane and 0.28 mL of 4 M HCl in dioxane, stirred overnight at room temperature, and the solvents removed by evaporation to provide the crude product. The crude product was dissolved in water and purified using an automatic purification system equipped with a reverse phase column and eluted with a water/acetonitrile gradient (containing 0.1% formic acid). The appropriate fractions were collected and the solvent removed by evaporation to provide an orange solid that was characterized by LCMS ([M+1]=615.6).

Example 33

Figure 25:
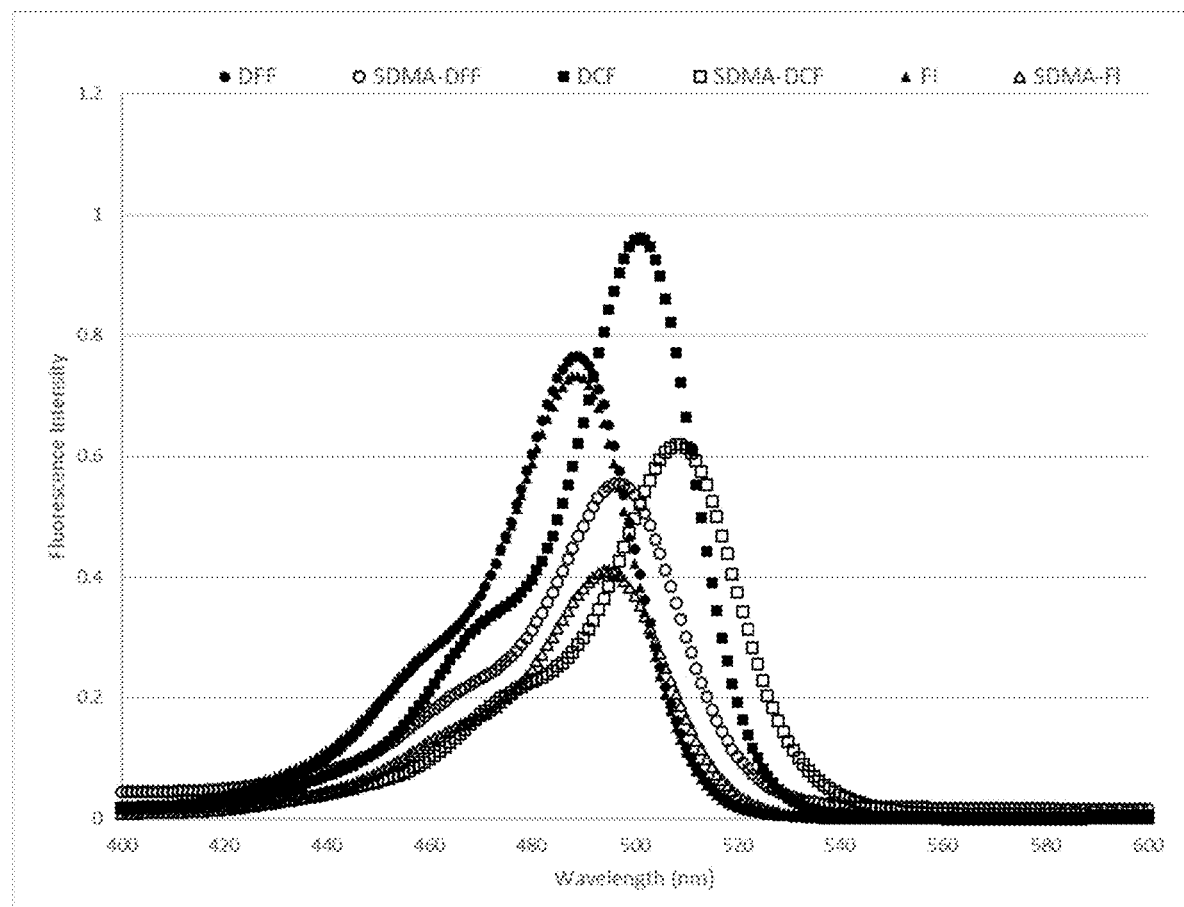
FIG. 25A depicts the absorption spectra of DFF, SDMA-DFF, DCF, SDMA-DCF, Fl, and SDMA-FL
FIG. 25B depicts the emission spectra of SDMA-DFF, SDMA-DCF, Fl, and SDMA-FL as described in Example 33.
Figure 25:
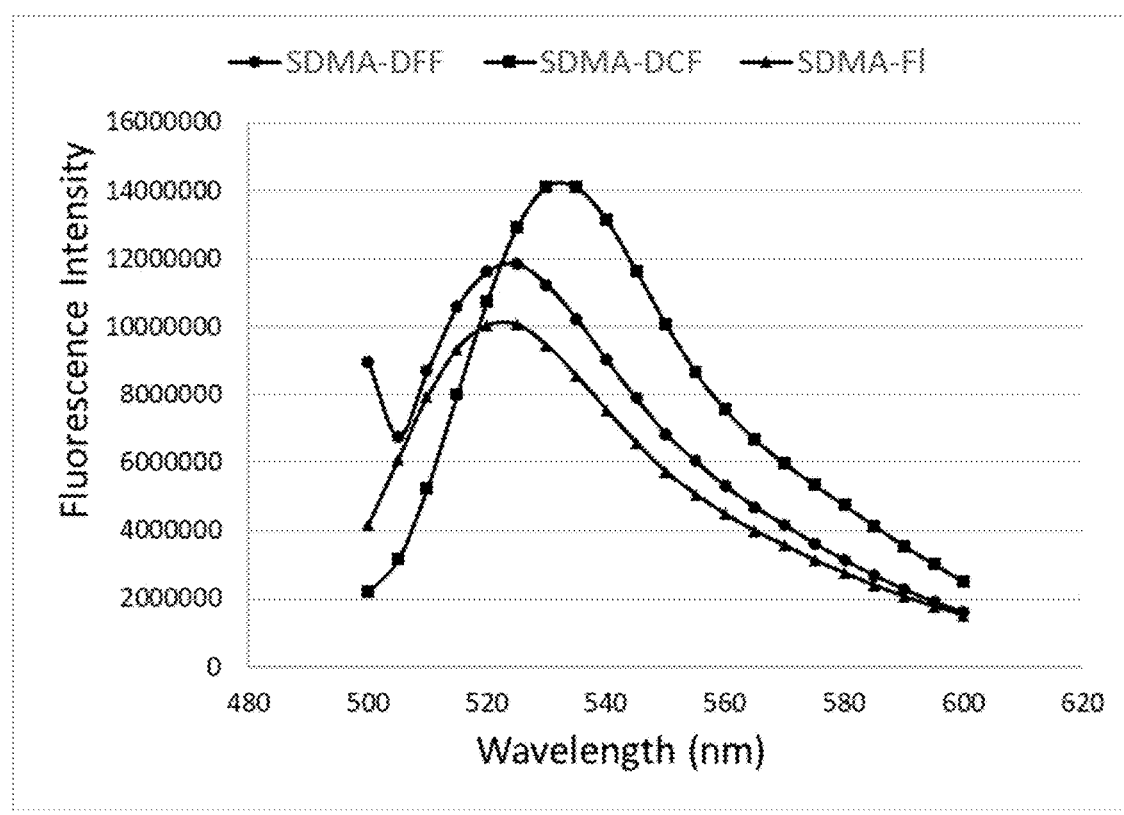

Absorption and Emission Spectra of DFF, SDMA-DFF, DCF, SDMA-DCF, Fl, and SDMA-FL The maximum absorption of fluorescein (Fl) in PBS buffer is at 489 nm and the maximum fluorescence emission is at 515 nm. When the fluorescein molecule is conjugated with an SDMA molecule via a —CH₂NH— linker (i.e., to provide SDMA-Fl), its maximum absorption and emission are shifted to 495 nm and 525 nm, respectively. When the fluorescein molecule is substituted by fluorine at the 2' and 7' positions (i.e., to provide DFF) there is no any change in the maximum absorption and emission compared to unsubstituted fluorescein. When the fluorescein molecule is substituted by chloride at the 2' and 7' positions (i.e., to provide DCF) the maximum absorption and emission are red-shifted to 500 nm and 525 nm, respectively. Also conjugating DFF or DCF to SDMA via a —CH$_2$NH— linker (i.e., to provide SDMA-DFF and SDMA DCF, respectively) results in the maximum absorption and emission being red-shifted. The maximum absorption and emission wavelengths of fluorescein (FL), 2',7'-difluorofluorescien (DFF), 2',7'-dichlorofluorescien (DCF), and their conjugates with SDMA via a —CH$_2$NH— linker (i.e., SDMA-Fl (i.e., structure A3), SDMA-DFF, and SDMA-DCF) are listed in the Table provided below. The absorption spectra of DFF, SDMA-DFF, DCF, SDMA-DCF, Fl, and SDMA-FL are depicted in FIG. 25A and the emission spectra of SDMA-DFF, SDMA-DCF, Fl, and SDMA-FL are depicted in FIG. 25B.

|  | Max Absorption (nm) | Max Emision (nm) |
|---|---|---|
| DFF | 489 | 515 |
| SDMA-DFF | 437 | 525 |
| DCF | 500 | 525 |
| SDMA-DCF | 510 | 535 |
| Fl | 483 | 515 |
| SDMA-Fl | 495 | 525 |

Example 34

Fluorescence of Mixtures of Various SDMA Fluorescent Tracers and Anti-SDMA Antibody Solutions of anti-SDMA antibody or anti-SDMA antibody conjugated to BHQ10 (4 eq.) in phosphate buffered saline (PBS) were prepared at concentrations of 0, 0.25, 0.5, 1, 2, 4, 8, and 16 µM (antibody solution). Solutions of an SDMA fluorescent tracer (i.e., SDMA-Fl, SDMA-DFF, or SDMA-DCF) in PBS were prepared at a concentration of 100 nM (tracer solution). 50 µL of antibody solution and 50 µL of tracer solution were combined on a 96-well UV plate and incubated for 30 min. at room temperature. The fluorescence intensity of each mixture was read using an excitation wavelength of 490 nm and an emission wavelength of 525 nm for SDMA-DFF and SDMA-Fl conjugates and an emission wavelength of 535 nm for SDMA-DCF. The results are depicted in FIGS. 26 and 27.

Figure 26:
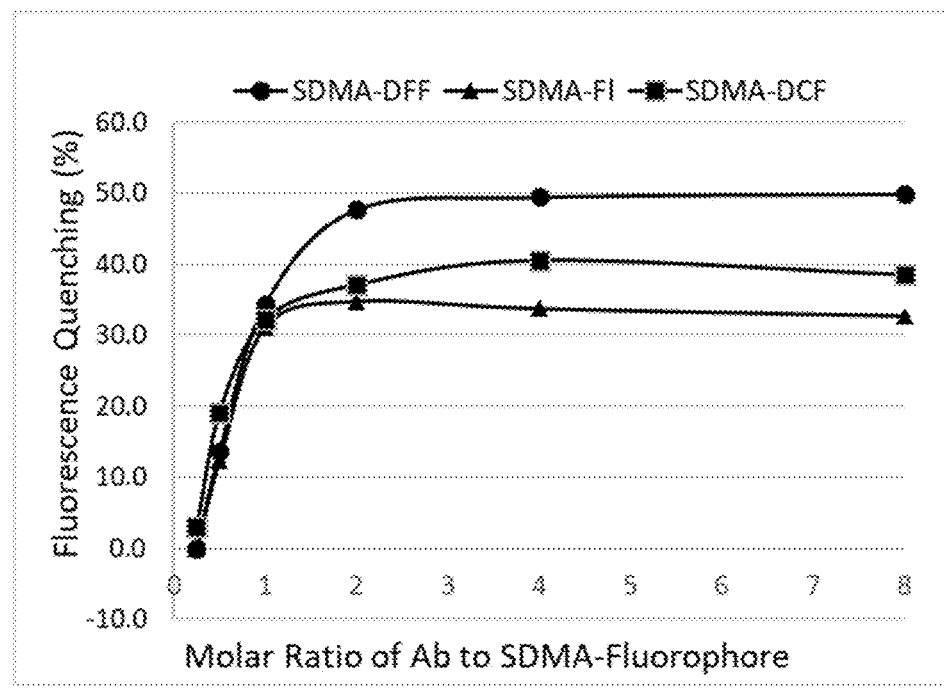
FIG. 26 depicts the percent of fluorescence quenching for different SDMA tracers as a function of increasing antibody concentration as described in Example 34.

FIG. 26 depicts the percent of fluorescence quenching for the different SDMA tracers as a function of increasing antibody concentration. FIG. 26 shows that about 50% of the fluorescence of the SDMA-DFF tracer is quenched by adding anti-SDMA antibody and about 30% of the fluorescence of the SDMA-Fl tracer is quenched by adding anti-SDMA antibody. FIG. 26 shows that with SDMA-DFF the quenching efficiency is almost saturated when the molar ratio of antibody to SDMA-DFF is greater than 2:1. The quenching efficiency of 50% for anti-SDMA antibody (not conjugated to a quencher) and SDMA-DFF tracer shows that the SDMA-DFF tracer can be used with anti-SDMA antibody that is not conjugated to a quencher as an assay reagent in a homogeneous SDMA assay.

Figure 27:
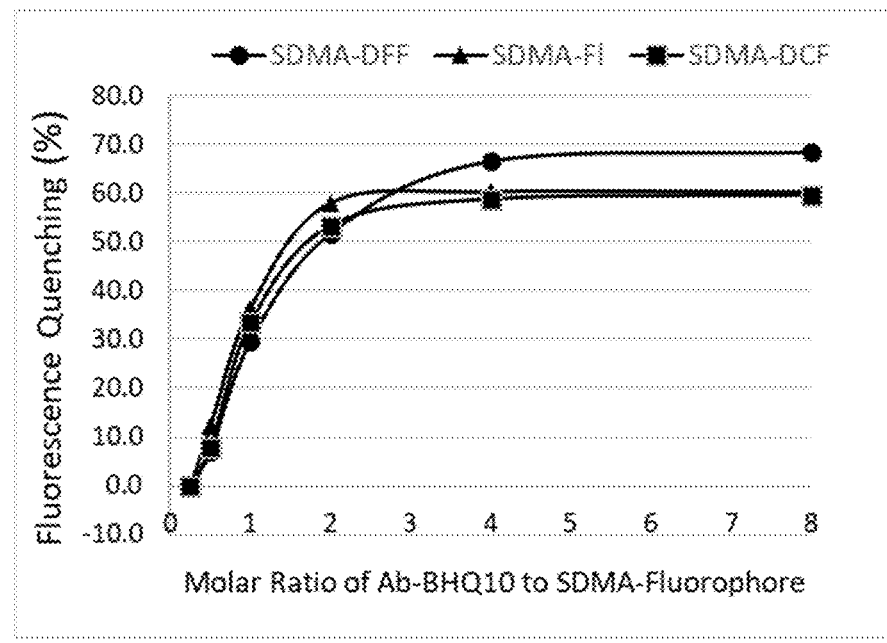
FIG. 27 depicts the percent of fluorescence quenching for different SDMA tracers as a function of increasing concentration of anti-SDMA antibody conjugated to BHQ10 (4 eq.) as described in Example 34.

FIG. 27 depicts the percent of fluorescence quenching for different SDMA tracers as a function of increasing concentration of anti-SDMA antibody conjugated to BHQ10 (4 eq.). FIG. 27 shows that the quenching efficiency is slightly greater for SDMA-DFF in comparison with SDMA-Fl.

Solutions of various SDMA tracers (SDMA-Fl, SDMA-DFF, and SDMA-DCF) in PBS (with 0.1% Tween) were prepared at a concentrations 400 nM. Solutions of anti-SDMA antibody or anti-SDMA antibody conjugated to BHQ10 (4 eq.) in PBS were prepared at concentrations of 400 and 800 nM, respectively. The solution of SDMA tracer was mixed with the solution of anti-SDMA antibody or anti-SDMA antibody conjugated to BHQ10 in a ratio of 1:1 (v/v) and incubated at room temperature for 60 min. to provide an SDMA tracer/SDMA antibody solution.

SDMA standard solutions were prepared by serially diluting SDMA in PBS (with 0.1% Tween) to provide a final SDMA concentration of 100, 50, 25, 12,5, 6.26, 0 µg/dL.

50 µl of each SDMA standard solution was added to the well of a 96-well UV transparent plate. 50 µl of the SDMA tracer/SDMA antibody solution was then added to each well, the resulting solution mixed well by shaking, and incubated at room temperature for 30 min. The fluorescence of each solution was then read using a plate reader using an excitation wavelength of 490 nm and an emission wavelength of 525 nm for SDMA-DFF and SDMA-Fl and an emission wavelength of 535 nm for SDMA-DCF.

Figure 28:
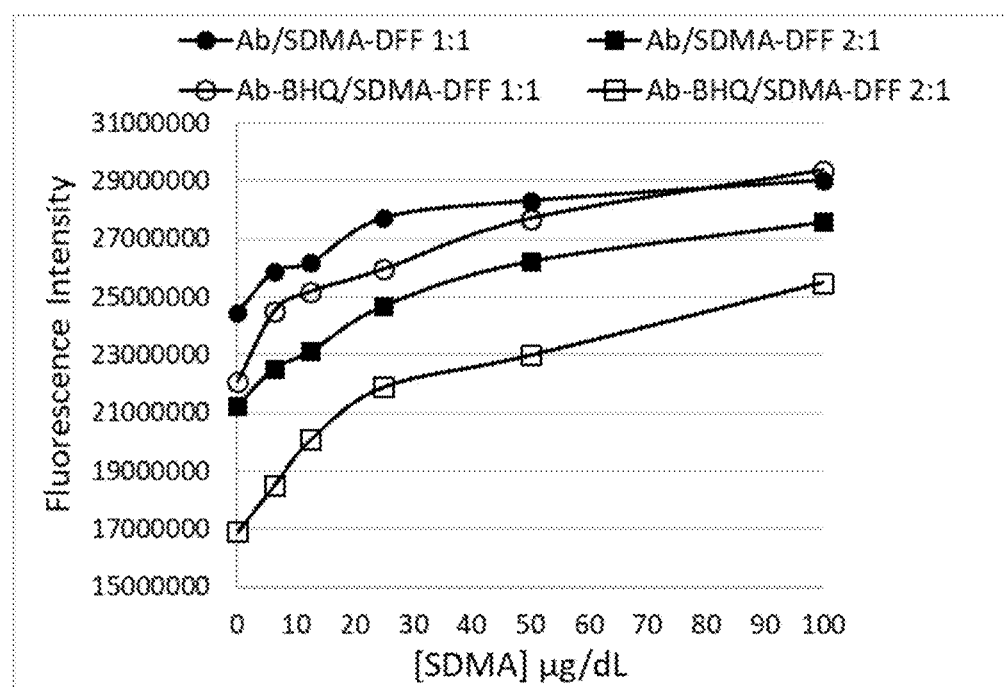
FIG. 28 depicts the increase in fluorescence intensity as a function of SDMA concentration when SDMA is combined with an SDMA-DFF tracer/SDMA antibody solution as described in Example 34.
Figure 29:
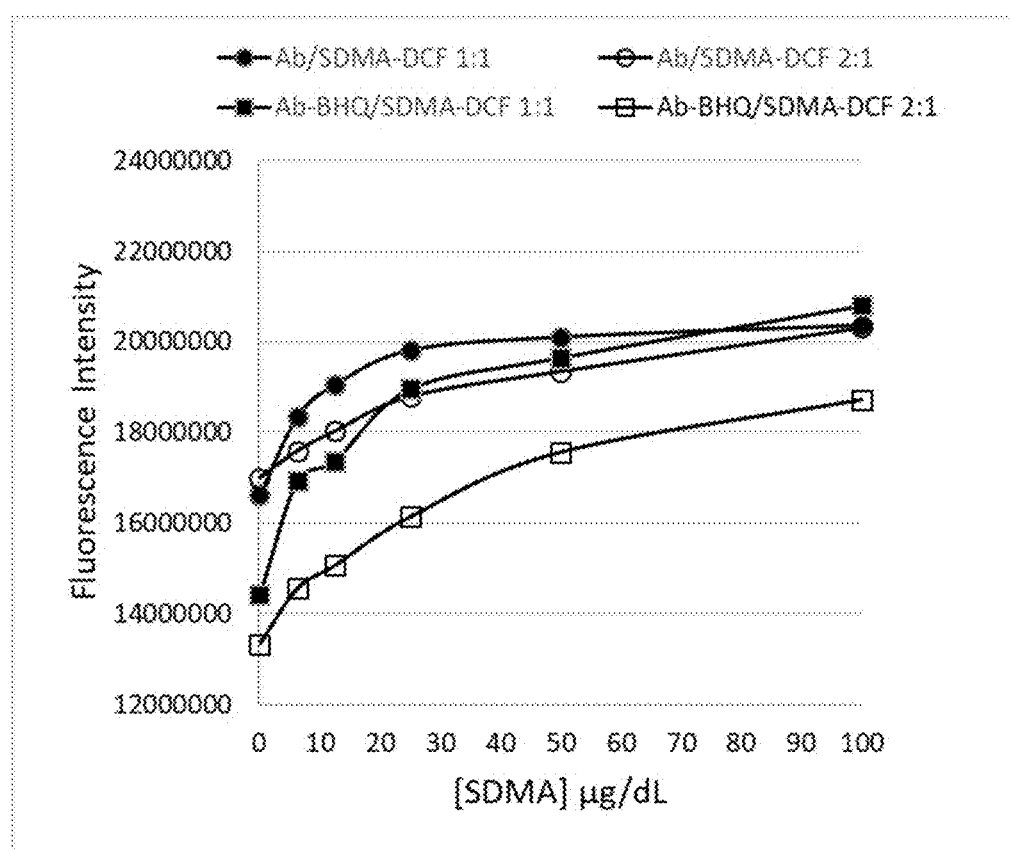
FIG. 29 depicts the increase in fluorescence intensity as a function of SDMA concentration when SDMA is combined with a SDMA-DCF tracer/SDMA antibody solution as described in Example 34.
Figure 30:
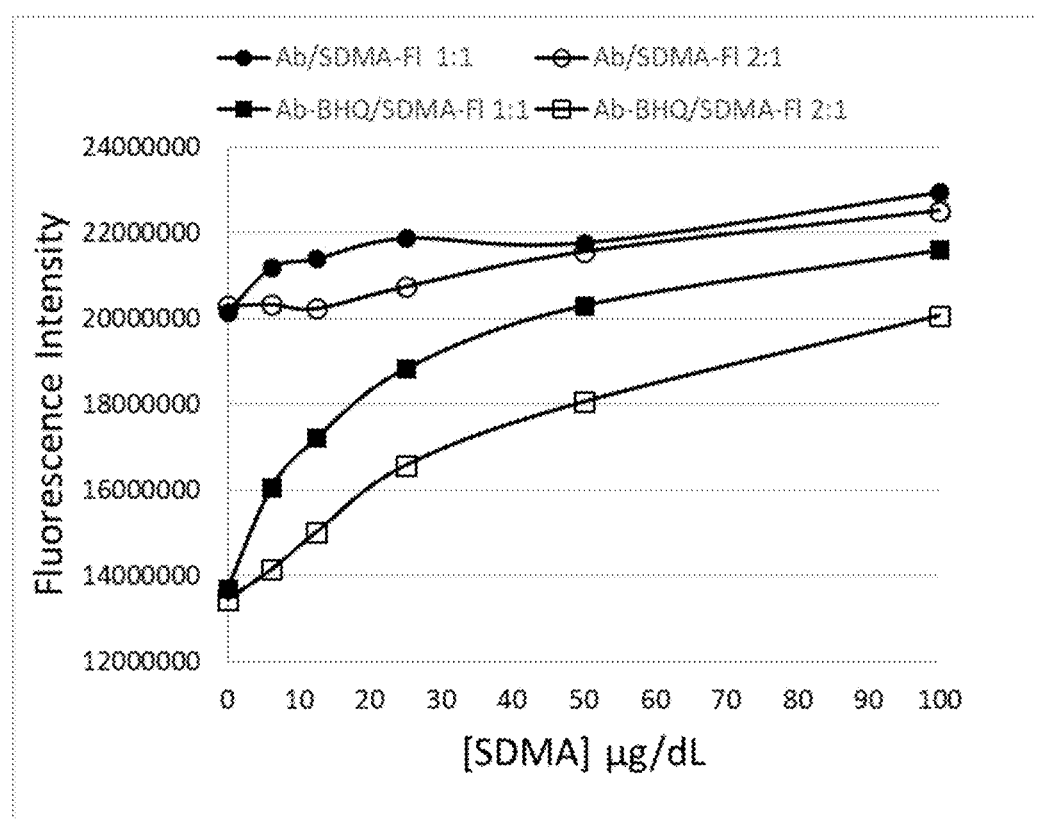
FIG. 30 depicts the increase in fluorescence intensity as a function of SDMA concentration when SDMA is combined with a SDMA-DCF tracer/SDMA antibody solution as described in Example 34.

The results are depicted in FIG. 28-30. FIG. 28-30 shows that there is an increase in fluorescence intensity as a function of SDMA concentration, i.e., a dose response is observed.

FIG. 28 shows the increase in fluorescence intensity when the SDMA tracer is SDMA-DFF. FIG. 28 shows that when the SDMA tracer/SDMA antibody solution is SDMA-DFF and antibody (i.e., antibody not conjugated to BHQ10) the increase in fluorescence intensity is greater when the ratio of antibody/SDMA-DFF is 2:1 than when the ratio is 1:1. FIG. 28 further shows that an increase in fluorescence intensity is observed when the SDMA tracer/SDMA antibody solution is SDMA-DFF and antibody conjugated to BHQ10.

FIG. 29 shows the increase in fluorescence intensity when the SDMA tracer is SDMA-DCF and FIG. 30 shows the increase in fluorescence intensity when the SDMA tracer is SDMA-DF1. FIG. 29 and FIG. 30 show that there is a greater increase in fluorescence intensity when the SDMA antibody is conjugated to BHQ10 compared to SDMA antibody that is not conjugated to BHQ10.

Example 35

Synthesis of SDMA-Fl

SDMA-F1, i.e.:

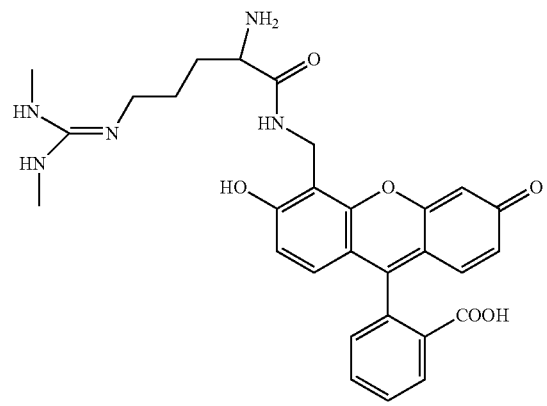 [SMILES: CNC(=NCCCC(N)C(=O)NCc1c(O)ccc2c(-c3ccccc3C(=O)O)c3ccc(=O)cc-3oc12)NC]

was prepared according to the following synthetic scheme:
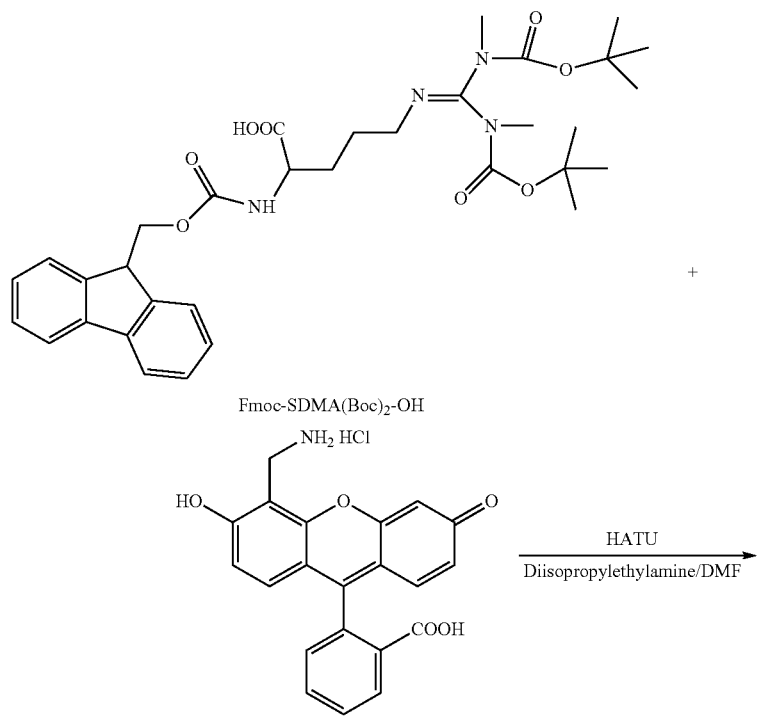
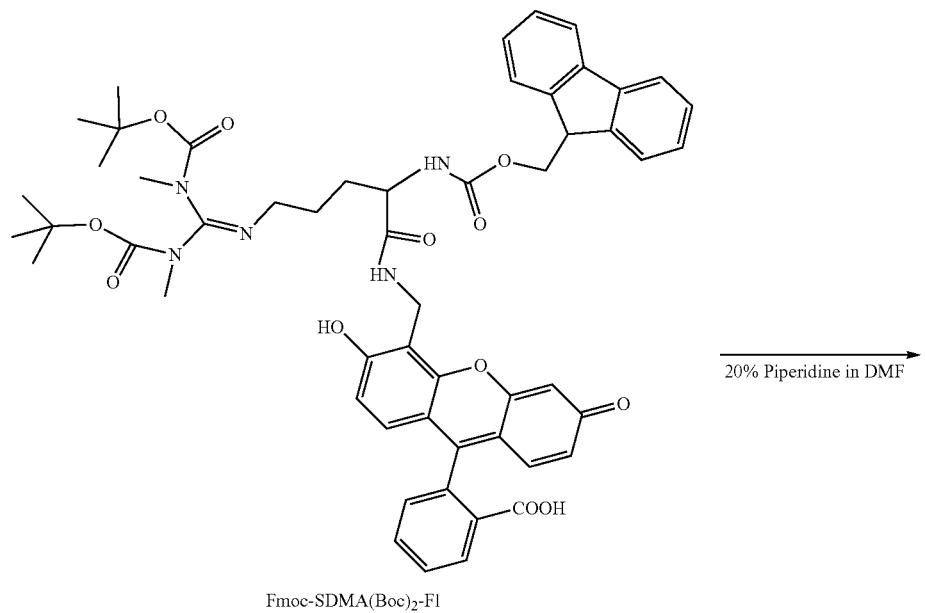

-continued

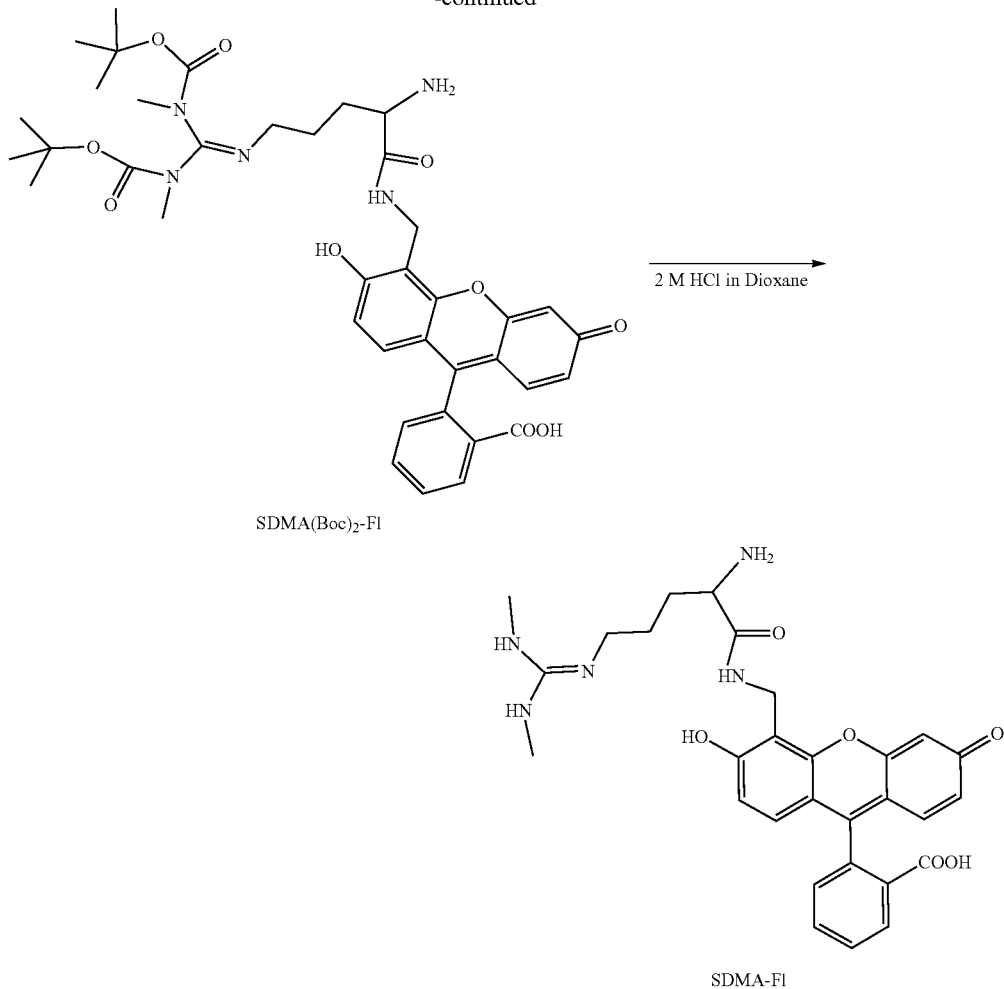

SDMA(Boc)₂-Fl

SDMA-Fl

Fmoc-SDMA(Boc)2-Fl

Fmoc-SDMA(Boc)₂—OH (47 mg, 0.075 mmol, commercially available from Novabiochem, a division of Sigma Aldrich of St. Louis, MO), 4-aminomethyl fluorescein (25 mg, 0.063, commercially available from ATT Bioquest of Sunnyvale, CA), HATU (28.7 mg, 0.075 mmol), N'N-diisopropylethylamine (23.6 mg, 0.189 mmol) were dissolved in anhydrous DMF (1.5 mL). The resulting mixture was stirred at room temperature for 18 hrs and then diluted in 15 mL of 40% acetonitrile in water (with 0.1% acetic acid) and purified by column chromatography using a C18 reverse phase column (5 g) that was eluted with a gradient of 20% to 50% acetonitrile in water. The fractions containing Fmoc-SDMA(Boc)2-Fl were combined and lyophilized to provide a yellow solid product, confirmed by LCMS (M+1:968.3).

SDMA(Boc)₂-Fl

The Fmoc-SDMA(Boc)₂-Fl (45 mg, 0.0465 mmol) was deprotected for 1 hr in 20% piperidine in DMF (8 mL). The solvent was then removed under reduced pressure to provide a residue. The resulting residue was dissolved in 40% acetonitrile in water containing 0.1% acetic acid and purified by column chromatography using a C18 reverse phase column (5 g) that was eluted with a 40% acetonitrile in water containing 0.1% acetic acid. The fractions containing SDMA(Boc)2-Fl were combined and lyophilized to provide an orange powder.

SDMA-Fl

The SDMA(Boc)₂-Fl (21 mg, 0.028 mmol) was dissolved in dioxane (2 mL) and 4 M HCl in dioxane (0.28 mL) was added to the solution. The resulting mixture was stirred overnight. The solvent was removed and the residue was dissolved into 20% acetonitrile in water and purified by column chromatography using a C18 reverse phase column (5 g) that was eluted 20% acetonitrile in water. The fractions containing SDMA-Fl were combined and lyophilized to provide SDMA-Fl as a yellow powder, structure confirmed by LCMS (M+1:546.9).

Example 36

Quenching of Riboflavin Fluoresence in Milk by Riboflavin Binding Protein

The following Example used "in-house" riboflavin binding protein that was purified from chicken egg white (i.e., "IDEXX in-house" riboflavin binding protein) and riboflavin binding protein that was commercially available (Sigma Aldrich, St. Louis, MO).

Figure 31:
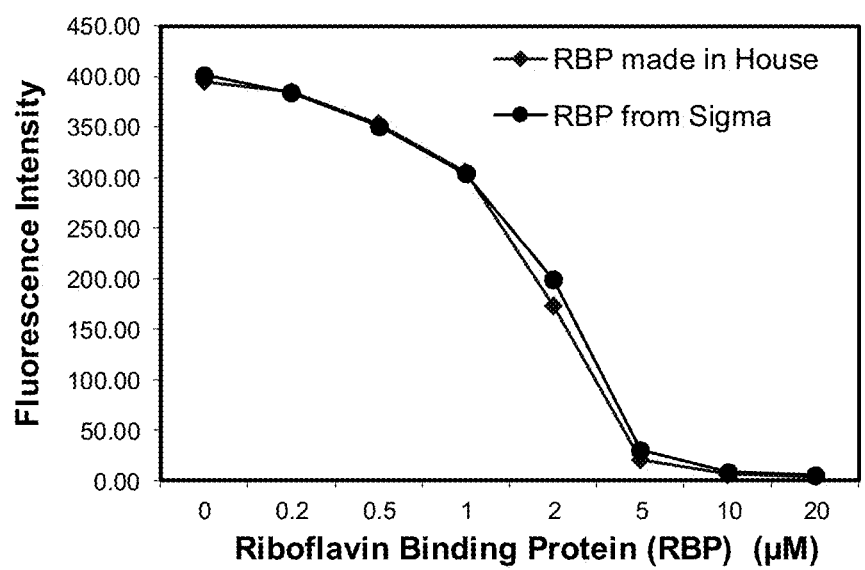
FIG. 31 depicts riboflavin fluorescence in milk as a function of riboflavin binding protein as described in Example 36.

Milk was spiked with a stock solution of riboflavin (1 mM) to provide a final riboflavin concentration of 4 µM. A stock solution of riboflavin binding protein ("RBP," 49.2 mg/mL in phosphate buffered saline ("PBS")), either IDEXX in-house or commercially available (Sigma), was serially diluted in PBS to provide solutions having an RBP concentration ranging from 0 to 1600 µM. 20 µL of the serially diluted RPB solution was added 2 mL of the riboflavin spiked milk to provide a RBP concentration from 0 to 20 µM. The resulting solutions were incubated at room temperature for 1 hour and the fluorescence intensities of a 90 µL volume of the resulting solutions were measured at an excitation wavelength of 350 nm and an emission wavelength of 538 nm. FIG. 31 depicts riboflavin fluorescence in milk as a function of the concentration of riboflavin binding protein.

The results show that adding riboflavin binding protein to milk at a concentration of 5 µM quenched over 95% of fluorescence of riboflavin, which significantly reduced milk fluorescence background. The results are depicted in FIG. 31.

Example 37

Preparation of a Dry Slide for Assaying SDMA

A dry slide for assaying SDMA was prepared in the following manner:

Onto a Melinex (10"×125 µm thick×24' long) sheet (commercially available from HiFi Film of Stevenage, United Kingdom, Part #506) was coated a solution containing about equal amounts by wt. of D4 Hydrogel (High Viscosity Polymer) and D4 Hydrogel (Low Viscosity Polymer) (both commercially available from AdvanSource Biomaterials Corp of Wilmington, MA) so as to provide a wet primer layer having a thickness of about 40 µm. Evaporation of the solvent provided a dry primer layer that contains about equal amounts by wt. of D4 Hydrogel (High Viscosity Polymer) and D4 Hydrogel (Low Viscosity Polymer).

Onto the dry primer layer was coated a solution containing a solution of SDMA-Fluorescein (prepared as described above in Example 35) and anti-SDMA antibody-BHQ10 conjugate (prepared as described below in Example 38) in a HEPES buffer (pH 8), HEPES buffer (pH 8), Merpol A, pullulan, and cellulose so as to provide a wet indicator layer having a thickness of about 93 µm. Evaporation of the solvent provided a dry indicator layer that contains about 1.4×10$^{-1}$% by wt. of anti-SDMA antibody-BHQ10 conjugate, about 1.1×10$^{-3}$% by wt. of SDMA-Fluorescein, about 13% by wt. of HEPES buffer, about 1.2% by wt. of Merpol A, about 28.5% by wt. of pullulan, and about 57% by wt. of cellulose.

Onto the dry indicator layer was coated a solution containing about equal amounts by wt. of D4 Hydrogel (High Viscosity Polymer) and D4 Hydrogel (Low Viscosity Polymer) (both commercially available from AdvanSource Biomaterials Corp of Wilmington, MA), cellulose (commercially available from Sigma Aldrich of St. Louis, MO), and Titania Microparticles (commercially available from Chemours of Fayetteville, NC Part #R-706) so as to provide a wet titanium oxide layer having a thickness of about 130 µm. Evaporation of the solvent provided a dry titanium oxide layer that contains about 37% by wt. of D4 Hydrogel (as about equal amounts by wt. of low viscosity and high viscosity D4 Hydrogel), about 20% by wt. of cellulose, and about 43% by wt. of titanium dioxide.

Onto the dry titanium oxide layer was coated a solution containing about equal amounts of D4 Hydrogel (High Viscosity Polymer) and D4 Hydrogel (Low Viscosity Polymer) (both commercially available from AdvanSource Biomaterials Corp of Wilmington, MA) and Carbon Black, Lamp Black 101 Powder (commercially available from Orion Specialty Carbon Blacks of Belpre, OH) so as to provide a wet carbon black layer having a thickness of about 140 µm. Evaporation of the solvent provided a dry carbon black layer contains about 95% by wt. of D4 Hydrogel (as about equal amounts by wt. of low viscosity and high viscosity D4 Hydrogel) and about 5% by wt. of carbon black.

Onto the dry carbon black layer was coated a solution containing cellulose, tetramethyl ammonium hydroxide (TMAH); polyacrylic acid (PAA), molecular weight about 1 million; and polyvinyl pyrrolidone (PVP) so as to provide a wet spreading layer having a thickness of about 310 µm. Evaporation of the solvent provided a dry spreading layer containing about 83% by wt. of cellulose, about 0.5% by weight of PAA, about 0.4% by wt. of TMAH, and about 16% by wt. of PVP.

Each wet layer was coated using a Slot Die Loop Coater with drying tunnel and heating pads.

The resulting Melinex sheet coated with the primer layer, indicator layer, titanium oxide layer, carbon black layer, and spreading layer was formed into 6.5 mm discs using a punch, and the resulting discs placed into and adhered to the adhesive pad of a slide housing for use in an IDEXX Catalyst Instrument (commercially available from IDEXX Laboratories Inc. of Westbrook, ME) so as to provide a slide, and the resulting slide wrapped in packaging.

Assay of a Panel of Serum Spiked with Various Levels of SDMA Using the Slide

Charcoal stripped canine serum (0 µg/dL SDMA), charcoal stripped canine serum spiked with SDMA (5 µg/dL), and canine serum spiked with SDMA (15, 30, 60, 100 µg/dL) were analyzed using an IDEXX Catalyst instrument (commercially available from IDEXX Laboratories Inc. of Westbrook, ME) configured with an IDEXX Catalyst pipette tip (commercially available from IDEXX Laboratories Inc. of Westbrook, ME), an IDEXX Catalyst sample cup (commercially available from IDEXX Laboratories Inc. of Westbrook, ME), and the above described slide. The following procedure was followed:

Remove SDMA slide from packaging and place in the IDEXX Catalyst instrument;
Pipette 300 µl of panel into the sample cup;
Allow the IDEXX Catalyst instrument to warm the slide to 37° C.;
After warming, the instrument measures and records the fluorescent intensity of the dry slide ($\lambda_{ex}$=470$_{nm}$, $\lambda_{em}$=525 nm) at 15 second intervals for 1.5 minutes;
The IDEXX Catalyst instrument then pipettes 8 µl of a sample onto the slide and then measures and records the fluorescent intensity as described above at 15 second intervals for 400 seconds;
The recorded measurement is compared to a calibration curve to generate the SDMA dose level.

Figure 32:
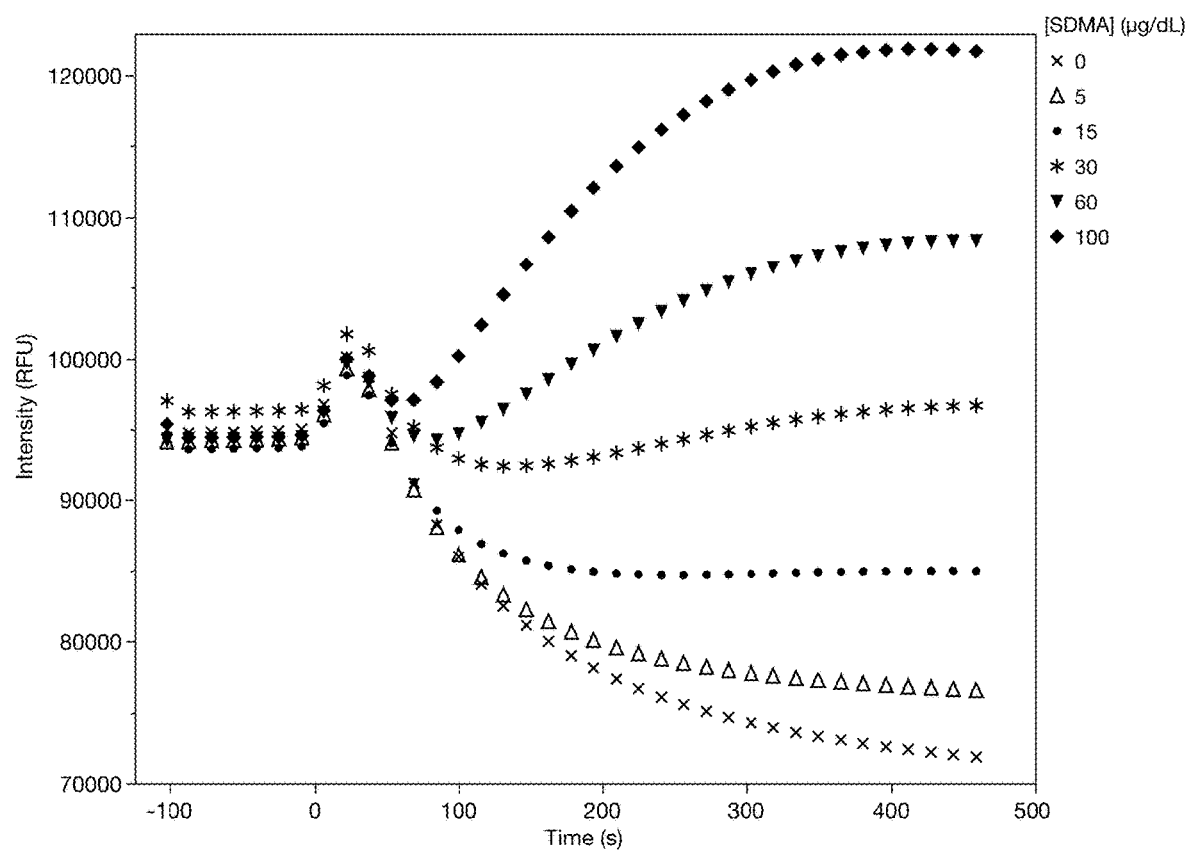
FIG. 32 depicts the output from an SMDA analysis using a dry slide as described in Example 37.

FIG. 32 depicts the assay results. FIG. 32 depicts the fluorescent intensity in the slide observed in the Catalyst instrument over time when different levels of SDMA are dispensed (legend). The Y axis is the intensity in Relative Fluorescent Units (unitless) and the x axis is time in seconds. Initially, fluorescent intensity readings of the dry slide are taken and then fluorescent intensity readings of the wet slide are measured at t=0 (i.e., when the sample is dispensed). The fluorescent intensity is read every 15 seconds. Each trace is an average of n=10 replicates.

Example 38

Preparation of Anti-SDMA Antibody-BHQ10 Conjugate

A stock solution of anti-mAb SDMA (custom made by Leinco Technologies of Fenton, MO) in 250 mM HEPES (pH 8) at a concentration of 5 mg/mL is created by diluting the anti-mAb SDMA to 2.5 mg/ml with 250 mM HEPES at pH 8 and 40% sucrose to provide an antibody solution in 250 mM HEPES and 20% sucrose. Lyophilized BHQ10-NHS ester (commercially available from LGC Biosearch Technologies of Middlesex, UK #BHQ10S) is solvated with anhydrous DMSO to a final concentration of 5 mg/ml. Then 20 molar equivalents of BHQ10 in anhydrous DMSO is added to the antibody solution with gentle mixing (for example, 52 µL of BHQ-10 solution to 1 mL of anti-mAb SDMA solution). The resulting solution is incubated at room temperature for 1 hr with no mixing, and the reaction quenched by adding 10 µL of 1M Tris buffer (commercially available from Alfa Aesar of Tewksbury, MA). The resulting solution is incubated for 10 minutes at room temperature, centrifuged to remove any precipitate, and used without further preparation.

Example 39

Determination of SDMA in the Presence of Various Interferents

In order to evaluate the impact of interferents (lipemia, bilirubin, hemolysis, and whole blood) on dry slide performance, fresh sample solutions of SDMA in pooled charcoal stripped mongrel serum (commercially available from BioIVT of Westbury, NY, #DOG42577) were made with a range of interferent levels. Each interferent level at each SDMA concentration was created through dilution. Samples having lipemia as the inteferent were created by forming a stock solution in charcoal stripped serum having the desired SDMA concentration (e.g., 100 µg/dL) and the highest interferent level, 1000 mg/dL lipemia (Intralipid 20% emulsion, commercially available from Sigma Aldrich, St. Louis, MO, #100267553). The resulting stock solution was then serially diluted with a control solution of 100 µg/dL SDMA in charcoal stripped serum to create solutions having lipemia concentrations of 0, 250, 500, 750, and 1000 mg/dL. In this manner, solutions at different interferent levels were prepared at SDMA concentrations of 0, 15, 30, and 100 µg/dL to evaluate the effect of interferents across a range of SDMA concentrations. For each solution, the SDMA concentration was determined by LCMS and the lipemia concentration was verified on a Beckman AU5812 Clinical Chemistry Analyzer (commercially available from Beckman Coulter, Brea CA).

A similar dilution protocol was used make bilirubin (bilirubin conjugate, commercially available from Scripps of La Jolla, CA #B011490604) solutions at SDMA concentrations of 0, 15, 30, and 100 µg/dL and bilirubin concentrations of 0, 7.5, 15, 22.5, and 30 mg/dL bilirubin. Bilirubin concentration was verified on a Beckman AU5812 Clinical Chemistry Analyzer (commercially available from Beckman Coulter of Brea CA). SDMA concentration was determined by LCMS.

Hemolysis interferent solutions were made from freshly drawn and hemolyzed blood samples (commercially available from Pet Food Solutions of Ward, SC) that were diluted as described above to provide hemolysate concentrations of 0, 125, 250, 375, and 500 mg/dL. Hemolysate concentration was verified on a Beckman AU5812 Clinical Chemistry Analyzer (commercially available from Beckman Coulter of Brea CA). SDMA concentration was determined by LCMS.

To create whole blood contaminated samples, lithium-heparinated anticoagulated whole blood (commercially available from Pet Food Solutions of Ward, SC) was diluted with stripped serum to provide SDMA concentrations of 0, 15, 60, and 100 µg/dL and whole blood percentages of 1, 5, and 10%. For each solution, whole blood percentages were determined by measuring hematocrit and SDMA concentrations were determined by LCMS.

FIG. 24 depicts the result of an assay (using a slide with a filtering layer) to determine the concentration of SDMA in a sample containing a fixed amount of SDMA. The results show that the interferents do not interfere with the analysis of SDMA.

Example 40

Synthesis of Cholic Acid-Fluorescein Conjugate (CA-Fl)

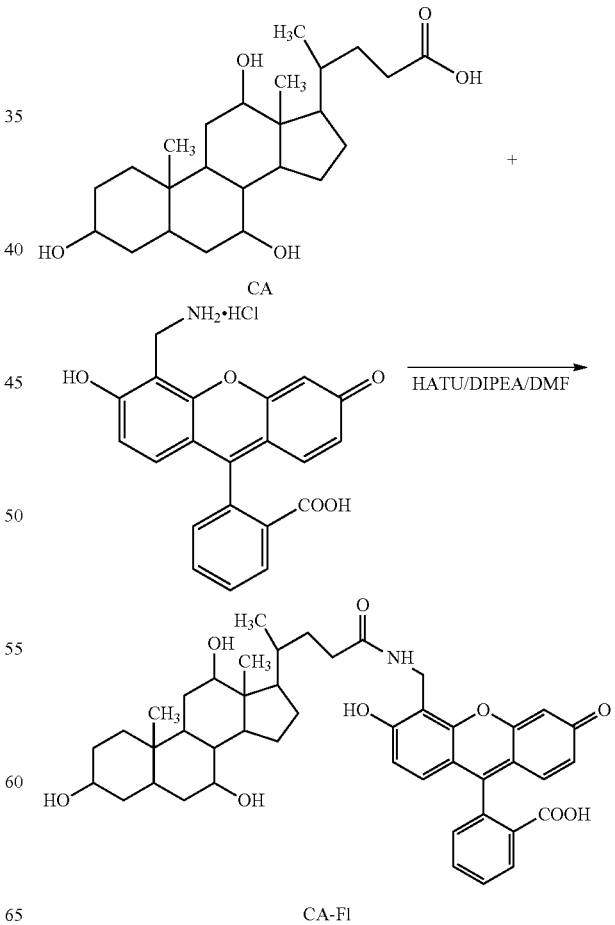

Cholic Acid (28 mg, 0.069 mmol, commercially available from Sigma Aldrich of St. Louis, MO), 4'-aminomethyl fluorescein (25 mg, 0.063 mmol, commercially available from AAT Bioquest of Sunnyvale, CA), HATU (29 mg, 0.075 mmol), and N'N-diisopropylethylamine (29 mg, 0.189 mmol) were dissolved in anhydrous DMF (1.5 ml). The resulting mixture was stirred at room temperature for over 20 hrs and the crude product purified using a Biotage Selekt System (commercially available from Biotage of Sweden) using a Teledyne Isco RediSep RF Gold C18AQ 5.5 gm column eluted with a mobile phase of a gradient of 50% to 100% acetonitrile in water containing 0.1% formic acid. The fractions containing CA-Fl were collected and lyophilized to provide a yellow solid that was characterized using LCMS (M+1:752.4).

Example 41

Fluorescence Quenching of CA-Fl with Anti-Cholic Acid Antibody in PBS

Figure 33:
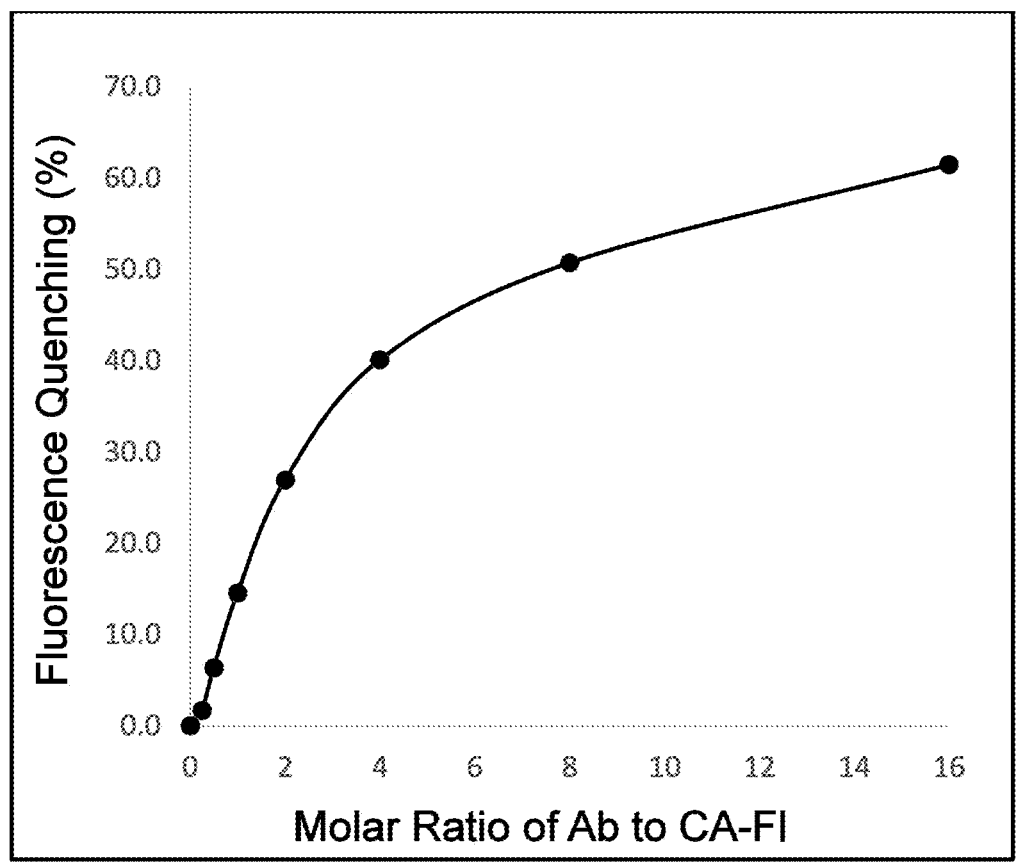
FIG. 33 is a plot of percent fluorescence quenching vs the ratio of antibody:CA-Fl ratio as described in Example 40.

A working solution of CA-Fl in PBS (100 nM) was prepared. The working solution was then combined with various equivalents of α-Cholic Acid antibody (1:1, v/v) (commercially available from Fitzgerald Industries of the Netherlands). The fluorescence was measured as a function of the ratio of antibody (Ab) to CA-Fl. The results are depicted in FIG. 33. The results show that the fluorescence of CA-Fl is quenched when it forms a complex with the antibody and that the amount of quenching is a function of the molar ratio of the antibody to the CA-Fl tracer. The higher the ratio of antibody to CA-Fl tracer, the greater the amount of quenching. The results also demonstrate that, quenching was saturated when the molar ratio of the antibody to the CA-Fl tracer was about 8:1.

Aliquots of CA-Fl in PBS (with 0.1% tween 20) (200 nM) were mixed 1:1 (v/v) with solutions of antibody at concentrations of 200, 400, or 800 nM, and the resulting mixtures incubated for 30 min at 4° C. to provide three assay reagents: Reagent 1 (Ab 100 nM/CA-Fl 100 nM), Reagent 2 (Ab 200 nM/CA-Fl 100 nM), and Reagent 3 (Ab 400 nM/CA-Fl 100 nM).

Figure 34A:
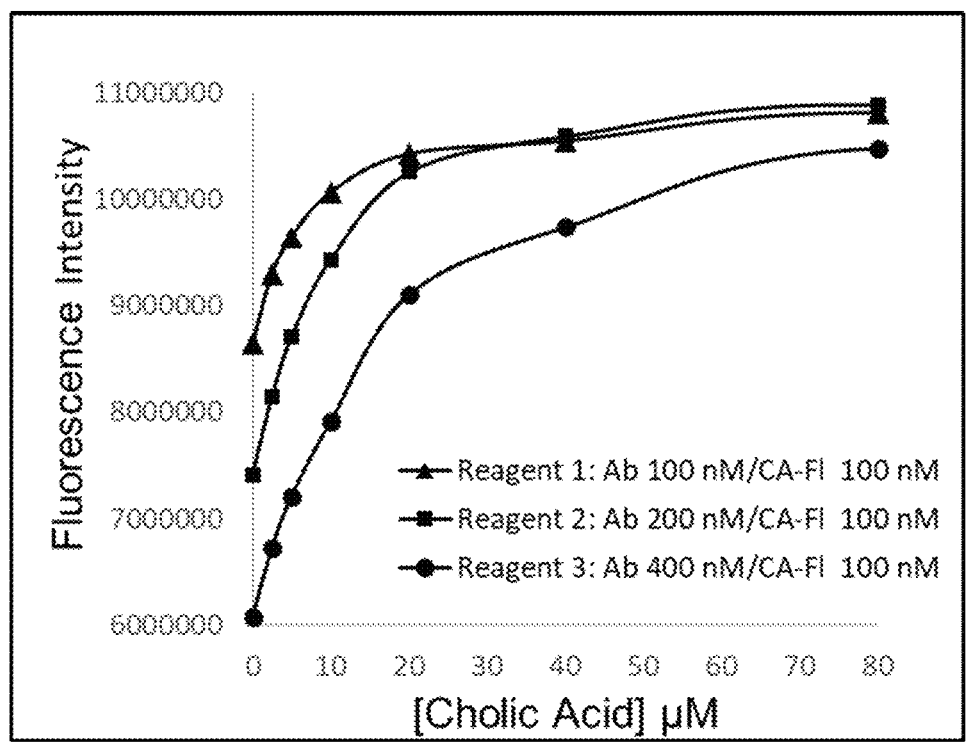
FIGS. 34A and B are plots of fluorescent intensity vs cholic acid concentration when cholic acid (FIG. 34A) or taurocholic acid (FIG. 34B) is added to a solution of CA-Fl and β-Cholic Acid antibody in PBS as described in Example 40.
Figure 34B:
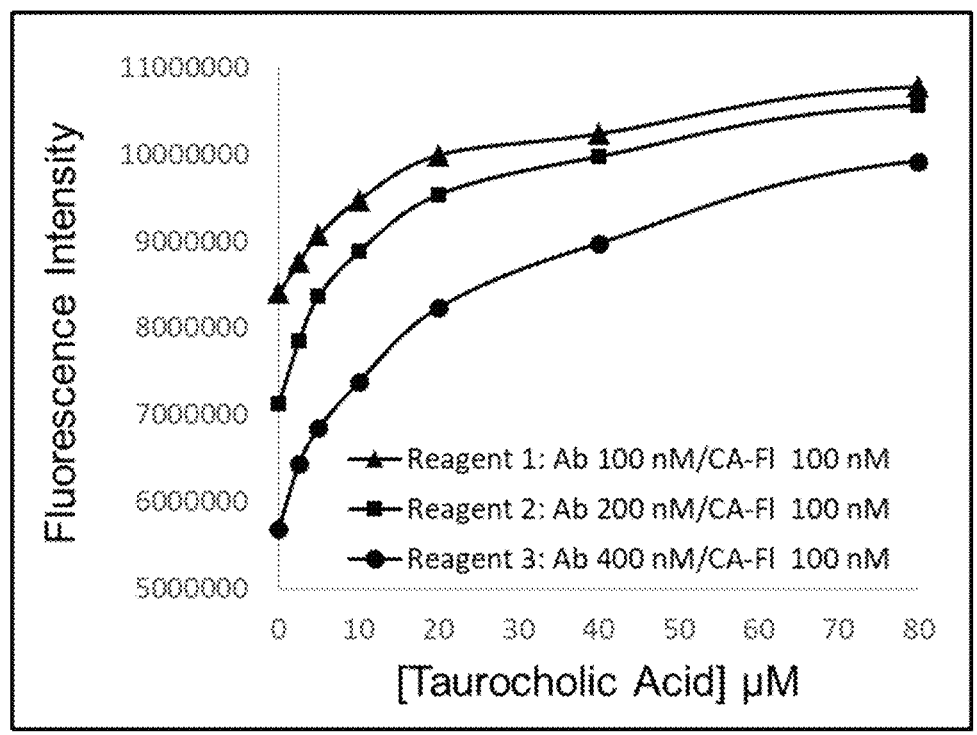

Bile acid (cholic acid or taurocholic acid) standard solutions at concentrations ranging from 0 to 80 μM were prepared in PBS (with 0.1% tween 20). Each bile acid standard solution (5 μl) was then added to a Reagent 1, 2, or 3 (95 μl) in a 96-well assay plate, and the resulting solution incubated for 30 min at room temperature with gentle shaking. Fluorescence intensities were then measured using an excitation wavelength of 490 nm and an emission wavelength of 520 nm. The results are shown in FIG. 34A (cholic acid) and FIG. 34B (taurocholic acid). FIGS. 34A and 34B depict the recovery of fluorescence as a function of bile acid concentration. The results show that reagent 3, which has an antibody: CA-Fl ratio of 4:1, exhibits the broadest dynamic range for bile acid in PBS at concentrations ranging from 0 to 80 μM.

Example 42

Fluorescence Quenching of CA-Fl with Anti-Cholic Acid Antibody as a Function of Bile Acid Concentration in Serum Charcoal stripped canine serum was adjusted to a pH of 7.3 with a phosphate buffer. The serum was then spiked with a bile acid (cholic acid or taurocholic acid) to provide bile acid concentrations ranging from between 0 to 40 μM.

A solution of CA-Fl in PBS (200 nM) was mixed with a solution of α-Cholic Acid antibody (400 nM) in a ratio of 1:1 (v/v) and incubated for 30 min at 4° C. to provide an assay reagent.

A solution of canine serum containing bile acid (5 μl) was then added to the assay reagent (95 μl) in a 96-well assay plate and the resulting mixture incubated for 30 min at room temperature with gentle shaking.

Figure 35A:
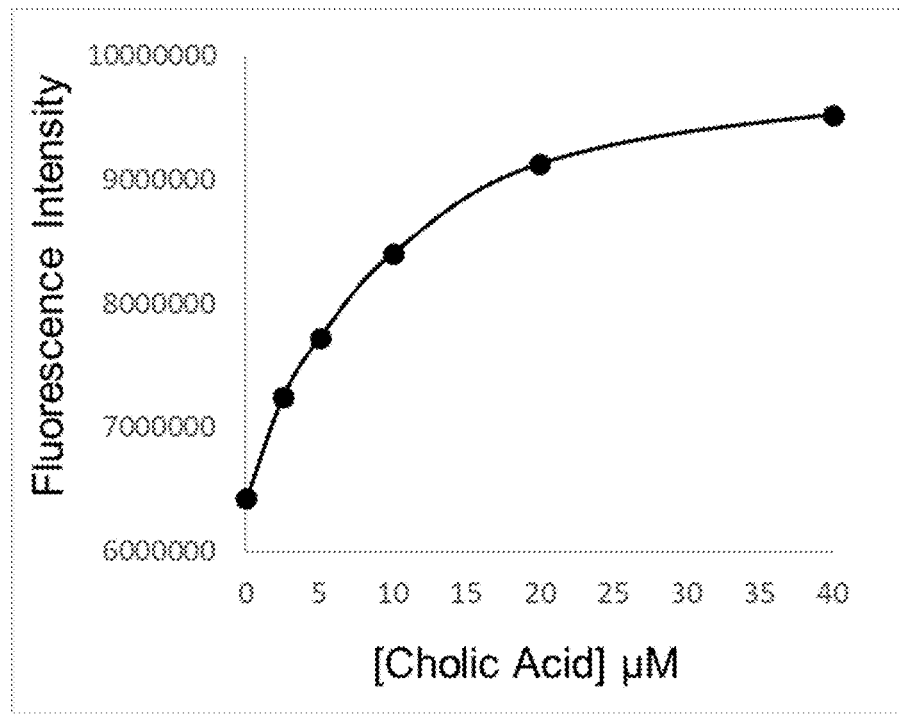
FIGS. 35A and B are plots of fluorescence of a solution of CA-Fl and α-Cholic Acid antibody containing different concentrations of cholic acid (FIG. 35A) or taurocholic acid (FIG. 35B) vs concentration of bile acid as described in Example 42.
Figure 35B:
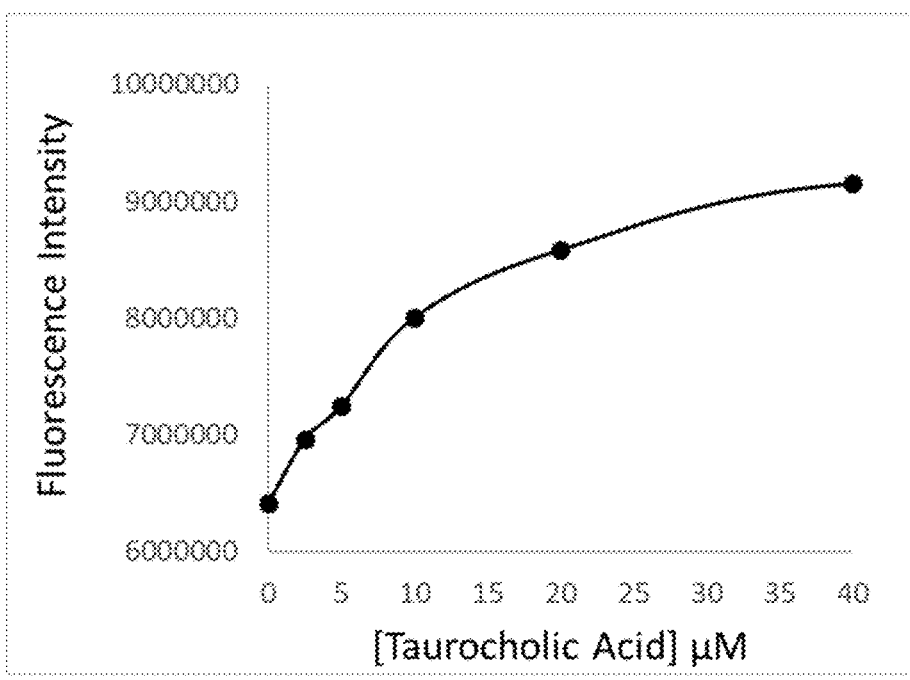

Fluorescence intensities were measured using an excitation wavelength of 490 nm and an emission wavelength of 520 nm. The results are shown in FIG. 35 for cholic acid (FIG. 35A) and taurocholic acid (FIG. 35B). FIGS. 35A and 35B depict the recovery of fluorescence as a function of the serum bile acid concentration. The results show that the assay for cholic acid and taurocholic acid in serum has a dynamic range of 0 to 40 μM.

Example 43

Synthesis of BHQ10-Labelled Cystatin-B (CysB): CysB-BHQ

Recombinant cystatin-B protein (4.0 mg) in PBS (1 mL) was mixed with 2.0 mg (8 eq, 204 uL of a 10 mg/mL stock) of BHQ10-NHS (the N-hydroxysuccinimide ester of BHQ10, commercially available from LGC Biosearch Technologies of Petaluma, CA) dissolved in DMSO (0.25 mL). The resulting solution was rotated end over end for 2 hours. The quencher-labeled protein was then purified by dialysis, against 3×4 L of PBS for a minimum of 2 hours for each exchange. A 10 kDa MWCO filter (G2 cassette available from Thermo Scientific of Waltham, MA) was used during the dialysis. The resulting product's protein concentration was determined using a BCA kit (commercially available from Thermo Scientific of Waltham, MA).

Example 44

Synthesis of Fluorescein-Labelled Anti-CysB (3114)-mAb, NHS Ester Route: AntiCysB-FL Monoclonal anti-CysB antibody (Anti-CysB (3H4)-mAb) (5 mg) in PBS (1 mL) was mixed with 0.025 mg (2 eq, 12.5 uL of a 2 mg/mL stock) of fluorescein-NHS (N-hydroxysuccinimide ester of fluorescein, commercially available from Sigma Aldrich of St. Louis, MO) dissolved in DMSO. The resulting solution was rotated end over end for 2 hours. The fluorescein-labeled antibody was then purified by dialysis, against 3×4 L of PBS for a minimum of 2 hours for each exchange. A 10 kDa MWCO filter (G2 cassette available from Thermo Scientific of Waltham, MA) was used during the dialysis. The resulting product's protein concentration was determined using a BCA kit (commercially available from Thermo Scientific of Waltham, MA).

Example 45

Synthesis of Fluorescein-Labelled Anti-CysB (3114)-mAb, Fluorescein Aldehyde Route: AntiCysB-FL-Ald Monoclonal anti-CysB antibody (Anti-CysB (3H4)-mAb) (5 mg) in PBS (1 mL) was mixed with 0.024 mg (2 eq) of fluorescein aldehyde dissolved in DMSO. To the resulting solution was added 0.02 mg (10 eq) of sodium cyanoborohydride dissolved in 1N NaOH. The mixture was rotated end over end for 2 hours. The fluorescein-labeled antibody was then purified by dialysis, against 3×4 L of PBS for a minimum of 2 hours for each exchange. A 10 kDa MWCO filter (G2 cassette available from Thermo Scientific of Waltham, MA) was used during the dialysis. The resulting product's protein concentration was determined using a BCA kit (commercially available from Thermo Scientific of Waltham, MA).

Example 46

Synthesis of BODIPY-Labelled Anti-CysB (3H4)-MAb: AntiCysB-BODIPY

Monoclonal anti-CysB antibody (Anti-CysB (3H4)-mAb) (5 mg) in PBS (1 mL) was mixed with 0.026 mg (2 eq) of BODIPY-NHS (commercially available from Thermo Scientific of Waltham, MA) dissolved in DMSO. The resulting solution was rotated end over end for 2 hours. The fluorescein-labeled antibody was then purified by dialysis, against 3×4 L of PBS for a minimum of 2 hours for each exchange. A 10 kDa MWCO filter (G2 cassette available from Thermo Scientific of Waltham, MA) was used during the dialysis. The resulting product's protein concentration was determined using a BCA kit (commercially available from Thermo Scientific of Waltham, MA).

Example 47

96-Well Plate Quenching and Dose Response Assay for CysB

The following example uses CysB-BHQ prepared as described in Example 41 and anti-CysB-FL prepared as described in Example 42.
1. Diluted BHQ—and fluorescein—conjugates, 10× from stock solution into PBS, pH=7.4, containing 1% BSA with 0.005% Tween 20 to make intermediate stock solutions.
2. Diluted the intermediate stock solutions to 4× working concentration in PBS, pH=7.4 containing 1% BSA with 0.005% Tween 20. [AntiCysB-FL]=400 nM and [CysB-BHQ]=800 nM.
3. Added 50 uL of CysB-BHQ solution and 50 uL of AntCysB-FL solution to the wells of a 96-well, black-bottom plate. The 96 well plate was shaken gently for 30 seconds, incubated at room temperature for 5 minutes, and read on a plate reader at 37° C. Final [AntiCysB-FL]=200 nM, final [CysB-BHQ]=200 nM; Excitation wavelength: 470 nm, and Emission wavelength: 520 nm.
4. Added 100 uL of 2× working solution of CysB recombinant standard (PBS, pH=7.4) at different concentrations to the wells. The 96 well plate is then shaken gently for 30 seconds, incubated for 30 minutes at 37° C., and the fluorescence measured. Final [AntiCysB-FL]=100 nM, [CysB-BHQ]=200 nM, [CysB]=0, 0.25, 0.5, 1, 2, 5 ug/mL. Excitation wavelength: 470 nm, Emission wavelength: 520 nm.

Figure 36:
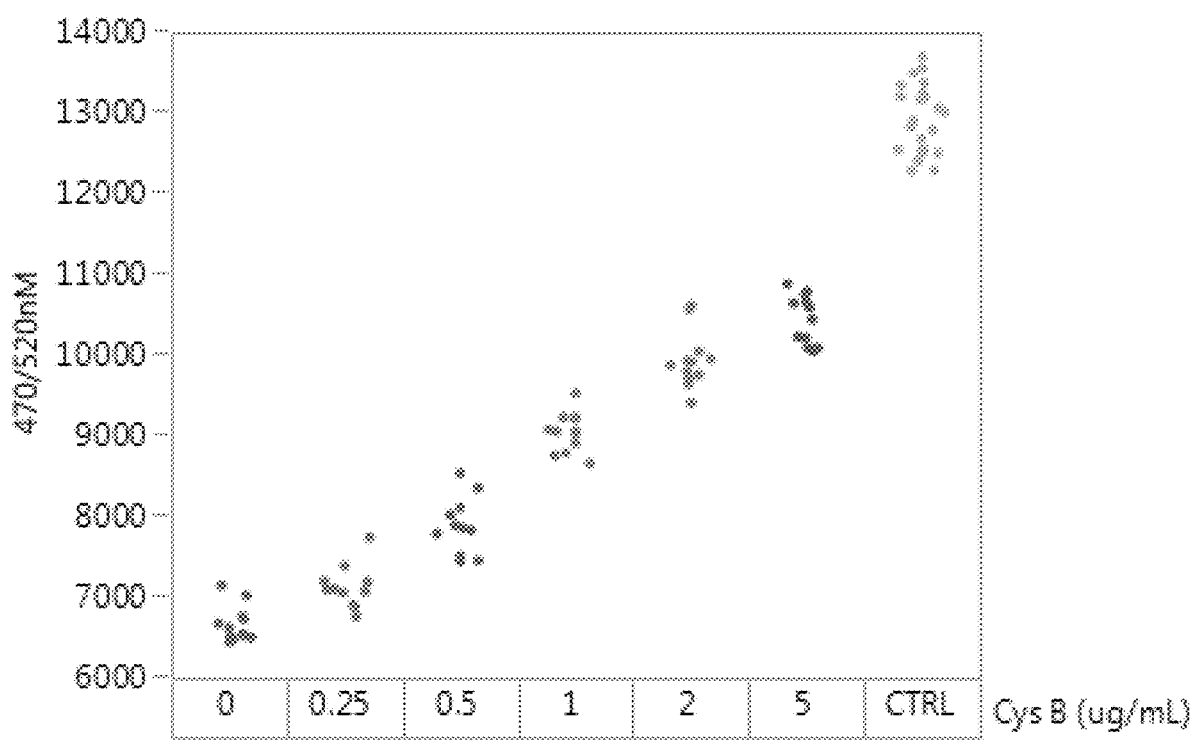
FIG. 36 is a plot of fluorescence intensity ($\lambda_{ex}=470_{nm}$, $\lambda_{em}=520$ nm) vs. CysB concentration (µg/mL) as described in Example 47.

FIG. 36 is a plot of fluorescence intensity ($\lambda ex=470_{nm}$, $\lambda_{em}=520$ nm) vs. CysB concentration (µg/mL). FIG. 36 shows the recovery of fluorescence as a function of the CysB concentration and illustrates that the assay can be used to measure CysB concentration in a sample. The assay has sensitivity down to 125 ng/mL and covers the clinically relevant range. The maximum recovery of fluorescence signal was 75% of the unbound AntiCysB-FL fluorescence"

Example 48

Catalyst Slide Dose Response Studies

A slide was prepared by the following procedure:
1. A mixture of CysB-BHQ (1600 nM), prepared as described in Example 41, and AntiCysB-FL (800 nM), prepared as described in Example 42, or AntiCysB-BODIPY (800 nM), prepared as described in Example 44, in PBS, pH=7.4, containing 1% BSA with 0.005% Tween 20, was spotted (12 uL) on a 7 mm diameter Fusion 5 membrane mounted on a plastic slide housing.
2. The spotted slides were dried at 40° C. for 30 minutes, protected from light.
3. The slides were then cooled to room temperature and loaded into a Catalyst Dx instrument (commercially available from IDEXX Laboratories of Portland, ME).
4. Serum samples were spiked with 0, 250, 500, 1000, and 2000 ng/mL recombinant CysB protein and loaded into the Catalyst Dx instrument.
5. Sample was then dispensed onto the slide (10 uL), and the fluorescence intensity measured over time.

Figure 37:
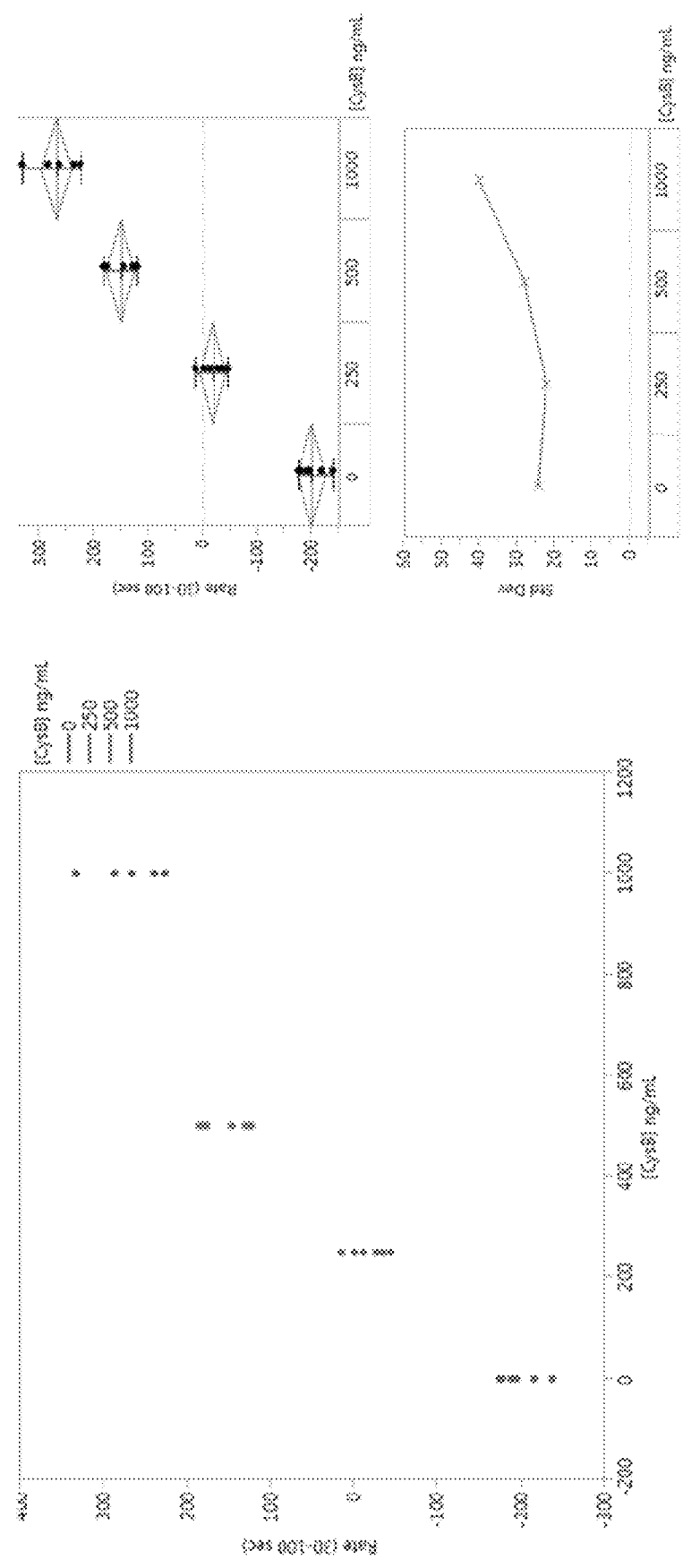
FIG. 37 is a plot of the rate of increase of fluorescence intensity (as measured over the time interval 30-100 sec) versus concentration of CysB in a dried slide format as described in Example 48.

FIG. 37 is a plot of the rate of increase of fluorescence intensity (as measured over the time interval 30-100 sec) versus concentration of CysB in a dried slide format. These results show that the AntiCysB-FL/CysB-BHQ immunocomplex remains intact after drying on a solid support and is able to generate a dose response in the clinically relevant range upon addition of sample to the dried slide.

Example 49

Synthesis of Fluorescein-Labelled Cystatin-B Conjugated to FL Through Lysine Residues Recombinant cystatin-B protein (4.0 mg) in PBS (1 mL) was mixed with 0.34 mg (2 eq, 17 uL of a 20 mg/mL stock) of Fluorescein-NHS (commercially available from Sigma Aldrich) dissolved in DMSO. The resulting solution was rotated end over end for 2 hours. The fluorescein-labeled CysB (lysine modified) was then purified by dialysis, against 3×4 L of PBS for a minimum of 2 hours for each exchange. A 10 kDa MWCO filter (G2 cassette available from Thermo Scientific of Waltham, MA) was used during the dialysis. The resulting product's protein concentration was determined using a BCA kit (commercially available from Thermo Scientific of Waltham, MA).

Example 50

Synthesis of Fluorescein-Labelled Cystatin-B Conjugated to FLT Through Cysteine Residues To recombinant cystatin-B protein (4.0 mg) in PBS (1 mL) was added 10 uL of 0.5 M EDTA (commercially available from Alfa Aesar of Haverhill, MA) to provide a final concentration of 5 mM EDTA. The resulting solution was added to 0.5 mL of TCEP-bound resin (commercially available from Thermofisher Scientific of Waltham, MA) in a centrifuge tube containing a 0.2 um filter, and allowed to rotate end over end at room temperature for 2 hours. The reaction mixture was then centrifuged briefly at 8,000 rpm for 1 minute. The flow through was collected to yield the reduced CysB (containing 1 activated cysteine residue) at a concentration of 4 mg/mL. This activated CysB was mixed with 0.31 mg (2 eq, 15 uL of a 20 mg/mL stock) of Fluorescein-maleimide (commercially available from Sigma Aldrich of St. Louis, MO) dissolved in DMSO. The resulting solution was rotated end over end for 2 hours. The fluorescein-labeled CysB (cysteine-modified) was then purified by dialysis, against 3×4 L of PBS for a minimum of 2 hours for each exchange. A 10 kDa MWCO filter (G2 cassette available from Thermo Scientific of Waltham, MA) was used during the dialysis. The resulting product's protein concentration was determined using a BCA kit (commercially available from Thermo Scientific of Waltham, MA).

Example 51

CysB Peptide-Fluorophore Conjugates

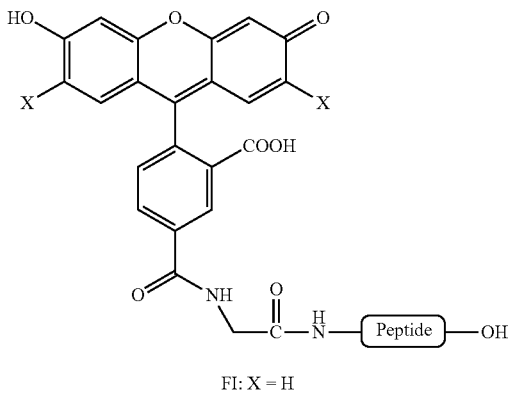

Fl: X = H
DFF: X = F
Peptide Conjugated at 5-Position of Fluorescein

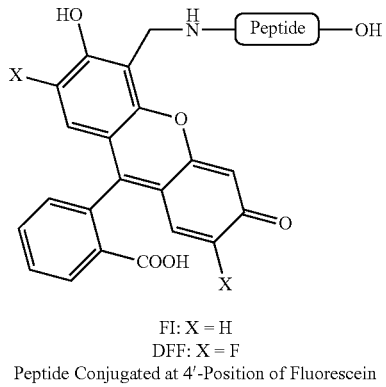

Fl: X = H
DFF: X = F
Peptide Conjugated at 4'-Position of Fluorescein

Canine CysB Sequences
Canine Cystatin-B, full-length:

[SEQ ID NO: 1]
MMCGAPSASQPATADTQAIADQVKAQLEERENKKYTTFKAVTFRSQVVAG
TPYFIKVQVDDDEFVHLRVFQSLPHENKPLALSSYQTNKAKHDELAYF

[SEQ ID NO: 2]
P9: QTNKAKHDELAYF

[SEQ ID NO: 3]
P14: YQTNKAKHDELAYF

[SEQ ID NO: 4]
P7: GHDELAYF

[SEQ ID NO: 5]
P6: GDELAYF

[SEQ ID NO: 6]
P5: GELAYF

[SEQ ID NO: 7]
P4: GLAYF

Preparation of Canine CysB Peptide-Fl Conjugates Conjugated at the 5-Position

CysB Peptides P7, P6, P5, and P4 were each conjugated to the 5-position of fluorescein as follows: CysB Peptide P6 with an amino acid sequence of GDELAYF [SEQ ID NO: 6] (15 mg, 0.0184 mmol, custom synthesized by GenScript of Piscataway, NJ), 5-carboxyfluorescein succinimidyl ester (9.2 mg, 0.0194 mmol, commercially available from Thermo Fisher of Waltham, MA), and N'N-diisopropylethylamine (9.67 µl, 0.055 mmol) were dissolved in anhydrous DMF (0.5 ml). The resulting mixture was stirred overnight at room temperature and then diluted in 1 ml of 30% ACN in water (containing 0.1% formic acid) and purified by column chromatography using a C18 reverse phase column (5 g) that was eluted with a gradient of 30% to 100% acetonitrile in water on a Biotage Isolera™ purification system. The fractions were collected automatically by monitoring the absorption at both 257 nm and 470 nm. The fractions with absorption at 470 nm were analyzed by LCMS to identify the fractions containing the target peptide P6-Fl conjugate and the desired fractions were combined and lyophilized to provide a final yellow, solid product confirmed by LCMS (M+1=1172).

CysB Peptides P7, P5, and P4 conjugates to fluorescein at the 5-position were synthesized using substantially the same synthetic and purification procedures as described above for CysB Peptide P6. The final conjugates were characterized by LCMS as: GHDELAYF, P7-Fl, LCMS (M+1=1309); GELAYF, P5-Fl, LCMS (M+1=1057); GLAYF, P4-Fl, LCMS (M+1=928).

Preparation of Canine CysB Peptide-DFF Conjugates Conjugated at the 5-Position

CysB Peptides P7, P6, P5, and P4 were each conjugated to the 5-position of DFF as follows: CysB peptide P6 with an amino acid sequence of GDELAYF [SEQ ID NO: 6] (4.2 mg, 0.0052 mmol, custom synthesized by GenScript of Piscataway, NJ), 5-difluorocarboxyfluorescein succinimidyl ester (2.5 mg, 0.0049 mmol, commercially available from ATT Bioquest of Sunnyvale, CA), and N'N-diisopropylethylamine (4.29 µl, 0.0245 mmol) were dissolved in anhydrous DMF (0.5 ml. The resulting mixture was stirred overnight at room temperature and then diluted in 1 ml of 30% ACN in water (containing 0.1% formic acid) and purified by column chromatography using a C18 reverse phase column (5 g) that was eluted with a gradient of 30% to 100% acetonitrile in water on a Biotage Isolera™ purification system. The fractions were collected automatically by monitoring the absorption at both 257 nm and 470 nm. The fractions with an absorption at 470 nm were analyzed by LCMS to identify the fractions containing the target peptide P6-DFF conjugate and the desired fractions were combined and lyophilized to provide final a yellow, solid product confirmed by LCMS (M+1=1208). Conjugates of CysB Peptides P7, P5, and P4 with DFF at the 5-position were synthesized using substantially the same synthetic and purification procedures and appropriate starting materials as described for CysB Peptide P6 above. The final conjugates were characterized by LCMS as: GHDELAYF, P7-DFF,

LCMS (M+1=1345); GELAYF, P5-DFF, LCMS (M+1=1093); GLAYF, P4-DFF, LCMS (M+1=964).

Preparation of Canine CysB Peptide-4-Fl Conjugates Conjugated at the 4'-Position CysB Peptides P6, P5, and P4 were each conjugated to the 4'-position of fluorescein as follows: In a 2 mL glass vial containing 1 mL of methanol was added fluorescein aldehyde (2.21 mg, 0.0061 mmol), CysB peptide P6 (5 mg, 0.0061 mmol) (custom synthesized by GenScript of Piscataway, NJ), and potassium carbonate (4.25 mg, 0.0307 mmol) and the resulting solution allowed to stir at room temperature for 1 hour. Sodium cyanoborohydride (0.77 mg, 0.0123 mmol) was then added to the solution and the resulting mixture stirred overnight at room temperature in the dark. The resulting crude product was diluted in 1 ml of 30% ACN in water (containing 0.1% formic acid) and purified by column chromatography using a C18 reverse phase column (5 g) that was eluted with a gradient of 30% to 100% acetonitrile in water on a Biotage Isolera™ purification system. The fractions were collected automatically by monitoring the absorption both at 257 nm and 470 nm. The fractions with an absorption at 470 nm were analyzed by LCMS and the fractions containing the target peptide P6-4-Fl conjugate were combined and lyophilized to provide a final yellow, solid product confirmed by LCMS (M+1=1158). Conjugates of CysB Peptides P5 and P4 with fluorescein at the 4'-position were synthesized using substantially the same synthetic and purification procedures as described above for CysB Peptide P6. The final conjugates were characterized by LCMS GELAYF, P5-4-Fl, LCMS (M+1=1043); GLAYF, P4-4-Fl, LCMS (M+1=914).

Preparation of Canine CysB Peptide-4-DFF Conjugate Conjugated at the 4'-Position CysB Peptides P6, P5, and P4 were each conjugated to the 4'-position of DFF as follows: In a 2 mL glass vial containing 1 mL of methanol was added difluorofluorescein aldehyde (2.43 mg, 0.0061 mmol), CysB peptide P6 (5 mg, 0.0061 mmol) (custom synthesized by GenScript of Piscataway, NJ), and potassium carbonate (4.25 mg, 0.0307 mmol) and the resulting solution allowed to stir at room temperature for 1 hour. Sodium cyanoborohydride (0.77 mg, 0.0123 mmol) was then added to the solution and the resulting mixture stirred overnight at room temperature in the dark. The resulting crude product was diluted in 1 ml of 30% ACN in water (containing 0.1% formic acid) and purified by column chromatography using a C18 reverse phase column (5 g) that was eluted with a gradient of 30% to 100% acetonitrile in water on a Biotage Isolera™ purification system. The fractions were collected automatically by monitoring the absorption at both 257 nm and 470 nm. The fractions with an absorption at 470 nm were analyzed by LCMS and the fractions containing the target peptide P6-4-DFF conjugate were combined and lyophilized to provide final a yellow, solid product, confirmed by LCMS (M+1=1194). Conjugates of CysB Peptides P5 and P4 with DFF at the 4'-position were synthesized using substantially the same synthetic and purification procedures and appropriate starting materials as described for CysB Peptide P6 above. The final conjugates were characterized by LCMS as: GELAYF, P5-4-DFF, LCMS (M+1=1079); GLAYF, P4-4-DFF, LCMS (M+1=950).

Fluorescence Quenching of Canine CysB P6-Fl and P6-DFF by Anti-CysB Mab or Anti-CysB Mab-BHQ10

CysB peptide-fluorescein (Fl) or -difluorofluorescein (DFF) conjugates were dissolved in DMSO (0.5 mM) and diluted with Tris Buffer (50 nM at pH8.0) to provide a stock solution (100 nM). Monoclonal anti-CysB antibody (7C2, raised against a peptide having the amino acid sequence of SEQ ID NO: 14) (8 mg/ml) was serially diluted in PBS buffer to provide solutions having an Anti-CysB-Mab concentration ranging from 0 to 800 nM in Tris buffer (50 mM at pH 8.0 with 0.5% sarkosyl (sodium lauroyl sarcosinate)). In a 96-well black assay plate containing the serially diluted Anti-CysB-Mab solution (50 µL) was added the peptide-Fl or peptide-DFF solution (50 µL), mixed well, incubated for 30 min and the fluorescence intensities recorded. The results are provided in FIG. 38, 39, 40, and Table 1.

Figure 38:
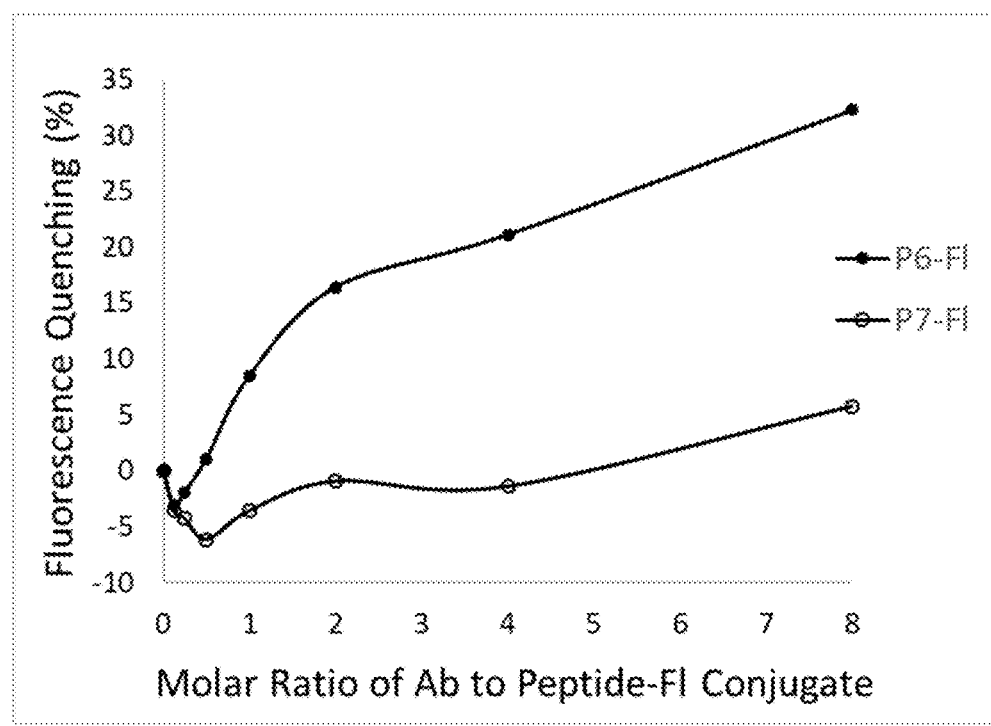
FIG. 38 is a plot of percent fluorescence quenching against the ratio of anti-CysB antibody to CysB peptide P6-Fl and against the ratio of antibody to P7-Fl and as described in Example 51.
Figure 39:
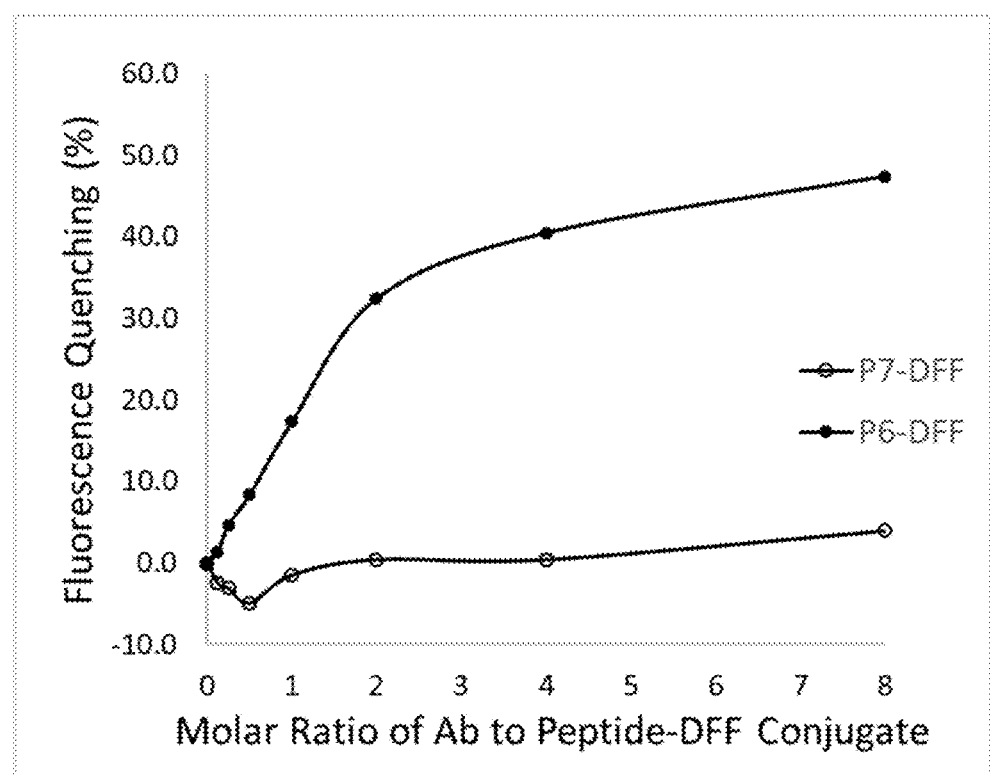
FIG. 39 is a plot of percent fluorescence quenching against the ratio of anti-CysB antibody to CysB peptide P6-DFF and against the ratio of antibody to P7-DFF and as described in Example 51.
Figure 40:
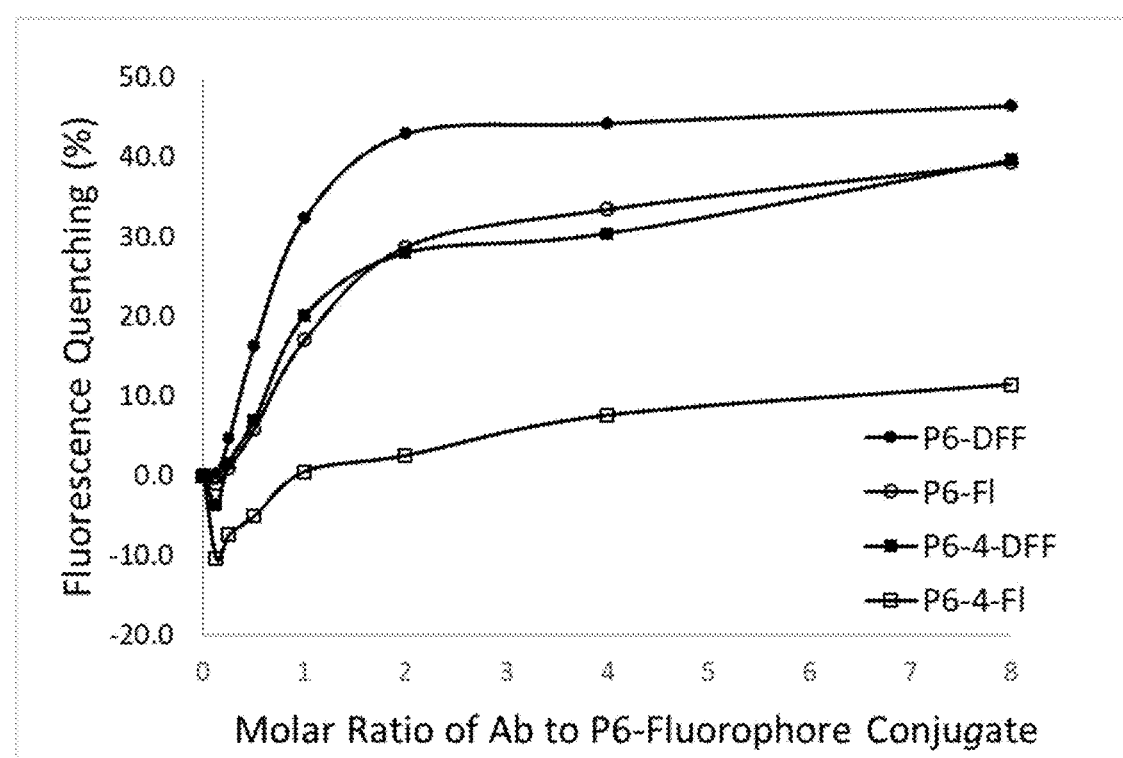
FIG. 40 is a plot of percent fluorescence quenching against the ratio of anti-CysB antibody to CysB peptide P6-Fl or P6-DFF and against the ratio of antibody to P6-4-Fl or P-4-DFF and as described in Example 52.
Figure 41:
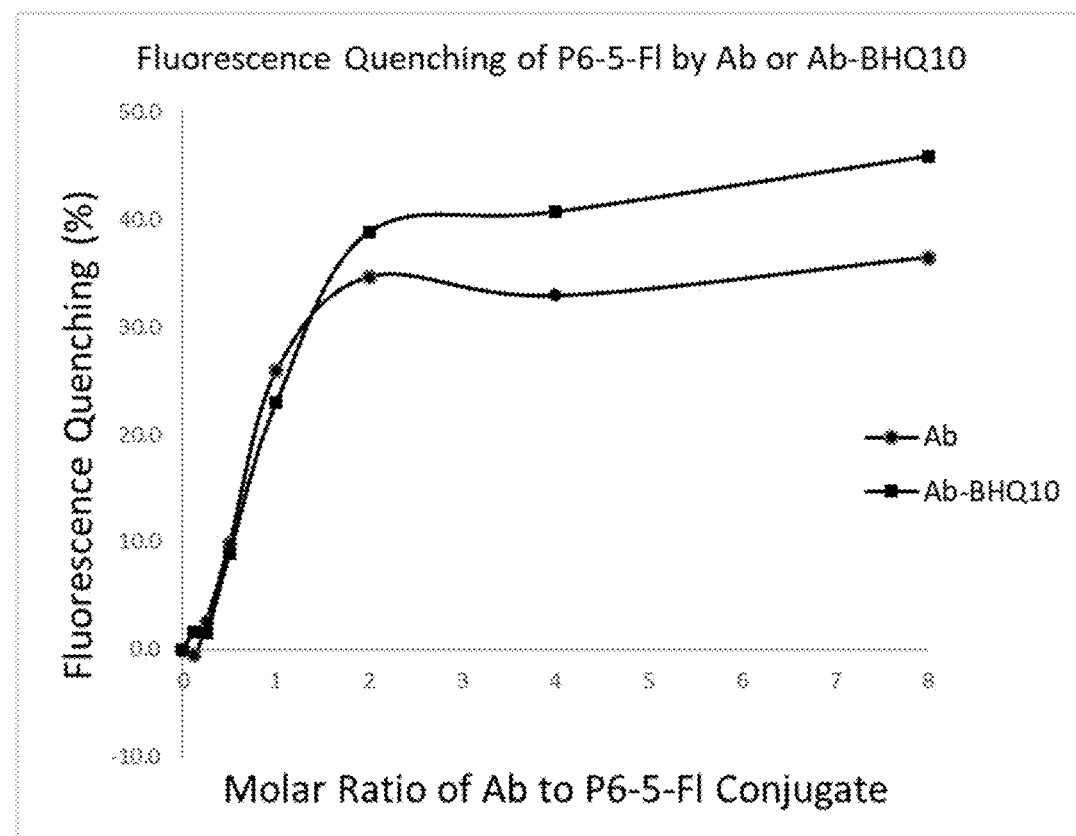
FIG. 41 is a plot of percent fluorescence quenching against the ratio of anti-CysB antibody (Ab) to CysB peptide P6-Fl and against the ratio of antibody-BHQ10 (Ab-BHQ10) to P6-Fl.
Figure 42:
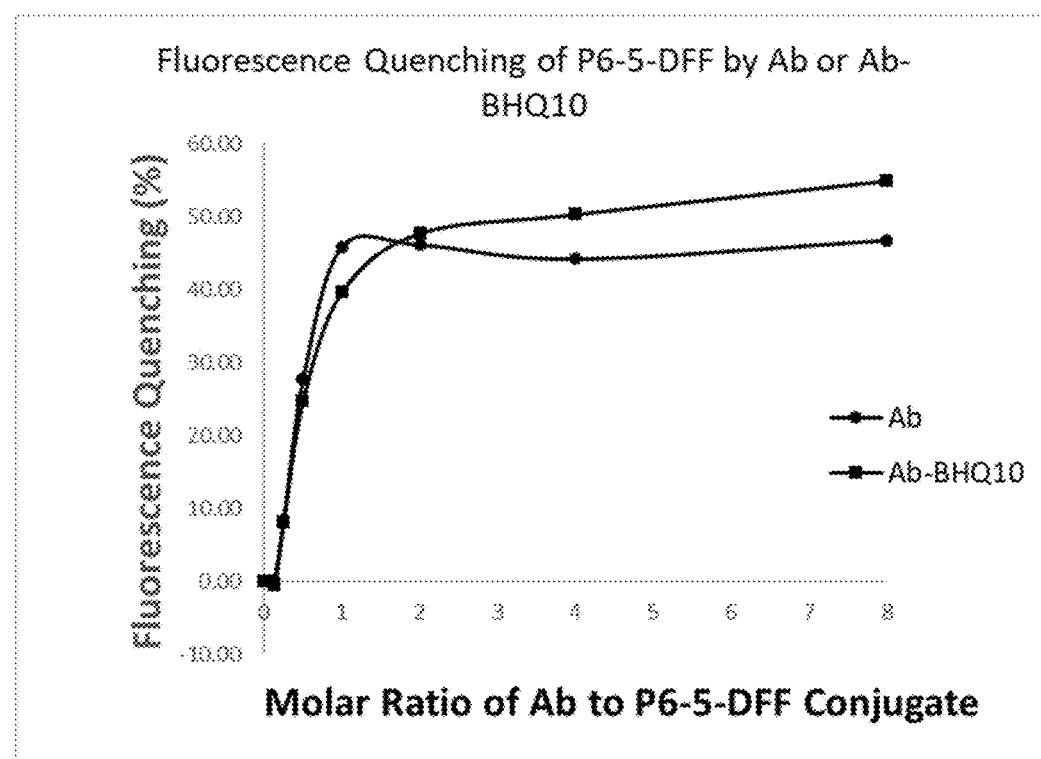
FIG. 42 is a plot of percent fluorescence quenching against the ratio of anti-CysB antibody to CysB peptide P6-DFF and against the ratio of antibody-BHQ10(Ab-BHQ10) to P6-DFF.

FIG. 38 shows that the fluorescence of P6-Fl was quenched in the presence of anti-CysB-Mab while weaker quenching for P7-Fl was observed. High quenching (~30%) was observed at a molar ratio of antibody to P6-Fl of about 8:1. FIG. 39 shows that fluorescence of P6-DFF was quenched in the presence of anti-CysB-Mab. Maximum quenching (~45%) was observed at a molar ratio of antibody to P7-Fl of about 4:1. FIG. 40 shows that the fluorescence of P6-Fl was quenched in the presence of anti-CysB Mab-BHQ10. Quenching in the presence of anti-CysB Mab-BHQ10 was slightly higher than that observed with unmodified mAb. Similar results are shown in FIG. 41 and FIG. 42 for P6-DFF in the presence of Ab-BHQ10.

The tracers of CysB peptide P6, P5, and P4 were conjugated to the 4'-position of fluorescein (Fl) or difluorofluorescein (DFF). The fluorescence quenching of the other CysB peptide-fluorophore conjugates by anti-CysB Mab is summarized in Table 1.

As shown in Table 1, fluorescence quenching of the peptide-Fl or DFF conjugated at the 4'-position of the fluorophore was observed when anti-CysB mAb was added. Generally, quenching of peptides conjugated at the 4'-position of the fluorophore was lower than that of peptides conjugated at the 5-position of the fluorophore, except for P5-Fl, which showed higher quenching with the 4' conjugated fluorescein.

TABLE 1

Percentage Fluorescence Quenching of CysB Peptide Fluorescein-Conjugates by Anti-CysB mAb (7C2) at Ab/Conjugate ratio = 2/1

| Peptide | F1 Conjugate | | DFF Conjugate | |
| --- | --- | --- | --- | --- |
| | At 5-Position | At 4'-Postion | At 5-Position | At 4'-Postion |
| P7 | 5% | — | 5% | — |
| P6 | 34% | 9.0% | 45% | 34% |
| P5 | 6.0% | 26.3% | 6.3% | 3.0% |
| P4 | 30% | 17.3% | 9.5% | 2% |

Peptide/Full Length Canine CysB Protein Dose Response in Tris Buffer and Serum

A mixture of CysB P6-Fl or P6-DFF in Tris buffer with 0.1% Tween 20 (200 nM, 25 µL) and anti-Cys-Mab in Tris buffer with 0.1% Tween 20 (400 nM, 25 µL) was incubated at room temperature for 30 min in the wells of a 96 well black assay plate. A series of CysB peptides P6, P7, and P14 standard solutions having peptide concentrations ranging from 0 to 3200 nM (50 µL) were then added to the mixtures of the P6-Fl or P6-DFF and anti-CysB Mab in Tris Buffer. The plate was then incubated for 30 min at room temperature and the fluorescence intensities recorded at an excitation of 485 nm and an emission of 520 nm. The results are shown in FIG. 43, FIG. 44, FIG. 45, and FIG. 46.

Figure 43:
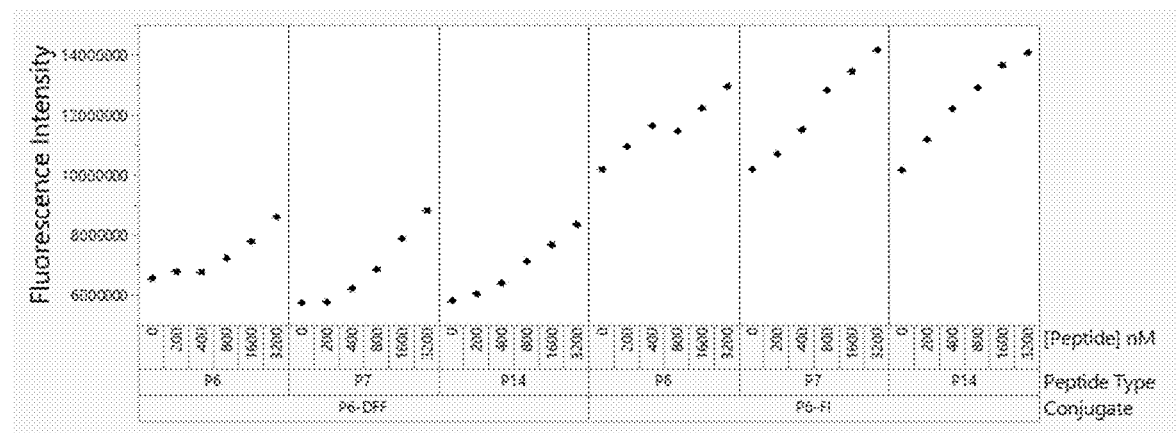
FIG. 43 is a plot of percent fluorescent recovery when CysB peptide P6, P7, or P14 is added to a solution of P6-Fl and anti-CysB antibody, or a solution of P6-DFF and anti-CysB antibody, as a function of the P6, P7 or P14 concentration as described in Example 51.
Figure 44A:
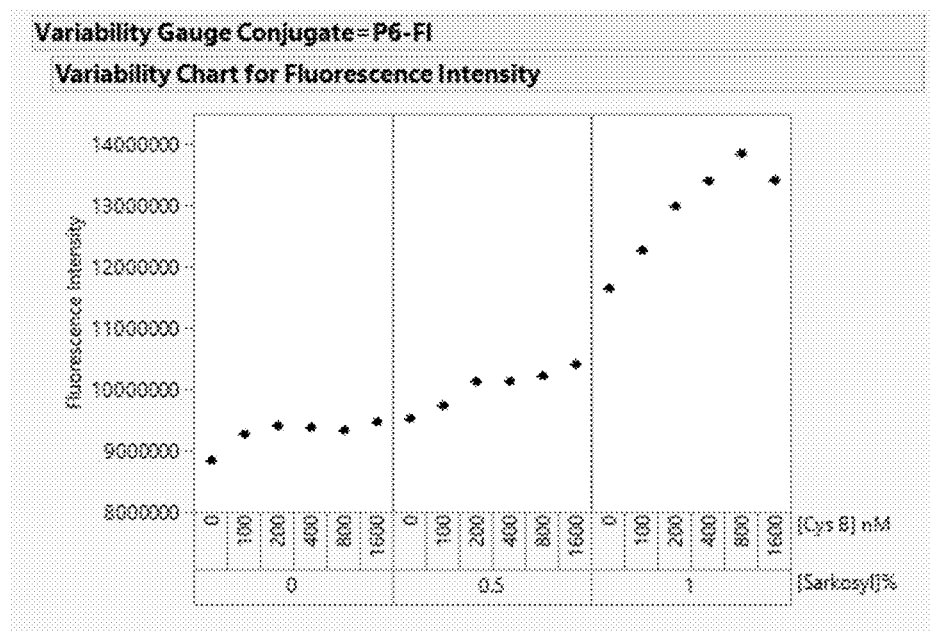
FIGS. 44A and B are plots of percent fluorescent recovery when CysB full length protein is added to a solution of P6-Fl and anti-CysB antibody (FIG. 44A), or a solution of P6-DFF and anti-CysB antibody (FIG. 44B), in the presence of detergent sarkosyl as a function of the CysB protein concentration as described in Example 51.
Figure 44B:
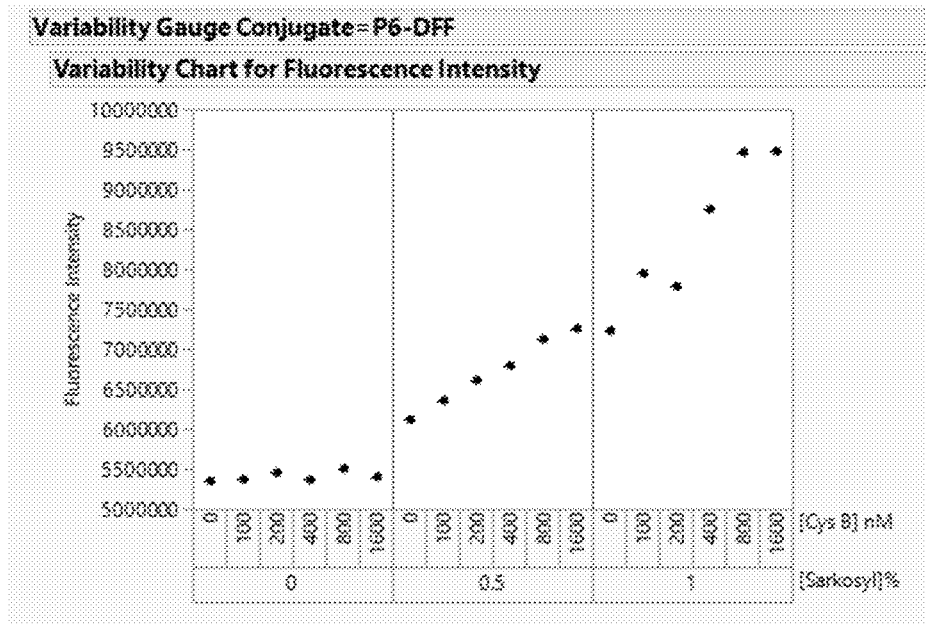
Figure 45:
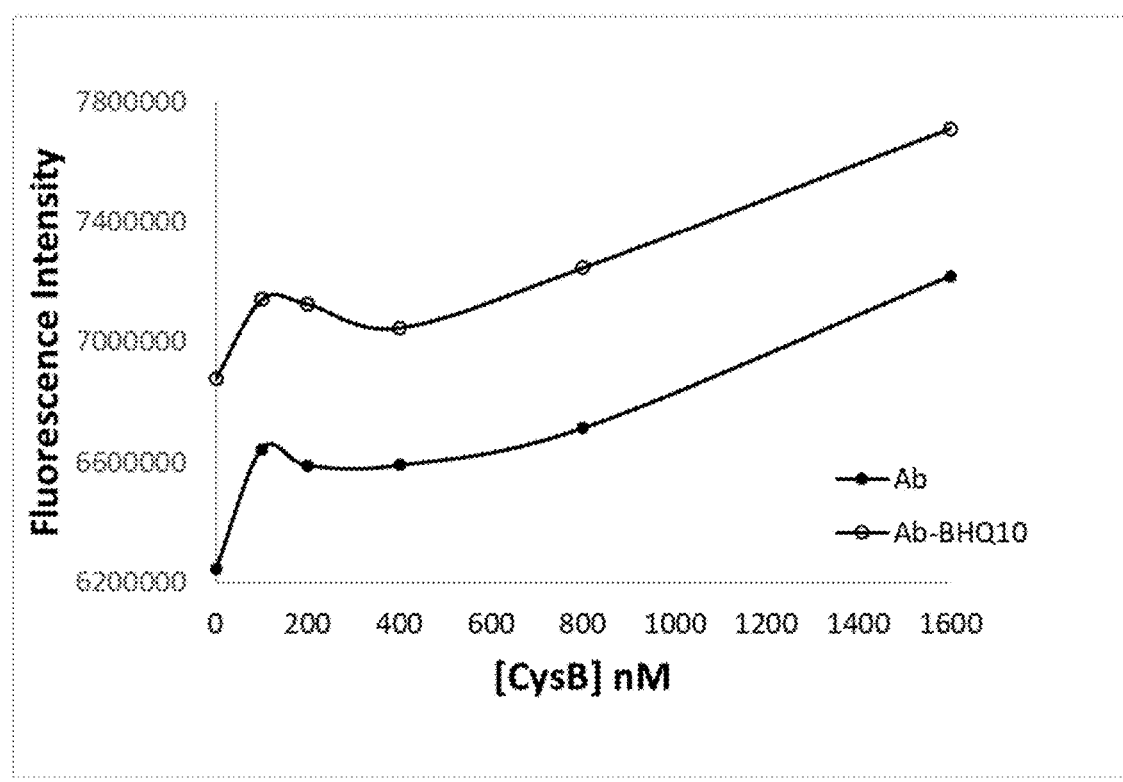
FIG. 45 is a plot of percent fluorescent recovery when CysB full length protein spiked into serum is added to a solution of P6-Fl and anti-CysB antibody (Ab), or a solution of P6-Fl and anti-CysB Antibody conjugated to BHQ10 (Ab-BHQ10), in the presence of the detergent sarkosyl as a function of the CysB protein concentration as described in Example 51.
Figure 46:
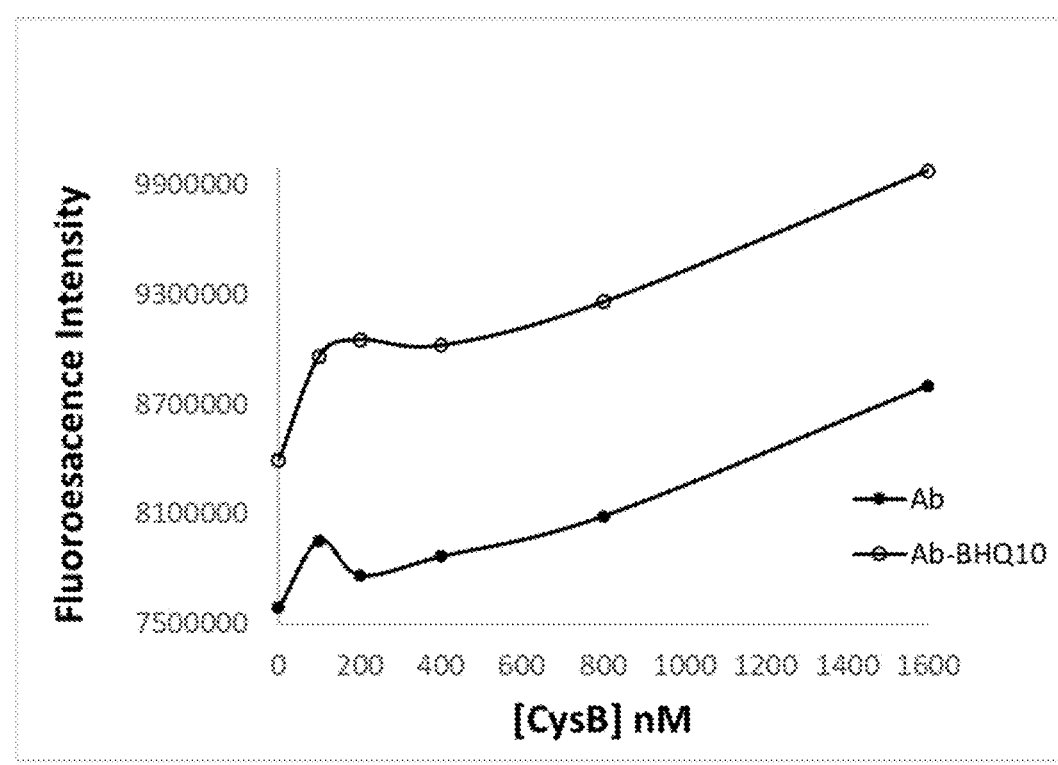
FIG. 46 is a plot of percent fluorescent recovery when CysB full length protein spiked into serum is added to a solution of P6-DFF and anti-CysB antibody (Ab), or a solution of P6-DFF and anti-CysB Antibody conjugated to BHQ10 (Ab-BHQ10), in the presence of detergent sarkosyl as a function of the CysB protein concentration as described in Example 51.

FIG. 43 shows that there is an increase in fluorescence intensity as a function of increasing concentration of CysB peptide P6, P7, or P14, i.e., a dose response was observed when each of these peptides was added to a mixture of antibody and P6-Fl or P6-DFF. FIG. 44 shows an increase of fluorescence intensity as a function of increasing concentration of CysB full length protein, i.e., a dose response was observed when this protein was added to a mixture of antibody and P6-Fl (FIG. 44A) or P1-DFF (FIG. 44B) in the presence of varying concentrations of sarkosyl. The magnitude of the dose response increased with increasing concentrations of sarkosyl. A dose response was also observed when CysB full length protein in serum was added to a mixture of antibody or antibody-BHQ10 with P6-Fl (FIG. 45) or P6-DFF (FIG. 46) in the presence of the detergent sarkosyl (1%).

Example 52

Canine NT-ProBNP Peptide Conjugates

Canine NT-ProBNP Sequences:

```
P1:    AEQLALEPLHRS    [SEQ ID NO: 8]

P2:    AEQLAL          [SEQ ID NO: 9]

P3:    EPLHRS          [SEQ ID NO: 10]

P4:    LALEPL          [SEQ ID NO: 11]

P5:    AEQLALE         [SEQ ID NO: 12]

P6:    LEPLHRS         [SEQ ID NO: 13]
```

Canine NT-proPNP, full length:

```
                                              [SEQ ID NO: 14]
HPLGGRSPASEASEASEASGLWAVQELLGRLKDAVSELQAEQLALEPLHR

SHSPAEAPEAGGTPRGVLAPHDSVLQALR
```

Canine NT-proPNP stable epitope:

```
GRSPASEASEASEASGLWAVQ    [SEQ ID NO: 15]
```

Canine NT-proPNP, stable epitope 2:

```
SHSPAEAPEAGGTPRGVLAPHDSVLQ    [SEQ ID NO: 16]
```

Preparation of Canine NT-ProBNP Peptide-Fl Conjugates Conjugated at the 5-Position NT-proBNP peptide P1 with an amino acid sequence of AEQLALEPLHRS [SEQ ID NO: 8] (3.02 mg, 0.0022 mmol, custom synthesized by GenScript of Piscataway, NJ), 5-carboxyfluorescein succinimidyl ester (1 mg, 0.0021 mmol, commercially available from Thermo Fisher of Waltham, MA), and N'N-diisopropylethylamine (1.6 µl, 0.0089 mmol) were dissolved in anhydrous DMSO (0.5 ml). The resulting mixture was stirred overnight at room temperature and then diluted in 1 ml of 30% ACN in water (containing 0.1% formic acid) and purified by column chromatography using a C18 reverse phase column (5 g) that was eluted with a gradient of 30% to 100% acetonitrile in water on a Biotage Isolera™ purification system. The fractions were collected automatically by monitoring the absorption at both 257 nm and 470 nm. The fractions with an absorption at 470 nm were analyzed by LCMS and the fractions containing the target peptide P1-Fl conjugate were combined and lyophilized to provide a final yellow, solid product confirmed by LCMS (M2+=861.7). Conjugates of NT-proBNP Peptides P2: AEQLAL [SEQ ID NO: 9]; P3: EPLHRS [SEQ ID NO: 10]; P4: LALEPL [SEQ ID NO: 11]; P5: AEQLALE [SEQ ID NO: 12]; and P6: LEPLHRS [SEQ ID NO: 13] with fluorescein at the 5 position were synthesized using substantially the same synthetic and purification procedures and starting materials as described above for NT-proBNP Peptide P1. The final conjugates were characterized by LCMS as: P2-Fl, (M+1=1002.5); P3-Fl, (M+1=1096.7); P4-Fl (M+1=1013.4): P5-Fl, (M+1=1131.8); P6-Fl (M+1=1209.9)

Preparation of Canine NT-ProBNP Peptide-DFF Conjugates Conjugated at the 5-Position NT-proBNP peptide P1 with an amino acid sequence of AEQLALEPLHRS (2.81 mg, 0.0021 mmol, custom synthesized by GenScript of Piscataway, NJ), 5-difluorocarboxyfluorescein succinimidyl ester (1.0 mg, 0.0021 mmol, commercially available from ATT Bioquest of Sunnyvale, CA), and N'N-diisopropylethylamine (1.5 µl, 0.0089 mmol) were dissolved in anhydrous DMSO (0.5 ml). The resulting mixture was stirred overnight at room temperature and then diluted in 1 ml of 30% ACN in water (containing 0.1% formic acid) and purified by column chromatography using a C18 reverse phase column (5 g) that was eluted with a gradient of 30% to 100% acetonitrile in water on a Biotage Isolera™ purification system. The fractions were collected automatically by monitoring the absorption at both 257 nm and 470 nm. The fractions with an absorption at 470 nm were analyzed by LCMS and the fractions containing the target peptide P1-DFF conjugate were combined and lyophilized to provide final a yellow, solid product confirmed by LCMS (M2+=879.8). Conjugates of NT-proBNP Peptides P2: AEQLAL [SEQ ID NO: 9]; P3: EPLHRS [SEQ ID NO: 10]; P4: LALEPL [SEQ ID NO: 11]; P5: AEQLALE [SEQ ID NO: 12] and P6: LEPLHRS [SEQ ID NO: 13] with DFF at the 5-position were synthesized using substantially the same synthetic and purification procedures and starting materials as described for NT-proBNP Peptide P1 above. The final conjugates were characterized by LCMS as: P2-DFF, (M+1=1039.1); P3-DFF, (M+1=1132.2); P4-DFF (M+1=1049.5): P5-DFF, (M+1=1167.9); P6-DFF(M+1=1245.9)

Fluorescence Quenching of Canine NT-proBNP P1-Fl and P1-DFF by Anti-NT-ProBNP Mab and Ab-BHQ10

NT-proBNP peptide-fluorescein (Fl) or -difluorofluorescein (DFF) conjugates were dissolved in DMSO (0.4 mM) and diluted with PBS to provide a stock solution (100 nM). Monoclonal anti-NT-proBNP antibody (ADX-15 Mab, IDEXX Laboratories Inc. of Westbrook, ME) (6.84 mg/ml) was serially diluted in PBS buffer to provide solutions having an antibody concentration ranging from 0 to 800 nM in PBS. In a 96 well black assay plate containing the serially diluted antibody solution (50 µL) was added the P1-Fl or P1-DFF, or other peptide-Fl or Peptide-DFF solution (50 µL), mixed well, incubated for 30 min and the fluorescence intensities recorded (excitation at 485 nm and emission at 520 nm). The results are provided in FIG. 47, FIG. 48, and Table 2.

Figure 47:
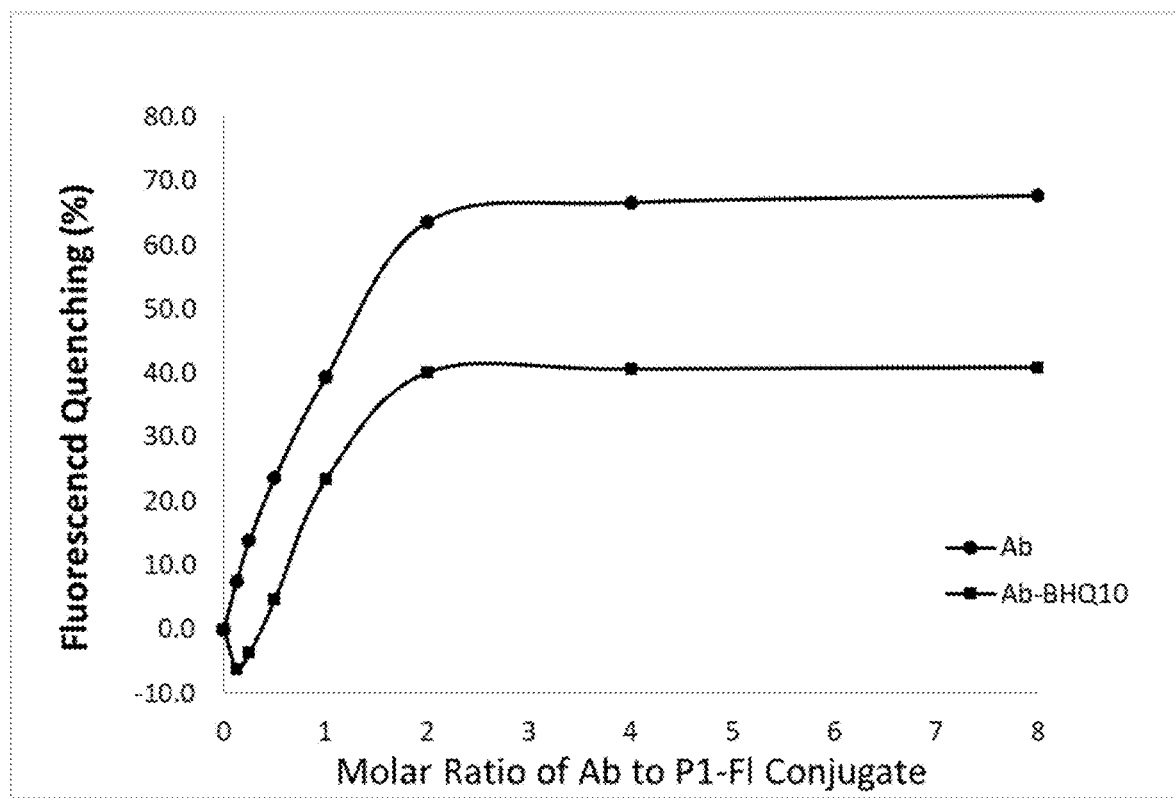
FIG. 47 is a plot of percent fluorescence quenching against the ratio of anti-NT-proBNP antibody to NT-proBNP peptide P1-Fl (Ab), and against the ratio of anti-NT-proBNP antibody-BHQ10 to peptide P1-F1, as described in Example 52.
Figure 48:
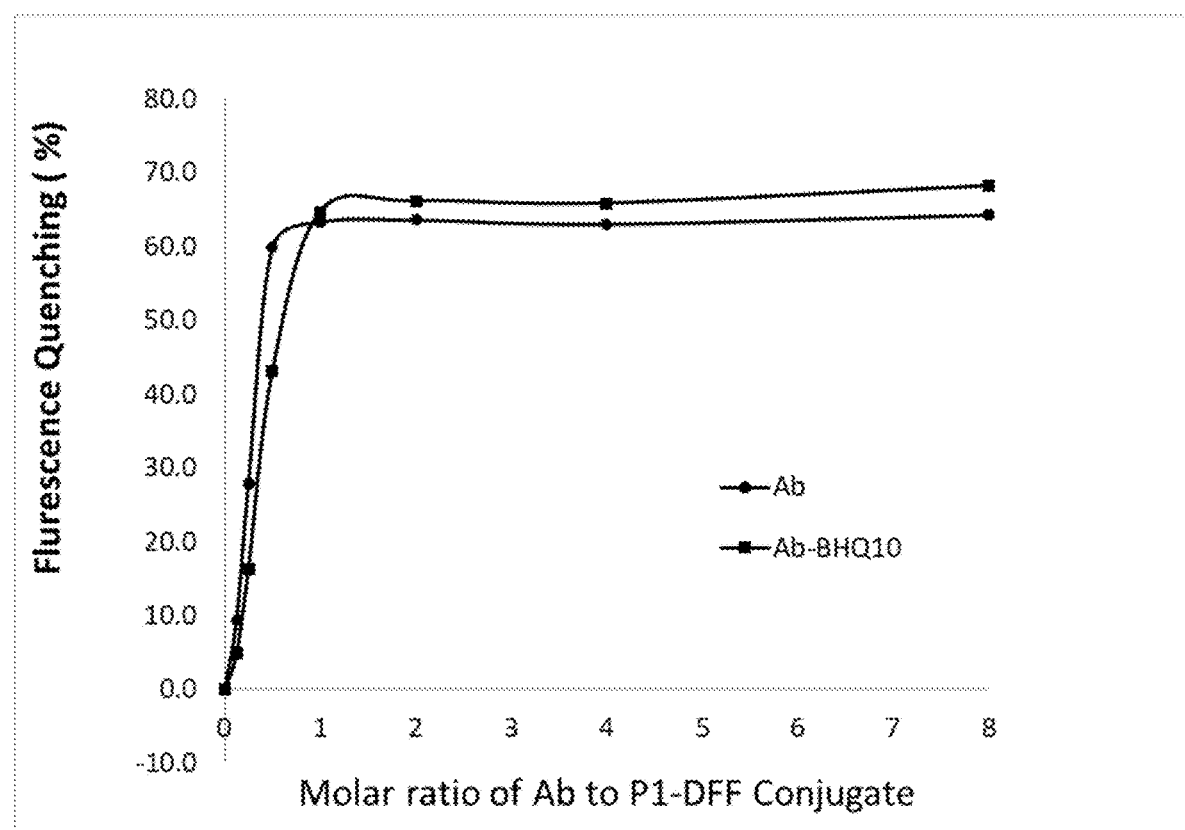
FIG. 48 is a plot of percent fluorescence quenching against the ratio of anti-NT-proBNP antibody to NT-proBNP peptide P1-DFF (Ab), and against the ratio of anti-NT-proBNP antibody-BHQ10 to P1-DFF (Ab-BHQ10), as described in Example 52.

FIG. 47 shows that a fluorescence quenching of P1-Fl by the addition of anti-NT-proBNP antibody reached up to 70%, and quenching approached a saturation point when the molar ratio of anti-NT-proBNP Ab to the P1-Fl was 2:1. Fluorescence quenching of P1-Fl by the addition of anti-NT-proBNP antibody-BHQ10 reached up to 40%, and quenching approached a saturation point when the molar ratio of anti-NT-proBNP Ab-BHQ10 to the P1-Fl was 2:1. FIG. 48 shows that the fluorescence of P1-DFF was quenched in the presence of anti-NT-proBNP-Mab up to approximately 70%, and quenching approached saturation at a molar ratio of antibody to P1-DFF at 1:1. The fluorescence of P1-DFF was quenched up to approximately 65% in the presence of Anti-NT-proBNP Ab-BHQ10. All other NT-proBNP peptide-Fl or -DFF conjugates (P2, P3, P4, P5) exhibited no quenching upon addition of the antibody or antibody-BHQ10 at any molar ratio from 1:1 to 8:1. NT-proBNP P6-Fl and P6-DFF exhibited slight fluorescence quenching (1.0 to 3.7%) at a ratio of 1:1, which increased to approximately 10% at a ratio of 8:1. The results at a 1:1 molar ratio are summarized in Table 2.

TABLE 2

Percentage Fluorescence Quenching of NP proBNP Peptide Fluorophore-Conjugates by Anti-NT-proBNP mAb (Ab)or Anti-NT-proBNP mAb-BHQ10 conjugate (Ab-BHQ10) at Ab/Conjugate molar ratio of 1:1.

| NP-proBNP Peptide | Fl Conjugate | | DFF Conjugate | |
|---|---|---|---|---|
| | Ab | Ab-BHQ10 | Ab | Ab-BHQ10 |
| P1 | 39.4% | 40.2% | 63.3% | 64.7% |
| P2 | No | No | No | No |
| P3 | No | No | No | No |
| P4 | No | No | No | No |
| P5 | No | No | No | No |
| P6 | 2.0% | 3.7% | 1.0% | 1.2% |

(No = No Quenching.)

Canine NT-ProBNP Peptide P1 Dose Response in PBS and Serum

A mixture of NT-proBNP P1-Fl or P1-DFF in PBS (100 nM, 25 µL) and anti-NT-proBNP-Mab in PBS (100 nM, 254 µL) were incubated at room temperature for 30 min in the wells of a 96 well black assay plate. A series of NT-proBNP peptide P1 standard solutions in PBS or charcoal stripped serum having peptide or protein concentrations ranging from 0 to 320 nM (50 µL) were then added to the mixtures of P1-Fl or P1-DFF and anti-NT-proBNP Mab in PBS. The plate was then incubated for 30 min at room temperature and the fluorescence intensities recorded at excitation at 485 nm and emission at 520 nm. The results are shown in FIG. 49, FIG. 50, FIG. 51, and FIG. 52.

Figure 49:
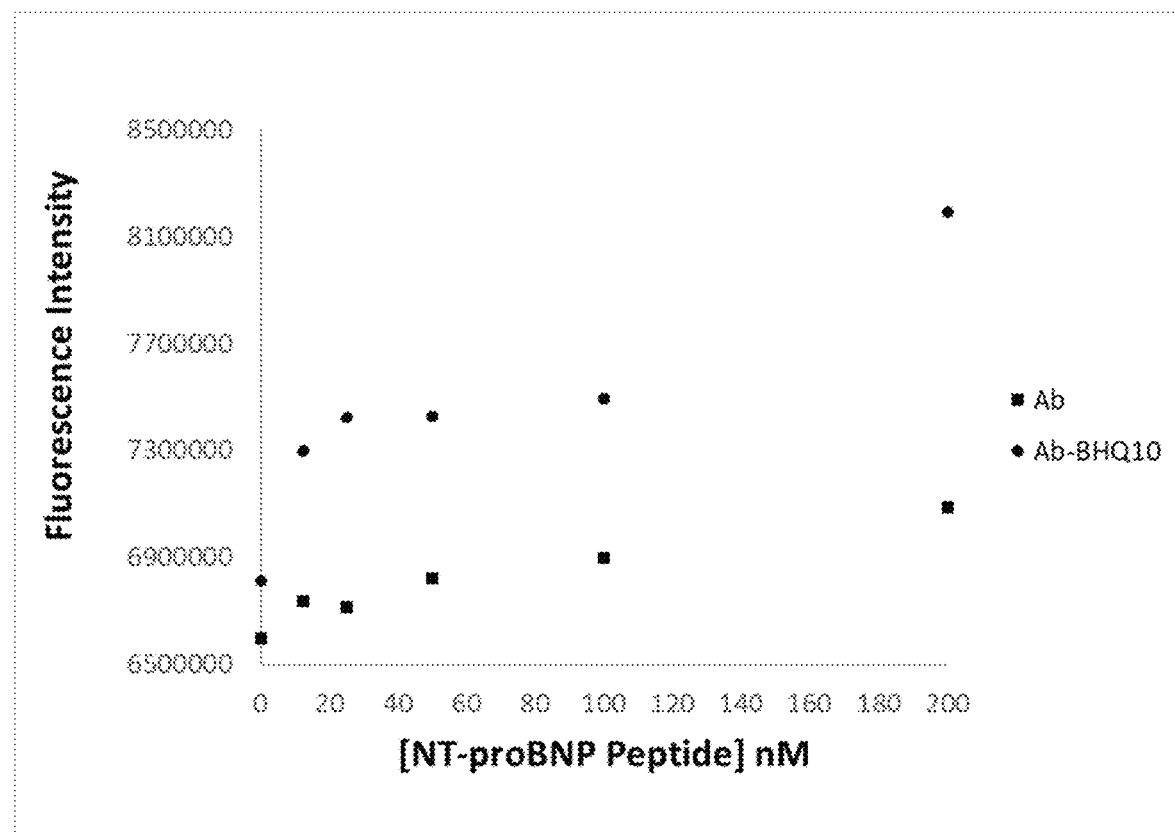
FIG. 49 is a plot of percent fluorescent recovery when NT-proBNP peptide P1 is added to a solution of P1-Fl and anti-NT-proBNP antibody (Ab), or a solution of P1-Fl and antibody-BHQ10 (Ab-BHQ10), as a function of the P1 concentration as described in Example 52.
Figure 50:
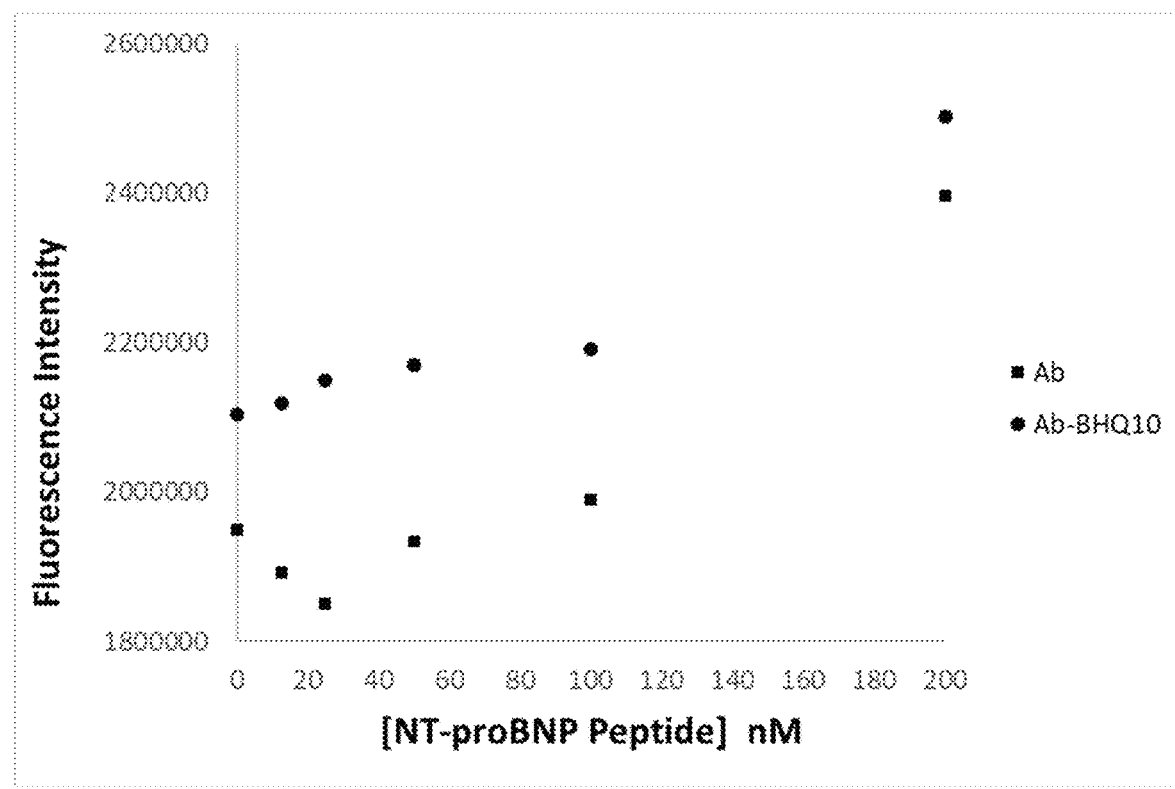
FIG. 50 is a plot of percent fluorescent recovery when NT-proBNP peptide P1 is added to a solution of P1-DFF and anti-NT-proBNP antibody (Ab), or to a solution of P1-DFF and anti-NT-proBNP antibody-BHQ10 as a function of the P1 concentration as described in Example 52.
Figure 51:
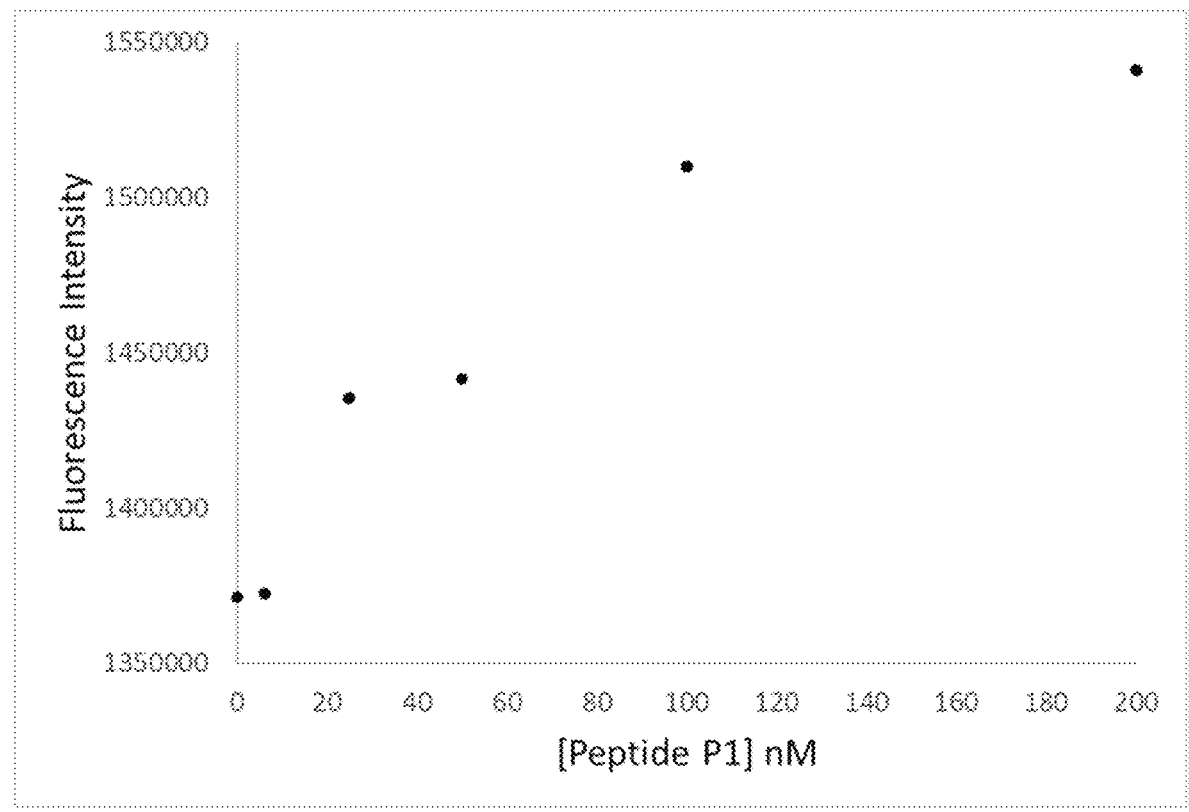
FIG. 51 is a plot of percent fluorescent recovery when NT-proBNP peptide P1 spiked into charcoal stripped serum is added to a solution of P1-Fl and anti-NT-proBNP antibody as a function of the P1 concentration as described in Example 52.
Figure 52:
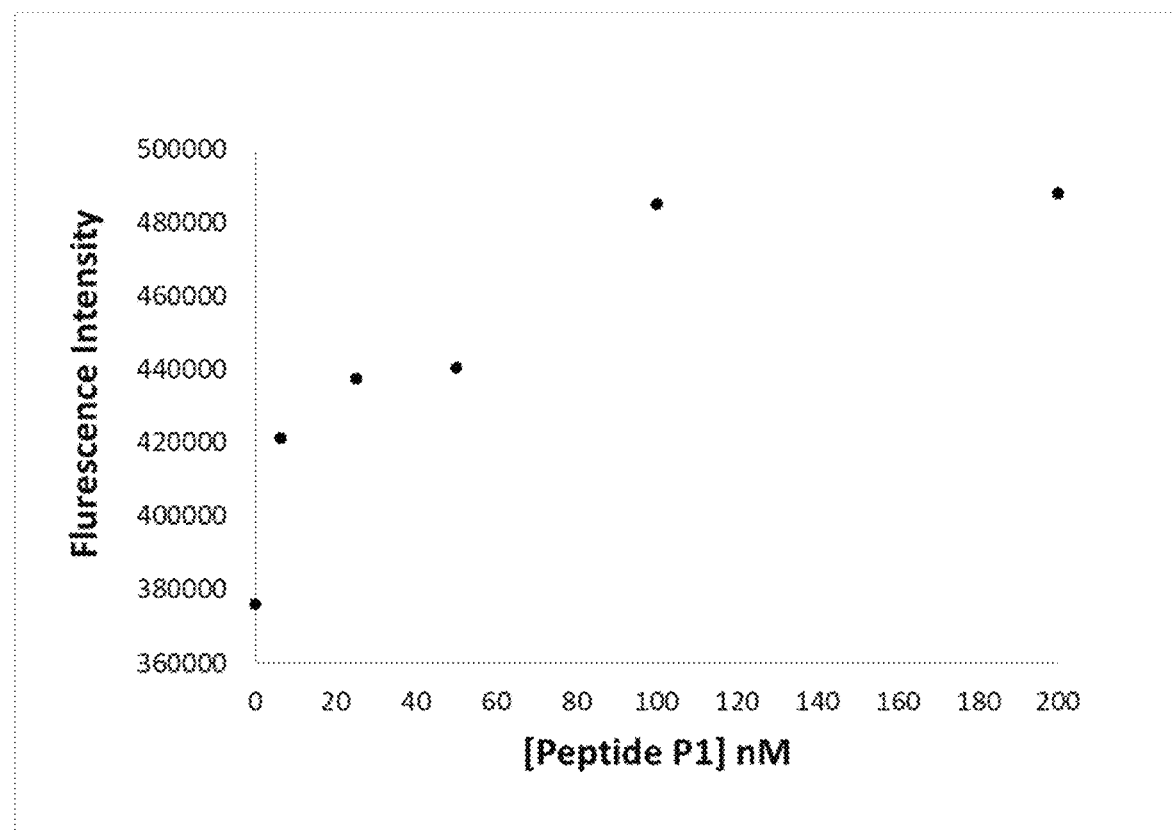
FIG. 52 is a plot of percent fluorescent recovery when NT-proBNP peptide P1 spiked into charcoal stripped serum is added to a solution of P1-DFF and anti-NT-proBNP antibody as a function of the P1 concentration as described in Example 52.

FIG. 49 shows an increase in fluorescence intensity as a function of increasing NT-proBNP peptide P1 concentration, i.e., a dose response was observed when the peptide was added to a mixture of P1-Fl with anti-NT-proBNP antibody (Ab), or antibody-BHQ10 (Ab-BHQ10). FIG. 50 also shows an increase in fluorescence intensity as a function of increasing NT-proBNP peptide P1 concentration, i.e., a dose response was observed when the peptide was added to a mixture of P1-DFF with anti-NT-proBNP antibody (Ab), or antibody-BHQ10 (Ab-BHQ10). P1 peptide also produced a dose response in serum with a mixture of antibody or antibody-BHQ10 with P1-Fl (FIG. 51) or P1-DFF (FIG. 52).

Canine NT-ProBNP Full Length Protein Dose Response

A mixture of NT-proBNP P1-Fl or P1-DFF in PBS (200 nM, 10 µL) and anti-NT-proBNP Mab in PBS (200 nM, 10 µL) were incubated at room temperature for 30 min in the wells of a 96 well black assay plate. A series of NT-proBNP peptide P1 standard solutions in PBS having NT-proBNP full length protein (lyophilized powder synthesized by New England Biolabs of Ipswich, MA) at concentrations ranging from 0 to 320 nM (80 µL) were then added to the mixtures of P1-Fl or P1-DFF and anti-NT-proBNP Mab in PBS. The plate was then incubated for 30 min at room temperature and the fluorescence intensities recorded at an excitation of 485 nm and an emission of 520 nm. The results are shown in FIG. 53 and FIG. 54.

Figure 53:
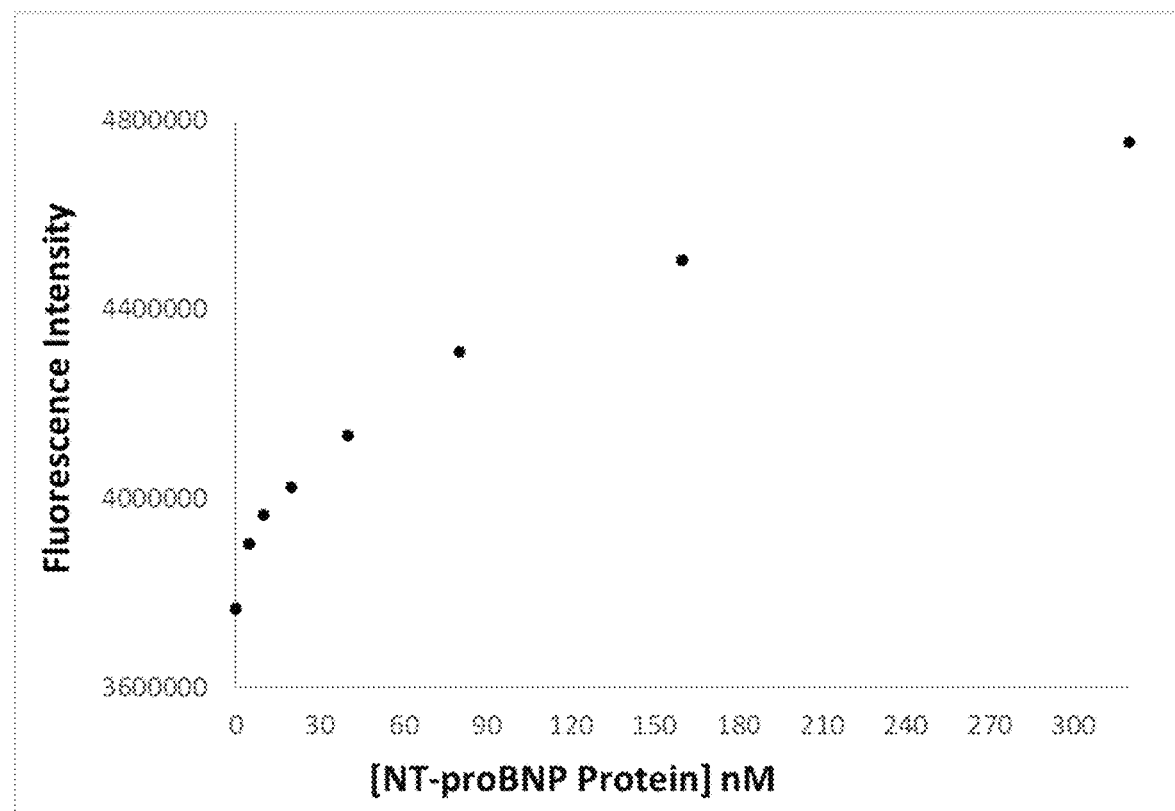
FIG. 53 is a plot of percent fluorescent recovery when NT-proBNP full length protein in PBS is added to a solution of P1-Fl and anti-NT-proBNP antibody (P1-Fl/Ab=1:1) as a function of the NT-proBNP protein concentration as described in Example 52.
Figure 54:
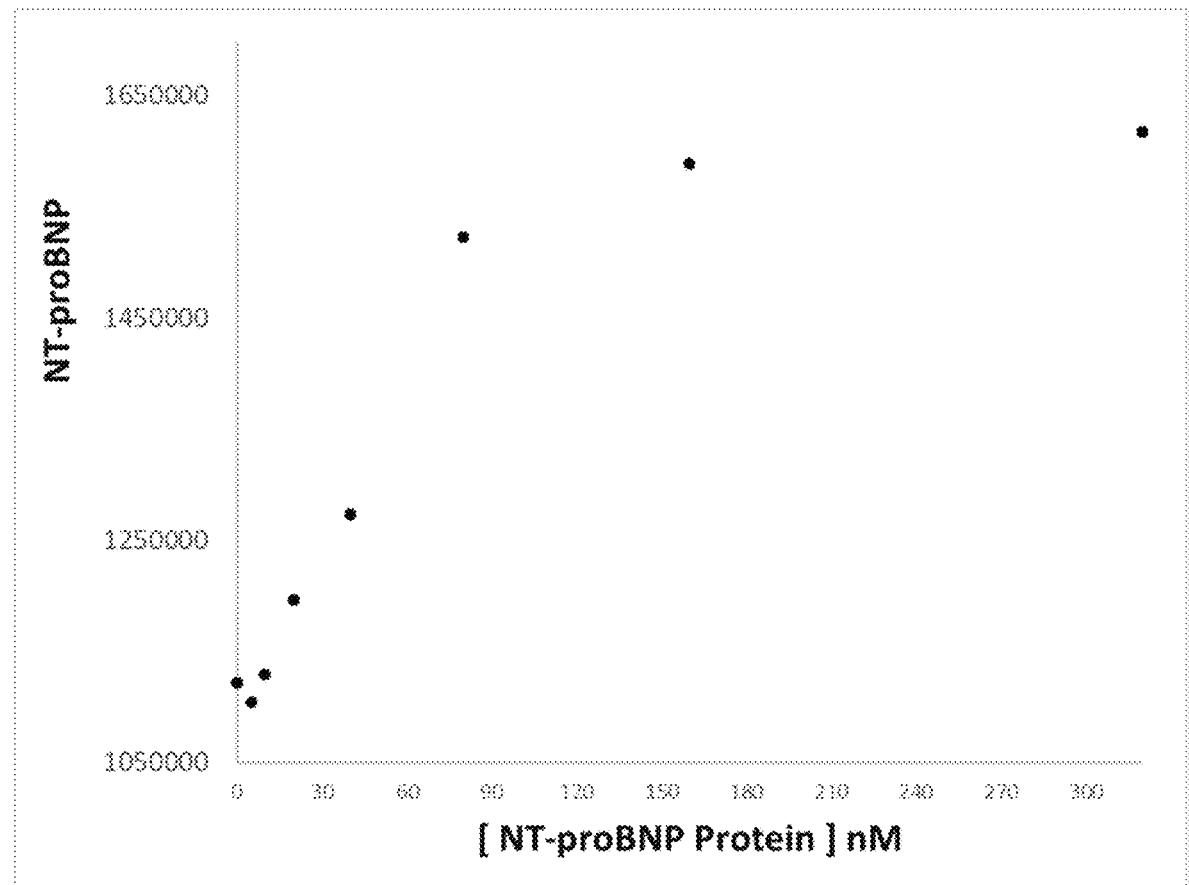
FIG. 54 is a plot of percent fluorescent recovery when NT-proBNP full length protein in PBS is added to a solution of P1-DFF and anti-NT-proBNP antibody (P1-DFF/Ab=1:1) as a function of the NT-proBNP protein concentration as described in Example 52.
Figure 55:
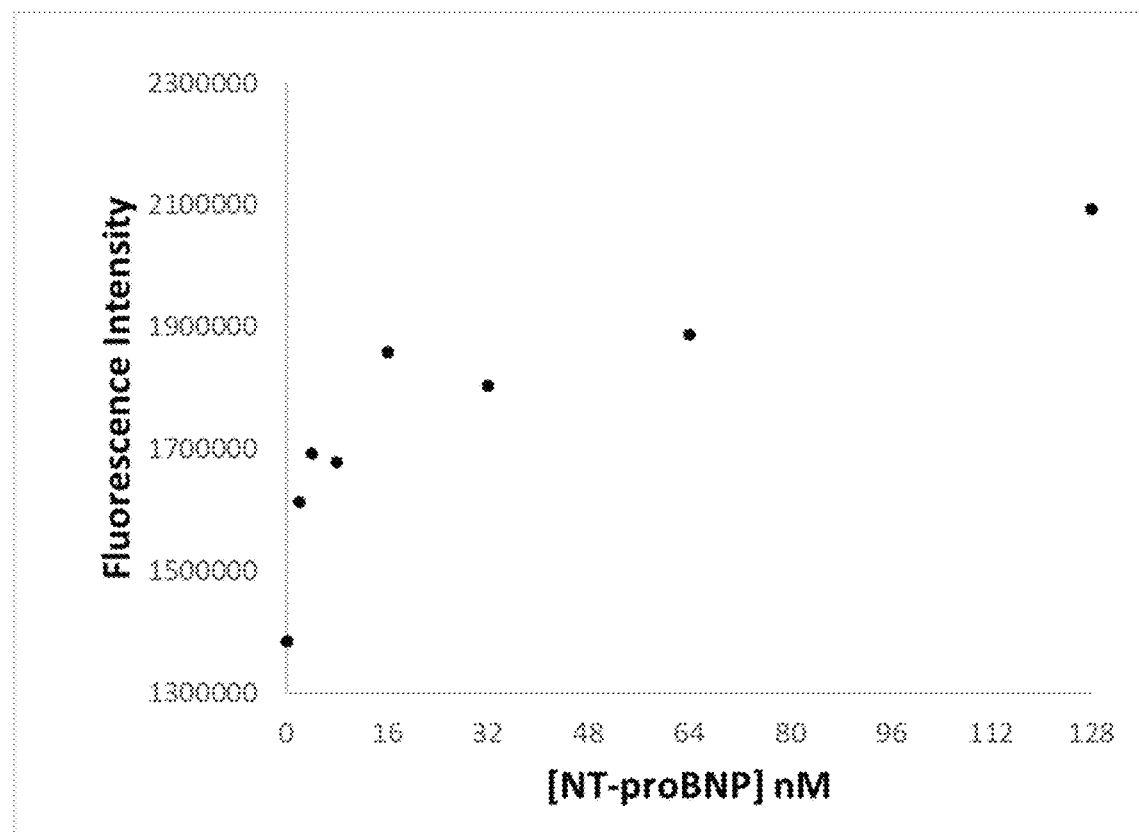
FIG. 55 is a plot of percent fluorescent recovery when NT-proBNP full length protein in serum is added to a solution of P1-Fl and anti-NT-proBNP antibody (P1-Fl/Ab=2:1) as a function of the NT-proBNP protein concentration as described in Example 52.
Figure 56:
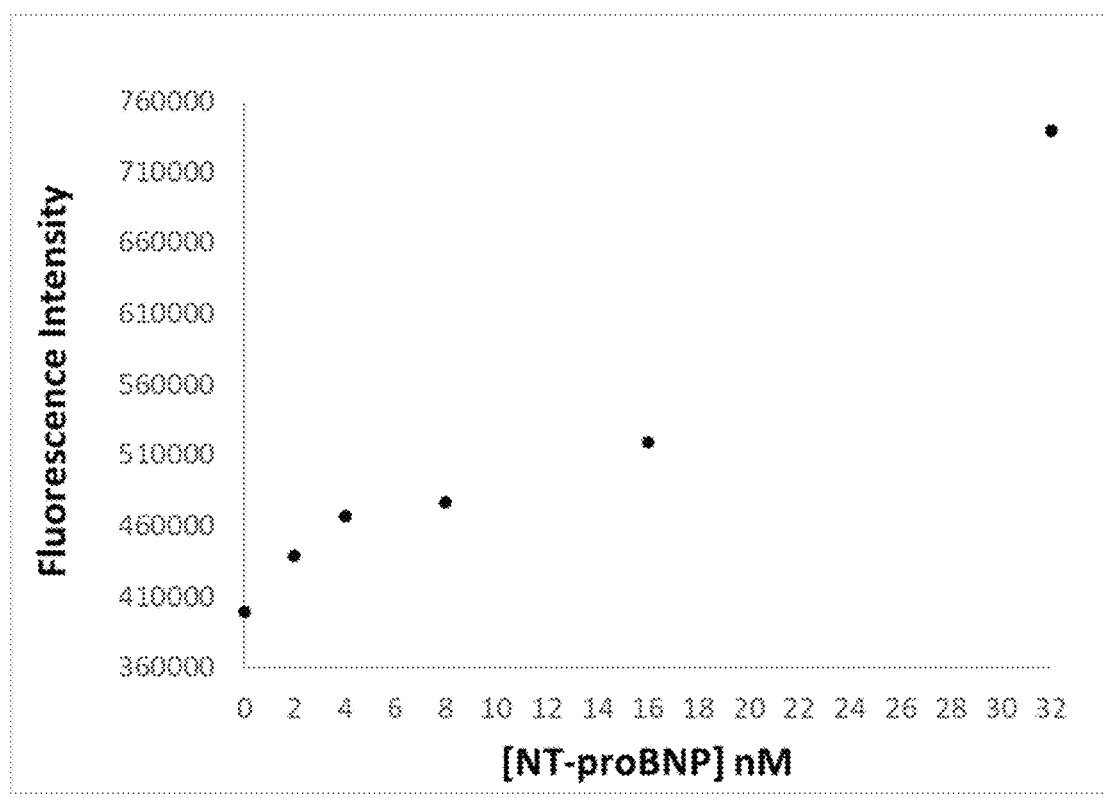
FIG. 56 is a plot of percent fluorescent recovery when NT-proBNP full length protein in serum is added to a solution of P1-DFF and anti-NT-proBNP antibody (P1-DFF/Ab=2:1) as a function of the NT-proBNP protein concentration as described in Example 52.

FIG. 53 shows an increase in fluorescence intensity as a function of increasing concentrations of full length NT-proBNP protein i.e., a dose response was observed when the protein was added to a mixture of P1-Fl and anti-NT-proBNP antibody at a ratio of P1-Fl/Ab at 1:1. Similarly, a dose response was observed when the protein was added to a mixture of P1-DFF and antibody at ratio of 1:1, as shown in FIG. 54. A dose response was also observed when full length NT-proBNP was spiked into charcoal stripped serum and added to a mixture of either P1-Fl/Ab (FIG. 55) or P1-DFF/Ab (FIG. 56). The assay sensitivity is improved by reducing the relative amount of antibody in the mixture, as shown in FIG. 55 for P1-Fl/Ab=2:1 and in FIG. 56 for P1-DFF/Ab at 2:1.

The entire disclosure of all references that have been cited are incorporated herein by reference.

What is claimed is:

1. A method for determining the presence of or the amount of an analyte in a sample comprising:
   (i) providing a sample suspected of containing an analyte;
   (ii) contacting the sample with a fluorescent tracer and a binding partner to provide an assay composition;
   wherein the binding partner is specific for the analyte and the fluorescent tracer;
   (iii) irradiating the assay composition with light at a first wavelength; and
   (iv) measuring the intensity of light emitted at a second wavelength,
   wherein
   (a) the intensity of the light emitted at the second wavelength is greater if the fluorescent tracer is not bound to the binding partner than if the fluorescent tracer is bound to the binding partner,
   (b) the light at the first wavelength is not linearly polarized, and
   (c) the fluorescent tracer is selected from the group consisting of:

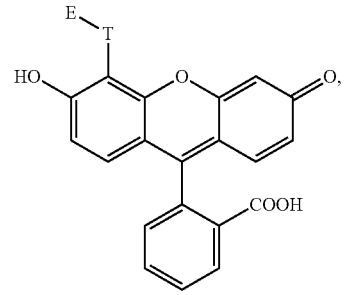

-continued

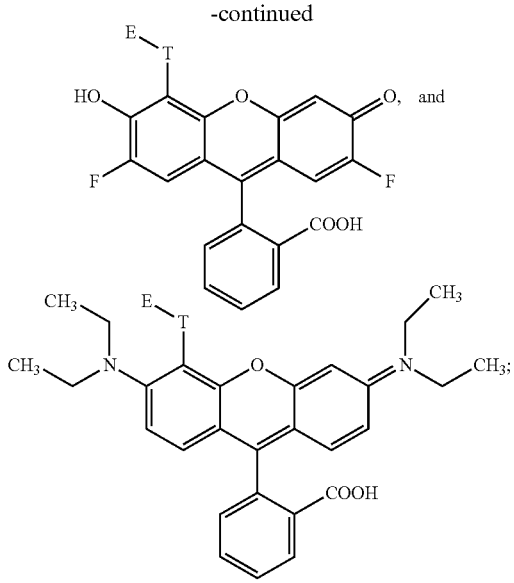

wherein T is a bond or a linking group and E is an epitopic moiety capable of specifically binding to the binding partner; and wherein the intensity of the light emitted at the second wavelength is directly proportional to the concentration of the analyte in the sample.

2. The method of claim 1, wherein the analyte is a macromolecule.

3. The method of claim 2, wherein the analyte is a protein.

4. The method of claim 3, wherein (i) the epitopic moiety is an amino acid chain and wherein the amino acid sequence of the amino acid chain comprises the amino acid sequence of an epitope on the protein that is responsible for complexing with the binding partner, and (ii) the binding partner is optionally conjugated to a quencher.

5. The method of claim 4, wherein the quencher is selected from the group consisting of

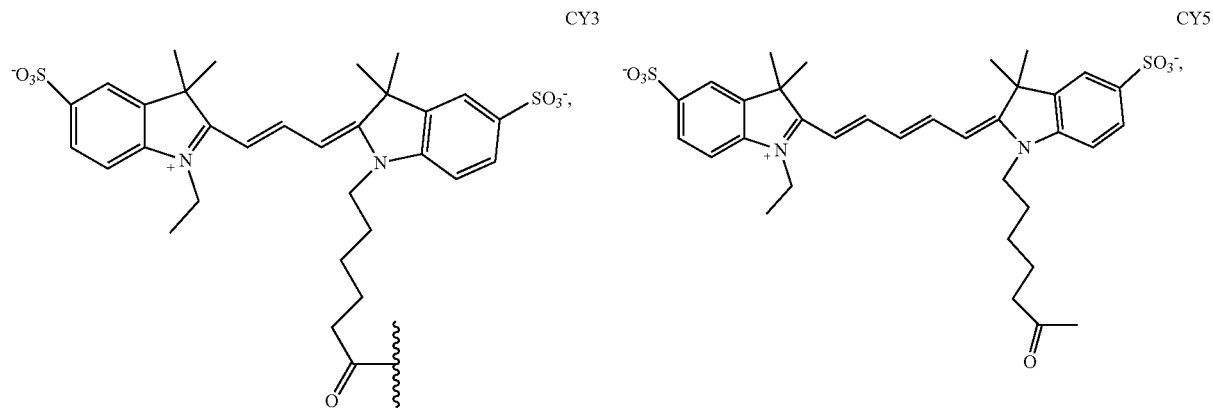

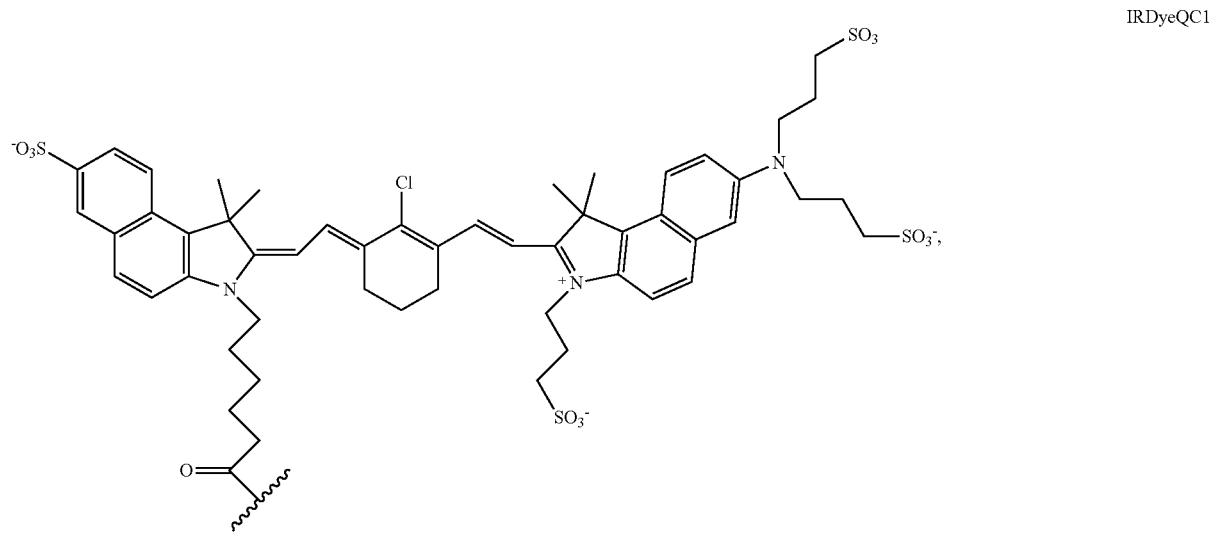

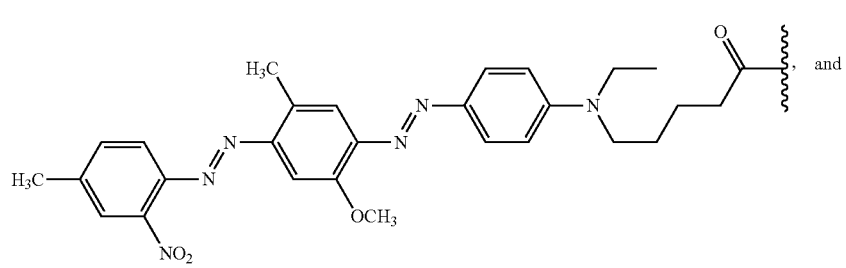

BHQ1

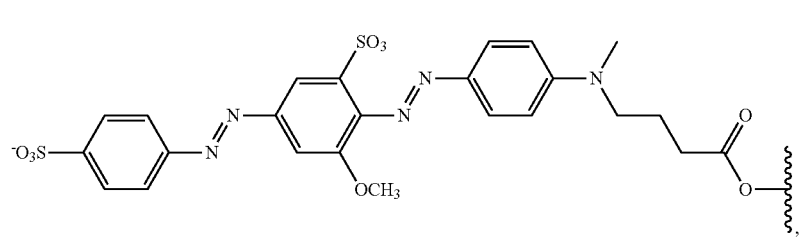

BHQ10 wherein the wavy line indicates the linkage point to the binding partner.

6. The method of claim 4, wherein the binding partner is an antibody.

7. The method of claim 4, wherein the protein is selected from the group consisting of canine CysB protein and canine NT-proBNP.

8. The method of claim 7, wherein the protein is canine CysB protein.

9. The method of claim 8, wherein the binding partner is an anti-cystatin-B antibody and the fluorescent tracer is fluorescein attached to an amino acid sequence selected from the group consisting of SEQ ID NO:2, SEQ ID NO:3, SEQ ID NO:4, SEQ ID NO:5, SEQ ID NO: 6, and SEQ ID NO:7.

10. The method of claim 1, wherein the amino acid sequence is attached to the 4'-position of the fluorescein with a —CH$_2$—linker.

11. The method of claim 9, wherein the anti-cystatin-B antibody is conjugated to the quencher.

12. The method of claim 1, wherein the analyte is an antigen and the binding partner is an antibody.

13. The method of claim 12, wherein the antigen is SDMA and the antibody is an antibody for SDMA.

14. The method of claim 13, wherein the fluorescent tracer is selected from the group consisting of:

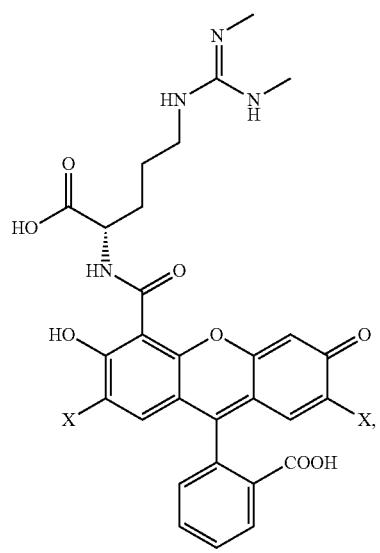

-continued

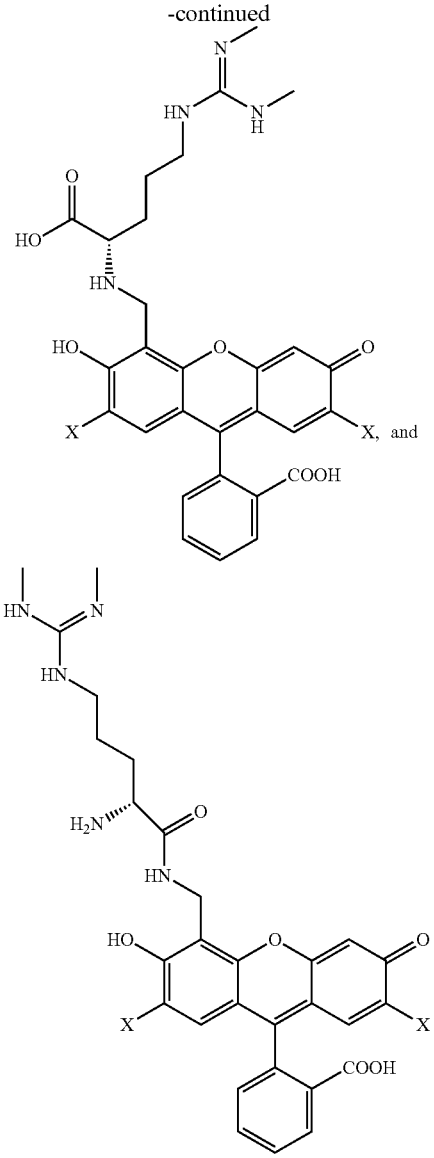

wherein each X is —H—, or each X is —F.

15. The method of claim 14, wherein the antibody for SDMA is conjugated to a quencher.

16. The method of claim 15, wherein the quencher is selected from the group consisting of CY3, CY5, IRDyeQC1, BHQ1, and BHQ10.

17. The method of claim 1, comprising:
(A) providing a slide, wherein the slide comprises sequentially:
(i) a support layer selected from the group consisting of glass, polystyrene, polyesters, polycarbonates, cellulose derivatives, polyethylene terephthalate, and mixtures thereof, wherein the support layer is optically clear to the first wavelength and the second wavelength;
(ii) a primer layer comprising polyurethane;
(ii an indicator layer comprising the fluorescent tracer and the binding partner dispersed in a second polymer, wherein the second polymer is selected from the group consisting of cellulose, cellulose derivatives, polysaccharides, gelatin, gelatin derivatives, polyvinyl alcohol, polyvinyl pyrrolidone, acrylamide polymers, polyurethane, alginate, xantham, and mixtures thereof,
(iv) a filtering layer comprising polyurethane and cellulose; and
(v) a spreading layer comprising a mixture of cellulose and a hydrophilic polymer, wherein the hydrophilic polymer is selected from the group consisting of polyacrylic acid, polyvinylpyrrolidone, polythylene glycol, polyethylene oxide, polyvinyl alcohol, polyacrylamides, and polethylenimines,
(B) depositing the sample on the spreading layer of the slide;
(C) allowing the sample to diffuse from the spreading layer into the indicator layer so that the sample can contact the fluorescent tracer and the binding partner;
(D) irradiating the support layer of the slide with the light that is not polarized at a first wavelength; and
(E) measuring the intensity of the light emitted at the second wavelength from the support layer of the slide.

18. The method of claim 17, wherein the analyte is SDMA and the antibody is an antibody for SDMA.

19. A method for determining the presence of or the amount of an analyte in a sample comprising:
(i) providing a sample suspected of containing an analyte;
(ii) contacting the sample with a fluorescent tracer and a binding partner to provide an assay composition;
wherein the binding partner is specific for the analyte and the fluorescent tracer;
(iii) irradiating the assay composition with light at a first wavelength; and
(iv) measuring the intensity of light emitted at a second wavelength,
wherein
(a) the intensity of the light emitted at the second wavelength is greater if the fluorescent tracer is not bound to the binding partner than if the fluorescent tracer is bound to the binding partner,
(b) the light at the first wavelength is not linearly polarized,
(c) the fluorescent tracer is selected from the group consisting of:

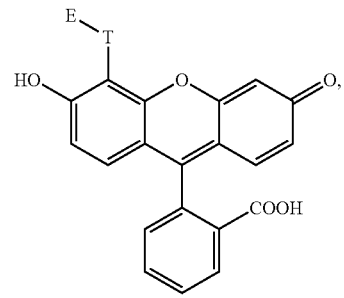

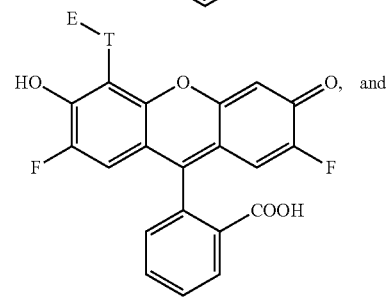

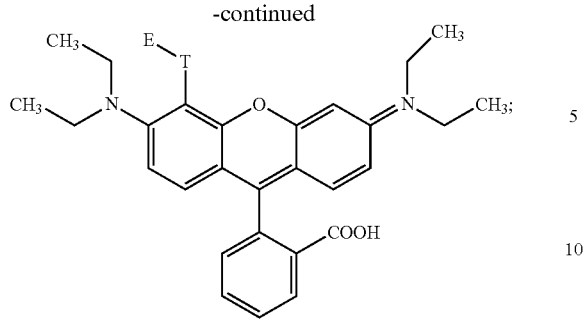

wherein T is a bond or a linking group and E is an epitopic moiety capable of specifically binding to the binding partner;
(d) the intensity of the light emitted at the second wavelength is directly proportional to the concentration of the analyte in the sample; and
(e) wherein the analyte is selected from the group consisting of SDMA, melamine, T4, bile acid, biotin, thyroxine, cystatin-B, NT-proBNP, antibiotics, sulfadimethoxine, cortisol, and progesterone.

* * * * *

UNITED STATES PATENT AND TRADEMARK OFFICE
CERTIFICATE OF CORRECTION

| | | |
|---|---|---|
| PATENT NO. | : 12,345,641 B2 | Page 1 of 1 |
| APPLICATION NO. | : 17/232647 | |
| DATED | : July 1, 2025 | |
| INVENTOR(S) | : Jennifer E. Gagner et al. | |

It is certified that error appears in the above-identified patent and that said Letters Patent is hereby corrected as shown below:

On the Title Page

Item [73], replace "IDEZZ Laboratories, Inc., Westbrook, ME (US)" with --IDEXX Laboratories Inc., Westbrook, ME (US)--

Signed and Sealed this
Twenty-sixth Day of August, 2025

Coke Morgan Stewart
*Acting Director of the United States Patent and Trademark Office*

SEQUENCE LISTING

```
<160> NUMBER OF SEQ ID NOS: 16

<210> SEQ ID NO 1
<211> LENGTH: 98
<212> TYPE: PRT
<213> ORGANISM: Canis familiaris

<400> SEQUENCE: 1

Met Met Cys Gly Ala Pro Ser Ala Ser Gln Pro Ala Thr Ala Asp Thr
1               5                   10                  15

Gln Ala Ile Ala Asp Gln Val Lys Ala Gln Leu Glu Glu Arg Glu Asn
            20                  25                  30

Lys Lys Tyr Thr Thr Phe Lys Ala Val Thr Phe Arg Ser Gln Val Val
        35                  40                  45

Ala Gly Thr Pro Tyr Phe Ile Lys Val Gln Val Asp Asp Asp Glu Phe
    50                  55                  60

Val His Leu Arg Val Phe Gln Ser Leu Pro His Glu Asn Lys Pro Leu
65                  70                  75                  80

Ala Leu Ser Ser Tyr Gln Thr Asn Lys Ala Lys His Asp Glu Leu Ala
```

```
                        85                  90                  95

Tyr Phe

<210> SEQ ID NO 2
<211> LENGTH: 13
<212> TYPE: PRT
<213> ORGANISM: Artificial Sequence
<220> FEATURE:
<223> OTHER INFORMATION: Synthetic

<400> SEQUENCE: 2

Gln Thr Asn Lys Ala Lys His Asp Glu Leu Ala Tyr Phe
1               5                   10

<210> SEQ ID NO 3
<211> LENGTH: 14
<212> TYPE: PRT
<213> ORGANISM: Artificial Sequence
<220> FEATURE:
<223> OTHER INFORMATION: Synthetic

<400> SEQUENCE: 3

Tyr Gln Thr Asn Lys Ala Lys His Asp Glu Leu Ala Tyr Phe
1               5                   10

<210> SEQ ID NO 4
<211> LENGTH: 8
<212> TYPE: PRT
<213> ORGANISM: Artificial Sequence
<220> FEATURE:
<223> OTHER INFORMATION: Synthetic

<400> SEQUENCE: 4

Gly His Asp Glu Leu Ala Tyr Phe
1               5

<210> SEQ ID NO 5
<211> LENGTH: 7
<212> TYPE: PRT
<213> ORGANISM: Artificial Sequence
<220> FEATURE:
<223> OTHER INFORMATION: Synthetic

<400> SEQUENCE: 5

Gly Asp Glu Leu Ala Tyr Phe
1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic

<400> SEQUENCE: 6

Gly Glu Leu Ala Tyr Phe
1               5

<210> SEQ ID NO 7
<211> LENGTH: 5
<212> TYPE: PRT
<213> ORGANISM: Artificial Sequence
<220> FEATURE:
<223> OTHER INFORMATION: Synthetic

<400> SEQUENCE: 7
```

```
Gly Leu Ala Tyr Phe
1               5

<210> SEQ ID NO 8
<211> LENGTH: 12
<212> TYPE: PRT
<213> ORGANISM: Artificial Sequence
<220> FEATURE:
<223> OTHER INFORMATION: Synthetic

<400> SEQUENCE: 8

Ala Glu Gln Leu Ala Leu Glu Pro Leu His Arg Ser
1               5                   10

<210> SEQ ID NO 9
<211> LENGTH: 6
<212> TYPE: PRT
<213> ORGANISM: Artificial Sequence
<220> FEATURE:
<223> OTHER INFORMATION: Synthetic

<400> SEQUENCE: 9

Ala Glu Gln Leu Ala Leu
1               5

<210> SEQ ID NO 10
<211> LENGTH: 6
<212> TYPE: PRT
<213> ORGANISM: Artificial Sequence
<220> FEATURE:
<223> OTHER INFORMATION: Synthetic

<400> SEQUENCE: 10

Glu Pro Leu His Arg Ser
1               5

<210> SEQ ID NO 11
<211> LENGTH: 6
<212> TYPE: PRT
<213> ORGANISM: Artificial Sequence
<220> FEATURE:
<223> OTHER INFORMATION: Synthetic

<400> SEQUENCE: 11

Leu Ala Leu Glu Pro Leu
1               5

<210> SEQ ID NO 12
<211> LENGTH: 7
<212> TYPE: PRT
<213> ORGANISM: Artificial Sequence
<220> FEATURE:
<223> OTHER INFORMATION: Synthetic

<400> SEQUENCE: 12

Ala Glu Gln Leu Ala Leu Glu
1               5

<210> SEQ ID NO 13
<211> LENGTH: 7
<212> TYPE: PRT
<213> ORGANISM: Artificial Sequence
<220> FEATURE:
<223> OTHER INFORMATION: Synthetic
```

```
<400> SEQUENCE: 13

Leu Glu Pro Leu His Arg Ser
1               5

<210> SEQ ID NO 14
<211> LENGTH: 79
<212> TYPE: PRT
<213> ORGANISM: Canis familiaris

<400> SEQUENCE: 14

His Pro Leu Gly Gly Arg Ser Pro Ala Ser Glu Ala Ser Glu Ala Ser
1               5                   10                  15

Glu Ala Ser Gly Leu Trp Ala Val Gln Glu Leu Leu Gly Arg Leu Lys
                20                  25                  30

Asp Ala Val Ser Glu Leu Gln Ala Glu Gln Leu Ala Leu Glu Pro Leu
            35                  40                  45

His Arg Ser His Ser Pro Ala Glu Ala Pro Glu Ala Gly Gly Thr Pro
        50                  55                  60

Arg Gly Val Leu Ala Pro His Asp Ser Val Leu Gln Ala Leu Arg
65                  70                  75

<210> SEQ ID NO 15
<211> LENGTH: 21
<212> TYPE: PRT
<213> ORGANISM: Canis familiaris

<400> SEQUENCE: 15

Gly Arg Ser Pro Ala Ser Glu Ala Ser Glu Ala Ser Glu Ala Ser Gly
1               5                   10                  15

Leu Trp Ala Val Gln
                20

<210> SEQ ID NO 16
<211> LENGTH: 26
<212> TYPE: PRT
<213> ORGANISM: Canis familiaris

<400> SEQUENCE: 16

Ser His Ser Pro Ala Glu Ala Pro Glu Ala Gly Gly Thr Pro Arg Gly
1               5                   10                  15

Val Leu Ala Pro His Asp Ser Val Leu Gln
                20                  25
```